(12) United States Patent
Chan et al.

(10) Patent No.: US 8,765,757 B2
(45) Date of Patent: *Jul. 1, 2014

(54) 3-HETEROCYCLIC SUBSTITUTED INDOLE DERIVATIVES AND METHODS OF USE THEREOF

(75) Inventors: Tin-Yau Chan, Edison, NJ (US); Jose S. Duca, Cranford, NJ (US); Liwu Hong, Edison, NJ (US); Charles A. Lesburg, Short Hills, NJ (US); Brian A. McKittrick, New Vernon, NJ (US); Haiyan Pu, Livingston, NJ (US); Li Wang, Nanuet, NY (US); Henry M. Vaccaro, South Plainfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 995 days.

This patent is subject to a terminal disclaimer.

(21) Appl. No.: 12/743,016

(22) PCT Filed: Nov. 13, 2008

(86) PCT No.: PCT/US2008/083351
§ 371 (c)(1),
(2), (4) Date: Mar. 22, 2011

(87) PCT Pub. No.: WO2009/064848
PCT Pub. Date: May 22, 2009

(65) Prior Publication Data
US 2011/0165118 A1 Jul. 7, 2011

Related U.S. Application Data

(60) Provisional application No. 60/988,528, filed on Nov. 16, 2007.

(51) Int. Cl.
C07D 519/00 (2006.01)
A61P 31/20 (2006.01)

(52) U.S. Cl.
USPC .............. 514/249; 514/263.2; 514/266.2; 514/260.1; 514/274; 514/264.1; 514/406; 514/265.1; 514/262.1; 514/267; 514/389; 514/339; 544/265; 544/284; 544/278; 544/279; 544/280; 544/262; 544/257; 544/250; 544/253; 544/310; 546/278.1; 548/361.1; 548/312.1

(58) Field of Classification Search
None
See application file for complete search history.

(56) References Cited

U.S. PATENT DOCUMENTS

| | | | |
|---|---|---|---|
| 3,632,805 A | 1/1972 | Yamamoto et al. | |
| 4,634,697 A | 1/1987 | Hamashima | |
| 4,812,561 A | 3/1989 | Hamashima et al. | |
| 4,933,443 A | 6/1990 | Hamashima et al. | |
| 5,017,380 A | 5/1991 | Hamashima et al. | |
| 6,800,434 B2 | 10/2004 | Saksena et al. | |
| 6,838,475 B2 | 1/2005 | Arasappan et al. | |
| 6,846,802 B2 | 1/2005 | Chen et al. | |
| 6,911,428 B2 | 6/2005 | Zhu et al. | |
| 6,914,122 B2 | 7/2005 | Venkatraman et al. | |
| 7,012,066 B2 | 3/2006 | Saksena et al. | |
| 8,143,305 B2 * | 3/2012 | Anilkumar et al. | 514/412 |
| 2002/0160962 A1 | 10/2002 | Saksena et al. | |
| 2004/0077704 A1 | 4/2004 | Beight et al. | |
| 2005/0075331 A1 | 4/2005 | Pratt et al. | |
| 2005/0101770 A1 | 5/2005 | Presta | |
| 2005/0176648 A1 | 8/2005 | Saksena et al. | |
| 2005/0249702 A1 | 11/2005 | Njoroge et al. | |
| 2007/0274951 A1 | 11/2007 | Tong et al. | |
| 2010/0098661 A1 | 4/2010 | Chen et al. | |
| 2010/0196319 A1 | 8/2010 | Anilkumar et al. | |
| 2010/0239527 A1 | 9/2010 | Anilkumar et al. | |
| 2010/0260711 A1 | 10/2010 | Chen et al. | |
| 2010/0322901 A1 | 12/2010 | Bennett et al. | |
| 2011/0033417 A1 | 2/2011 | Anilkumar et al. | |
| 2011/0104109 A1 | 5/2011 | Bennett et al. | |
| 2011/0104110 A1 | 5/2011 | Anikumar et al. | |
| 2011/0165118 A1 | 7/2011 | Chan et al. | |

FOREIGN PATENT DOCUMENTS

| | | |
|---|---|---|
| AU | 2002313410 B2 | 7/2002 |
| DE | 648639 C | 8/1937 |
| EP | 0449196 A2 | 10/1991 |
| FR | 2768146 A1 | 3/1999 |
| JP | 4-149429 | 5/2004 |
| WO | 96/37619 A1 | 11/1996 |
| WO | 98/14181 A1 | 4/1998 |
| WO | 98/17679 A1 | 4/1998 |
| WO | 98/22496 A2 | 5/1998 |
| WO | 99/07734 A2 | 2/1999 |
| WO | 02/30895 A1 | 4/2002 |
| WO | 02/068412 A1 | 9/2002 |

(Continued)

OTHER PUBLICATIONS

Beaulieu et al., "Inhibitors of the HCV NS5B polymerase: New hope for the treatment of hepatitis C infections", Current Opinion in Investigational Drugs, 2004, vol. 5, pp. 838-850, No. 8.

Behrens et al., "Identification and properties of the RNA-dependent RNA polymerase of hepatitis C virus", The EMBO Journal, 1996, vol. 15, pp. 12-22, No. 1.

Bioworld Today, 9 (217):4 Nov. 10, 1998, pp. 1-5.

Birnbock et al., "Sulfate Derivatives of 2-Phenylindols as Novel Steroid Sulfatase Inhibitors", Biochemical Pharmacology, 1990, vol. 39, pp. 1709-1713, No. 11.

Bunker et al., "1,3-Diaryl-2-Carboxyindoles as Potent Non-Peptide Endothelin Antagonists", Bioorganic & Medicinal Chemistry Letters, 1996, vol. 6, pp. 1061-1066, No. 9.

(Continued)

*Primary Examiner* — Susanna Moore
(74) *Attorney, Agent, or Firm* — Alysia A. Finnegan; Sheldon O. Heber

(57) ABSTRACT

The present invention relates to 3-Heterocyclic Substituted Indole Derivatives, compositions comprising at least one 3-Heterocyclic Substituted Indole Derivative, and methods of using the 3-Heterocyclic Substituted Indole Derivatives for treating or preventing a viral infection or a virus-related disorder in a patient.

20 Claims, No Drawings

(56) References Cited

FOREIGN PATENT DOCUMENTS

| | | |
|---|---|---|
| WO | 2004/035571 A1 | 4/2004 |
| WO | 2004/106328 A1 | 12/2004 |
| WO | 2005/034941 A1 | 4/2005 |
| WO | 2005/084315 A2 | 9/2005 |
| WO | 2005/087731 A1 | 9/2005 |
| WO | 2005/111018 A1 | 11/2005 |
| WO | 2006/020082 A1 | 2/2006 |
| WO | 2006/032541 A1 | 3/2006 |
| WO | 2006/034337 A2 | 3/2006 |
| WO | 2006/046030 A2 | 5/2006 |
| WO | 2006/076529 A1 | 7/2006 |
| WO | 2007/029029 A2 | 3/2007 |
| WO | 2007/038209 A2 | 4/2007 |
| WO | 2007/084413 A2 | 7/2007 |
| WO | 2007/084435 A2 | 7/2007 |
| WO | 2008/082484 A1 | 7/2008 |

OTHER PUBLICATIONS

Chemical and Pharmaceutical Bulletin, vol. 19, 1971, p. 263-270.
Denmark et al., "Palladium-Catalyzed Cross-Coupling Reactions of Silanolates: A Paradigm Shift in Silicon-Based Cross-Coupling Reactions", Chem. Eur. J., 2006, vol. 12, pp. 4954-4963.
Dimasi et al., "Characterization of Engineered Hepatitis C Virus NS3 Protease Inhibitors Affinity Selected from Human Pancreatic Secretory Trypsin Inhibitor and Minibody Repertoires", Journal of Virology, 1997, vol. 71, pp. 7461-7469, No. 10.
Elzouki et al., "Serine protease inhibitors in patients with chronic viral hepatitis", Journal of Hepatology, 1997, vol. 27, pp. 42-48.
Ferrari et al., "Characterization of Soluble Hepatitis C Virus RNA-Dependent RNA Polymerase Expressed in *Escherichia coli*", Journal of Virology, 1999, vol. 73, pp. 1649-1654, No. 2.
Fonseca et al., "Synthesis and antiviral evaluation of benzimidazoles, quinoxalines and indoles from dehydroabietic acid", Bioorganic & Medicinal Chemistry, 2004, vol. 12, pp. 103-112.
Forbes et al., "Synthesis, Biological Activity, and Molecular Modeling Studies of Selective 5-HT2C/2B Receptor Antagonists", J. Med. Chem., 1996, vol. 39, pp. 4966-4977, No. 25.
Goldsmith et al., "Studies in the Benzindole Series", J. Org. Chem, 1952, vol. 18, pp. 507-514.
Gopalsamy et al., "Design and synthesis of 2,3,4,9-tetrahydro-1H-carbazole and 1,2,3,4-tetrahydro-cyclopenta[b] indole derivatives as non-nucleoside inhibitors of hepatitis C virus NS5B RNA-dependent RNA polymerase", Bioorganic & Medicinal Chemistry Letters, 2006, vol. 16, pp. 2532-2534.
Humphrey et al., "Practical Methodologies for the Synthesis of Indoles", Chem. Rev., 2006, vol. 106, pp. 2875-2911.
International Search Report for International Application No. PCT/US2007/025754, mailed May 13, 2008, (4 pages).
Written Opinion for PCT/US2007/025754, filed Dec. 17, 2007, (7 pages).
International Search Report for International Application No. PCT/US2007/025765, mailed May 13, 2008, (6 pages).
Written Opinion for PCT/US2007/025765, filed Dec. 17, 2007, (8 pages).
International Search Report for International Application No. PCT/US2007/025757, mailed Mar. 6, 2009, (8 pages).
Written Opinion for PCT/US2007/025757, filed Dec. 17, 2007 (12 pages).
International Search Report for International Application No. PCT/US2008/010130, mailed Jan. 22, 2009, (5 pages).
Written Opinion for PCT/US2008/010130, filed Aug. 27, 2008 (9 pages).
International Search Report for International Application No. PCT/US2008/010149, mailed Feb. 2, 2009, (5 pages).
Written Opinion for PCT/US2008/010149, filed Aug. 27, 2008 (6 pages).
International Search Report for International Application No. PCT/US2008/083351, mailed Feb. 27, 2009, (3 pages).
Written Opinion for PCT/US2008/083351, filed Nov. 13, 2008 (5 pages).
International Search Report for International Application No. PCT/US2008/010147, mailed May 4, 2009, (3 pages).
Written Opinion for PCT/US2008/010147, filed Aug. 27, 2008 (6 pages).
International Search Report for International Application No. PCT/US2008/083358, mailed Mar. 6, 2009, (2 pages).
Written Opinion for PCT/US2008/083358, filed Nov. 13, 2008 (5 pages).
International Search Report for International Application No. PCT/US2008/010148, mailed Dec. 9, 2008, (3 pages).
Written Opinion for PCT/US2008/010148, filed Aug. 27, 2008 (7 pages).
International Search Report for International Application No. PCT/US2009/046822, mailed Oct. 7, 2009, (5 pages).
Written Opinion for PCT/US2009/046822, filed Jun. 10, 2009 (8 pages).
Ingallinella et al., "Potent Peptide Inhibitors of Human Hepatitis C Virus NS3 Protease are Obtained by Optimizing the Cleavage Products", Biochemistry, 1998, vol. 37, pp. 8906-8914.
Journal of Heterocyclic Chemistry, vol. 12, 1975, pp. 351-358.
Journal of Medicinal Chemistry, vol. 23, No. 7, 1980, pp. 764-773.
Journal of Organic Chemistry, vol. 27, 1962, pp. 3782-3786.
Landro et al., "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", Biochemistry, 1997, vol. 36, pp. 9340-9348.
Lindsay et al., "SmI2-Promoted Radical Addition Reactions with N-(2-Indolylacyl)oxazolidinones: Synthesis of Bisindole Compounds", Journal of Organic Chemistry, 2007, vol. 72, pp. 4181-4188, No. 11.
Llinas-Brunet et al., "Peptide-Based Inhibitors of the Hepatitis C Virus Serine Protease", Bioorganic & Medicinal Chemistry Letters, 1998, vol. 8, pp. 1713-1718.
Malcolm et al., "SCH 503034, a Mechanism-Based Inhibitor of Hepatitis C Virus NS3 Protease, Suppresses Polyprotein Maturation and Enhances the Antiviral Activity of Alpha Interferon in Replicon Cells", Antimicrobial Agents and Chemotherapy, 2006, vol. 50, pp. 1013-1020, No. 3.
Martin, et al., "Affinity selection of a camelized VH domain antibody inhibitor of hepatitis C virus NS3 protease", Protein Engineering, 1997, vol. 10, pp. 607-614, No. 5.
Martin et al., "Design of Selective Eglin Inhibitors of HCV NS3 Proteinase", Biochemistry, 1998, vol. 37, pp. 11459-11468.
Muratake et al., "Synthesis of Duocarmycin SA by Way of Methyl 4-(Methoxycarbonyl)oxy-3H-pyrrolo[3,2-f] quinoline-2-carboxylate as a Tricyclic Heteroaromatic Intermediate", Chem. Pharm. Bulletin, 1998, vol. 46, pp. 400-412, No. 3.
Ni et al., "Progress and development of small molecule HCV antivirals", Current Opinion in Drug Discovery & Development, 2004, vol. 7, pp. 446-459, No. 4.
Rawal et al., "Photocyclization of Pyrrole Analogues of Stilbene: an Expedient Approach to Anti-tumour Agent CC-1065", Journal Chem. Soc., Chem. Commun., 1984, pp. 1526-1527.
Sechi et al., "Design and Synthesis of Novel Indole β-Diketo Acid Derivatives as HIV-1 Integrase Inhibitors", J. Med. Chem., 2004, vol. 47, pp. 5298-5310, No. 21.
Silvestri et al., "Synthesis and biological evaluation of 5H-indolo [3,2-b][1,5]benzothiazepine derivatives, designed as conformationally constrained analogues of the human immunodeficiency virus type 1 reverse transcriptase inhibitor L-737,126", Antiviral Chemistry & Chemotherapy, 1998, vol. 9, pp. 139-148.
Tan et al., "Hepatitis C Therapeutics: Current Status and Emerging Strategies", Nature Reviews, 2002, vol. 1, pp. 867-881.

\* cited by examiner

3-HETEROCYCLIC SUBSTITUTED INDOLE DERIVATIVES AND METHODS OF USE THEREOF

CROSS-REFERENCE TO RELATED APPLICATIONS

This application is a 371 National Stage Application of PCT/US2008/083351 with an international filing date of Nov. 13, 2008 and claims the benefit of U.S. Provisional Patent Application No. 60/988,528 filed Nov. 16, 2007, each of which is hereby incorporated by reference in its entirety.

FIELD OF THE INVENTION

The present invention relates to 3-Heterocyclic Substituted Indole Derivatives, compositions comprising at least one 3-Heterocyclic Substituted Indole Derivative, and methods of using the 3-Heterocyclic Substituted Indole Derivatives for treating or preventing a viral infection or a virus-related disorder in a patient.

BACKGROUND OF THE INVENTION

HCV is a (+)-sense single-stranded RNA virus that has been implicated as the major causative agent in non-A, non-B hepatitis (NANBH). NANBH is distinguished from other types of viral-induced liver disease, such as hepatitis A virus (HAV), hepatitis B virus (HBV), hepatitis delta virus (HDV), as well as from other forms of liver disease such as alcoholism and primary biliary cirrhosis.

Hepatitis C virus is a member of the hepacivirus genus in the family Flaviviridae. It is the major causative agent of non-A, non-B viral hepatitis and is the major cause of transfusion-associated hepatitis and accounts for a significant proportion of hepatitis cases worldwide. Although acute HCV infection is often asymptomatic, nearly 80% of cases resolve to chronic hepatitis. About 60% of patients develop liver disease with various clinical outcomes ranging from an asymptomatic carrier state to chronic active hepatitis and liver cirrhosis (occurring in about 20% of patients), which is strongly associated with the development of hepatocellular carcinoma (occurring in about 1-5% of patients). The World Health Organization estimates that 170 million people are chronically infected with HCV, with an estimated 4 million living in the United States.

HCV has been implicated in cirrhosis of the liver and in induction of hepatocellular carcinoma. The prognosis for patients suffering from HCV infection remains poor as HCV infection is more difficult to treat than other forms of hepatitis. Current data indicates a four-year survival rate below 50% for patients suffering from cirrhosis and a five-year survival rate below 30% for patients diagnosed with localized resectable hepatocellular carcinoma. Patients diagnosed with localized unresectable hepatocellular carcinoma fare even worse, having a five-year survival rate less than 1%.

HCV is an enveloped RNA virus containing a single-stranded positive-sense RNA genome approximately 9.5 kb in length. The RNA genome contains a 5'-nontranslated region (5' NTR) of 341 nucleotides, a large open reading frame (ORF) encoding a single polypeptide of 3,010 to 3,040 amino acids, and a 3'-nontranslated region (3'-NTR) of variable length of about 230 nucleotides. HCV is similar in amino acid sequence and genome organization to flaviviruses and pestiviruses, and therefore HCV has been classified as a third genus of the family Flaviviridae.

The 5' NTR, one of the most conserved regions of the viral genome, contains an internal ribosome entry site (IRES) which plays a pivotal role in the initiation of translation of the viral polyprotein. A single long open reading frame encodes a polyprotein, which is co- or post-translationally processed into structural (core, E1, E2 and p7) and nonstructural (NS2, NS3, NS4A, NS4B, NS5A, and NS5B) viral proteins by either cellular or viral proteinases. The 3' NTR consists of three distinct regions: a variable region of about 38 nucleotides following the stop codon of the polyprotein, a polyuridine tract of variable length with interspersed substitutions of cytidines, and 98 nucleotides (nt) at the very 3' end which are highly conserved among various HCV isolates. By analogy to other plus-strand RNA viruses, the 3'-NTR is thought to play an important role in viral RNA synthesis. The order of the genes within the genome is: $NH_2$-C-E1-E2-p7-NS2-NS3-NS4A-NS4B-NS5A-NS5B-COOH.

Processing of the structural proteins core (C), envelope protein 1 and (E1, E2), and the p7 region is mediated by host signal peptidases. In contrast, maturation of the nonstructural (NS) region is accomplished by two viral enzymes. The HCV polyprotein is first cleaved by a host signal peptidase generating the structural proteins C/E1, E1/E2, E2/p7, and p7/NS2. The NS2-3 proteinase, which is a metalloprotease, then cleaves at the NS2/NS3 junction. The NS3/4A proteinase complex (NS3 being a serine protease and NS4A acting as a cofactor of the NS3 protease), is then responsible for processing all the remaining cleavage junctions. RNA helicase and NTPase activities have also been identified in the NS3 protein. One-third of the NS3 protein functions as a protease, and the remaining two-thirds of the molecule acts as the helicase/ATPase that is thought to be involved in HCV replication. NS5A may be phosphorylated and acts as a putative cofactor of NS5B. The fourth viral enzyme, NS5B, is a membrane-associated RNA-dependent RNA polymerase (RdRp) and a key component responsible for replication of the viral RNA genome. NS5B contains the "GDD" sequence motif, which is highly conserved among all RdRps characterized to date.

Replication of HCV is thought to occur in membrane-associated replication complexes. Within these, the genomic plus-strand RNA is transcribed into minus-strand RNA, which in turn can be used as a template for synthesis of progeny genomic plus-strands. At least two viral enzymes appear to be involved in this reaction: the NS3 helicase/NTPase, and the NS5B RNA-dependent RNA polymerase. While the role of NS3 in RNA replication is less clear, NS5B is the key enzyme responsible for synthesis of progeny RNA strands. Using recombinant baculoviruses to express NS5B in insect cells and a synthetic nonviral RNA as a substrate, two enzymatic activities have been identified as being associated with it: a primer-dependent RdRp and a terminal transferase (TNTase) activity. It was subsequently confirmed and further characterized through the use of the HCV RNA genome as a substrate. Other studies have shown that NS5B with a C-terminal 21 amino-acid truncation expressed in *Escherichia coli* is also active for in vitro RNA synthesis. On certain RNA templates, NS5B has been shown to catalyze RNA synthesis via a de novo initiation mechanism, which has been postulated to be the mode of viral replication in vivo. Templates with single-stranded 3' termini, especially those containing a 3'-terminal cytidylate moiety, have been found to direct de novo synthesis efficiently. There has also been evidence for NS5B to utilize di- or tri-nucleotides as short primers to initiate replication.

It is well-established that persistent infection of HCV is related to chronic hepatitis, and as such, inhibition of HCV replication is a viable strategy for the prevention of hepatocellular carcinoma. Present treatment approaches for HCV infection suffer from poor efficacy and unfavorable side-effects and there is currently a strong effort directed to the discovery of HCV replication inhibitors that are useful for the treatment and prevention of HCV related disorders. New approaches currently under investigation include the development of prophylactic and therapeutic vaccines, the identification of interferons with improved pharmacokinetic characteristics, and the discovery of agents designed to inhibit the function of three major viral proteins: protease, helicase and polymerase. In addition, the HCV RNA genome itself, particularly the IRES element, is being actively exploited as an antiviral target using antisense molecules and catalytic ribozymes.

Particular therapies for HCV infection include α-interferon monotherapy and combination therapy comprising α-interferon and ribavirin. These therapies have been shown to be effective in some patients with chronic HCV infection. The use of antisense oligonucleotides for treatment of HCV infection has also been proposed as has the use of free bile acids, such as ursodeoxycholic acid and chenodeoxycholic acid, and conjugated bile acids, such as tauroursodeoxycholic acid. Phosphonoformic acid esters have also been proposed as potentially for the treatment of various viral infections including HCV. Vaccine development, however, has been hampered by the high degree of viral strain heterogeneity and immune evasion and the lack of protection against reinfection, even with the same inoculum.

The development of small-molecule inhibitors directed against specific viral targets has become a major focus of anti-HCV research. The determination of crystal structures for NS3 protease, NS3 RNA helicase, and NS5B polymerase has provided important structural insights that should assist in the rational design of specific inhibitors.

NS5B, the RNA-dependent RNA polymerase, is an important and attractive target for small-molecule inhibitors. Studies with pestiviruses have shown that the small molecule compound VP32947 (3-[((2-dipropylamino)ethyl)thio]-5H-1,2,4-triazino[5,6-b]indole) is a potent inhibitor of pestivirus replication and most likely inhibits the NS5B enzyme since resistant strains are mutated in this gene Inhibition of RdRp activity by (−)β-L-2',3'-dideoxy-3'-thiacytidine 5'-triphosphate (3TC; lamivudine triphosphate) and phosphonoacetic acid also has been observed.

Despite the intensive effort directed at the treatment and prevention of HCV and related viral infections, there exists a need in the art for non-peptide, small-molecule compounds having desirable or improved physicochemical properties that are useful for inhibiting viruses and treating viral infections and virus-related disorders.

SUMMARY OF THE INVENTION

In one aspect, the present invention provides compounds of formula (I):

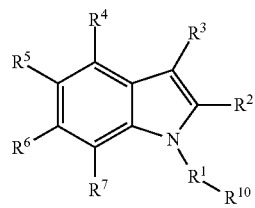

and pharmaceutically acceptable salts, solvates, esters and prodrugs thereof, wherein:

$R^1$ is a bond, $-[C(R^{12})_2]_r-$, $-[C(R^{12})_2]_r-O-[C(R^{12})_2]_q-$, $-[C(R^{12})_2]_r-N(R^9)-[C(R^{12})_2]_q-$, $-[C(R^{12})_2]_q-CH=CH-[C(R^{12})_2]_q-$, $-[C(R^{12})_2]_q-C\equiv C-[C(R^{12})_2]_q-$, or $-[C(R^{12})_2]_q-SO_2-[C(R^{12})_2]_q-$;

$R^2$ is $-[C(R^{12})_2]_q-C(O)N(R^9)SOR^{11}$, $-[C(R^{12})_2]_q-C(O)N(R^9)SO_2R^{11}$, $-[C(R^{12})_2]_q-C(O)N(R^9)SO_2N(R^{11})_2$,

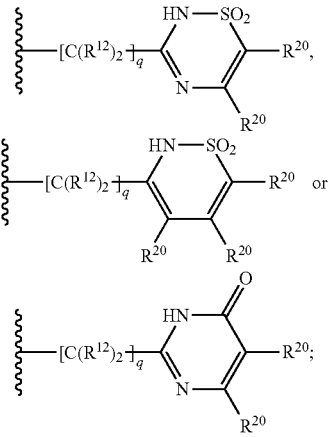

$R^3$ is:

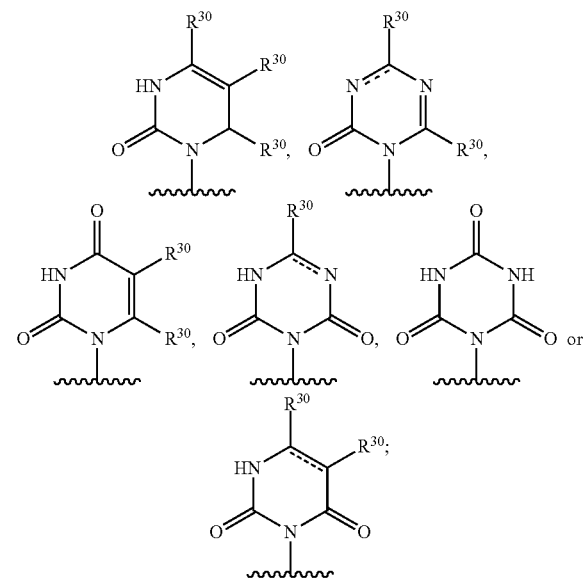

wherein the dotted line indicates an optional and additional bond such that when the optional and additional bond is absent, a hydrogen atom is understood to be present on the two ring atoms connected by the dotted line;

$R^4$, $R^5$, $R^6$ and $R^7$ are each, independently, H, alkyl, alkenyl, alkynyl, aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, $-[C(R^{12})_2]_q$-haloalkyl, $-[C(R^{12})_2]_q$-hydroxyalkyl, halo, hydroxy, $-OR^9$, $-CN$, $-[C(R^{12})_2]_q-C(O)R^8$, $-[C(R^{12})_2]_q-C(O)OR^9$, $-[C(R^{12})_2]_q-C(O)N(R^9)_2$, $-[C(R^{12})_2]_q-OR^9$, $-[C(R^{12})_2]_q-N(R^9)_2$, $-[C(R^{12})_2]_q-NHC(O)R^8$, $-[C(R^{12})_2]_q-NR^8C(O)N(R^9)_2$, $-[C(R^{12})_2]_q-NHSO_2R^{11}$, $-[C(R^{12})_2]_q-S(O)_pR^{11}$, $-[C(R^{12})_2]_q-SO_2N(R^9)_2$ or $-SO_2N(R^9)C(O)N(R^9)_2$;

each occurrence of $R^8$ is independently H, alkyl, alkenyl, alkynyl, —$[C(R^{12})_2]_q$-aryl, —$[C(R^{12})_2]_q$-cycloalkyl, —$[C(R^{12})_2]_q$-cycloalkenyl, —$[C(R^{12})_2]_q$-heterocycloalkyl, —$[C(R^{12})_2]_q$-heterocycloalkenyl, —$[C(R^{12})_2]_q$-heteroaryl, haloalkyl or hydroxyalkyl;

each occurrence of $R^9$ is independently H, alkyl, alkenyl, alkynyl, —$[C(R^{12})_2]_q$-aryl, —$[C(R^{12})_2]_q$-cycloalkyl, —$[C(R^{12})_2]_q$-cycloalkenyl, —$[C(R^{12})_2]_q$-heterocycloalkyl, —$[C(R^{12})_2]_q$-heterocycloalkenyl, —$[C(R^{12})_2]_q$-heteroaryl, haloalkyl or hydroxyalkyl;

$R^{10}$ is H, cycloalkyl, cycloalkenyl, heterocycloalkyl, heterocycloalkenyl, aryl, or heteroaryl, wherein a cycloalkyl, cycloalkenyl, heterocycloalkyl, heterocycloalkenyl, aryl or heteroaryl group can be optionally substituted with up to 4 substituents, which are each independently selected from H, alkyl, alkenyl, alkynyl, aryl, —$[C(R^{12})_2]_q$-cycloalkyl, —O—$[C(R^{12})_2]_q$-cycloalkyl, —$[C(R^{12})_2]_q$-cycloalkenyl, —$[C(R^{12})_2]_q$-heterocycloalkyl, —$[C(R^{12})_2]_q$-heterocycloalkenyl, —$[C(R^{12})_2]_q$-heteroaryl, —$[C(R^{12})_2]_q$-haloalkyl, —$[C(R^{12})_2]_q$-hydroxyalkyl, halo, hydroxy, —$NO_2$, —$OR^9$, —CN, —$[C(R^{12})_2]_q$—$C(O)R^8$, —$[C(R^{12})_2]_q$—$C(O)OR^9$, —$[C(R^{12})_2]_q$—$C(O)N(R^9)_2$, —$[C(R^{12})_2]_q$—$OR^9$, —$[C(R^{12})_2]_q$—$N(R^9)_2$, —$[C(R^{12})_2]_q$—$NHC(O)R^8$, —$[C(R^{12})_2]_q$—$NR^8C(O)N(R^9)_2$, —$[C(R^{12})_2]_q$—$NHSO_2R^{11}$, —$[C(R^{12})_2]_q$—$S(O)_pR^{11}$, —$[C(R^{12})_2]_q$—$SO_2N(R^9)_2$ and —$SO_2N(R^9)C(O)N(R^9)_2$, such that when $R^1$ is a bond, $R^{10}$ is not H;

each occurrence of $R^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally substituted with up to 4 substituents, which are each independently selected from H, alkyl, alkenyl, alkynyl, aryl, —$[C(R^{12})_2]_q$-cycloalkyl, —$[C(R^{12})_2]_q$-cycloalkenyl, —$[C(R^{12})_2]_q$-heterocycloalkyl, —$[C(R^{12})_2]_q$-heterocycloalkenyl, —$[C(R^{12})_2]_q$-heteroaryl, —$[C(R^{12})_2]_q$-haloalkyl, —$[C(R^{12})_2]_q$-hydroxyalkyl, halo, hydroxy, —$OR^9$, —CN, —$[C(R^{12})_2]_q$—$C(O)R^8$, —$[C(R^{12})_2]_q$—$C(O)OR^9$, —$[C(R^{12})_2]_q$—$C(O)N(R^9)_2$, —$[C(R^{12})_2]_q$—$OR^9$, —$[C(R^{12})_2]_q$—$N(R^9)_2$, —$[C(R^{12})_2]_q$—$NHC(O)R^8$, —$[C(R^{12})_2]_q$—$NR^8C(O)N(R^9)_2$, —$[C(R^{12})_2]_q$—$NHSO_2$alkyl, —$[C(R^{12})_2]_q$—$NHSO_2$cycloalkyl, —$[C(R^{12})_2]_q$—$NHSO_2$aryl, —$[C(R^{12})_2]_q$—$SO_2N(R^9)_2$ and —$SO_2N(R^9)C(O)N(R^9)_2$;

each occurrence of $R^{12}$ is independently H, halo, —$N(R^9)_2$, —$OR^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally substituted with up to 4 substituents, which are each independently selected from alkyl, halo, haloalkyl, hydroxyalkyl, hydroxy, —CN, —C(O)alkyl, —C(O)Oalkyl, —C(O)NHalkyl, —C(O)N(alkyl)$_2$, —O-alkyl, —$NH_2$, —NH(alkyl), —N(alkyl)$_2$, —NHC(O)alkyl, —NHSO$_2$alkyl, —SO$_2$alkyl or —SO$_2$NH-alkyl, or two $R^{12}$ groups, together with the carbon atoms to which they are attached, join to form a cycloalkyl, heterocycloalkyl or C═O group;

each occurrence of $R^{20}$ is independently alkyl, aryl, cycloalkyl, heterocycloalkyl or heteroaryl, or both $R^{20}$ groups and the carbon atoms to which they are attached, join to form a cycloalkyl, cycloheteroalkyl, aryl or heteroaryl group wherein a cycloalkyl, cycloheteroalkyl, aryl or heteroaryl group can be optionally substituted with up to 4 groups, which are each independently selected from alkyl, alkenyl, alkynyl, halo, hydroxy, —$OR^9$, —CN, —$[C(R^{12})_2]_q$-cycloalkyl, —$[C(R^{12})_2]_q$-cycloalkenyl, —$[C(R^{12})_2]_q$-heterocycloalkyl, —$[C(R^{12})_2]_q$-heterocycloalkenyl, —$[C(R^{12})_2]_q$-haloalkyl, —$[C(R^{12})_2]_q$-hydroxyalkyl, —$[C(R^{12})_2]_q$—$C(O)R^8$, —$[C(R^{12})_2]_q$—$C(O)OR^9$, —$[C(R^{12})_2]_q$—$C(O)N(R^9)_2$, —$[C(R^{12})_2]_q$—$OR^9$, —$[C(R^{12})_2]_q$—$N(R^9)_2$, —$[C(R^{12})_2]_q$—$NHC(O)R^8$, —$[C(R^{12})_2]_q$—$NR^8C(O)N(R^9)_2$, —$[C(R^{12})_2]_q$—$NHSO_2R^{11}$, —$[C(R^{12})_2]_q$—$S(O)_pR^{11}$, —$[C(R^{12})_2]_q$—$SO_2N(R^9)_2$ and —$SO_2N(R^9)C(O)N(R^9)_2$;

each occurrence of $R^{30}$ is independently, H, alkyl, alkenyl, alkynyl, aryl, —$[C(R^{12})_2]_q$-cycloalkyl, —$[C(R^{12})_2]_q$-cycloalkenyl, —$[C(R^{12})_2]_q$-heterocycloalkyl, —$[C(R^{12})_2]_q$-heterocycloalkenyl, —$[C(R^{12})_2]_q$-heteroaryl, —$[C(R^{12})_2]_q$-haloalkyl, —$[C(R^{12})_2]_q$-hydroxyalkyl, halo, hydroxy, —$OR^9$, —CN, —$[C(R^{12})_2]_q$—$C(O)R^8$, —$[C(R^{12})_2]_q$—$C(O)OR^9$, —$[C(R^{12})_2]_q$—$C(O)N(R^9)_2$, —$[C(R^{12})_2]_q$—$OR^9$, —$[C(R^{12})_2]_q$—$N(R^9)_2$, —$[C(R^{12})_2]_q$—$NHC(O)R^8$, —$[C(R^{12})_2]_q$—$NR^8C(O)N(R^9)_2$, —$[C(R^{12})_2]_q$—$NHSO_2R^{11}$, —$[C(R^{12})_2]_q$—$S(O)_pR^{11}$, —$[C(R^{12})_2]_q$—$SO_2N(R^9)_2$ or —$SO_2N(R^9)C(O)N(R^9)_2$, or two adjacent $R^{30}$ groups, together with the carbon atoms to which they are attached, join to form a cycloalkyl, heterocycloalkyl, aryl or heteroaryl group;

each occurrence of p is independently 0, 1 or 2;

each occurrence of q is independently an integer ranging from 0 to 4; and each occurrence of r is independently an integer ranging from 1 to 4.

In another aspect, the present invention provides compounds of formula (II):

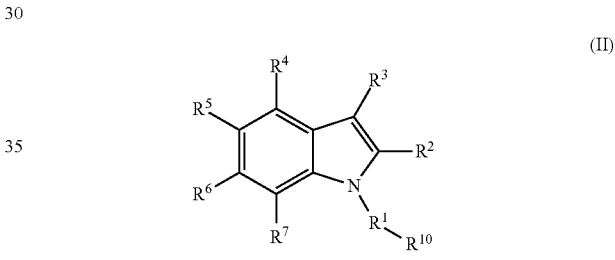

(II)

and pharmaceutically acceptable salts, solvates, esters and prodrugs thereof, wherein:

$R^1$ is a bond, —$[C(R^{12})_2]_r$—, —$[C(R^{12})_2]_r$—O—$[C(R^{12})_2]_q$—, —$[C(R^{12})_2]_r$—$N(R^9)$—$[C(R^{12})_2]_q$—, —$[C(R^{12})_2]_q$—CH═CH—$[C(R^{12})_2]_q$—, —$[C(R^{12})_2]_q$—C≡C—$[C(R^{12})_2]_q$—, or —$[C(R^{12})_2]_q$—$SO_2$—$[C(R^{12})_2]_q$—;

$R^2$ is —$C(O)R^9$, —$C(O)OR^9$, —$C(O)OCH_2OR^9$, —$C(O)N(R^9)_2$, —$[C(R^{12})_2]_q$—$C(O)OR^9$, —$[C(R^{12})_2]_q$—$C(O)N(R^9)_2$, —$[C(R^{12})_2]_q$—$C(O)N(R^9)C$═$N(R^9)_2$, -alkyl, —$[C(R^{12})_2]_q$-aryl, —$[C(R^{12})_2]_q$-cycloalkyl, —$[C(R^{12})_2]_q$-cycloalkenyl, —$[C(R^{12})_2]_q$-heterocycloalkyl, —$[C(R^{12})_2]_q$-heteroaryl or —$[C(R^{12})_2]_q$-heterocycloalkenyl, wherein an aryl, cycloalkyl, cycloalkenyl, heterocycloalkyl, heterocycloalkenyl or heteroaryl, group can be optionally substituted with up to 4 substituents, which are each independently selected from alkyl, alkenyl, alkynyl, aryl, —$[C(R^{12})_2]_q$-cycloalkyl, —$[C(R^{12})_2]_q$-cycloalkenyl, —$[C(R^{12})_2]_q$-heterocycloalkyl, —$[C(R^{12})_2]_q$-heterocycloalkenyl, —$[C(R^{12})_2]_q$-heteroaryl, —$[C(R^{12})_2]_q$-haloalkyl, —$[C(R^{12})_2]_q$-hydroxyalkyl, halo, hydroxy, —$OR^9$, —CN, —$[C(R^{12})_2]_q$—$C(O)R^8$, —$[C(R^{12})_2]_q$—$C(O)OR^9$, —$[C(R^{12})_2]_q$—$C(O)N(R^9)_2$, —$[C(R^{12})_2]_q$—$OR^9$, —$[C(R^{12})_2]_q$—$N(R^9)_2$, —$[C(R^{12})_2]_q$—$NHC(O)R^8$, —$[C(R^{12})_2]_q$—$NR^8C(O)N(R^9)_2$, —$[C(R^{12})_2]_q$—$NHSO_2R^{11}$, —$[C(R^{12})_2]_q$—$S(O)_pR^{11}$, —$[C(R^{12})_2]_q$—$SO_2N(R^9)_2$ and —$SO_2N(R^9)C(O)N(R^9)_2$;

$R^3$ is:

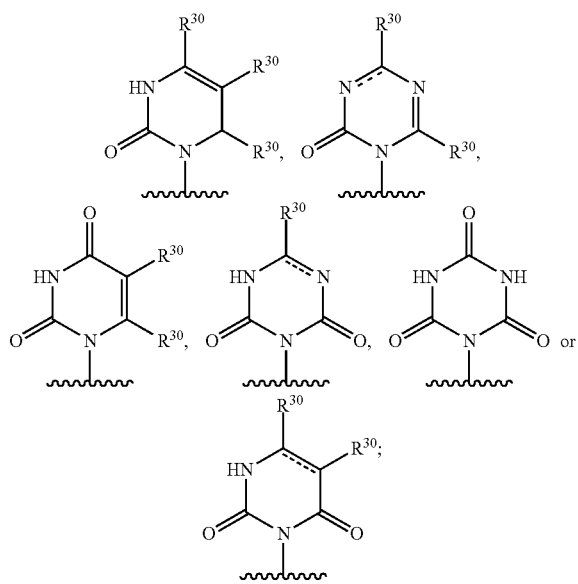

wherein the dotted line indicates an optional and additional bond such that when the optional and additional bond is absent, a hydrogen atom is understood to be present on the two ring atoms connected by the dotted line;

$R^4$, $R^5$, $R^6$ and $R^7$ are each, independently, H, alkyl, alkenyl, alkynyl, aryl, —$[C(R^{12})_2]_q$-cycloalkyl, —$[C(R^{12})_2]_q$-cycloalkenyl, —$[C(R^{12})_2]_q$-heterocycloalkyl, —$[C(R^{12})_2]_q$-heterocycloalkenyl, —$[C(R^{12})_2]_q$-heteroaryl, —$[C(R^{12})_2]_q$-haloalkyl, —$[C(R^{12})_2]_q$-hydroxyalkyl, halo, hydroxy, —$OR^9$, —CN, —$[C(R^{12})_2]_q$—C(O)$R^8$, —$[C(R^{12})_2]_q$—C(O)OR$^9$, —$[C(R^{12})_2]_q$—C(O)N(R$^9$)$_2$, —$[C(R^{12})_2]_q$—OR$^9$, —$[C(R^{12})_2]_q$—N(R$^9$)$_2$, —$[C(R^{12})_2]_q$—NHC(O)R$^8$, —$[C(R^{12})_2]_q$—NR$^8$C(O)N(R$^9$)$_2$, —$[C(R^{12})_2]_q$—NHSO$_2$R$^{11}$, —$[C(R^{12})_2]_q$—S(O)$_p$R$^{11}$, —$[C(R^{12})_2]_q$—SO$_2$N(R$^9$)$_2$ or —SO$_2$N(R$^9$)C(O)N(R$^9$)$_2$;

each occurrence of $R^8$ is independently H, alkyl, alkenyl, alkynyl, —$[C(R^{12})_2]_q$-aryl, —$[C(R^{12})_2]_q$-cycloalkyl, —$[C(R^{12})_2]_q$-cycloalkenyl, —$[C(R^{12})_2]_q$-heterocycloalkyl, —$[C(R^{12})_2]_q$-heterocycloalkenyl, —$[C(R^{12})_2]_q$-heteroaryl, haloalkyl or hydroxyalkyl;

each occurrence of $R^9$ is independently H, alkyl, alkenyl, alkynyl, —$[C(R^{12})_2]_q$-aryl, —$[C(R^{12})_2]_q$-cycloalkyl, —$[C(R^{12})_2]_q$-cycloalkenyl, —$[C(R^{12})_2]_q$-heterocycloalkyl, —$[C(R^{12})_2]_q$-heterocycloalkenyl, —$[C(R^{12})_2]_q$-heteroaryl, haloalkyl or hydroxyalkyl;

$R^{10}$ is H, cycloalkyl, cycloalkenyl, heterocycloalkyl, heterocycloalkenyl, aryl, or heteroaryl, wherein a cycloalkyl, cycloalkenyl, heterocycloalkyl, heterocycloalkenyl, aryl or heteroaryl group can be optionally substituted with up to 4 substituents, which are each independently selected from H, alkyl, alkenyl, alkynyl, aryl, —$[C(R^{12})_2]_q$-cycloalkyl, —$[C(R^{12})_2]_q$-cycloalkenyl, —$[C(R^{12})_2]_q$-heterocycloalkyl, —$[C(R^{12})_2]_q$-heterocycloalkenyl, —$[C(R^{12})_2]_q$-heteroaryl, —$[C(R^{12})_2]_q$-haloalkyl, —$[C(R^{12})_2]_q$-hydroxyalkyl, halo, hydroxy, —$OR^9$, —CN, —$[C(R^{12})_2]_q$—C(O)$R^8$, —$[C(R^{12})_2]_q$—C(O)OR$^9$, —$[C(R^{12})_2]_q$—C(O)N(R$^9$)$_2$, —$[C(R^{12})_2]_q$—OR$^9$, —$[C(R^{12})_2]_q$—N(R$^9$)$_2$, —$[C(R^{12})_2]_q$—NHC(O)R$^8$, —$[C(R^{12})_2]_q$—NR$^8$C(O)N(R$^9$)$_2$, —$[C(R^{12})_2]_q$—NHSO$_2$R$^{11}$, —$[C(R^{12})_2]_q$—S(O)$_p$R$^{11}$, —$[C(R^{12})_2]_q$—SO$_2$N(R$^9$)$_q$ and —SO$_2$N(R$^9$)C(O)N(R$^9$)$_2$, such that when $R^1$ is a bond, $R^{10}$ is not H;

each occurrence of $R^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally substituted with up to 4 substituents, which are each independently selected from H, alkyl, alkenyl, alkynyl, aryl, —$[C(R^{12})_2]_q$-cycloalkyl, —$[C(R^{12})_2]_q$-cycloalkenyl, —$[C(R^{12})_2]_q$-heterocycloalkyl, —$[C(R^{12})_2]_q$-heterocycloalkenyl, —$[C(R^{12})_2]_q$-heteroaryl, —$[C(R^{12})_2]_q$-haloalkyl, —$[C(R^{12})_2]_q$-hydroxyalkyl, halo, hydroxy, —$OR^9$, —CN, —$[C(R^{12})_2]_q$—C(O)$R^8$, —$[C(R^{12})_2]_q$—C(O)OR$^9$, —$[C(R^{12})_2]_q$—OR$^9$, —$[C(R^{12})_2]_q$—N(R$^9$)$_2$, —$[C(R^{12})_2]_q$—NHC(O)R$^8$, —$[C(R^{12})_2]_q$—NR$^8$C(O)N(R$^9$)$_2$, —$[C(R^{12})_2]_q$—NHSO$_2$alkyl, —$[C(R^{12})_2]_q$—NHSO$_2$cycloalkyl, —$[C(R^{12})_2]_q$—NHSO$_2$aryl, —$[C(R^{12})_2]_q$—SO$_2$N(R$^9$)$_2$ and —SO$_2$N(R$^9$)C(O)N(R$^9$)$_2$;

each occurrence of $R^{12}$ is independently H, halo, —N(R$^9$)$_2$, —OR$^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally substituted with up to 4 substituents, which are each independently selected from alkyl, halo, haloalkyl, hydroxyalkyl, hydroxy, —CN, —C(O)alkyl, —C(O)Oalkyl, —C(O)NHalkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two $R^{12}$ groups, together with the carbon atoms to which they are attached, join to form a cycloalkyl, heterocycloalkyl or C=O group;

each occurrence of $R^{30}$ is independently, H, alkyl, alkenyl, alkynyl, aryl, —$[C(R^{12})_2]_q$-cycloalkyl, —$[C(R^{12})_2]_q$-cycloalkenyl, —$[C(R^{12})_2]_q$-heterocycloalkyl, —$[C(R^{12})_2]_q$-heterocycloalkenyl, —$[C(R^{12})_2]_q$-heteroaryl, —$[C(R^{12})_2]_q$-haloalkyl, —$[C(R^{12})_2]_q$-hydroxyalkyl, halo, hydroxy, —$OR^9$, —CN, —$[C(R^{12})_2]_q$—C(O)$R^8$, —$[C(R^{12})_2]_q$—C(O)OR$^9$, —$[C(R^{12})_2]_q$—C(O)N(R$^9$)$_2$, —$[C(R^{12})_2]_q$—OR$^9$, —$[C(R^{12})_2]_q$—N(R$^9$)$_2$, —$[C(R^{12})_2]_q$—NHC(O)R$^8$, —$[C(R^{12})_2]_q$—NR$^8$C(O)N(R$^9$)$_2$, —$[C(R^{12})_2]_q$—NHSO$_2$R$^{11}$, —$[C(R^{12})_2]_q$—S(O)$_p$R$^{11}$, —$[C(R^{12})_2]_q$—SO$_2$N(R$^9$)$_2$ or —SO$_2$N(R$^9$)C(O)N(R$^9$)$_2$, or two adjacent $R^{30}$ groups, together with the carbon atoms to which they are attached, join to form a cycloalkyl, heterocycloalkyl, aryl or heteroaryl group;

each occurrence of p is independently 0, 1 or 2;

each occurrence of q is independently an integer ranging from 0 to 4; and each occurrence of r is independently an integer ranging from 1 to 4.

The compounds of formulas (I) and (II) (herein referred to collectively as the "3-Heterocyclic Substituted Indole Derivatives") and pharmaceutically acceptable salts, solvates, esters and prodrugs thereof can be useful for treating or preventing a viral infection or a virus-related disorder in a patient.

Also provided by the invention are methods for treating or preventing a viral infection or a virus-related disorder in a patient, comprising administering to the patient an effective amount of at least one 3-Heterocyclic Substituted Indole Derivative or a pharmaceutically acceptable salt, solvate, ester or prodrug thereof.

The present invention further provides pharmaceutical compositions comprising an effective amount of at least one 3-Heterocyclic Substituted Indole Derivative or a pharmaceutically acceptable salt, solvate, ester or prodrug thereof, and a pharmaceutically acceptable carrier. The compositions can be useful for treating or preventing a viral infection or a virus-related disorder in a patient.

The details of the invention are set forth in the accompanying detailed description below.

Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

In an embodiment, the present invention provides 3-Heterocyclic Substituted Indole Derivatives, pharmaceutical compositions comprising at least one 3-Heterocyclic Substituted Indole Derivative, and methods of using the 3-Heterocyclic Substituted Indole Derivatives for treating or preventing a viral infection or a virus-related disorder in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "alkyl" as used herein, refers to an aliphatic hydrocarbon group, wherein one of the aliphatic hydrocarbon group's hydrogen atoms is replaced with a single bond. An alkyl group can be straight or branched and can contain from about 1 to about 20 carbon atoms. In one embodiment, an alkyl group contains from about 1 to about 12 carbon atoms. In another embodiment, an alkyl group contains from about 1 to about 6 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or optionally substituted by one or more substituents which may be the same or different, each substituent being independently selected from the group consisting of halo, alkenyl, alkynyl, —O-aryl, aryl, heteroaryl, cycloalkyl, cycloalkenyl, cyano, hydroxy, —O-alkyl, —O-haloalkyl, -alkylene-O-alkyl, alkylthio, —NH$_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)-cycloalkyl, —C(O)alkyl, —C(O)NH$_2$, —C(O)NH-alkyl, —C(O)OH and —C(O)O-alkyl. In one embodiment, an alkyl group is unsubstituted. In another embodiment, an alkyl group is a straight chain alkyl group. In another embodiment, an alkyl group is a branched alkyl group.

The term "alkylene" as used herein, refers to an alkyl group, as defined above, wherein one of the alkyl group's hydrogen atoms is replaced with a bond. Illustrative examples of alkylene include, but are not limited to, —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH$_2$CH(CH$_3$)CH$_2$— and —CH$_2$CH$_2$CH(CH$_3$)—. In one embodiment, an alkylene group is a straight chain alkylene group. In another embodiment, an alkylene group is a branched alkylene group.

The term "alkenyl" as used herein, refers to an aliphatic hydrocarbon group having at least one carbon-carbon double bond, wherein one of the aliphatic hydrocarbon group's hydrogen atoms is replaced with a single bond. An alkenyl group can be straight or branched and can contain from about 2 to about 15 carbon atoms. In one embodiment, an alkenyl group contains from about 2 to about 10 carbon atoms. In another embodiment, an alkenyl group contains from about 2 to about 6 carbon atoms. Non-limiting examples of illustrative alkenyl groups include ethenyl, propenyl, n-butenyl, 3-methylbut-2-enyl, n-pentenyl, octenyl and decenyl. An alkenyl group may be unsubstituted or optionally substituted by one or more substituents which may be the same or different, each substituent being independently selected from the group consisting of halo, alkyl, alkynyl, —O-aryl, aryl, cycloalkyl, cycloalkenyl, cyano, hydroxy, —O-alkyl, —O-haloalkyl, -alkylene-O-alkyl, alkylthio, —NH$_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)-cycloalkyl, —C(O)alkyl, —C(O)NH$_2$, —C(O)NH-alkyl, —C(O)OH and —C(O)O-alkyl. In one embodiment, an alkenyl group is unsubstituted. In another embodiment, an alkenyl group is a straight chain alkenyl group. In another embodiment, an alkyl group is a branched alkenyl group.

The term "alkynyl" as used herein, refers to an aliphatic hydrocarbon group having at least one carbon-carbon triple bond, wherein one of the aliphatic hydrocarbon group's hydrogen atoms is replaced with a single bond. An alkynyl group can be straight or branched and can contain from about 2 to about 15 carbon atoms. In one embodiment, an alkynyl group contains from about 2 to about 10 carbon atoms. In another embodiment, an alkynyl group contains from about 2 to about 6 carbon atoms. Non-limiting examples of illustrative alkynyl groups include ethynyl, propynyl, 2-butynyl and 3-methylbutynyl. An alkynyl group may be unsubstituted or optionally substituted by one or more substituents which may be the same or different, each substituent being independently selected from the group consisting of halo, alkyl, alkenyl, —O-aryl, aryl, cycloalkyl, cycloalkenyl, cyano, hydroxy, —O-alkyl, -alkylene-O-alkyl, —O-haloalkyl, -alkylthio, —NH$_2$, —NH(alkyl), —N(alkyl)$_2$, —NH-aryl, —NH-heteroaryl, -NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)-cycloalkyl, —C(O)alkyl, —C(O)NH$_2$, —C(O)NH-alkyl, —C(O)OH and —C(O)O-alkyl. In one embodiment, an alkynyl group is unsubstituted. In another embodiment, an alkynyl group is a straight chain alkynyl group. In another embodiment, an alkynyl group is a branched alkynyl group.

"Aryl" means an aromatic monocyclic or multicyclic ring system having from about 6 to about 14 ring carbon atoms. In one embodiment, an aryl group has from about 6 to about 10 ring carbon atoms. An aryl group can be optionally substituted with one or more "ring system substituents" which may be the same or different, and are as defined herein below. Non-limiting examples of illustrative aryl groups include phenyl and naphthyl. In one embodiment, an aryl group is unsubstituted. In another embodiment, an aryl group is a phenyl group.

The term "arylene" as used herein, refers to an aryl group, as defined above herein, wherein a hydrogen atom connected to one of the aryl group's ring carbon atoms is replaced with a bond.

The term "cycloalkyl" as used herein, refers to a non-aromatic mono- or multicyclic ring system having from about 3 to about 10 ring carbon atoms. In one embodiment, a cycloalkyl has from about 5 to about 10 ring carbon atoms. In another embodiment, a cycloalkyl has from about 5 to about 7 ring carbon atoms. Non-limiting examples of illustrative monocyclic cycloalkyls include cyclopropyl, cyclopentyl, cyclohexyl, cycloheptyl and the like. Non-limiting examples of illustrative multicyclic cycloalkyls include 1-decalinyl, norbornyl, adamantyl and the like. A cycloalkyl group can be optionally substituted with one or more "ring system substituents" which may be the same or different, and are as defined herein below. In one embodiment, a cycloalkyl group is unsubstituted.

The term "cycloalkylene" as used herein, refers to a cycloalkyl group, as defined above herein, wherein a hydrogen atom connected to one of the cycloalkyl group's ring carbon atoms is replaced with a bond.

The term "cycloalkenyl" as used herein, refers to a non-aromatic mono- or multicyclic ring system comprising from about 3 to about 10 ring carbon atoms and containing at least one endocyclic double bond. In one embodiment, a cycloalkenyl contains from about 5 to about 10 ring carbon atoms. In another embodiment, a cycloalkenyl contains 5 or 6 ring carbon atoms. Non-limiting examples of illustrative monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. In one embodiment, a cycloalkenyl group is unsubstituted.

The term "halo" as used herein, means —F, —Cl, —Br or —I. In one embodiment, halo refers to —Cl or —F.

The term "haloalkyl" as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of illustrative haloalkyl groups include —CH$_2$F, —CHF$_2$, —CF$_3$, —CH$_2$Cl and —CCl$_3$.

The term "hydroxyalkyl" as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of illustrative hydroxyalkyl groups include hydroxymethyl, 2-hydroxyethyl, 3-hydroxypropyl, 4-hydroxybutyl and —CH(OH)CH$_2$CH$_3$.

The term "heteroaryl" as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is monocyclic and has 5 or 6 ring atoms and at least one nitrogen ring atom. A heteroaryl group can be optionally substituted by one or more "ring system substituents" which may be the same or different, and are as defined herein below. A heteroaryl group is joined via a ring carbon atom and any nitrogen atom of a heteroaryl can be optionally oxidized to the corresponding N-oxide. The term "heteroaryl" also encompasses a heteroaryl group, as defined above, which has been fused to a benzene ring. Non-limiting examples of illustrative heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. In one embodiment, a heteroaryl group is a 6-membered heteroaryl group. In another embodiment, a heteroaryl group is a 5-membered heteroaryl group.

The term "heteroarylene" as used herein, refers to a heteroaryl group, as defined above herein, wherein a hydrogen atom connected to one of the heteroaryl group's ring carbon atoms is replaced with a bond.

The term "heterocycloalkyl" as used herein, refers to a non-aromatic saturated monocyclic or multicyclic ring system comprising 3 to about 10 ring atoms, wherein from 1 to 4 of the ring atoms are independently O, S or N and the remainder of the ring atoms are carbon atoms. In one embodiment, a heterocycloalkyl group has from about 5 to about 10 ring atoms.

In another embodiment, a heterocycloalkyl group has 5 or 6 ring atoms. There are no adjacent oxygen and/or sulfur atoms present in the ring system. Any —NH group in a heterocycloalkyl ring may exist protected such as, for example, as an —N(Boc), —N(CBz), —N(Tos) group and the like; such protected heterocycloalkyl groups are considered part of this invention. A heterocycloalkyl group can be optionally substituted by one or more "ring system substituents" which may be the same or different, and are as defined herein below. The nitrogen or sulfur atom of the heterocyclyl can be optionally oxidized to the corresponding N-oxide, S-oxide or S,S-dioxide. Non-limiting examples of illustrative monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. A ring carbon atom of a heterocycloalkyl group may be functionalized as a carbonyl group. An illustrative example of such a heterocycloalkyl group is pyrrolidonyl:

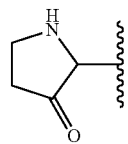

In one embodiment, a heterocycloalkyl group is a 6-membered heterocycloalkyl group. In another embodiment, a heterocycloalkyl group is a 5-membered heterocycloalkyl group.

The term "heterocycloalkylene" as used herein, refers to a heterocycloalkylene group, as defined above herein, wherein a hydrogen atom connected to one of the heterocycloalkylene group's ring carbon atoms is replaced with a bond.

The term "heterocycloalkenyl" as used herein, refers to a heterocycloalkyl group, as defined above, wherein the heterocycloalkyl group contains from 3 to 10 ring atoms, and at least one endocyclic carbon-carbon or carbon-nitrogen double bond. In one embodiment, a heterocycloalkenyl group has from 5 to 10 ring atoms. In another embodiment, a heterocycloalkenyl group is monocyclic and has 5 or 6 ring atoms. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of illustrative heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. A ring carbon atom of a heterocyclenyl group may be functionalized as a carbonyl group. An illustrative example of such a heterocyclenyl group is:

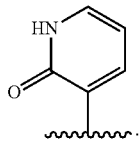

In one embodiment, a heterocycloalkenyl group is a 6-membered heterocycloalkenyl group. In another embodiment, a heterocycloalkenyl group is a 5-membered heterocycloalkenyl group.

The term "ring system substituent" as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, haloalkyl, —O-alkyl, —O-haloalkyl, -alkylene-O-alkyl, —O-aryl, aralkoxy, acyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —OC(O)-alkyl, —OC(O)-aryl, —OC(O)-cycloalkyl, —C(=N—CN)—NH$_2$, —C(=NH)—NH$_2$, —C(=NH)—NH(alkyl), —NY$_1$Y$_2$, -alkylene-NY$_1$Y$_2$, —C(O)NY$_1$Y$_2$ and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on the same carbon atom (such as to form a carbonyl group) or replaces two available hydrogen atome on two adjacent carbon atoms (one H on each carbon) on a ring system. Examples of such moiety are =O, methylene dioxy, ethylenedioxy, —C(CH$_3$)$_2$— and the like which form moieties such as, for example:

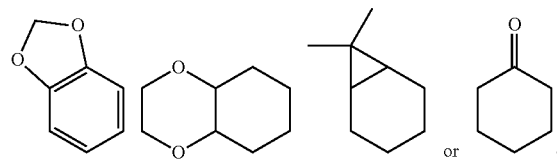

The term "substituted," as used herein, means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" as used herein, means optional substitution with the specified groups, radicals or moieties.

The terms "purified", "in purified form" or "in isolated and purified form" as used herein, for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, R$^{11}$, etc.) occurs more than one time in any constituent or in Formula (I), its definition on each occurrence is independent of its definition at every other occurrence, unless otherwise noted.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" as used herein, refers to a compound (e.g, a drug precursor) that is transformed in vivo to yield a 3-Heterocyclic Substituted Indole Derivative or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S.

Symposium Series, and in Bioreversible Carriers in Drug Design, ed. Edward B. Roche, American Pharmaceutical Association and Pergamon Press, 1987.

For example, if a 3-Heterocyclic Substituted Indole Derivative or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino ($C_2$-$C_3$)alkyl, and the like.

Similarly, if a 3-Heterocyclic Substituted Indole Derivative contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)$ alkyl$)_2$ or glycosyl (the radical resulting from the removal of a hydroxyl group of the hemiacetal form of a carbohydrate), and the like.

If a 3-Heterocyclic Substituted Indole Derivative incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)$OY^1$ wherein $Y^1$ is H, ($C_1$-$C_6$)alkyl or benzyl, —C($OY^2$)$Y^3$ wherein $Y^2$ is ($C_1$-$C_4$) alkyl and $Y^3$ is ($C_1$-$C_6$)alkyl, carboxy ($C_1$-$C_6$)alkyl, amino($C_1$-$C_4$)alkyl or mono-N— or di-N,N—($C_1$-$C_6$)alkylaminoalkyl, —C($Y^4$)$Y^5$ wherein $Y^4$ is H or methyl and $Y^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of illustrative solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "effective amount" or "therapeutically effective amount" is meant to describe an amount of compound or a composition of the present invention that is effective to treat or prevent a viral infection or a virus-related disorder.

Metabolic conjugates, such as glucuronides and sulfates which can undergo reversible conversion to the 3-Heterocyclic Substituted Indole Derivatives are contemplated in the present invention.

The 3-Heterocyclic Substituted Indole Derivatives may form salts, and all such salts are contemplated within the scope of this invention. Reference to a 3-Heterocyclic Substituted Indole Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a 3-Heterocyclic Substituted Indole Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a 3-Heterocyclic Substituted Indole Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, *Camille G.* (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, choline, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

The 3-Heterocyclic Substituted Indole Derivatives may contain asymmetric or chiral centers, and, therefore, exist in different stereoisomeric forms. It is intended that all stereoisomeric forms of the 3-Heterocyclic Substituted Indole Derivatives as well as mixtures thereof, including racemic mixtures, form part of the present invention. In addition, the present invention embraces all geometric and positional isomers. For example, if a 3-Heterocyclic Substituted Indole Derivative incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the 3-Heterocyclic Substituted Indole Derivatives may be atropisomers (e.g., substituted biaryls) and are considered as part of this invention. Enantiomers can also be separated by use of chiral HPLC column.

The straight line — as a bond generally indicates a mixture of, or either of, the possible isomers, non-limiting example(s) include, containing (R)- and (S)-stereochemistry. For example,

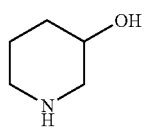

means containing both

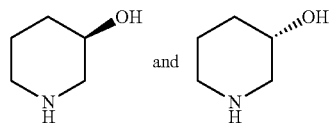 [SMILES: O[C@@H]1CCCNC1 ; O[C@H]1CCCNC1]

A dashed line (-----) represents an optional bond.
Lines drawn into the ring systems, such as, for example:

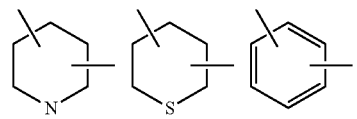

indicate that the indicated line (bond) may be attached to any of the substitutable ring atoms, non limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

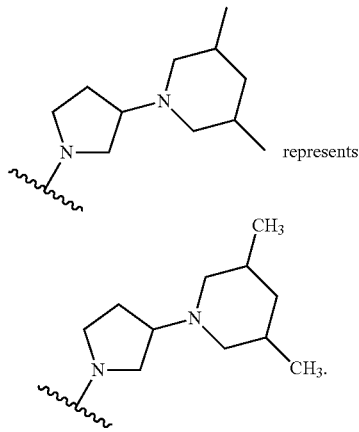

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a 3-Heterocyclic Substituted Indole Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Such compounds are useful as therapeutic, diagnostic or research reagents. Examples of isotopes that can be incorporated into compounds of the invention include isotopes of hydrogen, carbon, nitrogen, oxygen, phosphorus, fluorine and chlorine, such as $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled 3-Heterocyclic Substituted Indole Derivatives (e.g., those labeled with $^{3}$H and $^{14}$C) are useful in compound and/or substrate tissue distribution assays. Tritiated (i.e., $^{3}$H) and carbon-14 (i.e., $^{14}$C) isotopes are particularly preferred for their ease of preparation and detectability. Further, substitution with heavier isotopes such as deuterium (i.e., $^{2}$H) may afford certain therapeutic advantages resulting from greater metabolic stability (e.g., increased in vivo half-life or reduced dosage requirements) and hence may be preferred in some circumstances. Isotopically labelled 3-Heterocyclic Substituted Indole Derivatives can generally be prepared by following procedures analogous to those disclosed in the Schemes and/or in the Examples herein below, by substituting an appropriate isotopically labelled reagent for a non-isotopically labelled reagent.

Polymorphic forms of the 3-Heterocyclic Substituted Indole Derivatives, and of the salts, solvates, hydrates, esters and prodrugs of the 3-Heterocyclic Substituted Indole Derivatives, are intended to be included in the present invention.

The following abbreviations are used below and have the following meanings: BINAP is racemic-2,2'-bis(diphenylphosphino)-1,1'-binaphthyl; CSA is camphorsulfonic acid; DBPD is 2-(Di-t-butylphosphino)biphenyl, DBU is 1,8-diazabicyclo[5.4.0]undec-7-ene, DBN is 1,5-diazabicyclo[4.3.0]non-5-ene; DCC is dicyclohexylcarbodiimide; DCM is dichloromethane; Dibal-His diisobutylaluminum hydride; DMF is dimethylformamide; EDCI is 1-(3-dimethylaminopropyl)-3-ethylcarbodiimide; HATU is N-(diethylamino)-1H-1,2,3-triazolo[4,5-b]pyridine-1-ylmethylene]-N-methylmethanaminium Hexafluorophosphate N-oxide; HOBT is 1-hydroxybenzotriazole; LAH is lithium aluminum hydride; LDA is lithium diisopropylamide; m-CPBA is m-chloroperbenzoic acid; NaBH(OAc)$_3$ is sodium triacetoxyborohydride; NaBH$_4$ is sodium borohydride; NaBH$_3$CN is sodium cyanoborohydride; NaHMDS is sodium hexamethyl disilylazide; p-TsOH is p-toluenesulfonic acid; p-TsCl is p-toluenesulfonyl chloride; PPTS is pyridinium p-toluenesulfonate; TMAD is N,N,N',N'-tetramethylazodicarboxamide; HRMS is high resolution mass spectrometry; HPLC is high performance liquid chromatography; LRMS is low resolution mass spectrometry; Tr is triphenylmethyl; Tris is tris (hydroxymethyl)aminomethane; THF is tetrahydrofuran; TFA is trifluoroacetic acid; Ci/mmol is Curie/mmol (a measure of specific activity); and Ki represents the dissociation constant for a substrate/receptor complex.

The 3-Heterocyclic Substituted Indole Derivatives of Formula (I)

The present invention provides 3-Heterocyclic Substituted Indole Derivatives having the formula:

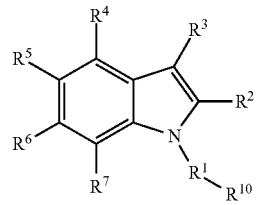

(I)

and pharmaceutically acceptable salts, solvates, esters and prodrugs thereof, wherein $R^1$, $R^2$, $R^3$, $R^4$, $R^5$, $R^6$, $R^7$ and $R^{16}$ are defined above for the compounds of formula (I).

In one embodiment, $R^1$ is bond.

In another embodiment, $R^1$ is —[C(R$^{12}$)$_2$]$_r$—.

In another embodiment, $R^1$ is —[C(R$^{12}$)$_2$]$_r$—O—[C(R$^{12}$)$_2$]$_q$—.

In still another embodiment, $R^1$ is —[C(R$^{12}$)$_2$]$_r$—N(R$^9$)—[C(R$^{12}$)$_2$]$_q$—.

In yet another embodiment, $R^1$ is —[C(R$^{12}$)$_2$]$_q$—CH=CH—[C(R$^{12}$)$_2$]$_q$—.

In another embodiment, $R^1$ is —[C(R$^{12}$)$_2$]$_q$—C≡C—[C(R$^{12}$)$_2$]$_4$—.

In a further embodiment, $R^1$ is —[C(R$^{12}$)$_2$]$_q$—SO$_2$—[C(R$^{12}$)$_2$]$_q$—.

In another embodiment, $R^1$ is —CH$_2$—.

In one embodiment, $R^{10}$ is H and $R^1$ is other than a bond.

In another embodiment, $R^{10}$ is aryl.

In another embodiment, $R^{10}$ is cycloalkyl.

In still another embodiment, $R^{10}$ is cycloalkenyl.

In another embodiment, $R^{10}$ is heterocycloalkenyl.

In another embodiment, $R^{10}$ is heteroaryl.

In yet another embodiment, $R^{10}$ is heterocycloalkyl.

In another embodiment, $R^{10}$ is phenyl.

In a further embodiment, $R^{10}$ is phenyl, which is substituted with from 1-3 groups independently selected from: alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl.

In one embodiment, $R^{10}$ is pyridyl.

In another embodiment, $R^{10}$ is furanyl.

In another embodiment, $R^{10}$ is thiophenyl.

In still another embodiment, $R^{10}$ is thiophenyl.

In another embodiment, $R^{10}$ is thiazolyl.

In another embodiment, $R^{10}$ is quinolinyl.

In a further embodiment, $R^{10}$ is

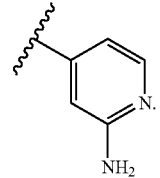 [SMILES: *c1ccnc(N)c1]

In another embodiment, —$R^{10}$ is:

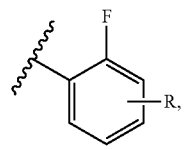

wherein R represents up to 2 optional and additional phenyl substituents, each independently selected from alkyl, —O-alkyl, halo, —O-haloalkyl, —OH, —$NH_2$, —NH(alkyl), —N(alkyl)$_2$, —$NO_2$, —CN, —NHC(O)-alkyl, —O-alkylene-heterocycloalkyl —C(O)O-alkyl and —O-haloalkyl.

In another embodiment, —$R^{10}$ is:

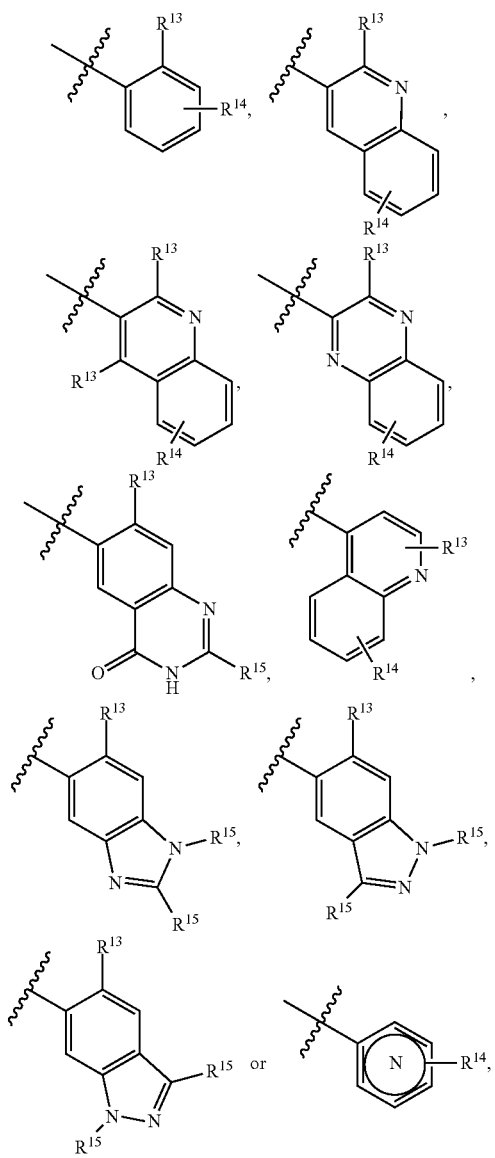

wherein $R^{13}$ is H, F, Br or Cl; $R^{14}$ represents up to 4 optional and additional substituents, each independently selected from alkyl, cycloalkyl, $CF_3$, —CN, halo, —O-alkyl, —O-haloalkyl, —$NHSO_2$-alkyl, —$NO_2$, —C(O)$NH_2$, —C(O)NH-alkyl, —C(O)OH, hydroxy, —$NH_2$, —$SO_2$alkyl, —$SO_2$NHalkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and

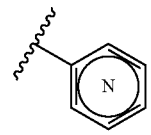

represents a pyridyl group, wherein the ring nitrogen atom can be at any of the five unsubstituted ring atom positions.

In another embodiment, —$R^{10}$ is:

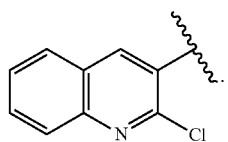 [SMILES: *c1cc2ccccc2nc1Cl]

In one embodiment, $R^{10}$ is H, alkyl, alkenyl, aryl, cycloalkyl, —CN, aryl, cycloalkyl or heteroaryl.

In another embodiment, $R^{10}$ is aryl, cycloalkyl or heteroaryl, any of which can be optionally and substituted with up to 3 groups, each independently selected from —$NH_2$, alkyl, alkenyl, halo, —$NO_2$ or —C(O)O-alkyl.

In another embodiment, $R^{10}$ is phenyl, cyclopropyl, furanyl, pyridyl or thiophenyl, any of which can be optionally and independently substituted with up to 3 groups selected from alkyl, —O-alkyl, halo, —O-haloalkyl, —OH, —$NH_2$, —NH(alkyl), —N(alkyl)$_2$, —$NO_2$, —CN, —NHC(O)-alkyl, —O-alkylene-heterocycloalkyl —C(O)O-alkyl and —O-haloalkyl.

In one embodiment, —$R^1$-$R^{10}$ is alkyl.

In another embodiment, $R^1$ is —$CH_2$— and $R^{10}$ is H, alkyl, alkenyl, aryl, cycloalkyl, —CN, aryl, cycloalkyl or heteroaryl.

In another embodiment, $R^1$ is —$CH_2$— and $R^{10}$ is aryl, cycloalkyl or heteroaryl, any of which can be optionally and substituted with up to 3 groups, each independently selected from alkyl, —O-alkyl, halo, —O-haloalkyl, —OH, —$NH_2$, —NH(alkyl), —N(alkyl)$_2$, —$NO_2$, —CN, —NHC(O)-alkyl, —O-alkylene-heterocycloalkyl —C(O)O-alkyl and —O-haloalkyl.

In yet another embodiment, $R^1$ is —$CH_2$— and $R^{10}$ is phenyl, cyclopropyl, furanyl, pyridyl, isoxazolyl or thiophenyl, any of which can be optionally and independently substituted with up to 3 groups selected from alkyl, —O-alkyl, halo, —O-haloalkyl, —OH, —$NH_2$, —NH(alkyl), —N(alkyl)$_2$, —$NO_2$, —CN, —NHC(O)-alkyl, —O-alkylene-heterocycloalkyl —C(O)O-alkyl and —O-haloalkyl.

In another embodiment, $R^1$ is —$CH_2$— and —$R^{10}$ is:

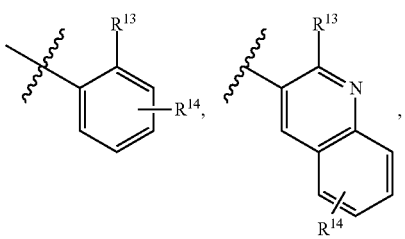

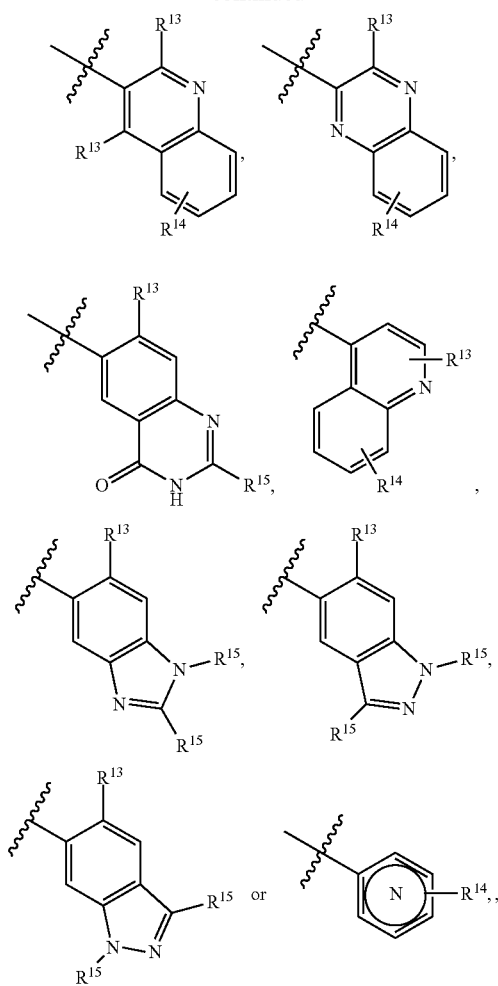

wherein $R^{13}$ is H, F, Br or Cl; $R^{14}$ represents up to 4 optional and additional substituents, each independently selected from alkyl, cycloalkyl, $CF_3$, —CN, halo, —O-alkyl, —O-haloalkyl, —NHSO$_2$-alkyl, —NO$_2$, —C(O)NH$_2$, —C(O)NH-alkyl, —C(O)OH, hydroxy, —NH$_2$, —SO$_2$alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and

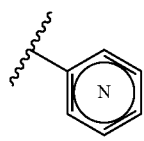

represents a pyridyl group, wherein the ring nitrogen atom can be at any of the five unsubstituted ring atom positions.

In one embodiment, —R$^1$-R$^{10}$ is benzyl.

In another embodiment, —R$^1$-R$^{10}$ is benzyl, wherein the phenyl moiety of the benzyl group is substituted with from 1-4 groups independently selected from: alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl.

In still another embodiment, —R$^1$-R$^{10}$ is

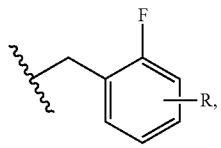

wherein R represents up to 2 optional and additional phenyl substituents, each independently selected from alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl.

In another embodiment, —R$^1$-R$^{10}$ is

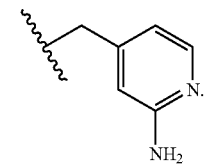

In still another embodiment, —R$^1$-R$^{10}$ is alkyl.

In another embodiment, —R$^1$-R$^{10}$ is benzyl, wherein the phenyl moiety of the benzyl group is substituted with 1 or 2 fluorine atoms.

In yet another embodiment, —R$^1$-R$^{10}$ is benzyl, wherein the phenyl moiety of the benzyl group is substituted with 1 or 2 methyl groups.

In one another embodiment, —R$^1$-R$^{10}$ is benzyl, wherein the phenyl moiety of the benzyl group is substituted with one fluorine atom and one methyl group.

In another embodiment, —R$^1$— R$^{10}$ is haloalkyl.

In a further embodiment, —R$^1$-R$^{10}$ is —CH$_2$-cycloalkyl.

In another embodiment, —R$^1$-R$^{10}$ is —CH$_2$-heteroaryl.

In another embodiment, —R$^1$-R$^{10}$ is:

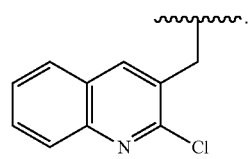

In one embodiment, $R^2$ is —[C(R$^{12}$)$_2$]-C(O)N(R$^9$)SO$_2$R$^{11}$.

In another embodiment, $R^2$ is —[C(R$^{12}$)$_2$]$_q$—C(O)N(R$^9$)SOR$^{11}$.

In another embodiment, $R^2$ is —[C(R$^{12}$)$_2$]$_q$—C(O)N(R$^9$)SO$_2$N(R$^{11}$)$_2$.

In still another embodiment, $R^2$ is —C(O)N(R$^9$)SO$_2$R$^{11}$.

In another embodiment, $R^2$ is —C(O)NHSO$_2$R$^{11}$.

In another embodiment, $R^2$ is —C(O)NHSO$_2$R$^{11}$ and R$^{11}$ is -alkylene-alkyl.

In yet another embodiment, $R^2$ is —C(O)NHSO$_2$R$^{11}$ and R$^{11}$ is -alkylene-aryl.

In another embodiment, $R^2$ is —C(O)NHSO$_2$R$^{11}$ and R$^{11}$ is -alkylene-cycloalkyl.

In a further embodiment, $R^2$ is —C(O)NHSO$_2$R$^{11}$ and R$^{11}$ is -alkylene-heterocycloalkyl.

In another embodiment, $R^2$ is —C(O)NHSO$_2$R$^{11}$ and R$^{11}$ is -alkylene-heteroaryl.

In another embodiment, $R^2$ is —C(O)NHSO$_2$R$^{11}$ and R$^{11}$ is -alkylene-haloalkyl.

In still another embodiment, $R^2$ is —C(O)NHSO$_2$R$^{11}$ and R$^{11}$ is -alkylene-hydroxyalkyl.

In still another embodiment, $R^2$ is —C(O)NHSO$_2$R$^{11}$ and R$^{11}$ is alkyl.

In yet another embodiment, $R^2$ is —C(O)NHSO$_2$R$^{11}$ and R$^{11}$ is aryl.

In another embodiment, $R^2$ is —C(O)NHSO$_2$R$^{11}$ and R$^{11}$ is cycloalkyl.

In a further embodiment, $R^2$ is —C(O)NHSO$_2$R$^{11}$ and R$^{11}$ is heterocycloalkyl.

In another embodiment, $R^2$ is —C(O)NHSO$_2$R$^{11}$ and R$^{11}$ is heteroaryl.

In another embodiment, $R^2$ is —C(O)NHSO$_2$R$^{11}$ and R$^{11}$ is haloalkyl.

In still another embodiment, $R^2$ is —C(O)NHSO$_2$R$^{11}$ and R$^{11}$ is hydroxyalkyl.

In another embodiment, $R^2$ is —C(O)NHSO$_2$R$^{11}$ and R$^{11}$ is -alkylene-phenyl.

In one embodiment, $R^2$ is —C(O)NHSO$_2$R$^{11}$ and R$^{11}$ is benzyl.

In another embodiment, $R^2$ is —C(O)NHSO$_2$R$^{11}$ and R$^{11}$ is naphthyl.

In one embodiment, $R^2$ is —C(O)NHSO$_2$R$^{11}$ and R$^{11}$ is methyl, ethyl, —CH$_2$CH$_2$NH$_2$, —CH$_2$CH$_2$N(CH$_3$)$_2$, —CH$_2$CH$_2$CH$_2$NH$_2$, —CH$_2$CH$_2$CH$_2$N(CH$_3$)$_2$, phenyl or cyclopropyl.

In yet another embodiment, $R^2$ is —C(O)NHSO$_2$R$^{11}$ and R$^{11}$ is —NH$_2$ or —N(CH$_3$)$_2$.

In another embodiment, $R^2$ is —C(O)NHSO$_2$CH$_3$.

In another embodiment, $R^2$ is —C(O)NHSO$_2$CH$_2$CH$_3$.

In one embodiment, $R^2$ is —C(O)NHSO$_2$R$^{11}$ and R$^{11}$ is phenyl.

In still another embodiment, $R^2$ is —C(O)NHSO$_2$R$^{11}$ and R$^{11}$ is phenyl, which is optionally substituted with up to 3 groups independently selected from: alkyl, F, Cl, methyl, —NH$_2$, —NO$_2$, methoxy, —SO$_2$NH$_2$, —COOH, -(alkylene)$_s$—C(O)O-alkyl, hydroxy, —NHSO$_2$-alkyl, -(alkylene)$_s$-SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, -(alkylene)$_s$-NHC(O)-alkyl, pyrazolyl or —OCH$_2$C(O)NH$_2$.

In yet another embodiment, $R^2$ is —C(O)NHSO$_2$R$^{11}$ and R$^{11}$ is cyclopropyl, cyclobutyl, cyclopentyl or cyclohexyl.

In one embodiment, $R^2$ is:

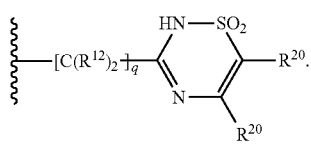

In another embodiment, $R^2$ is:

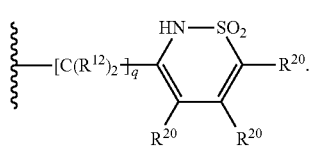

In another embodiment, $R^2$ is:

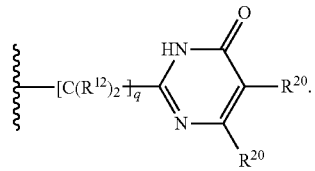

In one embodiment, $R^3$ is

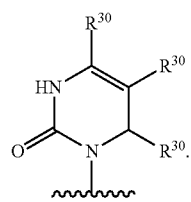

In another embodiment, $R^3$ is

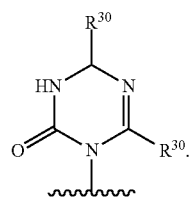

In another embodiment, $R^3$ is

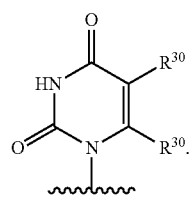

In still another embodiment, $R^3$ is

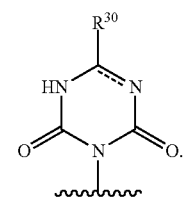

In another embodiment, $R^3$ is

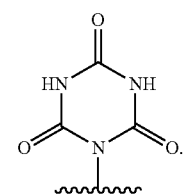

In yet another embodiment, $R^3$ is

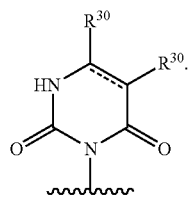

In another embodiment, $R^3$ is

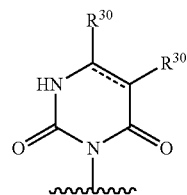

and both $R^{30}$ groups, together with the carbon atoms to which they are attached, join to form an aryl or heteroaryl group.

In another embodiment, $R^3$ is

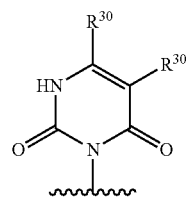

and each $R^{30}$ group is independently selected from H and alkyl.

In one embodiment, $R^3$ is:

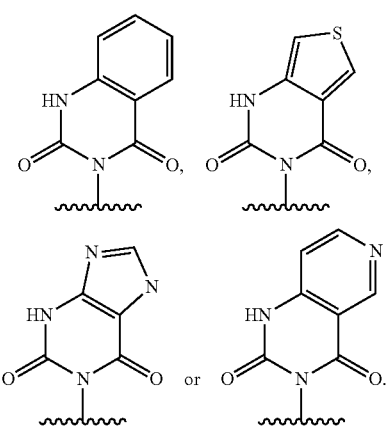

In another embodiment, $R^3$ is:

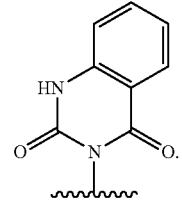 [SMILES: *n1c(=O)[nH]c2ccccc2c1=O]

In another embodiment, $R^3$ is:

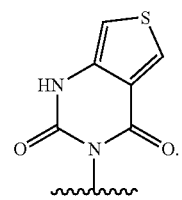 [SMILES: *n1c(=O)[nH]c2cscc2c1=O]

In yet another embodiment, $R^3$ is:

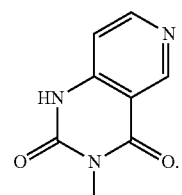

In a further embodiment, $R^3$ is:

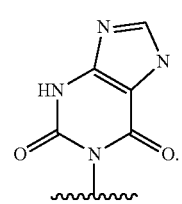

In one embodiment, $R^4$ is H.
In another embodiment, $R^4$ is H or F.
In another embodiment, $R^4$ is F.
In still another embodiment, $R^5$ is H.
In another embodiment, $R^6$ is H.
In yet another embodiment, $R^6$ is H or F.
In another embodiment, $R^6$ is F.
In still another embodiment, $R^5$ is H.
In another embodiment, $R^5$ is other than H.
In still another embodiment, $R^5$ is alkyl.
In another embodiment, $R^5$ is halo or haloalkyl.
In yet another embodiment, $R^5$ is halo.
In yet another embodiment, $R^5$ is haloalkyl.
In still another embodiment, $R^5$ is methyl.
In another embodiment, $R^5$ is ethyl.
In another embodiment, $R^5$ is Cl, Br or $CF_3$.
In another embodiment, $R^6$ is H.
In yet another embodiment, $R^6$ is H or F.
In another embodiment, $R^6$ is other than H.
In a further embodiment, $R^6$ is alkyl.

In yet another embodiment, $R^6$ is halo.

In still another embodiment, $R^6$ is methyl.

In another embodiment, $R^6$ is F.

In a further embodiment, $R^7$ is H.

In one embodiment, $R^4$ and $R^7$ are each H.

In yet another embodiment, $R^4$, $R^6$ and $R^7$ are each H.

In another embodiment, $R^4$, $R^5$, $R^6$ and $R^7$ are each H.

In a further embodiment, $R^4$, $R^6$ and $R^7$ are each H and $R^5$ is other than H.

In another embodiment, $R^4$, $R^6$ and $R^7$ are each H and $R^5$ is haloalkyl.

In still another embodiment, $R^4$, $R^6$ and $R^7$ are each H and $R^5$ is halo.

In another embodiment, $R^4$, $R^6$ and $R^7$ are each H and $R^5$ is Cl.

In a further embodiment, $R^4$, $R^6$ and $R^7$ are each H and $R^5$ is Br.

In another embodiment, $R^4$, $R^6$ and W are each H and $R^5$ is $CF_3$.

In one embodiment, $R^2$ is —C(O)NHSO$_2$R$^{11}$ and $R^3$ is

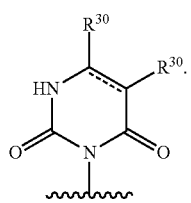

In another embodiment, $R^2$ is —C(O)NHSO$_2$R$^{11}$, $R^{11}$ is alkyl, and $R^3$ is

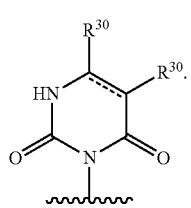

In one embodiment, $R^2$ is —C(O)NHSO$_2$CH$_3$, and $R^3$ is

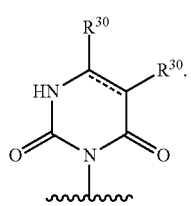

In another embodiment, $R^2$ is —C(O)NHSO$_2$R$^{11}$; $R^{11}$ is phenyl, which is optionally substituted with up to 3 groups independently selected from: alkyl, F, Cl, methyl, —NH$_2$, —NO$_2$, methoxy, —SO$_2$NH$_2$, —COOH, -(alkylene)$_s$-C(O)O-alkyl, hydroxy, —NHSO$_2$-alkyl, -(alkylene)$_s$-SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, -(alkylene)$_s$-NHC(O)-alkyl, pyrazolyl or —OCH$_2$C(O)NH$_2$; and $R^3$ is

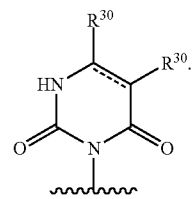

In another embodiment, $R^1$-$R^{10}$ is

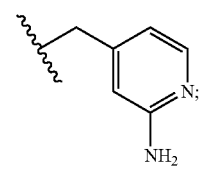

$R^2$ is —C(O)NHSO$_2$R$^{11}$; and $R^3$ is

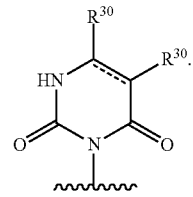

In still another embodiment, $R^1$-$R^{10}$ is

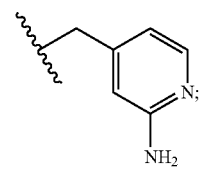

$R^2$ is —C(O)NHSO$_2$R$^{11}$; $R^{11}$ is alkyl; and $R^3$ is

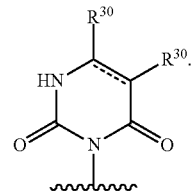

In one embodiment, $R^1$-$R^{10}$ is

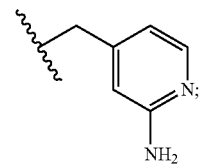

$R^2$ is —C(O)NHSO$_2$CH$_3$; and $R^3$ is

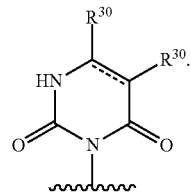

In another embodiment, $R^1$-$R^{10}$ is

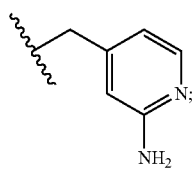

$R^2$ is —C(O)NHSO$_2$R$^{11}$, $R^{11}$ is phenyl, which is optionally substituted with up to 3 groups independently selected from: alkyl, F, Cl, methyl, —NH$_2$, —NO$_2$, methoxy, —SO$_2$NH$_2$, —COOH, -(alkylene)$_s$-C(O)O-alkyl, hydroxy, —NHSO$_2$-alkyl, -(alkylene)$_s$-SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, -(alkylene)$_s$-NHC(O)-alkyl, pyrazolyl or —OCH$_2$C(O)NH$_2$; and $R^3$ is

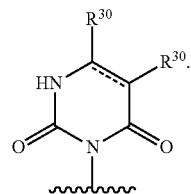

In another embodiment, $R^1$-$R^{10}$ is

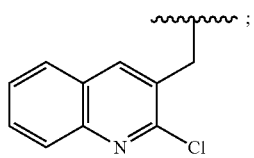 [SMILES: *Cc1cc2ccccc2nc1Cl]

$R^2$ is —C(O)NHSO$_2$R$^{11}$; and $R^3$ is

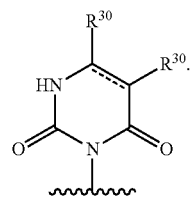

In still another embodiment, $R^1$-$R^{10}$ is

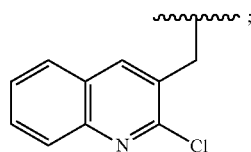

$R^2$ is —C(O)NHSO$_2$R$^{11}$; $R^{11}$ is alkyl; and $R^3$ is

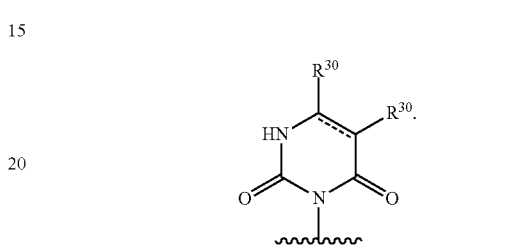

In one embodiment, $R^1$-$R^{10}$ is

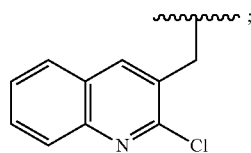 [SMILES: *Cc1cc2ccccc2nc1Cl]

$R^2$ is —C(O)NHSO$_2$CH$_3$; and $R^3$ is

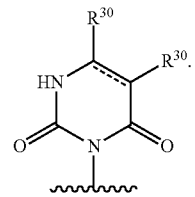

In another embodiment, $R^1$-$R^{10}$ is

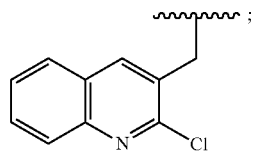 [SMILES: *Cc1cc2ccccc2nc1Cl]

$R^2$ is —C(O)NHSO$_2$R$^{11}$, $R^{11}$ is phenyl, which is optionally substituted with up to 3 groups independently selected from: alkyl, F, Cl, methyl, —NH$_2$, —NO$_2$, methoxy, —SO$_2$NH$_2$, —COOH, -(alkylene)$_s$-C(O)O-alkyl, hydroxy, —NHSO$_2$-alkyl, -(alkylene)$_s$-SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, -(alkylene)$_s$-NHC(O)-alkyl, pyrazolyl or —OCH$_2$C(O)NH$_2$; and $R^3$ is

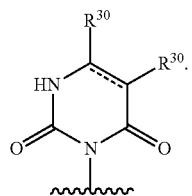

In another embodiment, $R^1$-$R^{10}$ is —CH$_2$-heteroaryl or alkyl; $R^2$ is —C(O)NHSO$_2$R$^{11}$; and $R^3$ is

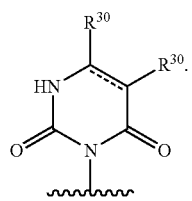

In still another embodiment, $R^1$-$R^{10}$ is —CH$_2$-heteroaryl or alkyl; $R^2$ is —C(O)NHSO$_2$R$^{11}$; $R^{11}$ is alkyl; and $R^3$ is

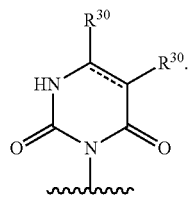

In another embodiment, $R^1$-$R^{10}$ is —CH$_2$-heteroaryl or alkyl; $R^2$ is —C(O)NHSO$_2$CH$_3$; and $R^3$ is

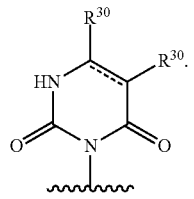

In yet another embodiment, $R^1$-$R^{10}$ is —CH$_2$-heteroaryl or alkyl; $R^2$ is —C(O)NHSO$_2$R$^{11}$, $R^{11}$ is phenyl, which is optionally substituted with up to 3 groups independently selected from: alkyl, F, Cl, methyl, —NH$_2$, —NO$_2$, methoxy, —SO$_2$NH$_2$, —COOH, -(alkylene)$_s$-C(O)O-alkyl, hydroxy, —NHSO$_2$-alkyl, -(alkylene)$_s$-SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, -(alkylene)$_s$-NHC(O)-alkyl, pyrazolyl or —OCH$_2$C(O)NH$_2$; and $R^3$ is

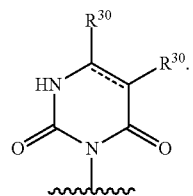

In a further embodiment, $R^1$-$R^{10}$ is benzyl, wherein the phenyl moiety of the benzyl group is optionally substituted with from 1-4 groups independently selected from: alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl; $R^2$ is —C(O)NHSO$_2$R$^{11}$; and $R^3$ is

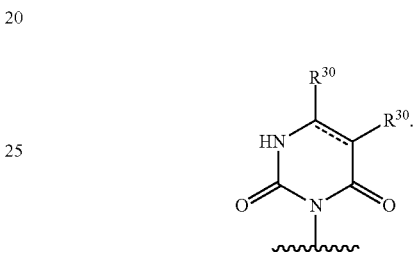

In one embodiment, $R^1$-$R^{10}$ is benzyl, wherein the phenyl moiety of the benzyl group is optionally substituted with from 1-4 groups independently selected from: alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl; $R^2$ is —C(O)NHSO$_2$-alkyl; and $R^3$ is

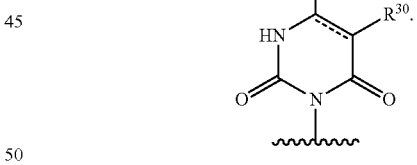

In another embodiment, $R^1$-$R^{10}$ is benzyl, wherein the phenyl moiety of the benzyl group is optionally substituted with from 1-4 groups independently selected from: alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl; $R^2$ is —C(O)NHSO$_2$R$^{11}$, $R^{11}$ is phenyl, which is optionally substituted with up to 3 groups independently selected from: alkyl, F, Cl, methyl, —NH$_2$, —NO$_2$, methoxy, —SO$_2$NH$_2$, —COOH, -(alkylene)$_s$-C(O)O-alkyl, hydroxy, —NHSO$_2$-alkyl, -(alkylene)$_s$-SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, -(alkylene)$_s$-NHC(O)-alkyl, pyrazolyl or —OCH$_2$C(O)NH$_2$; and $R^3$ is

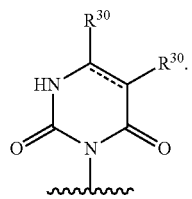

In another embodiment, $R^1$-$R^{10}$ is

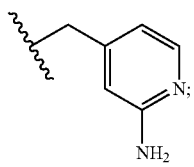

$R^2$ is —C(O)NHSO$_2$R$^{11}$, R$^{11}$ is phenyl, which is optionally substituted with up to 3 groups independently selected from: alkyl, F, Cl, methyl, —NH$_2$, —NO$_2$, methoxy, —SO$_2$NH$_2$, —COOH, -(alkylene)$_s$-C(O)O-alkyl, hydroxy, —NHSO$_2$-alkyl, -(alkylene)$_s$-SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, -(alkylene)$_s$-NHC(O)-alkyl, pyrazolyl or —OCH$_2$C(O)NH$_2$; R$^3$ is

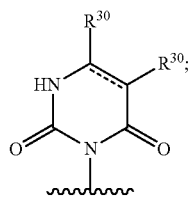

R$^4$, R$^6$ and R$^7$ are each H; and R$^5$ is halo or haloalkyl.

In another embodiment, R$^1$-R$^{10}$ is

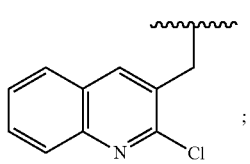 [SMILES: *Cc1cc2ccccc2nc1Cl]

R$^2$ is —C(O)NHSO$_2$R$^{11}$, R$^{11}$ is phenyl, which is optionally substituted with up to 3 groups independently selected from: alkyl, F, Cl, methyl, —NH$_2$, —NO$_2$, methoxy, —SO$_2$NH$_2$, —COOH, -(alkylene)$_s$-C(O)O-alkyl, hydroxy, —NHSO$_2$-alkyl, -(alkylene)$_s$-SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, -(alkylene)$_s$-NHC(O)-alkyl, pyrazolyl or —OCH$_2$C(O)NH$_2$; R$^3$ is

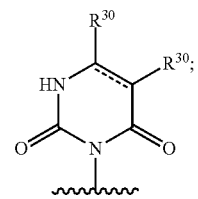

R$^4$, R$^6$ and R$^7$ are each H; and R$^5$ is halo or haloalkyl.

In another embodiment, R$^1$-R$^{10}$ is —CH$_2$-heteroaryl or alkyl; R$^2$ is —C(O)NHSO$_2$R$^{11}$; R$^3$ is

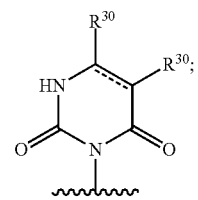

R$^4$, R$^6$ and R$^7$ are each H; and R$^5$ is halo or haloalkyl.

In still another embodiment. R$^1$-R$^{10}$ is —CH$_2$-heteroaryl or alkyl; R$^2$ is —C(O)NHSO$_2$R$^{11}$; R$^{11}$ is alkyl; R$^3$ is

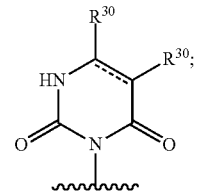

R$^4$, R$^6$ and R$^7$ are each H; and R$^5$ is halo or haloalkyl.

In another embodiment, R$^1$-R$^{10}$ is —CH$_2$-heteroaryl or —CH$_2$-cycloalkyl; R$^2$ is —C(O)NHSO$_2$CH$_3$; R$^3$ is

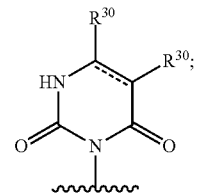

R$^4$, R$^6$ and R$^7$ are each H; and R$^5$ is halo or haloalkyl.

In yet another embodiment, R$^1$-R$^{10}$ is —CH$_2$-heteroaryl or alkyl; R$^2$ is —C(O)NHSO$_2$R$^{11}$, R$^{11}$ is phenyl, which is optionally substituted with up to 3 groups independently selected from: alkyl, F, Cl, methyl, —NH$_2$, —NO$_2$, methoxy, —SO$_2$NH$_2$, —COOH, -(alkylene)$_s$-C(O)O-alkyl, hydroxy, —NHSO$_2$-alkyl, -(alkylene)$_s$-SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, -(alkylene)$_s$-NHC(O)-alkyl, pyrazolyl or —OCH$_2$C(O)NH$_2$; R$^3$ is

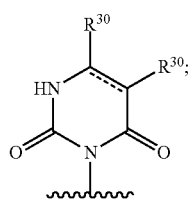

$R^4$, $R^6$ and $R^7$ are each H; and $R^5$ is halo or haloalkyl.

In a further embodiment, $R^1$-$R^{10}$ is benzyl, wherein the phenyl moiety of the benzyl group is optionally substituted with from 1-4 groups independently selected from: alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl; $R^2$ is —C(O)NHSO$_2$R$^{11}$; $R^3$ is

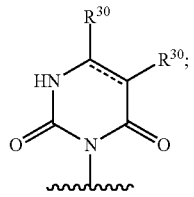

$R^4$, $R^6$ and $R^7$ are each H; and $R^5$ is halo or haloalkyl.

In one embodiment, $R^1$-$R^{10}$ is benzyl, wherein the phenyl moiety of the benzyl group is optionally substituted with from 1-4 groups independently selected from: alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl; $R^2$ is —C(O)NHSO$_2$-alkyl; $R^3$ is

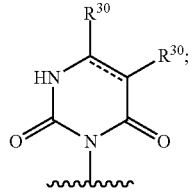

$R^4$, $R^6$ and $R^7$ are each H; and $R^5$ is halo or haloalkyl.

In another embodiment, $R^1$-$R^{10}$ is benzyl, wherein the phenyl moiety of the benzyl group is optionally substituted with from 1-4 groups independently selected from: alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl; $R^2$ is —C(O)NHSO$_2$R$^{11}$, $R^{11}$ is phenyl, which is optionally substituted with up to 3 groups independently selected from: alkyl, F, Cl, methyl, —NH$_2$, —NO$_2$, methoxy, —SO$_2$NH$_2$, —COOH, -(alkylene)$_s$-C(O)O-alkyl, hydroxy, —NHSO$_2$-alkyl, -(alkylene)$_s$-SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, -(alkylene)$_s$-NHC(O)-alkyl, pyrazolyl or —OCH$_2$C(O)NH$_2$; $R^3$ is

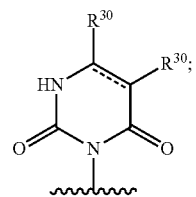

$R^4$, $R^6$ and $R^7$ are each H; and $R^5$ is halo or haloalkyl.

In one embodiment, the compounds of formula (I) have the formula (Ia):

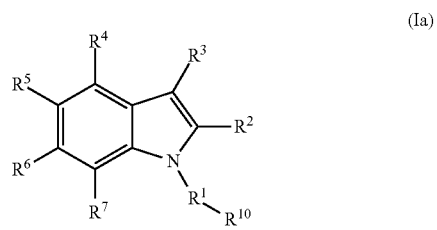

(Ia)

wherein:

$R^1$ is —[C(R$^{12}$)$_2$]$_r$-;

$R^2$ is —C(O)NHSO$_2$R$^{11}$;

$R^3$ is:

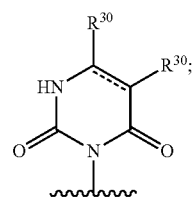

$R^4$, $R^5$, $R^6$ and $R^7$ are each, independently, H, alkyl, —O-alkyl, halo, haloalkyl or hydroxyalkyl;

$R^{10}$ is H, aryl, cycloalkyl, heterocycloalkyl or heteroaryl, wherein a cycloalkyl, heterocycloalkyl, aryl or heteroaryl group can be optionally substituted with one or more substituents, which are each independently selected from alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl;

$R^{11}$ is alkyl, aryl or cycloalkyl;

each occurrence of $R^{12}$ is H, alkyl or halo, or two geminal $R^{12}$ groups, together with the common carbon atom to which they are attached, join to form a 3- to 6-membered cycloalkyl group;

each occurrence of $R^{30}$ is independently, H, alkyl, aryl, halo, hydroxy, hydroxyalkyl, haloalkyl, —O-alkyl or —CN, or two adjacent $R^{30}$ groups, together with the carbon atoms to which they are attached, join to form a cycloalkyl, heterocycloalkyl, aryl or heteroaryl group; and r is an integer ranging from 1 to 4.

In one embodiment, for the compounds of formula (Ia):

$R^1$ is —CH$_2$—;

$R^2$ is —C(O)NHSO$_2$R$^{11}$;

$R^3$ is:

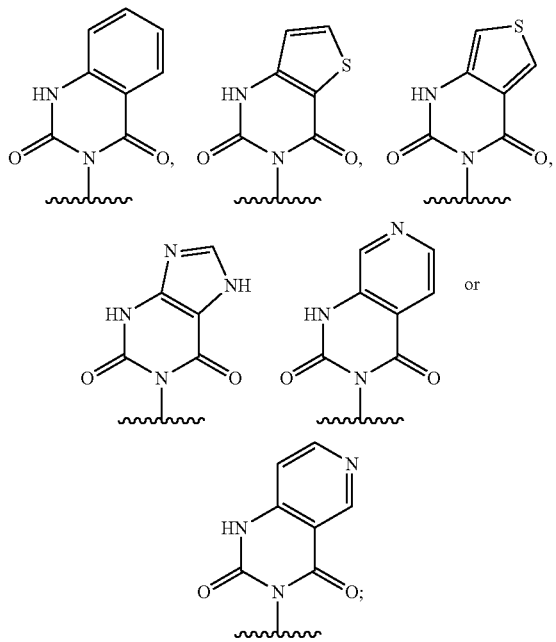

$R^4$, $R^6$ and $R^7$ are each H;

$R^5$ is H, alkyl, —O-alkyl, halo or haloalkyl;

$R^{10}$ is H aryl, cycloalkyl or heteroaryl, wherein a cycloalkyl, aryl or heteroaryl group can be optionally substituted with one or more substituents, which are each independently selected from alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl;

$R^{11}$ is alkyl, aryl or cycloalkyl; and r is an integer ranging from 1 to 4.

In another embodiment, for the compounds of formula (Ia):

$R^1$ is —CH$_2$—;

$R^2$ is —C(O)NHSO$_2R^{11}$;

$R^3$ is:

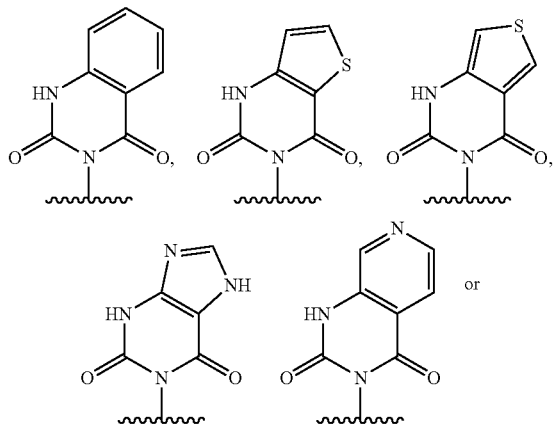

-continued

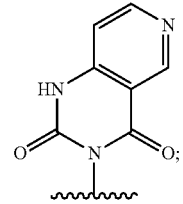

$R^4$, $R^6$ and $R^7$ are each H;

$R^5$ is H, halo or haloalkyl;

$R^{10}$ is phenyl, which can be optionally substituted with one or more substituents, which are each independently selected from alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl;

$R^{11}$ is alkyl, aryl or cycloalkyl; and r is an integer ranging from 1 to 4.

In another embodiment, for the compounds of formula (Ia):

$R^1$ is —CH$_2$—;

$R^2$ is —C(O)NHSO$_2R^{11}$;

$R^3$ is:

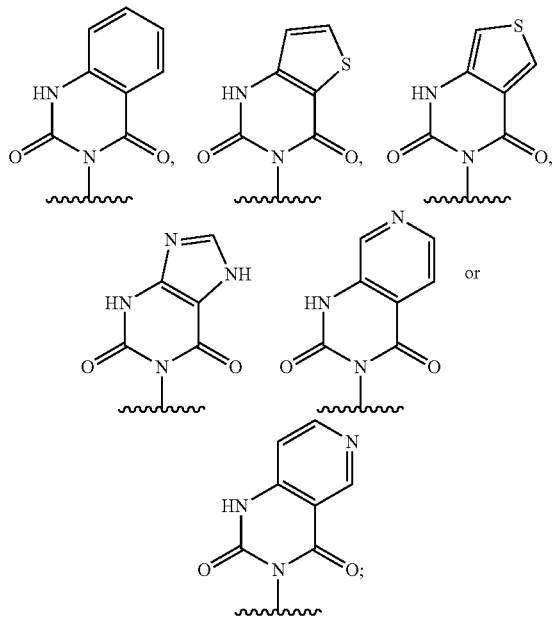

$R^4$, $R^6$ and $R^7$ are each H;

$R^5$ is H, halo or haloalkyl;

$R^{10}$ is phenyl, which can be optionally substituted with one or more substituents, which are each independently selected from alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl;

$R^{11}$ is alkyl, aryl or cycloalkyl; and r is an integer ranging from 1 to 4.

In another embodiment, for the compounds of formula (Ia):

$R^1$ is —CH$_2$—;

$R^2$ is —C(O)NHSO$_2R^{11}$;

$R^3$ is:

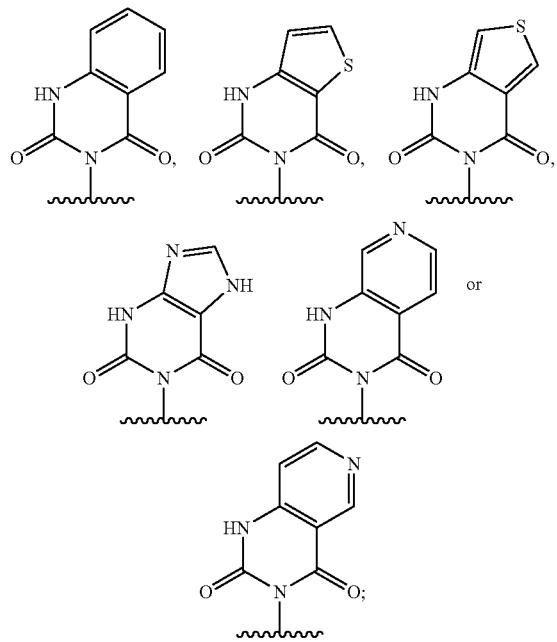

$R^4$, $R^6$ and $R^7$ are each H;

$R^5$ is Cl, Br or $CF_3$;

$R^{10}$ is phenyl, which can be optionally substituted with one or more substituents, which are each independently selected from alkyl, —O-alkyl, halo, —O-haloalkyl, —OH, —$NH_2$, —NH(alkyl), —N(alkyl)$_2$, —$NO_2$, —CN, —NHC(O)-alkyl, —O-alkylene-heterocycloalkyl —C(O)O-alkyl and —O-haloalkyl;

$R^{11}$ is methyl, ethyl, —$CH_2CH_2NH_2$, —$CH_2CH_2N(CH_3)_2$, —$CH_2CH_2CH_2NH_2$, —$CH_2CH_2CH_2N(CH_3)_2$, phenyl or cyclopropyl;

each occurrence of $R^{12}$ is H, alkyl or halo, or two geminal $R^{12}$ groups, together with the common carbon atom to which they are attached, join to form a 3- to 6-membered cycloalkyl group; and r is an integer ranging from 1 to 4.

In a further embodiment, for the compounds of formula (Ia):

$R^1$ is —$CH_2$—;

$R^2$ is —C(O)NHSO$_2R^{11}$;

$R^3$ is:

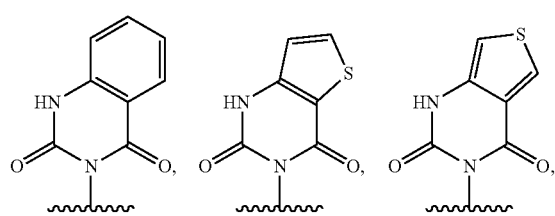

-continued

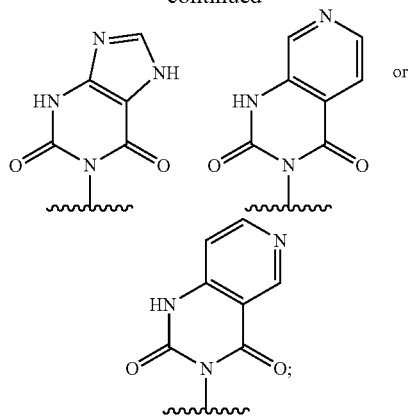

$R^4$, $R^6$ and $R^7$ are each H;

$R^5$ is H, halo or haloalkyl;

$R^{10}$ is phenyl, which can be optionally substituted with one or more substituents, which are each independently selected from alkyl, —O-alkyl, halo, —O-haloalkyl, —OH, —$NH_2$, —NH(alkyl), —N(alkyl)$_2$, —$NO_2$, —CN, —NHC(O)-alkyl, —O-alkylene-heterocycloalkyl —C(O)O-alkyl and —O-haloalkyl;

$R^{11}$ is methyl, phenyl or cyclopropyl; and r is an integer ranging from 1 to 4.

In one embodiment, for the compounds of formula (I), $R^1$, $R^2$, $R^3$, $R^4$, $R^5$, $R^6$, $R^7$ and $R^{10}$ are selected independently of each other.

In another embodiment, a compound of formula (I) is in purified form.

The 3-Heterocyclic Substituted Indole Derivatives of Formula (II)

The present invention also provides 3-Heterocyclic Substituted Indole Derivatives having the formula:

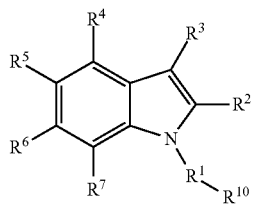

(II)

and pharmaceutically acceptable salts, solvates, esters and prodrugs thereof, wherein $R^1$, $R^2$, $R^3$, $R^4$, $R^5$, $R^6$, $R^7$ and $R^{16}$ are defined above for the compounds of formula (II).

In one embodiment, $R^1$ is bond.

In another embodiment, $R^1$ is —[C($R^{12}$)$_2$]$_r$—.

In another embodiment, $R^1$ is —[C($R^{12}$)$_2$]$_r$—O—[C($R^{12}$)$_2$]$_q$—.

In still another embodiment, $R^1$ is —[C($R^{12}$)$_2$]$_r$—N($R^9$)—[C($R^{12}$)$_2$]$_q$—.

In yet another embodiment, $R^1$ is —[C($R^{12}$)$_2$]$_q$—CH=CH—[C($R^{12}$)$_2$]$_4$—.

In another embodiment, $R^1$ is —[C($R^{12}$)$_2$]$_q$—C≡C—[C($R^{12}$)$_2$]$_4$—.

In a further embodiment, $R^1$ is —[C($R^{12}$)$_2$]$_q$—SO$_2$—[C($R^{12}$)$_2$]$_q$—.

In another embodiment, $R^1$ is —$CH_2$—.

In one embodiment, $R^{10}$ is H and $R^1$ is other than a bond.

In another embodiment, $R^{10}$ is aryl.

In another embodiment, $R^{10}$ is cycloalkyl.

In still another embodiment, $R^{10}$ is cycloalkenyl.

In another embodiment, $R^{10}$ is heterocycloalkenyl.

In another embodiment, $R^{10}$ is heteroaryl.

In yet another embodiment, $R^{10}$ is heterocycloalkyl.

In another embodiment, $R^{10}$ is phenyl.

In a further embodiment, $R^{10}$ is phenyl, which is substituted with from 1-3 groups independently selected from: alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl.

In one embodiment, $R^{10}$ is pyridyl.

In another embodiment, $R^{10}$ is furanyl.

In another embodiment, $R^{10}$ is thiophenyl.

In still another embodiment, $R^{10}$ is thiophenyl.

In another embodiment, $R^{10}$ is thiazolyl.

In another embodiment, $R^{10}$ is quinolinyl.

In a further embodiment, $R^{10}$ is

In another embodiment, —$R^{10}$ is:

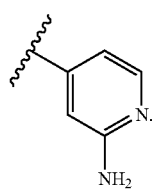

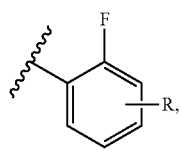

wherein R represents up to 2 optional and additional phenyl substituents, each independently selected from alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl.

In another embodiment, —$R^{10}$ is:

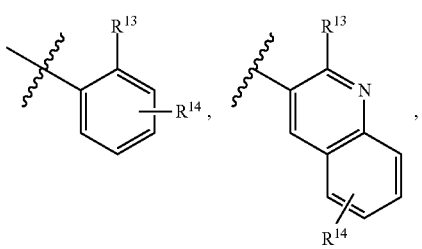

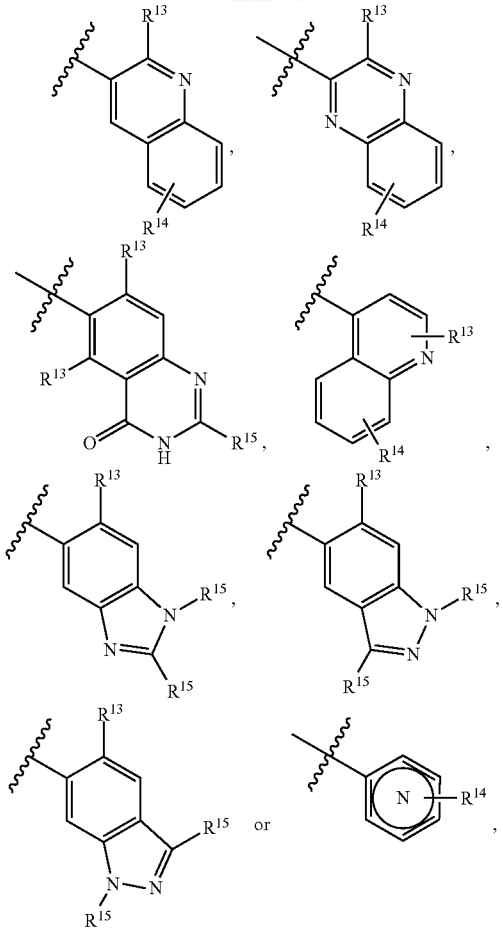

wherein $R^{13}$ is H, F, Br or Cl; $R^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, hydroxy, —NH$_2$, —SO$_2$alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and

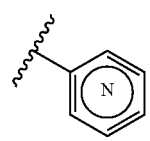

represents a pyridyl group, wherein the ring nitrogen atom can be at any of the five unsubstituted ring atom positions.

In another embodiment, —$R^{10}$ is:

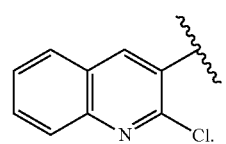 [SMILES: *c1cc2ccccc2nc1Cl]

In one embodiment, $R^{10}$ is H, alkyl, alkenyl, aryl, cycloalkyl, —CN, aryl, cycloalkyl or heteroaryl.

In another embodiment, $R^{10}$ is aryl, cycloalkyl or heteroaryl, any of which can be optionally and substituted with up to 3 groups, each independently selected from —NH$_2$, alkyl, alkenyl, halo, —NO$_2$ or —C(O)O-alkyl.

In another embodiment, $R^{10}$ is phenyl, cyclopropyl, furanyl, pyridyl or thiophenyl, any of which can be optionally and independently substituted with up to 3 groups selected from alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl.

In one embodiment, —$R^1$-$R^{10}$ is alkyl.

In another embodiment, $R^1$ is —CH$_2$— and $R^{10}$ is H, alkyl, alkenyl, aryl, cycloalkyl, —CN, aryl, cycloalkyl or heteroaryl.

In another embodiment, $R^1$ is —CH$_2$— and $R^{10}$ is aryl, cycloalkyl or heteroaryl, any of which can be optionally and substituted with up to 3 groups, each independently selected from alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl.

In yet another embodiment, $R^1$ is —CH$_2$— and $R^{10}$ is phenyl, cyclopropyl, furanyl, pyridyl, isoxazolyl or thiophenyl, any of which can be optionally and independently substituted with up to 3 groups selected from alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl.

In another embodiment, $R^1$ is —CH$_2$— and —$R^{10}$ is:

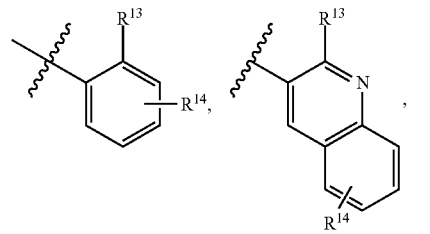

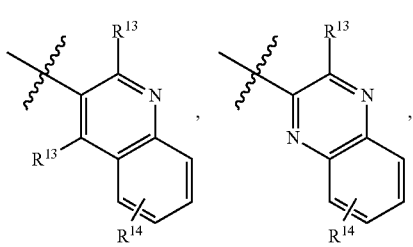

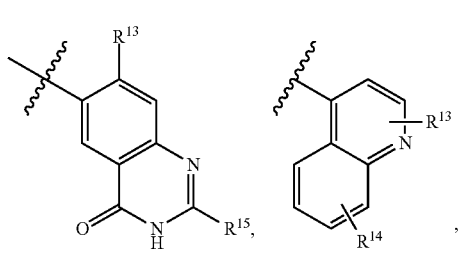

-continued

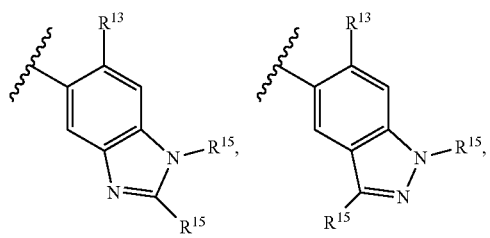

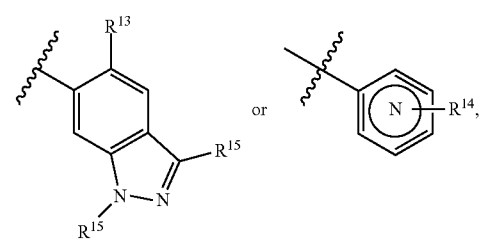

wherein $R^{13}$ is H, F, Br or Cl; $R^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, hydroxy, —NH$_2$, —SO$_2$alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and

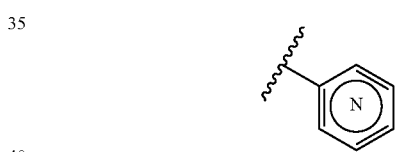

represents a pyridyl group, wherein the ring nitrogen atom can be at any of the five unsubstituted ring atom positions.

In one embodiment, —$R^1$-$R^{10}$ is benzyl.

In another embodiment, —$R^1$-$R^{10}$ is benzyl, wherein the phenyl moiety of the benzyl group is substituted with from 1-4 groups independently selected from: alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl.

In still another embodiment, —$R^1$-$R^{10}$ is

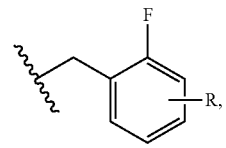

wherein R represents up to 2 optional and additional phenyl substituents, each independently selected from alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl.

In another embodiment, —R$^1$-R$^{10}$ is

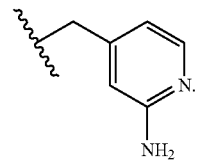

In still another embodiment, —R$^1$-R$^{10}$ is alkyl.

In another embodiment, —R$^1$-R$^{10}$ is benzyl, wherein the phenyl moiety of the benzyl group is substituted with 1 or 2 fluorine atoms.

In yet another embodiment, —R$^1$-R$^{10}$ is benzyl, wherein the phenyl moiety of the benzyl group is substituted with 1 or 2 methyl groups.

In one another embodiment, —R$^1$-R$^{10}$ is benzyl, wherein the phenyl moiety of the benzyl group is substituted with one fluorine atom and one methyl group.

In another embodiment, —R$^1$-R$^{10}$ is haloalkyl.

In a further embodiment, —R$^1$—R$^{10}$ is —CH$_2$-cycloalkyl.

In another embodiment, —R$^1$-R$^{10}$ is —CH$_2$-heteroaryl.

In another embodiment, —R$^1$-R$^{10}$ is:

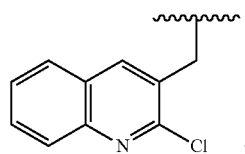

In one embodiment, R$^2$ is —C(O)R$^9$.

In another embodiment, R$^2$ is —C(O)OR$^9$.

In still another embodiment, R$^2$ is —C(O)N(R$^9$)$_2$.

In yet another embodiment, R$^2$ is —[C(R$^{12}$)$_2$]$_r$—C(O)OR$^9$.

In another embodiment, R$^2$ is —[C(R$^{12}$)$_2$]$_r$—C(O)N(R$^9$)$_2$.

In a further embodiment, R$^2$ is -alkyl.

In another embodiment, R$^2$ is —[C(R$^{12}$)$_2$]$_q$-aryl.

In another embodiment, R$^2$ is —[C(R$^{12}$)$_2$]$_q$-cycloalkyl.

In still another embodiment, R$^2$ is —[C(R$^{12}$)$_2$]$_q$-cycloalkenyl.

In still another embodiment, R$^2$ is —[C(R$^{12}$)$_2$]$_q$-heterocycloalkyl.

In yet another embodiment, R$^2$ is —[C(R$^{12}$)$_2$]$_q$-heteroaryl.

In another embodiment, R$^2$ is —[C(R$^{12}$)$_2$]$_q$-heterocycloalkenyl.

In a further embodiment, R$^2$ is —C(O)OR$^9$ or —C(O)N(R$^9$)$_2$.

In another embodiment, R$^2$ is —C(O)OH.

In another embodiment, R$^2$ is —C(O)NH$_2$.

In still another embodiment, R$^2$ is —C(O)R$^9$, —C(O)OR$^9$, —C(O)OCH$_2$OR$^9$, —C(O)N(R$^9$)$_2$, —[C(R$^{12}$)$_2$]$_q$—C(O)OR$^9$, —[C(R$^{12}$)$_2$]$_q$—C(O)N(R$^9$)$_2$ or —[C(R$^{12}$)$_2$]$_q$-heteroaryl wherein a heteroaryl group can be optionally substituted with up to 4 substituents, which are the same or different, and are selected from alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, hydroxyalkyl, halo, hydroxy, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^6$)$_2$.

In one embodiment, R$^3$ is

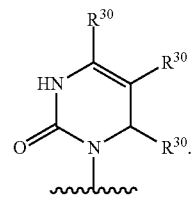

In another embodiment, R$^3$ is

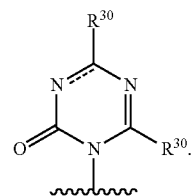

In another embodiment, R$^3$ is

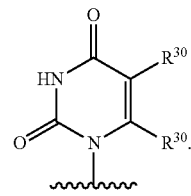

In still another embodiment, R$^3$ is

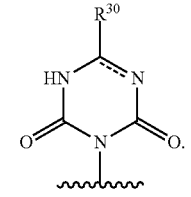

In another embodiment, R$^3$ is

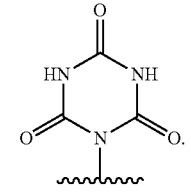 [SMILES: *n1c(=O)[nH]c(=O)[nH]c1=O]

In yet another embodiment, $R^3$ is

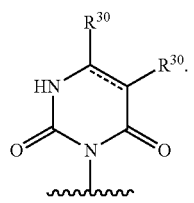

In another embodiment, $R^3$ is

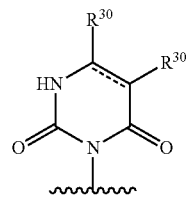

and both $R^{30}$ groups, together with the carbon atoms to which they are attached, join to form an aryl or heteroaryl group.

In another embodiment, $R^3$ is

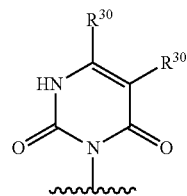

and each $R^{30}$ group is independently selected from H and alkyl.

In one embodiment, $R^3$ is:

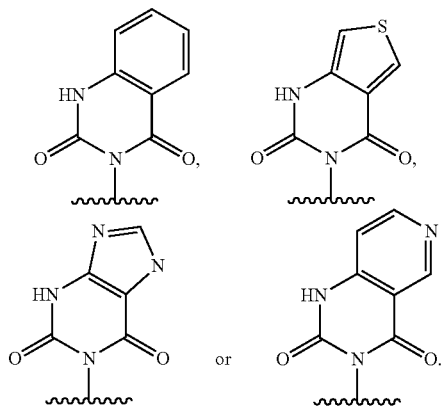

In another embodiment, $R^3$ is:

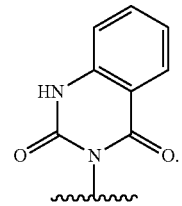 [SMILES: *n1c(=O)[nH]c2ccccc2c1=O]

In another embodiment, $R^3$ is:

In yet another embodiment, $R^3$ is:

In a further embodiment, $R^3$ is:

In one embodiment, $R^4$ is H.
In another embodiment, $R^4$ is H or F.
In another embodiment, $R^4$ is F.
In still another embodiment, $R^5$ is H.
In another embodiment, $R^6$ is H.
In yet another embodiment, $R^6$ is H or F.
In another embodiment, $R^6$ is F.
In still another embodiment, $R^5$ is H.
In another embodiment, $R^5$ is other than H.
In still another embodiment, $R^5$ is alkyl.
In another embodiment, $R^5$ is halo or haloalkyl.
In yet another embodiment, $R^5$ is halo.
In yet another embodiment, $R^5$ is haloalkyl.
In still another embodiment, $R^5$ is methyl.
In another embodiment, $R^5$ is ethyl.
In another embodiment, $R^5$ is Cl, Br or $CF_3$.
In another embodiment, $R^6$ is H.
In yet another embodiment, $R^6$ is H or F.
In another embodiment, $R^6$ is other than H.

In a further embodiment, $R^6$ is alkyl.
In yet another embodiment, $R^6$ is halo.
In still another embodiment, $R^6$ is methyl.
In another embodiment, $R^6$ is F.
In a further embodiment, $R^7$ is H.
In one embodiment, $R^4$ and $R^7$ are each H.
In yet another embodiment, $R^4$, $R^6$ and $R^7$ are each H.
In another embodiment, $R^4$, $R^5$, $R^6$ and $R^7$ are each H.
In a further embodiment, $R^4$, $R^6$ and $R^7$ are each H and $R^5$ is other than H.
In another embodiment, $R^4$, $R^6$ and $R^7$ are each H and $R^5$ is haloalkyl.
In still another embodiment, $R^4$, $R^6$ and $R^7$ are each H and $R^5$ is halo.
In another embodiment, $R^4$, $R^6$ and $R^7$ are each H and $R^5$ is Cl.
In a further embodiment, $R^4$, $R^6$ and $R^7$ are each H and $R^5$ is Br.
In another embodiment, $R^4$, $R^6$ and $R^7$ are each H and $R^5$ is $CF_3$.
In one embodiment, $R^2$ is —C(O)OR$^9$ and $R^3$ is

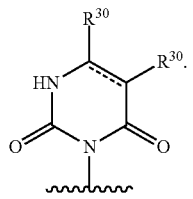

In another embodiment, $R^2$ is —C(O)OH and $R^3$ is

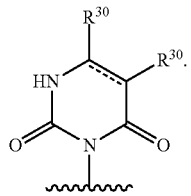

In one embodiment, $R^2$ is —C(O)N(R$^9$)$_2$ and $R^3$ is

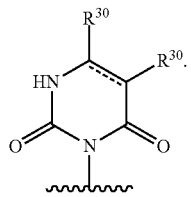

In another embodiment, $R^2$ is —C(O)NH$_2$ and $R^3$ is

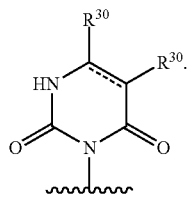

In another embodiment, $R^1$-$R^{10}$ is

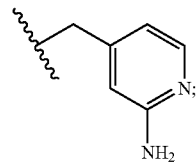

$R^2$ is —C(O)OR$^9$; and $R^3$ is

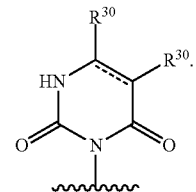

In still another embodiment, $R^1$-$R^{10}$ is

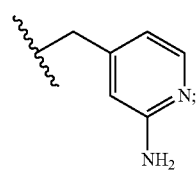

$R^2$ is —C(O)OH; and $R^3$ is

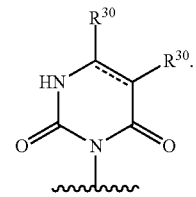

In one embodiment, $R^1$-$R^{10}$ is

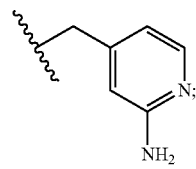

$R^2$ is —C(O)N(R$^9$)$_3$; and $R^3$ is

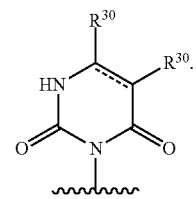

In another embodiment, $R^1$-$R^{10}$ is

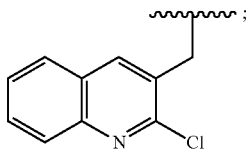 [SMILES: *Cc1cc2ccccc2nc1Cl]

$R^2$ is —C(O)$R^9$; and $R^3$ is

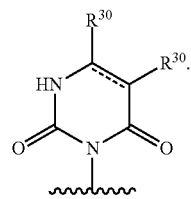

In still another embodiment, $R^1$-$R^{10}$ is

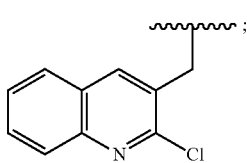 [SMILES: *Cc1cc2ccccc2nc1Cl]

$R^2$ is —C(O)OH; and $R^3$ is

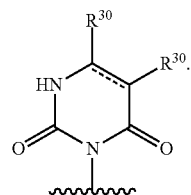

In one embodiment, $R^1$-$R^{10}$ is

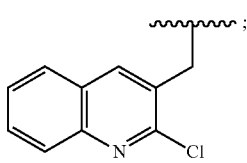 [SMILES: *Cc1cc2ccccc2nc1Cl]

$R^2$ is —C(O)N($R^9$)$_2$; and $R^3$ is

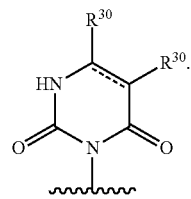

In another embodiment, $R^1$-$R^{10}$ is

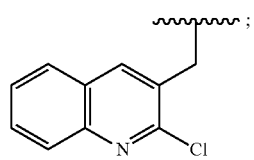 [SMILES: *Cc1cc2ccccc2nc1Cl]

$R^2$ is —C(O)NH$_2$; and $R^3$ is

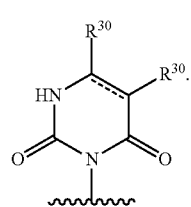

In another embodiment, $R^1$-$R^{10}$ is —CH$_2$-heteroaryl or alkyl; $R^2$ is —C(O)O$R^9$; and $R^3$ is

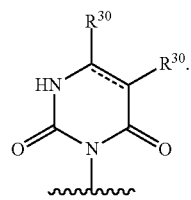

In still another embodiment, $R^1$-$R^{10}$ is —CH$_2$-heteroaryl or alkyl; $R^2$ is —C(O)OH; and $R^3$ is

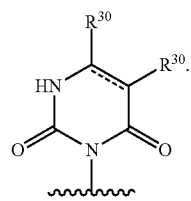

In another embodiment, $R^1$-$R^{10}$ is —CH$_2$-heteroaryl or alkyl; $R^2$ is —C(O)N($R^9$)$_2$; and $R^3$ is

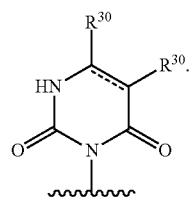

In another embodiment, $R^1$-$R^{10}$ is —CH$_2$-heteroaryl or alkyl; $R^2$ is —C(O)NH$_2$; and $R^3$ is

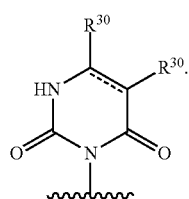

In one embodiment, $R^1$-$R^{10}$ is benzyl, wherein the phenyl moiety of the benzyl group is optionally substituted with from 1-4 groups independently selected from: alkyl, —O-alkyl, halo, —O-haloalkyl, —OH, —$NH_2$, —NH(alkyl), —N(alkyl)$_2$, —$NO_2$, —CN, —NHC(O)-alkyl, —O-alkylene-heterocycloalkyl —C(O)O-alkyl and —O-haloalkyl; $R^2$ is —C(O)OR$^9$; and $R^3$ is

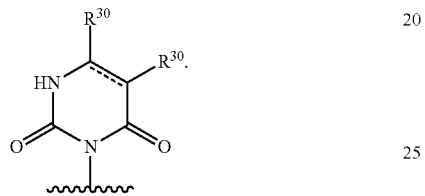

In another embodiment, $R^1$-$R^{10}$ is benzyl, wherein the phenyl moiety of the benzyl group is optionally substituted with from 1-4 groups independently selected from: alkyl, —O-alkyl, halo, —O-haloalkyl, —OH, —$NH_2$, —NH(alkyl), —N(alkyl)$_2$, —$NO_2$, —CN, —NHC(O)-alkyl, —O-alkylene-heterocycloalkyl —C(O)O-alkyl and —O-haloalkyl; $R^2$ is —C(O)OH; and $R^3$ is

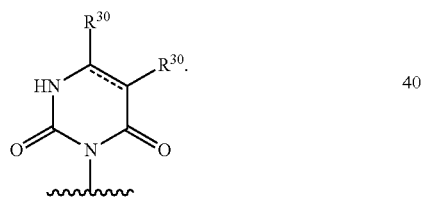

In another embodiment, $R^1$-$R^{10}$ is benzyl, wherein the phenyl moiety of the benzyl group is optionally substituted with from 1-4 groups independently selected from: alkyl, —O-alkyl, halo, —O-haloalkyl, —OH, —$NH_2$, —NH(alkyl), —N(alkyl)$_2$, —$NO_2$, —CN, —NHC(O)-alkyl, —O-alkylene-heterocycloalkyl —C(O)O-alkyl and —O-haloalkyl; $R^2$ is —C(O)N(R$^9$)$_2$; and $R^3$ is

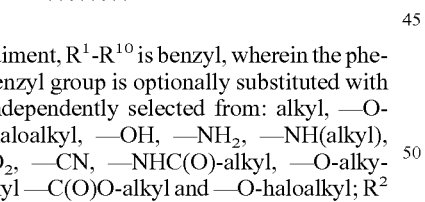

In another embodiment, $R^1$-$R^{10}$ is benzyl, wherein the phenyl moiety of the benzyl group is optionally substituted with from 1-4 groups independently selected from: alkyl, —O-alkyl, halo, —O-haloalkyl, —OH, —$NH_2$, —NH(alkyl), —N(alkyl)$_2$, —$NO_2$, —CN, —NHC(O)-alkyl, —O-alkylene-heterocycloalkyl —C(O)O-alkyl and —O-haloalkyl; $R^2$ is —C(O)$NH_2$; and $R^3$ is

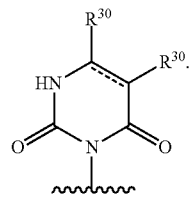

In another embodiment, $R^1$-$R^{10}$ is

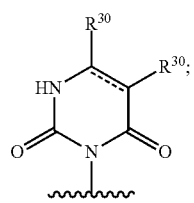

$R^2$ is —C(O)OH or —C(O)$NH_2$; $R^3$ is

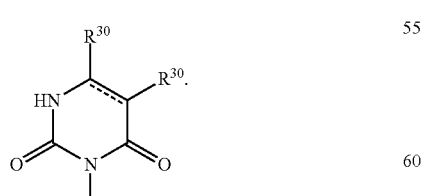

and $R^4$, $R^6$ and $R^7$ are each H; and $R^5$ is halo or haloalkyl.

In another embodiment, $R^1$-$R^{10}$ is

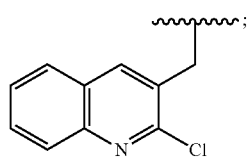 [SMILES: *Cc1cc2ccccc2nc1Cl]

$R^2$ is —C(O)OH or —C(O)$NH_2$; $R^3$ is

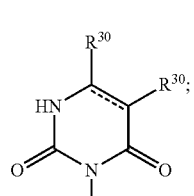

and $R^4$, $R^6$ and $R^7$ are each H; and $R^5$ is halo or haloalkyl.

In another embodiment, $R^1$-$R^{10}$ is —$CH_2$-heteroaryl or alkyl; $R^2$ is —C(O)OH or —C(O)$NH_2$; $R^3$ is

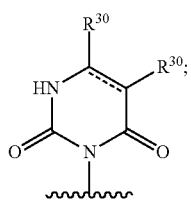

and $R^4$, $R^6$ and $R^7$ are each H; and $R^5$ is halo or haloalkyl.

In a further embodiment, $R^1$-$R^{10}$ is benzyl, wherein the phenyl moiety of the benzyl group is optionally substituted with from 1-4 groups independently selected from: alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl; $R^2$ is —C(O)OH or —C(O)NH$_2$; $R^3$ is

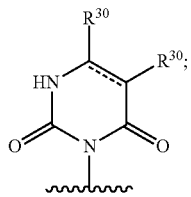

and $R^4$, $R^6$ and $R^7$ are each H; and $R^5$ is halo or haloalkyl.

In one embodiment, the compounds of formula (II) have the formula (IIa):

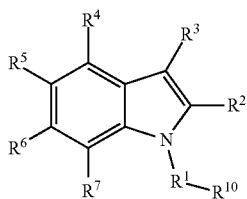

(IIa)

wherein:
$R^1$ is —[C($R^{12}$)$_2$]$_r$—;
$R^2$ is —C(O)OH, —C(O)NH$_2$, —C(O)OCH$_2$CH$_2$NH$_2$, —C(O)OCH$_2$CH$_2$N(CH$_3$)$_2$, C(O)OCH$_2$CH$_2$CH$_2$NH$_2$ or —C(O)OCH$_2$CH$_2$CH$_2$N(CH$_3$)$_2$;
$R^3$ is:

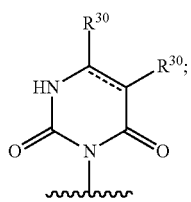

$R^4$, $R^5$, $R^6$ and $R^7$ are each, independently, H, alkyl, —O-alkyl, halo, haloalkyl or hydroxyalkyl;
$R^{10}$ is H, aryl, cycloalkyl, heterocycloalkyl or heteroaryl, wherein a cycloalkyl, heterocycloalkyl, aryl or heteroaryl group can be optionally substituted with one or more substituents, which are each independently selected from alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl;

$R^9$ is H, alkyl or aryl;

each occurrence of $R^{12}$ is H, alkyl or halo, or two geminal $R^{12}$ groups, together with the common carbon atom to which they are attached, join to form a 3- to 6-membered cycloalkyl group;

each occurrence of $R^{30}$ is independently, H, alkyl, aryl, halo, hydroxy, hydroxyalkyl, haloalkyl, —O-alkyl or —CN, or two adjacent $R^{30}$ groups, together with the carbon atoms to which they are attached, join to form a cycloalkyl, heterocycloalkyl, aryl or heteroaryl group; and r is an integer ranging from 1 to 4.

In another embodiment, for the compounds of formula (IIa):
$R^1$ is —CH$_2$—;
$R^2$ is —C(O)OH or —C(O)NH$_2$;
$R^3$ is:

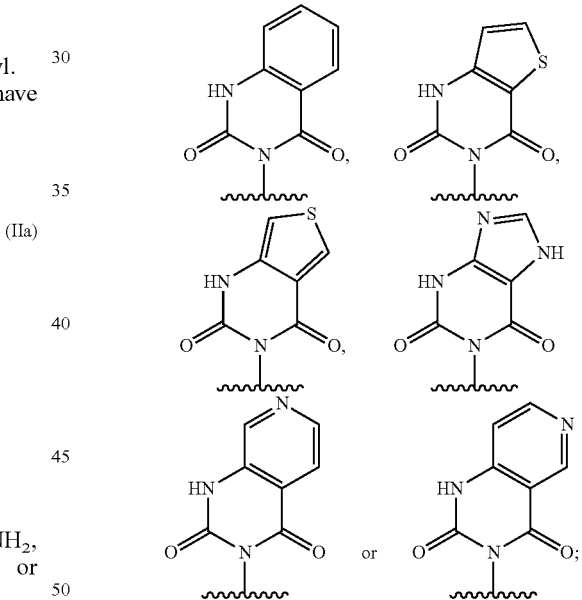

$R^4$, $R^6$ and $R^7$ are each H;

$R^5$ is H, halo or haloalkyl;

$R^{10}$ is H aryl, cycloalkyl or heteroaryl, wherein a cycloalkyl, aryl or heteroaryl group can be optionally substituted with one or more substituents, which are each independently selected from alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl; and r is an integer ranging from 1 to 4.

In another embodiment, for the compounds of formula (IIa):
$R^1$ is —CH$_2$—;
$R^2$ is —C(O)OH;

$R^3$ is:

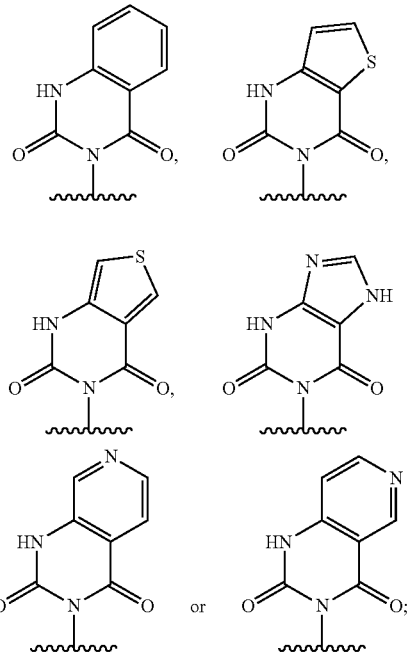

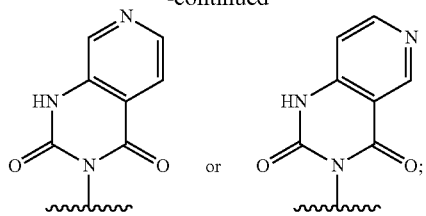

$R^4$, $R^6$ and $R^7$ are each H;

$R^5$ is H, halo or haloalkyl;

$R^{10}$ is phenyl, which can be optionally substituted with one or more substituents, which are each independently selected from alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl; and r is an integer ranging from 1 to 4.

In one embodiment, for the compounds of formula (IIa):

$R^1$ is —CH$_2$—;

$R^2$ is —C(O)OH;

$R^3$ is:

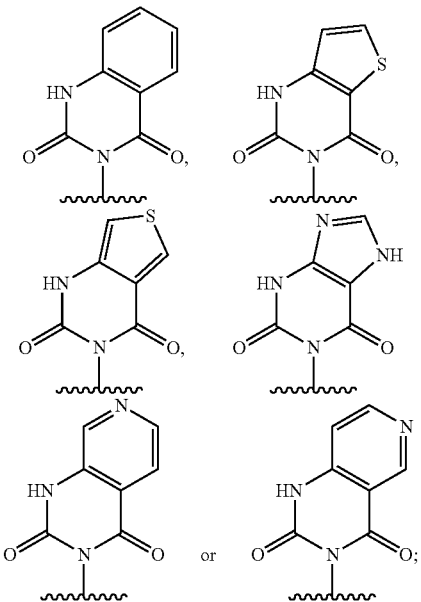

$R^4$, $R^6$ and $R^7$ are each H;

$R^5$ is H, halo or haloalkyl;

$R^{10}$ is H aryl, cycloalkyl or heteroaryl, wherein a cycloalkyl, aryl or heteroaryl group can be optionally substituted with one or more substituents, which are each independently selected from alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl; and r is an integer ranging from 1 to 4.

In still another embodiment, for the compounds of formula (IIa):

$R^1$ is —CH$_2$—;

$R^2$ is —C(O)OH;

$R^3$ is:

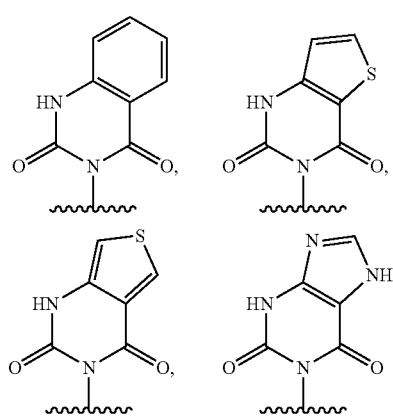

$R^4$, $R^6$ and $R^7$ are each H;

$R^5$ is Cl, Br, methyl, ethyl, —OCH$_3$ or CF$_3$;

$R^{10}$ is phenyl, which can be optionally substituted with one or more substituents, which are each independently selected from alkyl, —O-alkyl, halo, —O-haloalkyl, —OH, —NH$_2$, —NH(alkyl), —N(alkyl)$_2$, —NO$_2$, —CN, —NHC(O)-alkyl, —O-alkylene-heterocycloalkyl —C(O)O-alkyl and —O-haloalkyl; and r is an integer ranging from 1 to 4.

In one embodiment, for the compounds of formula (II), $R^1$, $R^2$, $R^3$, $R^4$, $R^5$, $R^6$, $R^7$ and $R^{10}$ are selected independently of each other.

In another embodiment, a compound of formula (II) is in purified form.

Non-limiting illustrative examples of the 3-Heterocyclic Substituted Indole Derivatives are set forth in the following table and in the Examples section below.

| Compound No. | Structure | LCMS (M + H) |
|---|---|---|
| 1 | 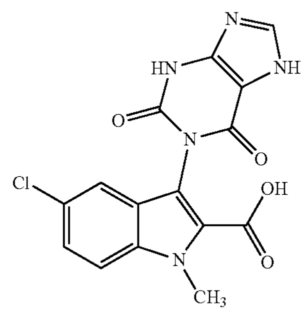 [SMILES: Cn1c(C(=O)O)c(-n2c(=O)[nH]c3nc[nH]c3c2=O)c2cc(Cl)ccc21] | 359.7 |
| 2 | 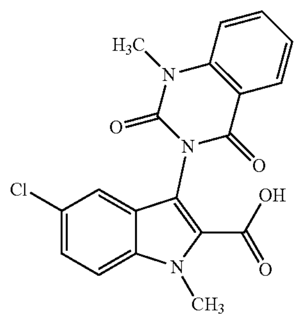 [SMILES: Cn1c(C(=O)O)c(-n2c(=O)c3ccccc3n(C)c2=O)c2cc(Cl)ccc21] | 383.8 |
| 3 | 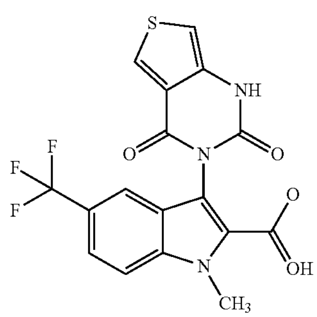 [SMILES: Cn1c(C(=O)O)c(-n2c(=O)[nH]c3cscc3c2=O)c2cc(C(F)(F)F)ccc21] | 409.3 |
| 4 | 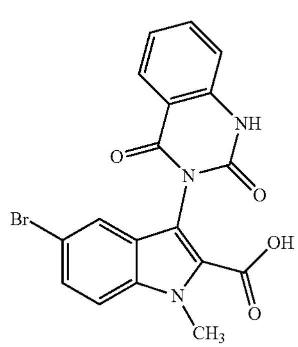 [SMILES: Cn1c(C(=O)O)c(-n2c(=O)[nH]c3ccccc3c2=O)c2cc(Br)ccc21] | 414.2 |

-continued

| Compound No. | Structure | LCMS (M + H) |
|---|---|---|
| 5 | 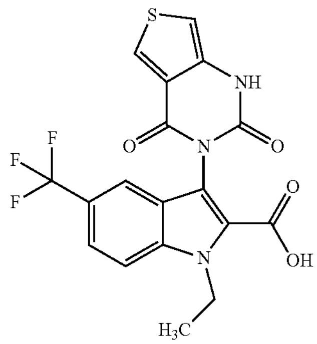 [SMILES: CCn1c(C(=O)O)c(-n2c(=O)[nH]c3cscc3c2=O)c2cc(C(F)(F)F)ccc21] | 423.4 |
| 6 | 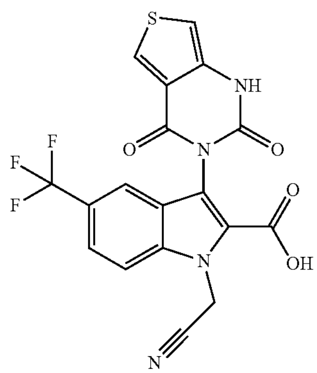 [SMILES: N#CCn1c(C(=O)O)c(-n2c(=O)[nH]c3cscc3c2=O)c2cc(C(F)(F)F)ccc21] | 434.4 |
| 7 | 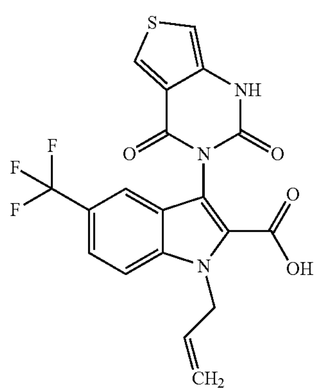 [SMILES: C=CCn1c(C(=O)O)c(-n2c(=O)[nH]c3cscc3c2=O)c2cc(C(F)(F)F)ccc21] | 435.4 |
| 8 | 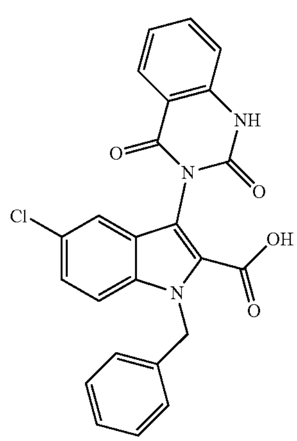 [SMILES: O=C(O)c1c(-n2c(=O)[nH]c3ccccc3c2=O)c2cc(Cl)ccc2n1Cc1ccccc1] | 445.9 |

-continued

| Compound No. | Structure | LCMS (M + H) |
|---|---|---|
| 9 | 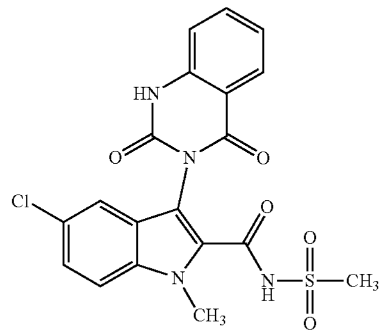 [SMILES: Cn1c(C(=O)NS(C)(=O)=O)c(-n2c(=O)[nH]c3ccccc3c2=O)c2cc(Cl)ccc21] | 446.9 |
| 10 | 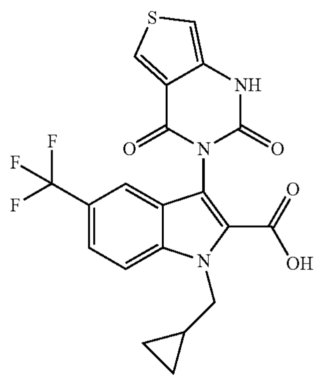 [SMILES: O=C(O)c1c(-n2c(=O)[nH]c3cscc3c2=O)c2cc(C(F)(F)F)ccc2n1CC1CC1] | 449.4 |
| 11 | 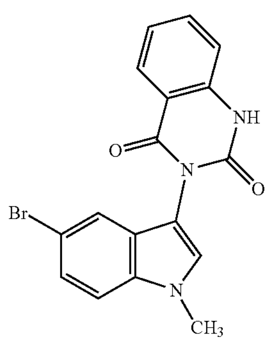 [SMILES: Cn1cc(-n2c(=O)[nH]c3ccccc3c2=O)c2cc(Br)ccc21] | 370.2 |
| 12 | 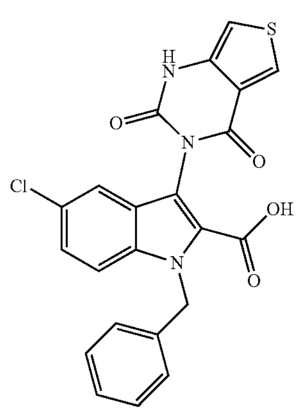 [SMILES: O=C(O)c1c(-n2c(=O)[nH]c3cscc3c2=O)c2cc(Cl)ccc2n1Cc1ccccc1] | 451.9 |

-continued
| Compound No. | Structure | LCMS (M + H) |
|---|---|---|
| 13 | 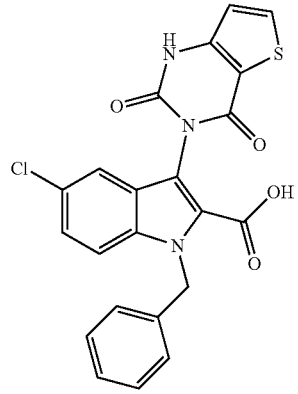 [SMILES: O=C(O)c1c(-n2c(=O)[nH]c3ccsc3c2=O)c2cc(Cl)ccc2n1Cc1ccccc1] | 451.9 |
| 14 | 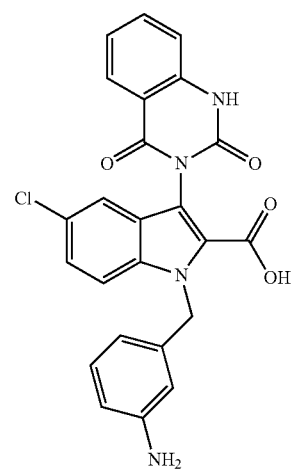 [SMILES: Nc1cccc(Cn2c(C(=O)O)c(-n3c(=O)[nH]c4ccccc4c3=O)c3cc(Cl)ccc32)c1] | 460.9 |
| 15 | 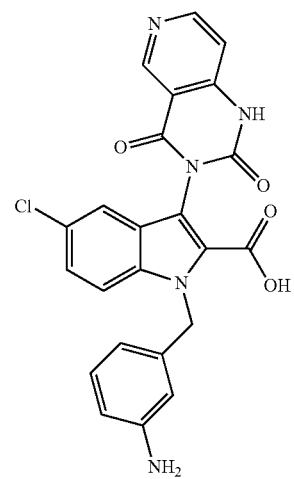 [SMILES: Nc1cccc(Cn2c(C(=O)O)c(-n3c(=O)[nH]c4ccncc4c3=O)c3cc(Cl)ccc32)c1] | 461.9 |

-continued

| Compound No. | Structure | LCMS (M + H) |
|---|---|---|
| 16 | 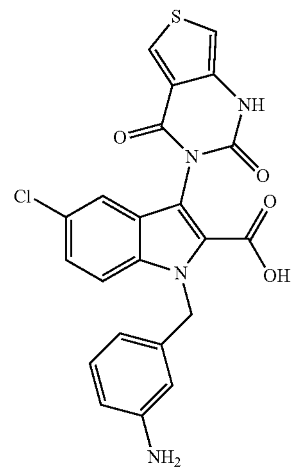 [SMILES: Nc1cccc(Cn2c(C(=O)O)c(-n3c(=O)[nH]c4cscc4c3=O)c3cc(Cl)ccc32)c1] | 466.9 |
| 17 | 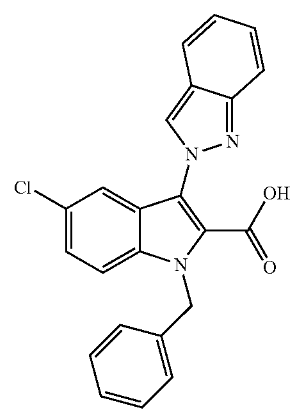 [SMILES: O=C(O)c1c(-n2cc3ccccc3n2)c2cc(Cl)ccc2n1Cc1ccccc1] | 401.9 |
| 18 | 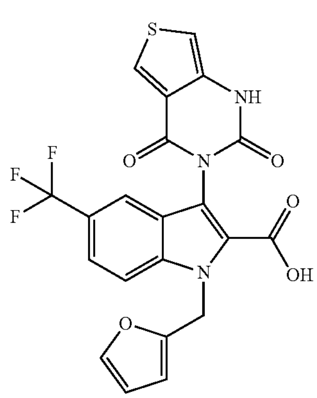 [SMILES: O=C(O)c1c(-n2c(=O)[nH]c3cscc3c2=O)c2cc(C(F)(F)F)ccc2n1Cc1ccco1] | 475.4 |

-continued

| Compound No. | Structure | LCMS (M + H) |
|---|---|---|
| 19 | 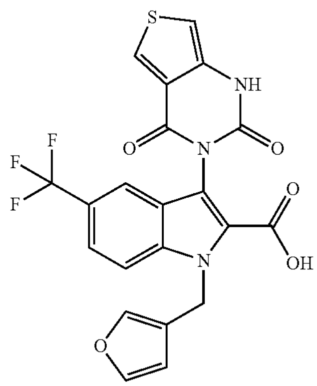 [SMILES: O=C(O)c1c(-n2c(=O)[nH]c3cscc3c2=O)c2cc(C(F)(F)F)ccc2n1Cc1ccoc1] | 475.4 |
| 20 | 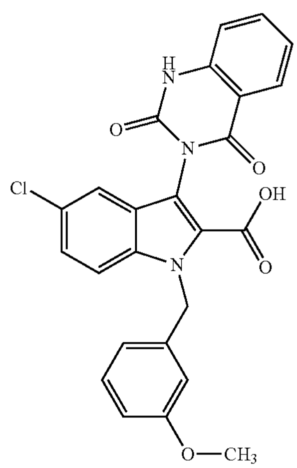 [SMILES: COc1cccc(Cn2c(C(=O)O)c(-n3c(=O)[nH]c4ccccc4c3=O)c3cc(Cl)ccc32)c1] | 475.9 |
| 21 | 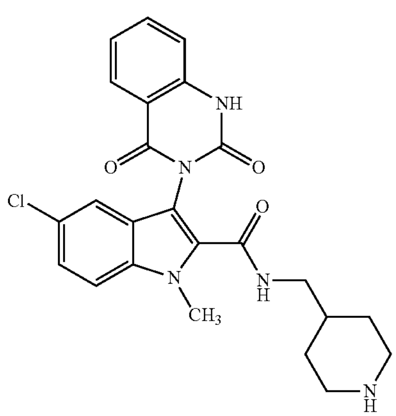 [SMILES: Cn1c(C(=O)NCC2CCNCC2)c(-n2c(=O)[nH]c3ccccc3c2=O)c2cc(Cl)ccc21] | 465.9 |

-continued
| Compound No. | Structure | LCMS (M + H) |
|---|---|---|
| 22 | 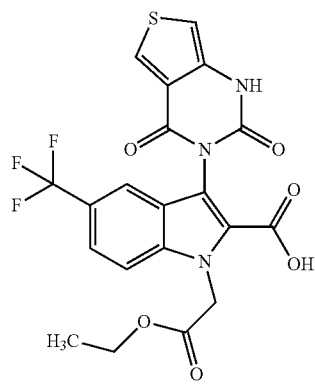 [SMILES: CCOC(=O)Cn1c(C(=O)O)c(-n2c(=O)[nH]c3cscc3c2=O)c2cc(C(F)(F)F)ccc21] | 481.4 |
| 23 | 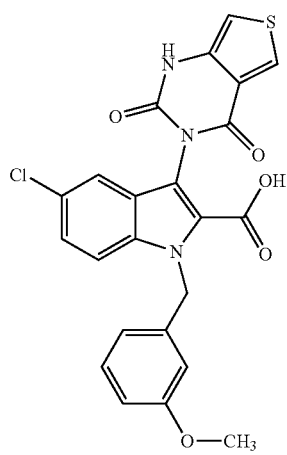 [SMILES: COc1cccc(Cn2c(C(=O)O)c(-n3c(=O)[nH]c4cscc4c3=O)c3cc(Cl)ccc32)c1] | 481.9 |
| 24 | 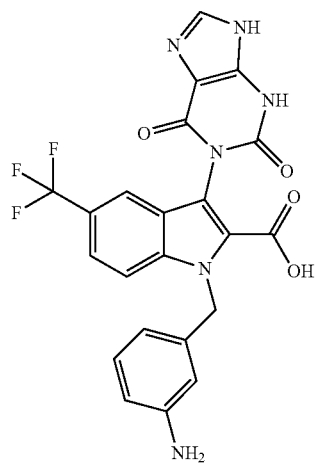 [SMILES: Nc1cccc(Cn2c(C(=O)O)c(-n3c(=O)[nH]c4[nH]cnc4c3=O)c3cc(C(F)(F)F)ccc32)c1] | 484.4 |

-continued
| Compound No. | Structure | LCMS (M + H) |
|---|---|---|
| 25 | 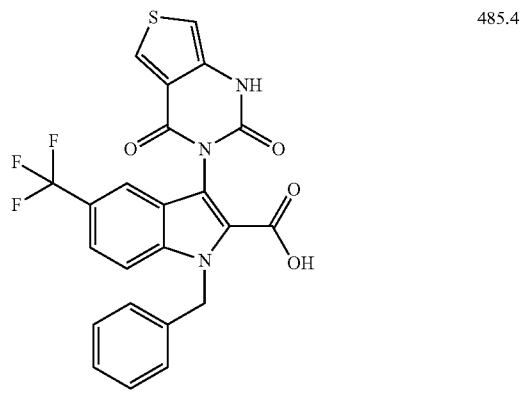 | 485.4 |
| 26 | 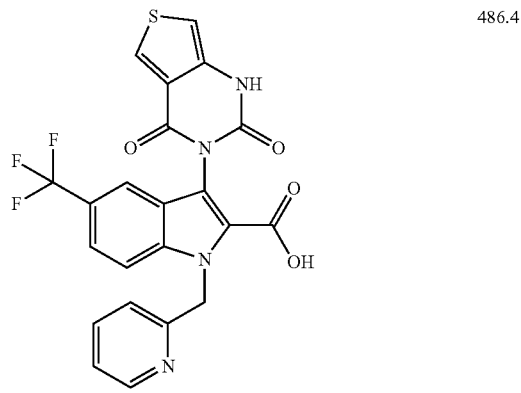 | 486.4 |
| 27 | 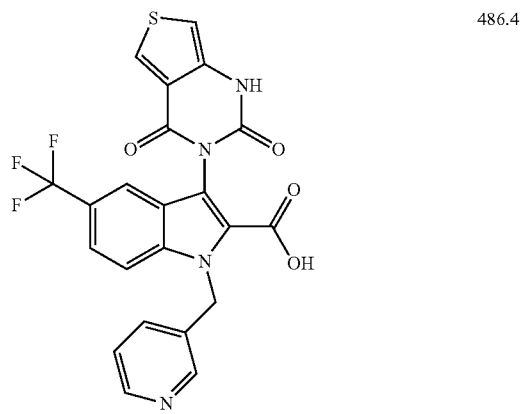 | 486.4 |

-continued
| Compound No. | Structure | LCMS (M + H) |
|---|---|---|
| 28 | 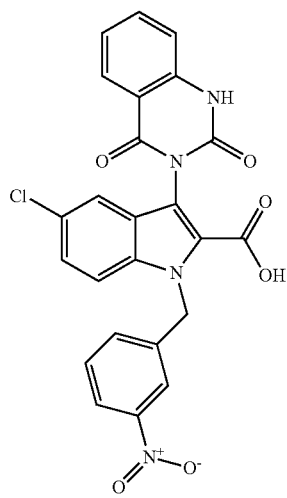 [SMILES: O=C(O)c1c(-n2c(=O)[nH]c3ccccc3c2=O)c2cc(Cl)ccc2n1Cc1cccc([N+](=O)[O-])c1] | 490.9 |
| 29 | 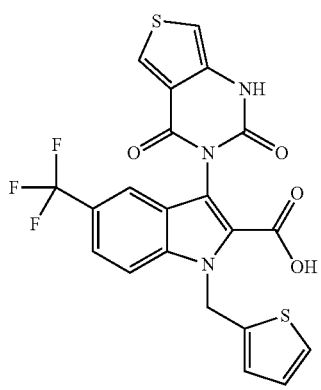 [SMILES: O=C(O)c1c(-n2c(=O)[nH]c3cscc3c2=O)c2cc(C(F)(F)F)ccc2n1Cc1cccs1] | 491.5 |
| 30 | 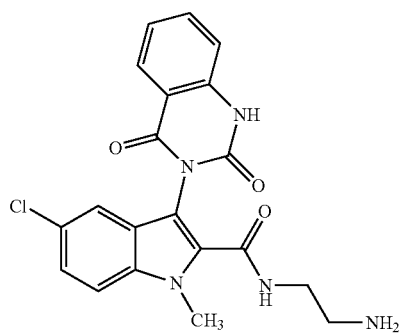 [SMILES: Cn1c(C(=O)NCCN)c(-n2c(=O)[nH]c3ccccc3c2=O)c2cc(Cl)ccc21] | 411.9 |

| Compound No. | Structure | LCMS (M + H) |
|---|---|---|
| 31 | 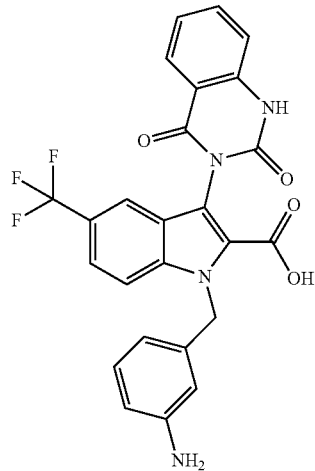 [SMILES: Nc1cccc(Cn2c(C(=O)O)c(-n3c(=O)[nH]c4ccccc4c3=O)c3cc(C(F)(F)F)ccc32)c1] | 494.4 |
| 32 | 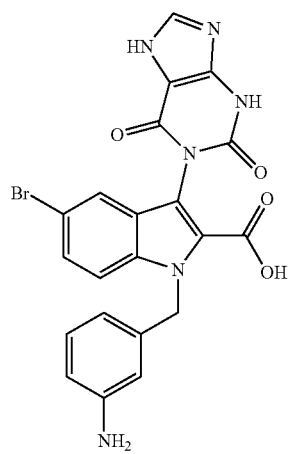 [SMILES: Nc1cccc(Cn2c(C(=O)O)c(-n3c(=O)[nH]c4nc[nH]c4c3=O)c3cc(Br)ccc32)c1] | 495.3 |
| 33 | 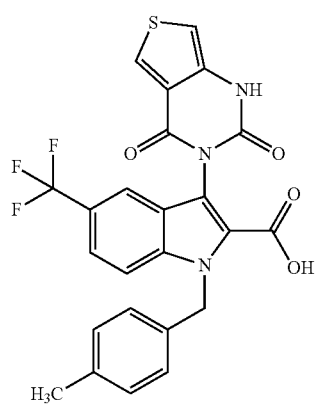 [SMILES: Cc1ccc(Cn2c(C(=O)O)c(-n3c(=O)[nH]c4cscc4c3=O)c3cc(C(F)(F)F)ccc32)cc1] | 499.5 |

-continued

| Compound No. | Structure | LCMS (M + H) |
|---|---|---|
| 34 | 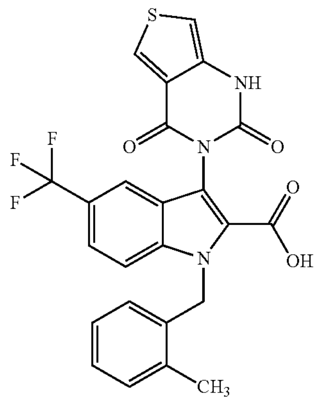 [SMILES: Cc1ccccc1Cn1c(C(=O)O)c(-n2c(=O)[nH]c3cscc3c2=O)c2cc(C(F)(F)F)ccc21] | 499.5 |
| 35 | 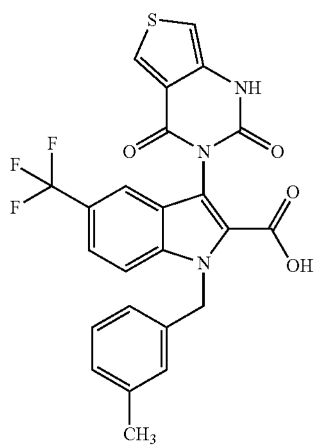 [SMILES: Cc1cccc(Cn2c(C(=O)O)c(-n3c(=O)[nH]c4cscc4c3=O)c3cc(C(F)(F)F)ccc32)c1] | 499.5 |
| 36 | 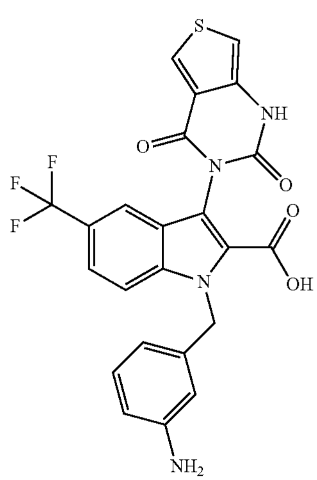 [SMILES: Nc1cccc(Cn2c(C(=O)O)c(-n3c(=O)[nH]c4cscc4c3=O)c3cc(C(F)(F)F)ccc32)c1] | 500.5 |

| Compound No. | Structure | LCMS (M + H) |
|---|---|---|
| 37 | 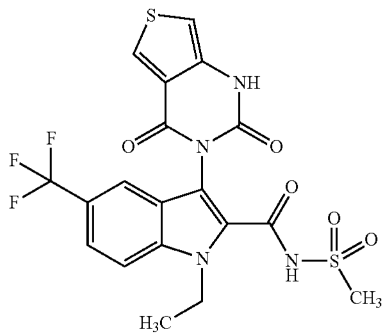 [SMILES: CCn1c(C(=O)NS(C)(=O)=O)c(-n2c(=O)[nH]c3cscc3c2=O)c2cc(C(F)(F)F)ccc21] | 500.5 |
| 38 | 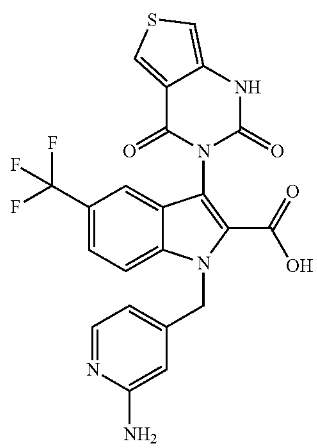 [SMILES: Nc1cc(Cn2c(C(=O)O)c(-n3c(=O)[nH]c4cscc4c3=O)c3cc(C(F)(F)F)ccc32)ccn1] | 501.4 |
| 39 | 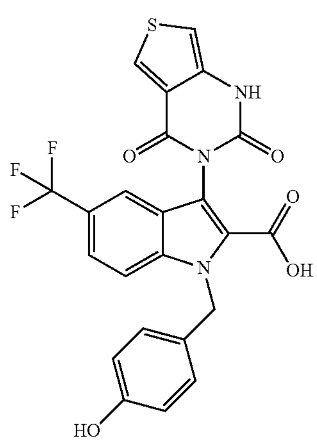 [SMILES: O=C(O)c1c(-n2c(=O)[nH]c3cscc3c2=O)c2cc(C(F)(F)F)ccc2n1Cc1ccc(O)cc1] | 501.4 |

-continued
| Compound No. | Structure | LCMS (M + H) |
|---|---|---|
| 40 | 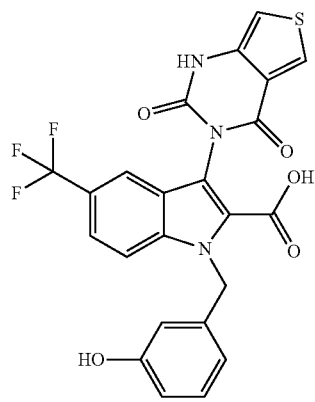 [SMILES: O=C(O)c1c(-n2c(=O)[nH]c3cscc3c2=O)c2cc(C(F)(F)F)ccc2n1Cc1cccc(O)c1] | 501.4 |
| 41 | 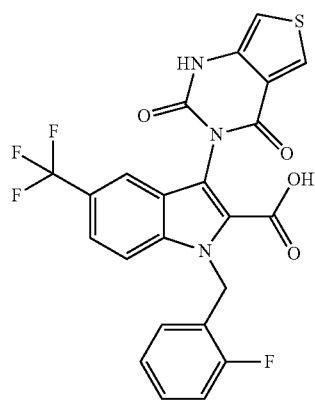 [SMILES: O=C(O)c1c(-n2c(=O)[nH]c3cscc3c2=O)c2cc(C(F)(F)F)ccc2n1Cc1ccccc1F] | 503.4 |
| 42 | 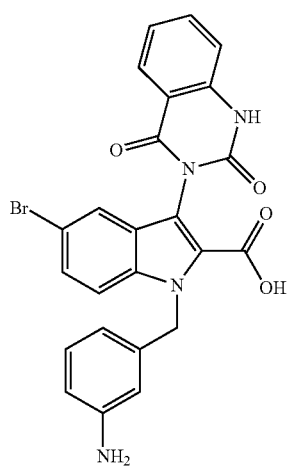 [SMILES: Nc1cccc(Cn2c(C(=O)O)c(-n3c(=O)[nH]c4ccccc4c3=O)c3cc(Br)ccc32)c1] | 505.3 |

-continued

| Compound No. | Structure | LCMS (M + H) |
|---|---|---|
| 43 | 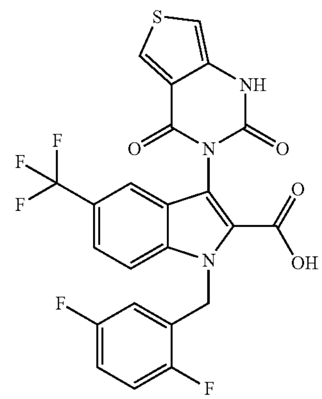 [SMILES: O=C(O)c1c(-n2c(=O)[nH]c3cscc3c2=O)c2cc(C(F)(F)F)ccc2n1Cc1cc(F)ccc1F] | 521.4 |
| 44 | 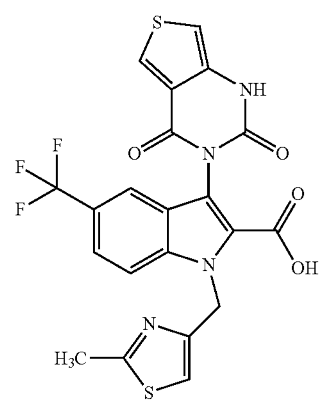 [SMILES: Cc1nc(Cn2c(C(=O)O)c(-n3c(=O)[nH]c4cscc4c3=O)c3cc(C(F)(F)F)ccc32)cs1] | 506.5 |
| 45 | 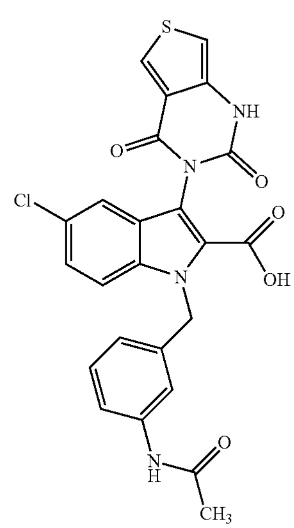 [SMILES: CC(=O)Nc1cccc(Cn2c(C(=O)O)c(-n3c(=O)[nH]c4cscc4c3=O)c3cc(Cl)ccc32)c1] | 508.9 |

-continued
| Compound No. | Structure | LCMS (M + H) |
|---|---|---|
| 46 | 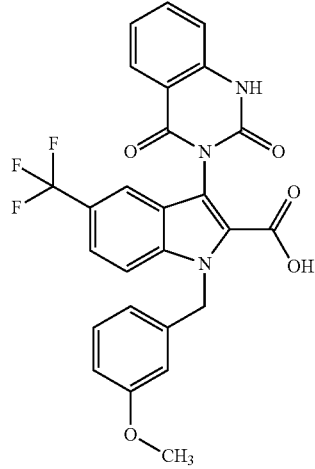 [SMILES: COc1cccc(Cn2c(C(=O)O)c(-n3c(=O)[nH]c4ccccc4c3=O)c3cc(C(F)(F)F)ccc32)c1] | 509.4 |
| 47 | 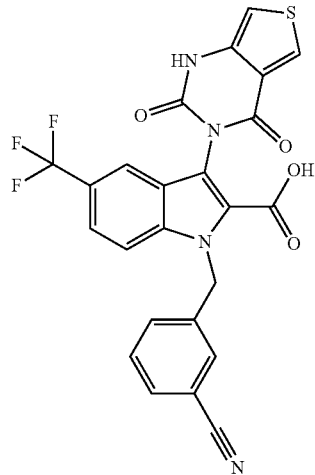 [SMILES: N#Cc1cccc(Cn2c(C(=O)O)c(-n3c(=O)[nH]c4cscc4c3=O)c3cc(C(F)(F)F)ccc32)c1] | 510.5 |
| 48 | 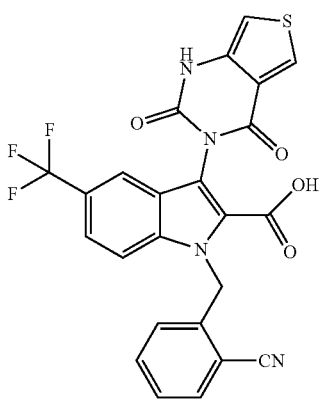 [SMILES: N#Cc1ccccc1Cn1c(C(=O)O)c(-n2c(=O)[nH]c3cscc3c2=O)c2cc(C(F)(F)F)ccc21] | 510.5 |

-continued

| Compound No. | Structure | LCMS (M + H) |
|---|---|---|
| 49 | 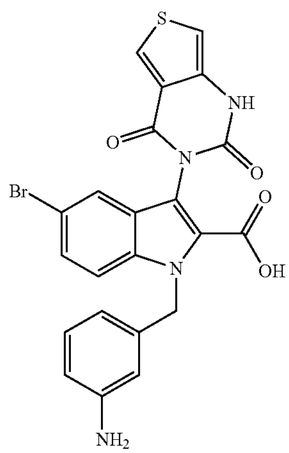 [SMILES: Nc1cccc(Cn2c(C(=O)O)c(-n3c(=O)[nH]c4cscc4c3=O)c3cc(Br)ccc32)c1] | 511.4 |
| 50 | 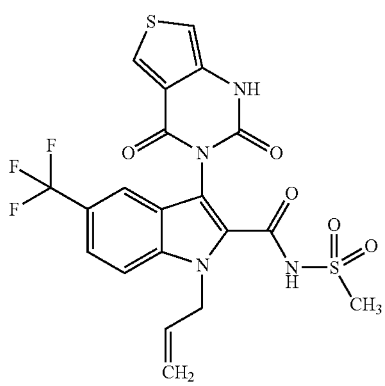 [SMILES: C=CCn1c(C(=O)NS(C)(=O)=O)c(-n2c(=O)[nH]c3cscc3c2=O)c2cc(C(F)(F)F)ccc21] | 512.5 |
| 51 | 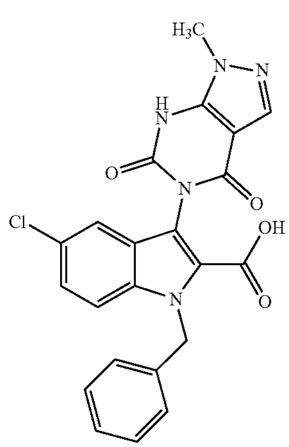 [SMILES: Cn1ncc2c(=O)n(-c3c(C(=O)O)n(Cc4ccccc4)c4ccc(Cl)cc34)c(=O)[nH]c21] | 449.9 |

| Compound No. | Structure | LCMS (M + H) |
|---|---|---|
| 52 | 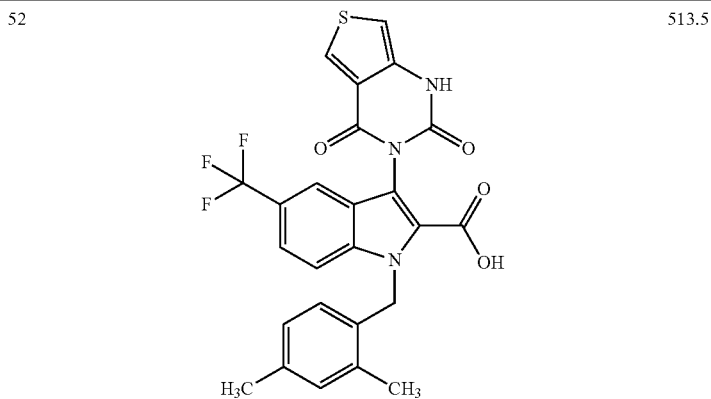 | 513.5 |
| 53 | 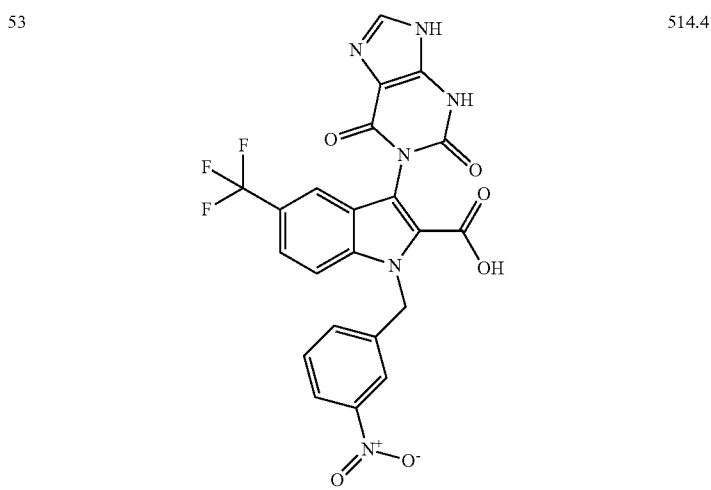 | 514.4 |
| 54 | 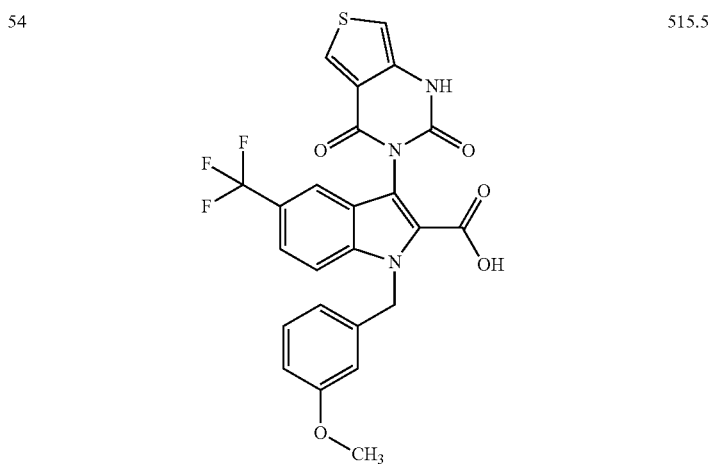 | 515.5 |

-continued
| Compound No. | Structure | LCMS (M + H) |
|---|---|---|
| 55 | 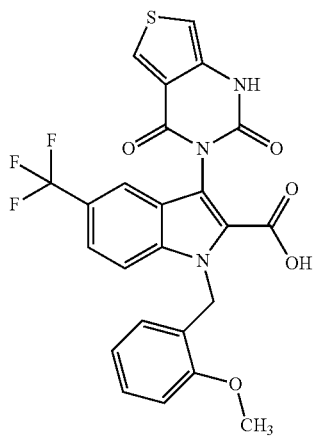 [SMILES: COc1ccccc1Cn1c(C(=O)O)c(-n2c(=O)[nH]c3cscc3c2=O)c2cc(C(F)(F)F)ccc21] | 515.5 |
| 56 | 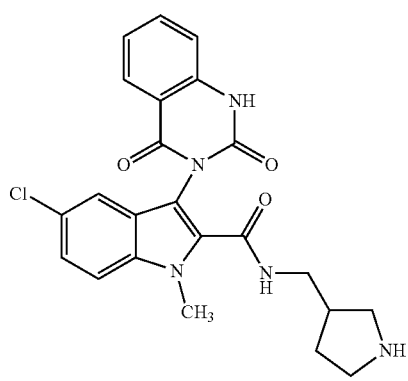 [SMILES: Cn1c(C(=O)NCC2CCNC2)c(-n2c(=O)[nH]c3ccccc3c2=O)c2cc(Cl)ccc21] | 451.9 |
| 57 | 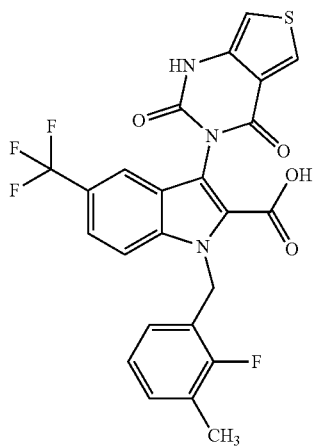 [SMILES: Cc1cccc(Cn2c(C(=O)O)c(-n3c(=O)[nH]c4cscc4c3=O)c3cc(C(F)(F)F)ccc32)c1F] | 517.5 |

-continued

| Compound No. | Structure | LCMS (M + H) |
|---|---|---|
| 58 | 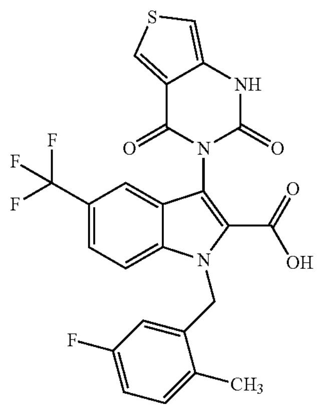 [SMILES: Cc1ccc(F)cc1Cn1c(C(=O)O)c(-n2c(=O)[nH]c3cscc3c2=O)c2cc(C(F)(F)F)ccc21] | 517.5 |
| 59 | 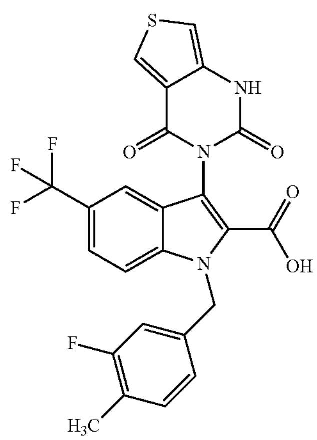 [SMILES: Cc1ccc(Cn2c(C(=O)O)c(-n3c(=O)[nH]c4cscc4c3=O)c3cc(C(F)(F)F)ccc32)cc1F] | 517.5 |
| 60 | 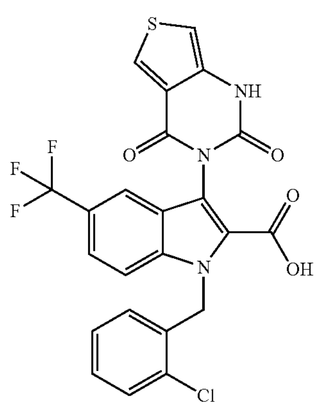 [SMILES: O=C(O)c1c(-n2c(=O)[nH]c3cscc3c2=O)c2cc(C(F)(F)F)ccc2n1Cc1ccccc1Cl] | 519.9 |

-continued

| Compound No. | Structure | LCMS (M + H) |
|---|---|---|
| 61 | 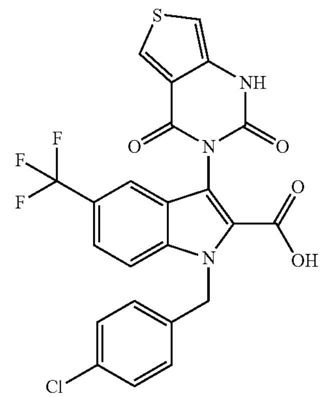 [SMILES: O=C(O)c1c(-n2c(=O)[nH]c3cscc3c2=O)c2cc(C(F)(F)F)ccc2n1Cc1ccc(Cl)cc1] | 519.9 |
| 62 | 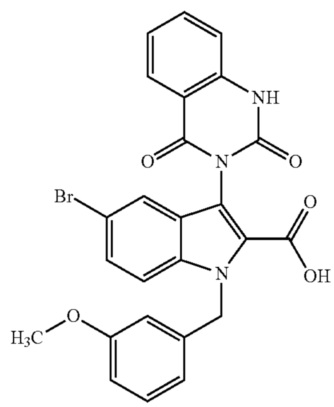 [SMILES: COc1cccc(Cn2c(C(=O)O)c(-n3c(=O)[nH]c4ccccc4c3=O)c3cc(Br)ccc32)c1] | 520.3 |
| 63 | 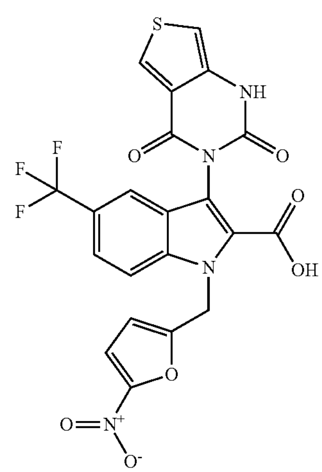 [SMILES: O=C(O)c1c(-n2c(=O)[nH]c3cscc3c2=O)c2cc(C(F)(F)F)ccc2n1Cc1ccc([N+](=O)[O-])o1] | 520.4 |
| 64 | 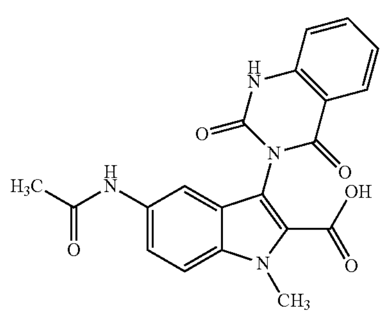 [SMILES: CC(=O)Nc1ccc2c(c1)c(-n1c(=O)[nH]c3ccccc3c1=O)c(C(=O)O)n2C] | 392.4 |

| Compound No. | Structure | LCMS (M + H) |
|---|---|---|
| 65 | 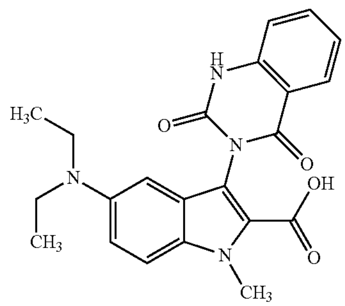 [SMILES: CCN(CC)c1ccc2c(c1)c(-n1c(=O)[nH]c3ccccc3c1=O)c(C(=O)O)n2C] | 406.4 |
| 66 | 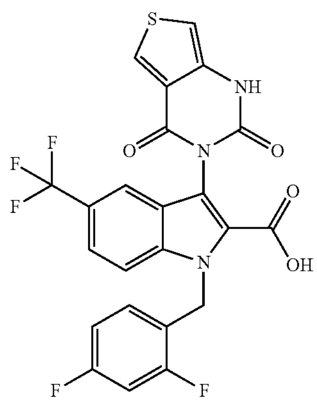 [SMILES: O=C(O)c1c(-n2c(=O)[nH]c3cscc3c2=O)c2cc(C(F)(F)F)ccc2n1Cc1ccc(F)cc1F] | 521.4 |
| 67 | 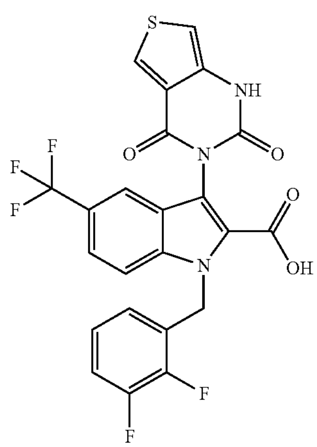 [SMILES: O=C(O)c1c(-n2c(=O)[nH]c3cscc3c2=O)c2cc(C(F)(F)F)ccc2n1Cc1cccc(F)c1F] | 521.4 |
| 68 | 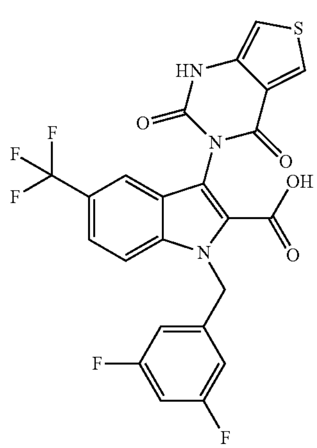 [SMILES: O=C(O)c1c(-n2c(=O)[nH]c3cscc3c2=O)c2cc(C(F)(F)F)ccc2n1Cc1cc(F)cc(F)c1] | 521.4 |

| Compound No. | Structure | LCMS (M + H) |
|---|---|---|
| 69 | 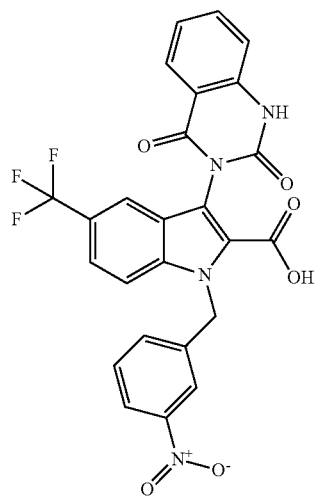 [SMILES: O=C(O)c1c(-n2c(=O)[nH]c3ccccc3c2=O)c2cc(C(F)(F)F)ccc2n1Cc1cccc([N+](=O)[O-])c1] | 524.4 |
| 70 | 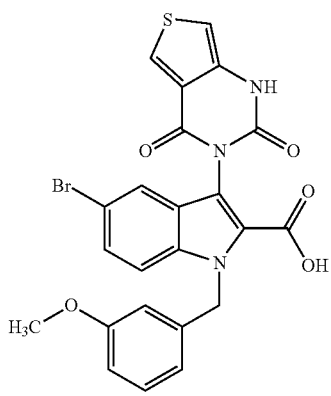 [SMILES: COc1cccc(Cn2c(C(=O)O)c(-n3c(=O)[nH]c4cscc4c3=O)c3cc(Br)ccc32)c1] | 526.4 |
| 71 | 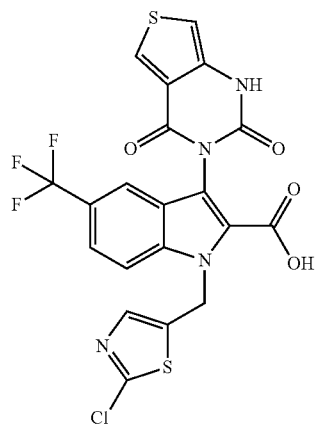 [SMILES: O=C(O)c1c(-n2c(=O)[nH]c3cscc3c2=O)c2cc(C(F)(F)F)ccc2n1Cc1cnc(Cl)s1] | 526.9 |

-continued
| Compound No. | Structure | LCMS (M + H) |
|---|---|---|
| 72 | 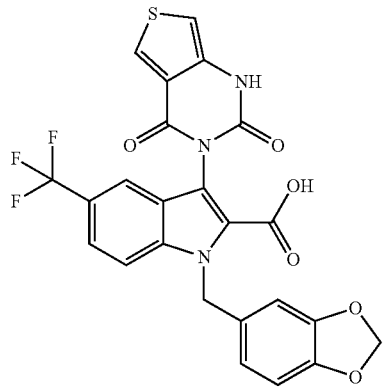 [SMILES: O=C(O)c1c(-n2c(=O)[nH]c3cscc3c2=O)c2cc(C(F)(F)F)ccc2n1Cc1ccc2c(c1)OCO2] | 529.5 |
| 73 | 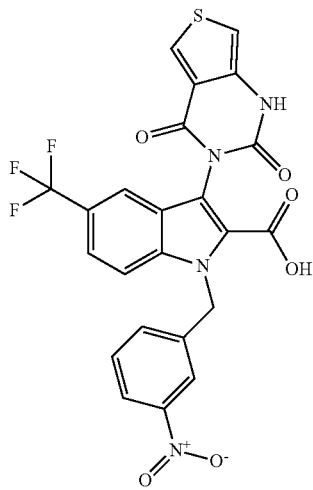 [SMILES: O=C(O)c1c(-n2c(=O)[nH]c3cscc3c2=O)c2cc(C(F)(F)F)ccc2n1Cc1cccc([N+](=O)[O-])c1] | 530.4 |
| 74 | 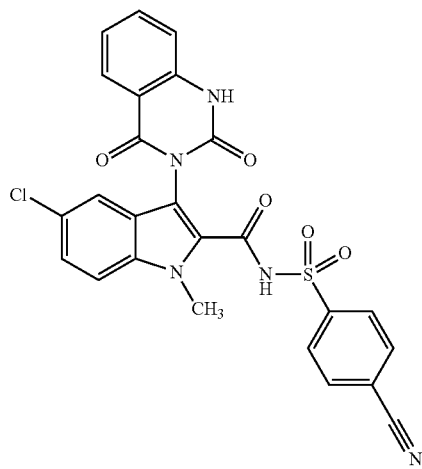 [SMILES: Cn1c(C(=O)NS(=O)(=O)c2ccc(C#N)cc2)c(-n2c(=O)[nH]c3ccccc3c2=O)c2cc(Cl)ccc21] | 533.9 |

-continued

| Compound No. | Structure | LCMS (M + H) |
|---|---|---|
| 75 | 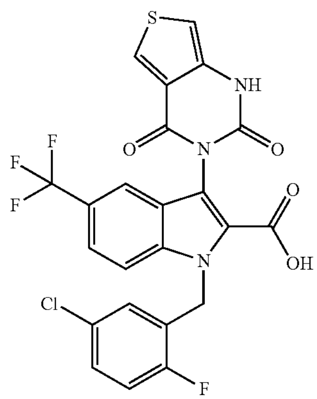 [SMILES: O=C(O)c1c(-n2c(=O)[nH]c3cscc3c2=O)c2cc(C(F)(F)F)ccc2n1Cc1cc(Cl)ccc1F] | 537.9 |
| 76 | 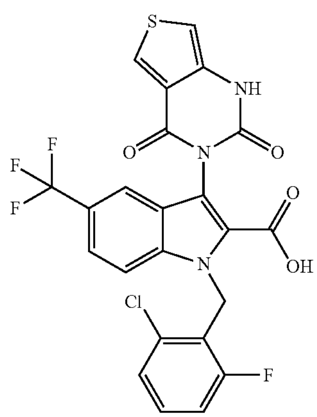 [SMILES: O=C(O)c1c(-n2c(=O)[nH]c3cscc3c2=O)c2cc(C(F)(F)F)ccc2n1Cc1c(F)cccc1Cl] | 537.9 |
| 77 | 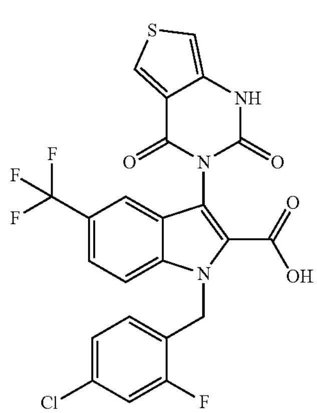 [SMILES: O=C(O)c1c(-n2c(=O)[nH]c3cscc3c2=O)c2cc(C(F)(F)F)ccc2n1Cc1ccc(Cl)cc1F] | 537.9 |

-continued
| Compound No. | Structure | LCMS (M + H) |
|---|---|---|
| 78 | 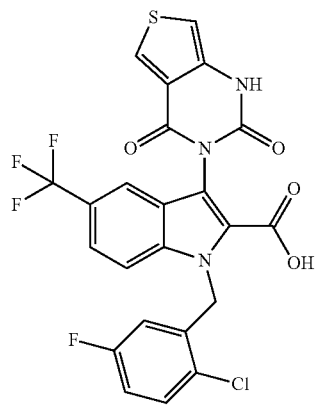 [SMILES: O=C(O)c1c(-n2c(=O)[nH]c3cscc3c2=O)c2cc(C(F)(F)F)ccc2n1Cc1cc(F)ccc1Cl] | 537.9 |
| 79 | 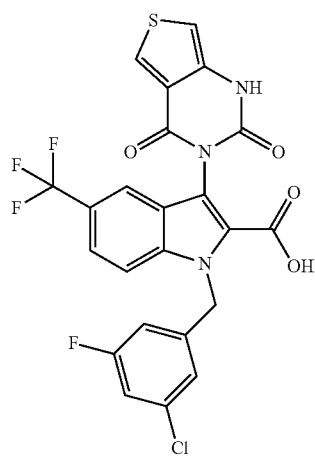 [SMILES: O=C(O)c1c(-n2c(=O)[nH]c3cscc3c2=O)c2cc(C(F)(F)F)ccc2n1Cc1cc(F)cc(Cl)c1] | 537.9 |
| 80 | 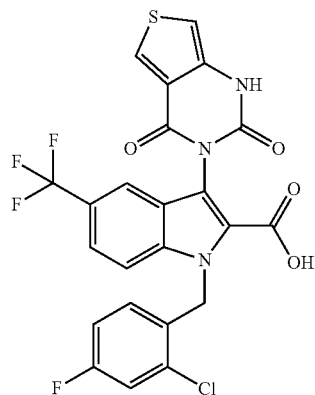 | 537.9 |

| Compound No. | Structure | LCMS (M + H) |
|---|---|---|
| 81 | 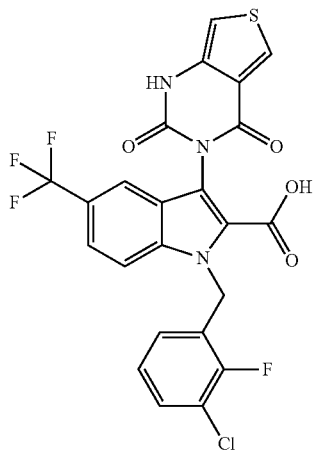 [SMILES: O=C(O)c1c(-n2c(=O)[nH]c3cscc3c2=O)c2cc(C(F)(F)F)ccc2n1Cc1cccc(Cl)c1F] | 537.9 |
| 82 | 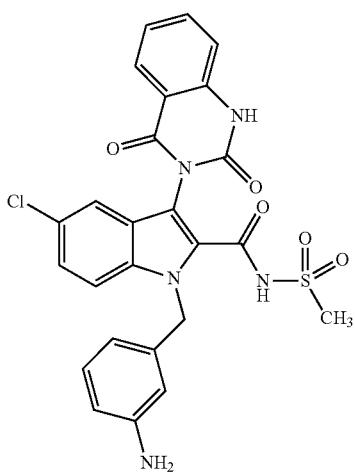 [SMILES: CS(=O)(=O)NC(=O)c1c(-n2c(=O)[nH]c3ccccc3c2=O)c2cc(Cl)ccc2n1Cc1cccc(N)c1] | 537.9 |
| 83 | 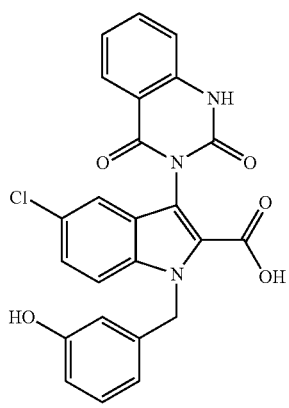 [SMILES: O=C(O)c1c(-n2c(=O)[nH]c3ccccc3c2=O)c2cc(Cl)ccc2n1Cc1cccc(O)c1] | 461.9 |

-continued

| Compound No. | Structure | LCMS (M + H) |
|---|---|---|
| 84 | 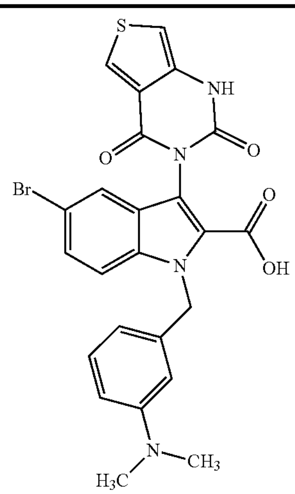 | 539.4 |
| 85 | 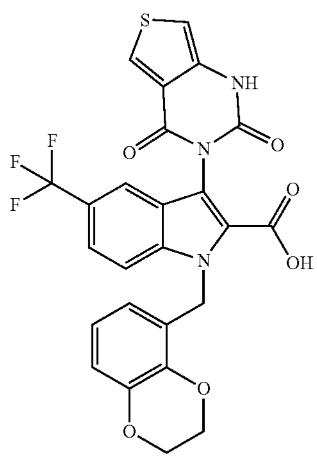 [SMILES: O=C(O)c1c(-n2c(=O)[nH]c3cscc3c2=O)c2cc(C(F)(F)F)ccc2n1Cc1cccc2c1OCCO2] | 543.5 |
| 86 | 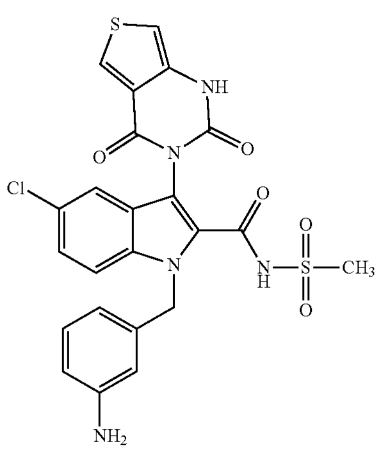 [SMILES: CS(=O)(=O)NC(=O)c1c(-n2c(=O)[nH]c3cscc3c2=O)c2cc(Cl)ccc2n1Cc1cccc(N)c1] | 544.0 |

| Compound No. | Structure | LCMS (M + H) |
|---|---|---|
| 87 | 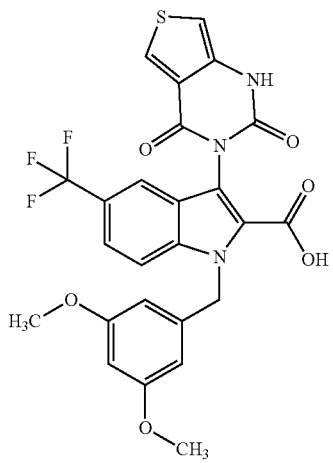 [SMILES: COc1cc(Cn2c(C(=O)O)c(-n3c(=O)[nH]c4cscc4c3=O)c3cc(C(F)(F)F)ccc32)cc(OC)c1] | 545.5 |
| 88 | 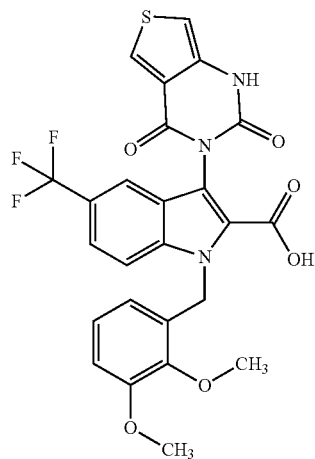 [SMILES: COc1cccc(Cn2c(C(=O)O)c(-n3c(=O)[nH]c4cscc4c3=O)c3cc(C(F)(F)F)ccc32)c1OC] | 545.5 |
| 89 | 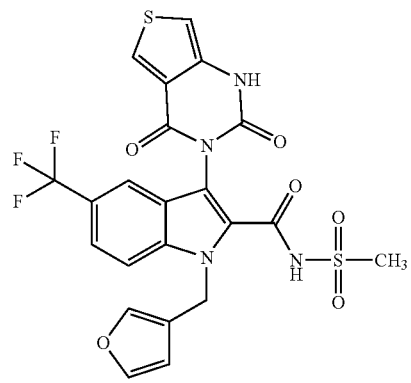 [SMILES: CS(=O)(=O)NC(=O)c1c(-n2c(=O)[nH]c3cscc3c2=O)c2cc(C(F)(F)F)ccc2n1Cc1ccoc1] | 552.5 |

-continued
| Compound No. | Structure | LCMS (M + H) |
|---|---|---|
| 90 | 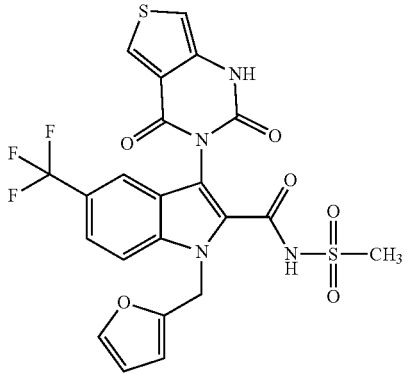 [SMILES: CS(=O)(=O)NC(=O)c1c(-n2c(=O)[nH]c3cscc3c2=O)c2cc(C(F)(F)F)ccc2n1Cc1ccco1] | 552.5 |
| 91 | 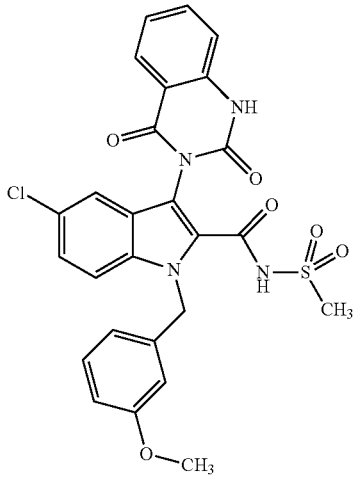 [SMILES: COc1cccc(Cn2c(C(=O)NS(C)(=O)=O)c(-n3c(=O)[nH]c4ccccc4c3=O)c3cc(Cl)ccc32)c1] | 552.9 |
| 92 | 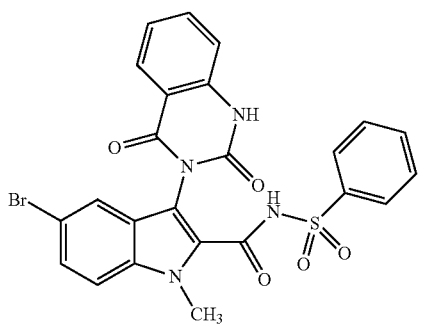 [SMILES: Cn1c(C(=O)NS(=O)(=O)c2ccccc2)c(-n2c(=O)[nH]c3ccccc3c2=O)c2cc(Br)ccc21] | 553.4 |

| Compound No. | Structure | LCMS (M + H) |
|---|---|---|
| 93 | 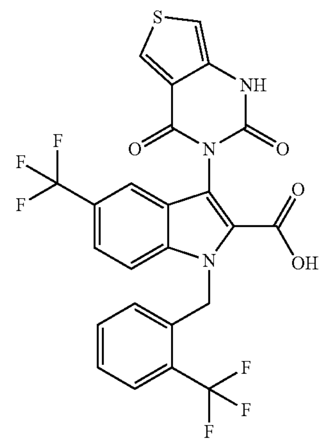 [SMILES: O=C(O)c1c(-n2c(=O)[nH]c3cscc3c2=O)c2cc(C(F)(F)F)ccc2n1Cc1ccccc1C(F)(F)F] | 553.4 |
| 94 | 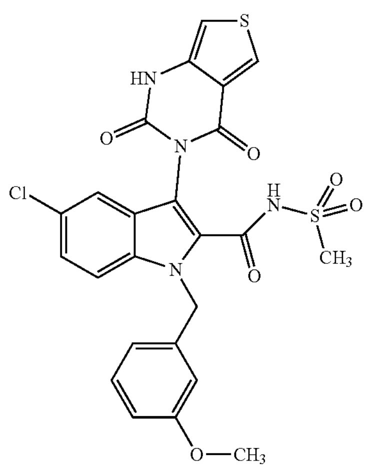 [SMILES: COc1cccc(Cn2c(C(=O)NS(C)(=O)=O)c(-n3c(=O)[nH]c4cscc4c3=O)c3cc(Cl)ccc32)c1] | 559.0 |
| 95 | 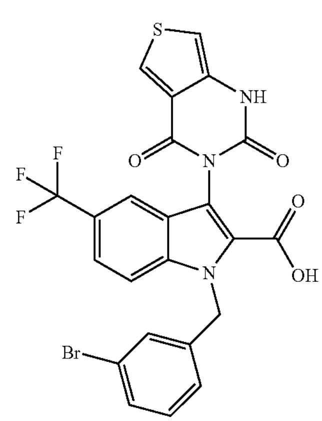 [SMILES: O=C(O)c1c(-n2c(=O)[nH]c3cscc3c2=O)c2cc(C(F)(F)F)ccc2n1Cc1cccc(Br)c1] | 564.341 |

-continued

| Compound No. | Structure | LCMS (M + H) |
|---|---|---|
| 96 | 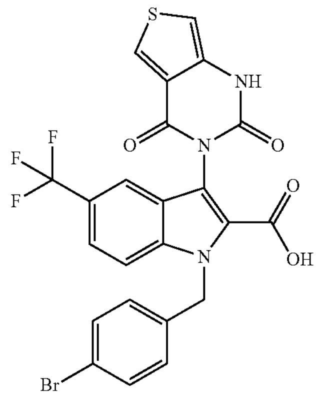 | 564.3 |
| 97 | 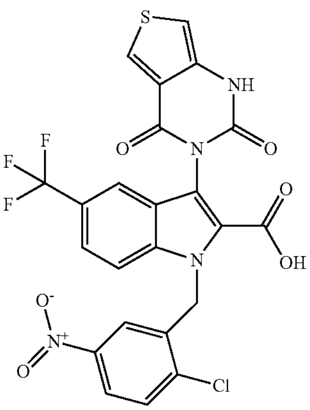 [SMILES: O=C(O)c1c(-n2c(=O)[nH]c3cscc3c2=O)c2cc(C(F)(F)F)ccc2n1Cc1cc([N+](=O)[O-])ccc1Cl] | 564.9 |
| 98 | 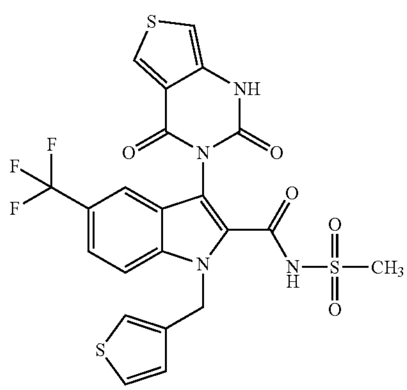 [SMILES: CS(=O)(=O)NC(=O)c1c(-n2c(=O)[nH]c3cscc3c2=O)c2cc(C(F)(F)F)ccc2n1Cc1ccsc1] | 568.6 |
| 99 | 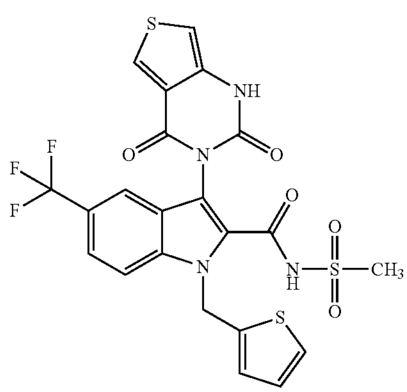 [SMILES: CS(=O)(=O)NC(=O)c1c(-n2c(=O)[nH]c3cscc3c2=O)c2cc(C(F)(F)F)ccc2n1Cc1cccs1] | 568.6 |

-continued
| Compound No. | Structure | LCMS (M + H) |
|---|---|---|
| 100 | 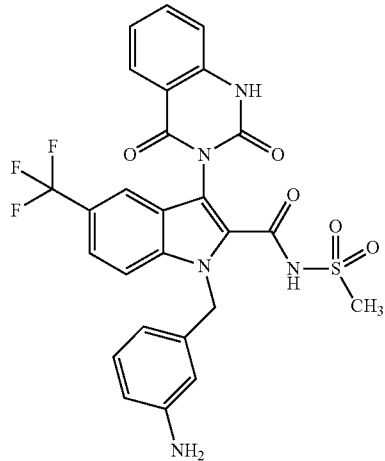 [SMILES: CS(=O)(=O)NC(=O)c1c(-n2c(=O)[nH]c3ccccc3c2=O)c2cc(C(F)(F)F)ccc2n1Cc1cccc(N)c1] | 571.5 |
| 101 | 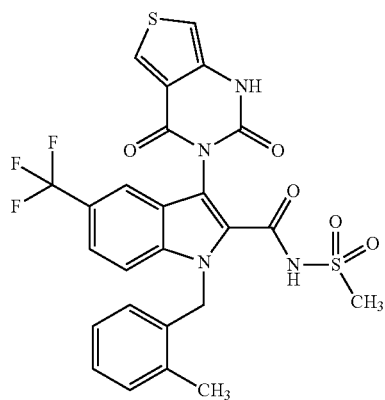 [SMILES: Cc1ccccc1Cn1c(C(=O)NS(C)(=O)=O)c(-n2c(=O)[nH]c3cscc3c2=O)c2cc(C(F)(F)F)ccc21] | 576.6 |
| 102 | 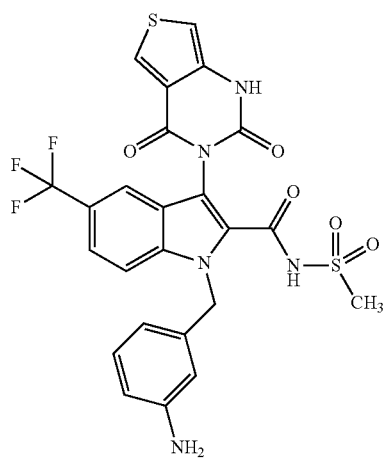 [SMILES: CS(=O)(=O)NC(=O)c1c(-n2c(=O)[nH]c3cscc3c2=O)c2cc(C(F)(F)F)ccc2n1Cc1cccc(N)c1] | 577.6 |

-continued
| Compound No. | Structure | LCMS (M + H) |
|---|---|---|
| 103 | 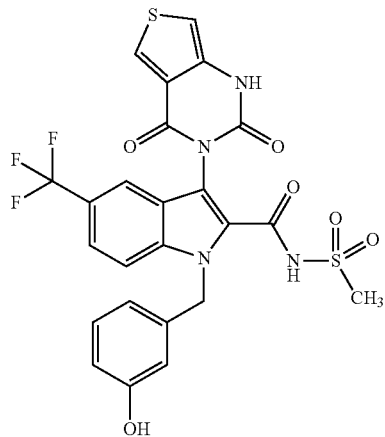 [SMILES: CS(=O)(=O)NC(=O)c1c(-n2c(=O)[nH]c3cscc3c2=O)c2cc(C(F)(F)F)ccc2n1Cc1cccc(O)c1] | 578.5 |
| 104 | 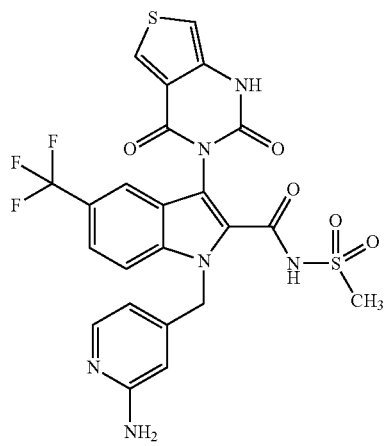 [SMILES: CS(=O)(=O)NC(=O)c1c(-n2c(=O)[nH]c3cscc3c2=O)c2cc(C(F)(F)F)ccc2n1Cc1ccnc(N)c1] | 578.6 |
| 105 | 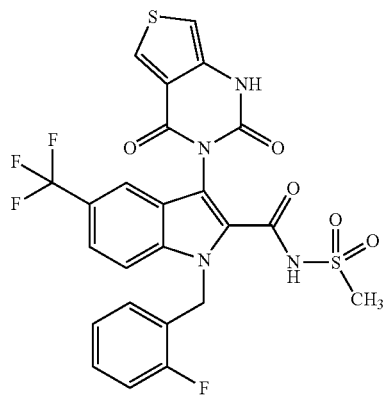 | 580.5 |

-continued
| Compound No. | Structure | LCMS (M + H) |
|---|---|---|
| 106 | 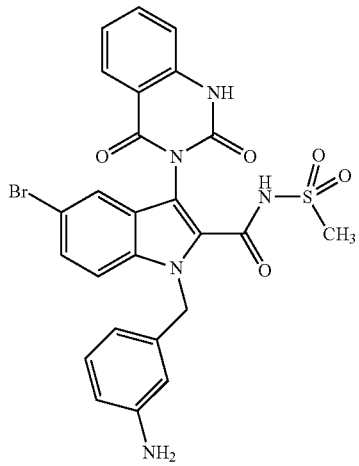 [SMILES: CS(=O)(=O)NC(=O)c1c(-n2c(=O)[nH]c3ccccc3c2=O)c2cc(Br)ccc2n1Cc1cccc(N)c1] | 582.4 |
| 107 | 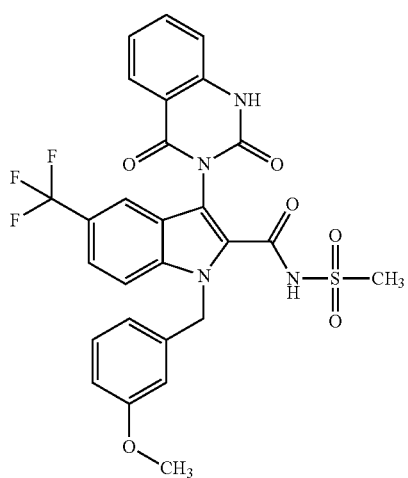 [SMILES: COc1cccc(Cn2c(C(=O)NS(C)(=O)=O)c(-n3c(=O)[nH]c4ccccc4c3=O)c3cc(C(F)(F)F)ccc32)c1] | 586.6 |
| 108 | 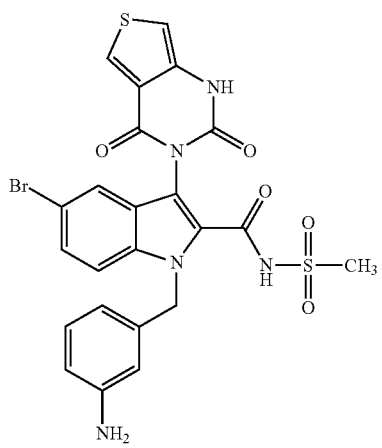 | 588.5 |

-continued

| Compound No. | Structure | LCMS (M + H) |
|---|---|---|
| 109 | 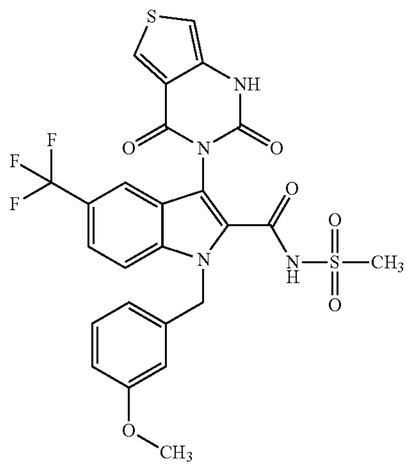 [SMILES: COc1cccc(Cn2c(C(=O)NS(C)(=O)=O)c(-n3c(=O)[nH]c4cscc4c3=O)c3cc(C(F)(F)F)ccc32)c1] | 592.6 |
| 110 | 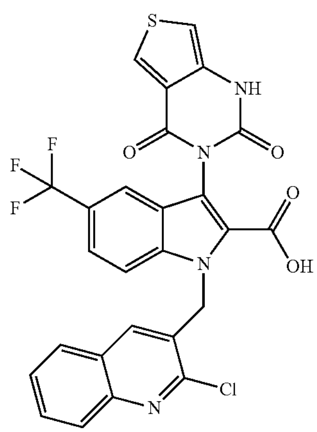 [SMILES: O=C(O)c1c(-n2c(=O)[nH]c3cscc3c2=O)c2cc(C(F)(F)F)ccc2n1Cc1cc2ccccc2nc1Cl] | 570.9 |
| 111 | 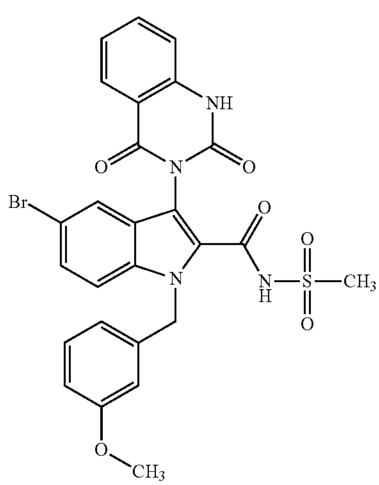 [SMILES: COc1cccc(Cn2c(C(=O)NS(C)(=O)=O)c(-n3c(=O)[nH]c4ccccc4c3=O)c3cc(Br)ccc32)c1] | 597.4 |

-continued

| Compound No. | Structure | LCMS (M + H) |
|---|---|---|
| 112 | 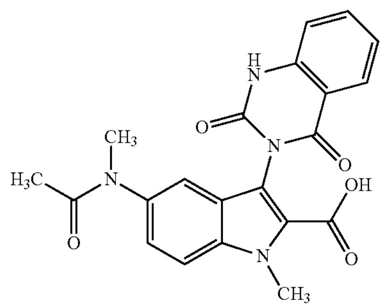 [SMILES: CC(=O)N(C)c1ccc2c(c1)c(-n1c(=O)[nH]c3ccccc3c1=O)c(C(=O)O)n2C] | 406.4 |
| 113 | 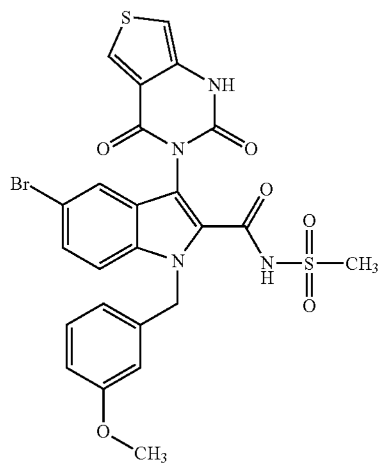 [SMILES: COc1cccc(Cn2c(C(=O)NS(C)(=O)=O)c(-n3c(=O)[nH]c4cscc4c3=O)c3cc(Br)ccc32)c1] | 603.5 |
| 114 | 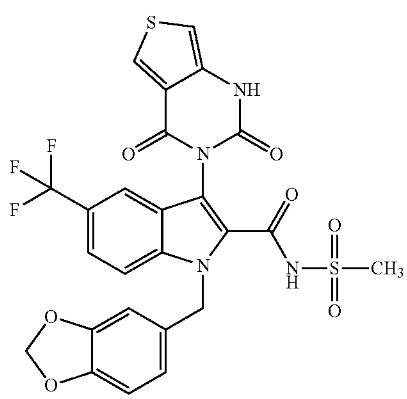 [SMILES: CS(=O)(=O)NC(=O)c1c(-n2c(=O)[nH]c3cscc3c2=O)c2cc(C(F)(F)F)ccc2n1Cc1ccc2c(c1)OCO2] | 606.6 |
| 115 | 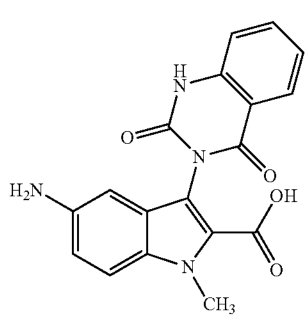 [SMILES: Cn1c(C(=O)O)c(-n2c(=O)[nH]c3ccccc3c2=O)c2cc(N)ccc21] | 350.3 |

-continued
| Compound No. | Structure | LCMS (M + H) |
|---|---|---|
| 116 | 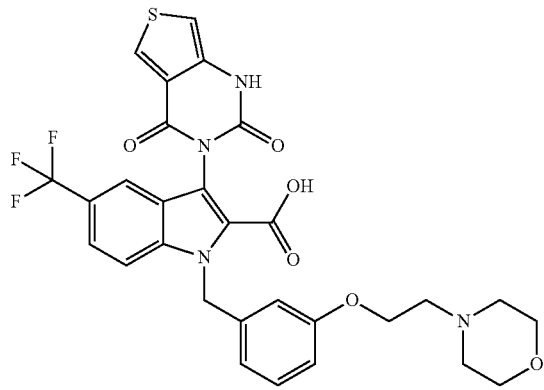 [SMILES: O=C(O)c1c(-n2c(=O)[nH]c3cscc3c2=O)c2cc(C(F)(F)F)ccc2n1Cc1cccc(OCCN2CCOCC2)c1] | 614.6 |
| 117 | 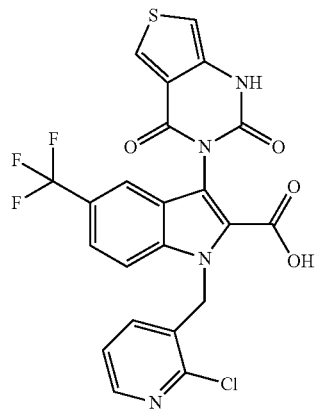 [SMILES: O=C(O)c1c(-n2c(=O)[nH]c3cscc3c2=O)c2cc(C(F)(F)F)ccc2n1Cc1cccnc1Cl] | 520.9 |
| 118 | 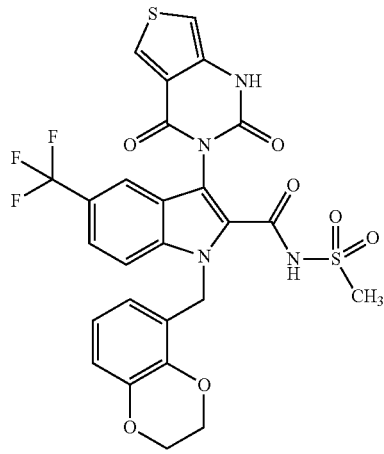 [SMILES: CS(=O)(=O)NC(=O)c1c(-n2c(=O)[nH]c3cscc3c2=O)c2cc(C(F)(F)F)ccc2n1Cc1cccc2c1OCCO2] | 620.6 |

-continued
| Compound No. | Structure | LCMS (M + H) |
|---|---|---|
| 119 | 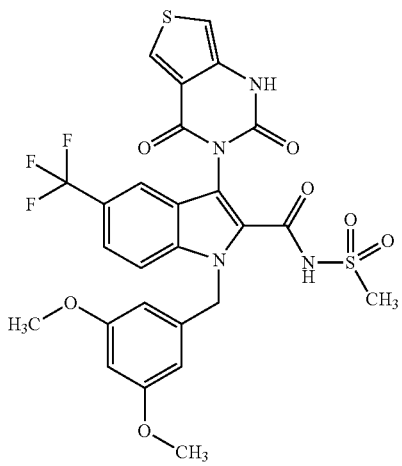 | 622.6 |
| 120 | 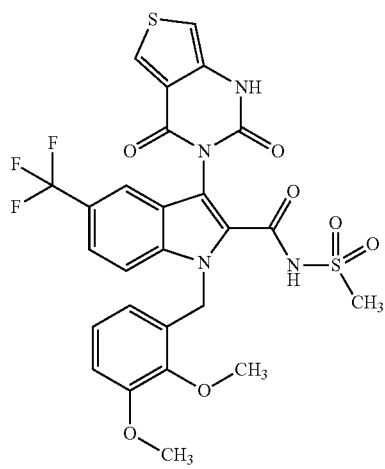 [SMILES: COc1cccc(Cn2c(C(=O)NS(C)(=O)=O)c(-n3c(=O)[nH]c4cscc4c3=O)c3cc(C(F)(F)F)ccc32)c1OC] | 622.6 |
| 121 | 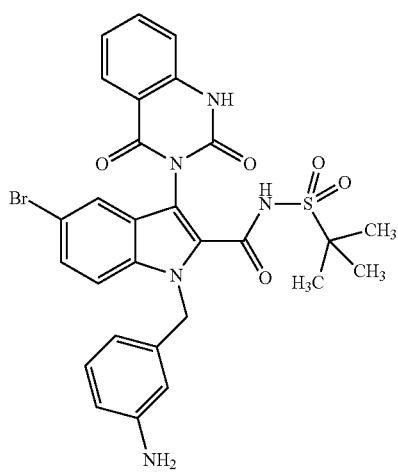 [SMILES: CC(C)(C)S(=O)(=O)NC(=O)c1c(-n2c(=O)[nH]c3ccccc3c2=O)c2cc(Br)ccc2n1Cc1cccc(N)c1] | 624.5 |

-continued
| Compound No. | Structure | LCMS (M + H) |
|---|---|---|
| 122 | 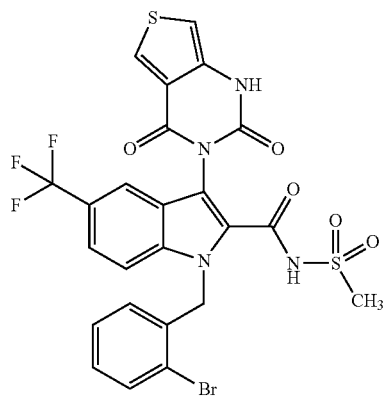 | 641.4 |
| 123 | 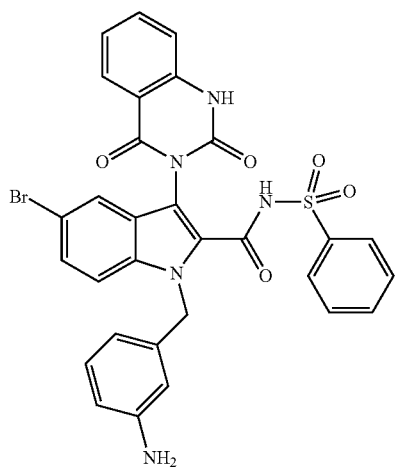 [SMILES: Nc1cccc(Cn2c(C(=O)NS(=O)(=O)c3ccccc3)c(-n3c(=O)[nH]c4ccccc4c3=O)c3cc(Br)ccc32)c1] | 644.5 |
| 124 | 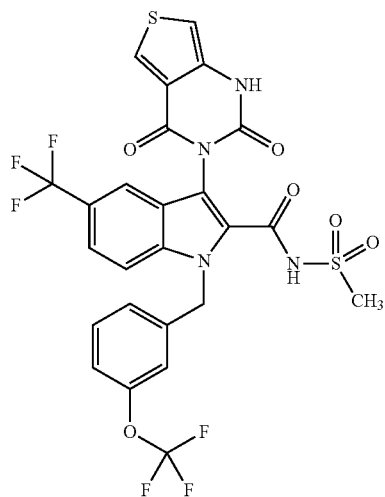 [SMILES: CS(=O)(=O)NC(=O)c1c(-n2c(=O)[nH]c3cscc3c2=O)c2cc(C(F)(F)F)ccc2n1Cc1cccc(OC(F)(F)F)c1] | 646.5 |

-continued
| Compound No. | Structure | LCMS (M + H) |
|---|---|---|
| 125 | 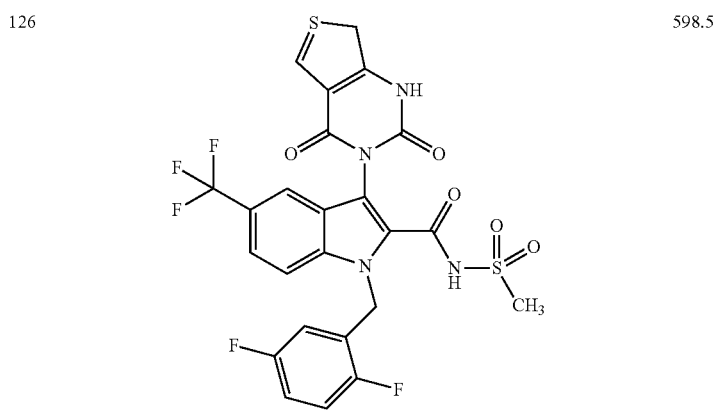 | 691.7 |
| 126 | 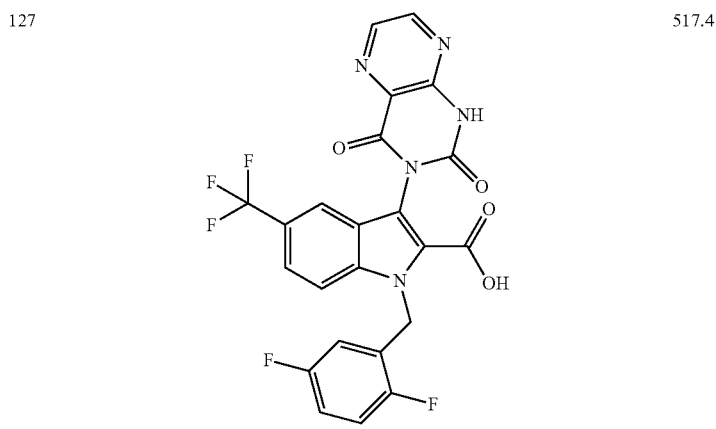 | 598.5 |
| 127 | 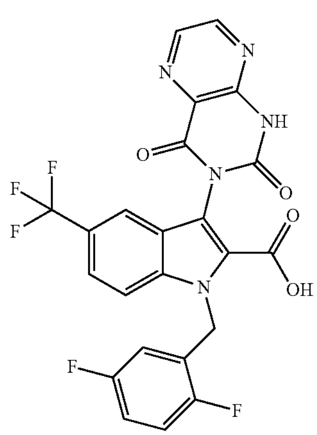 [SMILES: O=C(O)c1c(-n2c(=O)[nH]c3nccnc3c2=O)c2cc(C(F)(F)F)ccc2n1Cc1cc(F)ccc1F] | 517.4 |

-continued
| Compound No. | Structure | LCMS (M + H) |
|---|---|---|
| 128 | 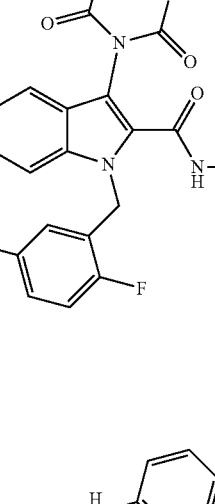 | 594.5 |
| 129 | 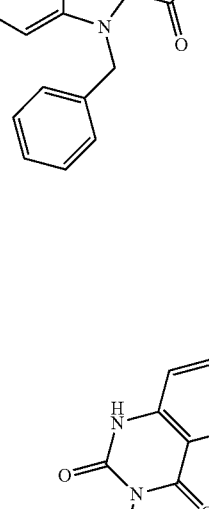 | 480.3 |
| 130 | 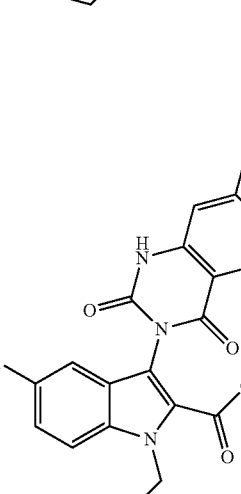 | 480.3 |

-continued
| Compound No. | Structure | LCMS (M + H) |
|---|---|---|
| 131 | 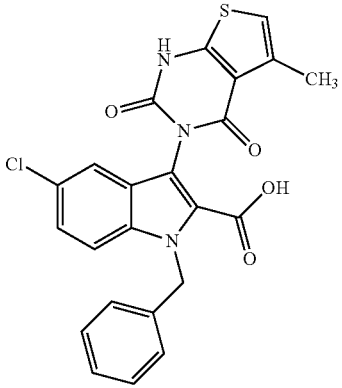 [SMILES: Cc1csc2[nH]c(=O)n(-c3c(C(=O)O)n(Cc4ccccc4)c4ccc(Cl)cc34)c(=O)c12] | 465.9 |
| 132 | 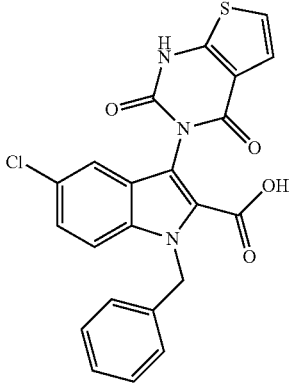 [SMILES: O=C(O)c1c(-n2c(=O)[nH]c3sccc3c2=O)c2cc(Cl)ccc2n1Cc1ccccc1] | 451.9 |
| 133 | 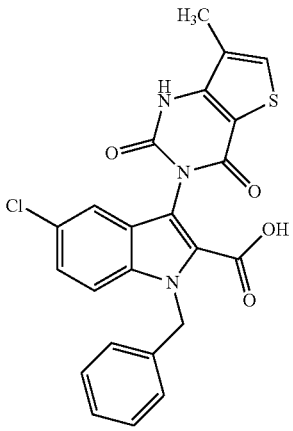 [SMILES: Cc1csc2c(=O)n(-c3c(C(=O)O)n(Cc4ccccc4)c4ccc(Cl)cc34)c(=O)[nH]c12] | 465.9 |

-continued
| Compound No. | Structure | LCMS (M + H) |
|---|---|---|
| 134 | 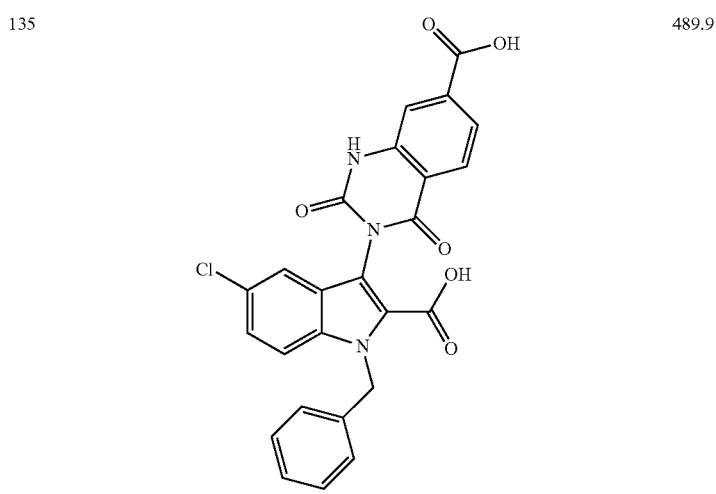 | 524.8 |
| 135 | 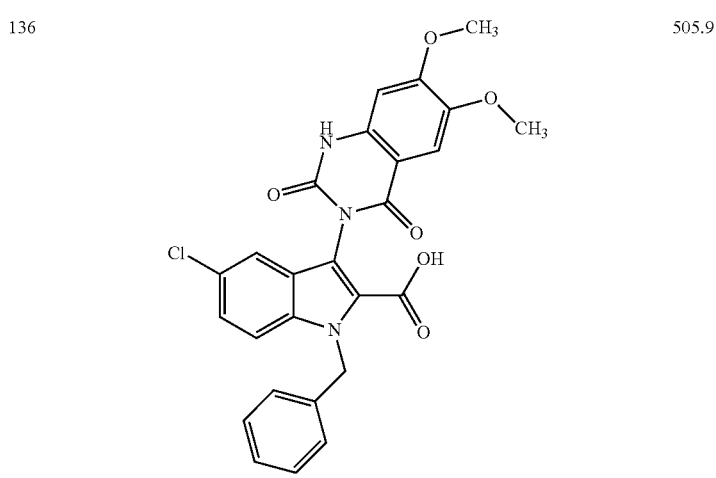 | 489.9 |
| 136 | 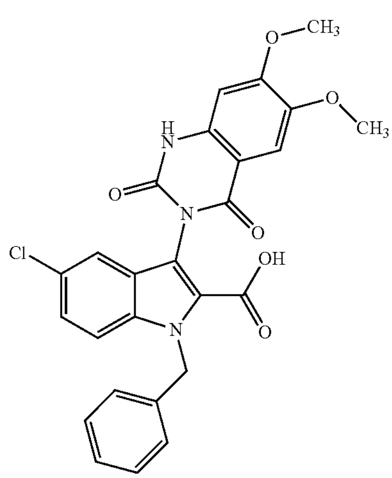 [SMILES: COc1cc2[nH]c(=O)n(-c3c(C(=O)O)n(Cc4ccccc4)c4ccc(Cl)cc34)c(=O)c2cc1OC] | 505.9 |

| Compound No. | Structure | LCMS (M + H) |
|---|---|---|
| 137 | 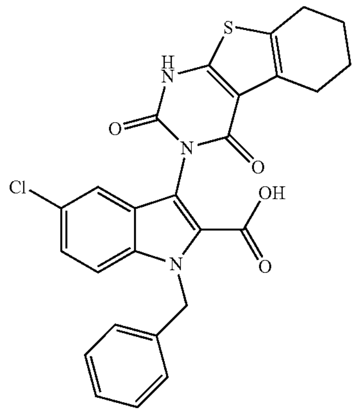 [SMILES: O=C(O)c1c(-n2c(=O)[nH]c3sc4c(c3c2=O)CCCC4)c2cc(Cl)ccc2n1Cc1ccccc1] | 505.9 |
| 138 | 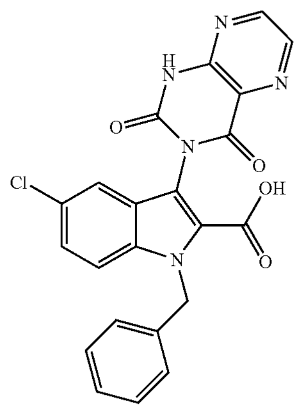 [SMILES: O=C(O)c1c(-n2c(=O)[nH]c3nccnc3c2=O)c2cc(Cl)ccc2n1Cc1ccccc1] | 447.8 |
| 139 | 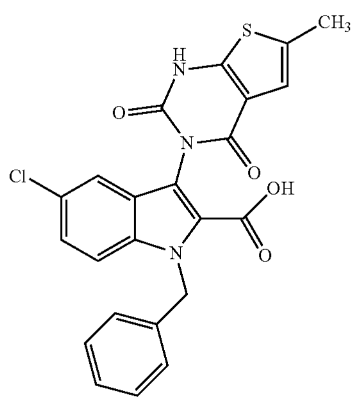 [SMILES: Cc1cc2c(=O)n(-c3c(C(=O)O)n(Cc4ccccc4)c4ccc(Cl)cc34)c(=O)[nH]c2s1] | 465.9 |
| 140 | 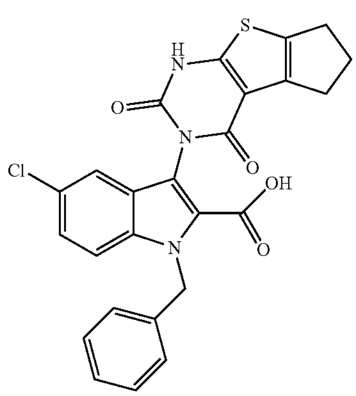 [SMILES: O=C(O)c1c(-n2c(=O)[nH]c3sc4c(c3c2=O)CCC4)c2cc(Cl)ccc2n1Cc1ccccc1] | 491.9 |

-continued

| Compound No. | Structure | LCMS (M + H) |
|---|---|---|
| 141 | 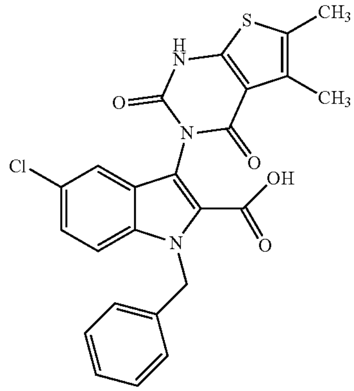 [SMILES: Cc1sc2[nH]c(=O)n(-c3c(C(=O)O)n(Cc4ccccc4)c4ccc(Cl)cc34)c(=O)c2c1C] | 479.9 |
| 142 | 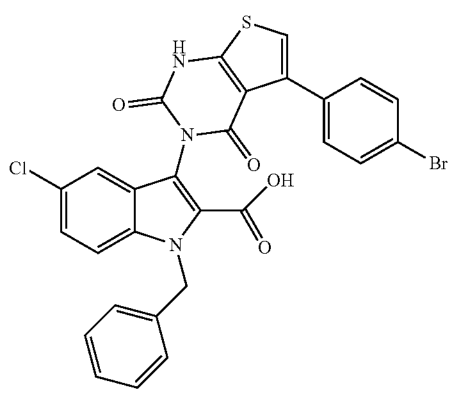 [SMILES: O=C(O)c1c(-n2c(=O)[nH]c3scc(-c4ccc(Br)cc4)c3c2=O)c2cc(Cl)ccc2n1Cc1ccccc1] | 606.9 |
| 143 | 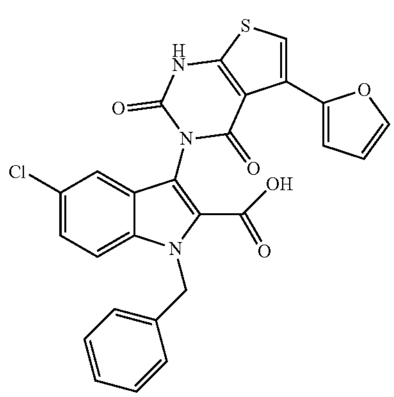 [SMILES: O=C(O)c1c(-n2c(=O)[nH]c3scc(-c4ccco4)c3c2=O)c2cc(Cl)ccc2n1Cc1ccccc1] | 517.9 |
| 144 | 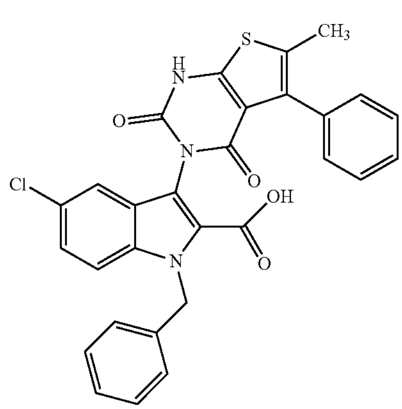 [SMILES: Cc1sc2[nH]c(=O)n(-c3c(C(=O)O)n(Cc4ccccc4)c4ccc(Cl)cc34)c(=O)c2c1-c1ccccc1] | 542.0 |

-continued

| Compound No. | Structure | LCMS (M + H) |
|---|---|---|
| 145 | 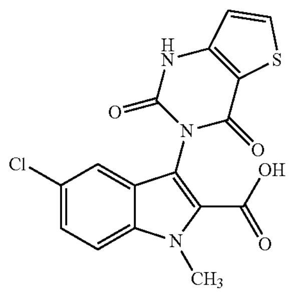 [SMILES: Cn1c(C(=O)O)c(-n2c(=O)[nH]c3ccsc3c2=O)c2cc(Cl)ccc21] | 375.8 |
| 146 | 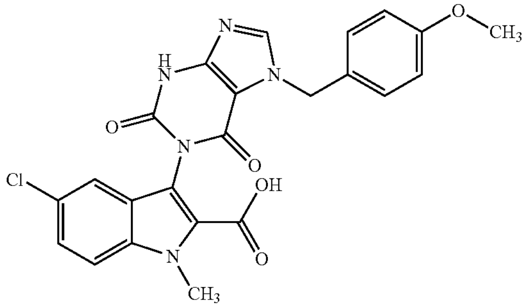 [SMILES: COc1ccc(Cn2cnc3[nH]c(=O)n(-c4c(C(=O)O)n(C)c5ccc(Cl)cc45)c(=O)c32)cc1] | 479.9 |
| 147 | 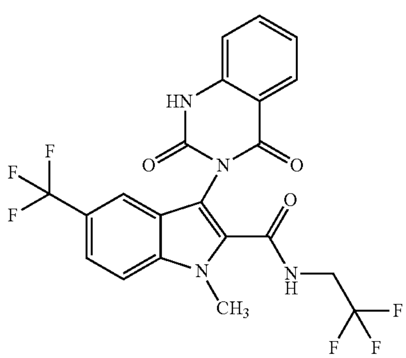 [SMILES: Cn1c(C(=O)NCC(F)(F)F)c(-n2c(=O)[nH]c3ccccc3c2=O)c2cc(C(F)(F)F)ccc21] | 484.4 |
| 148 | 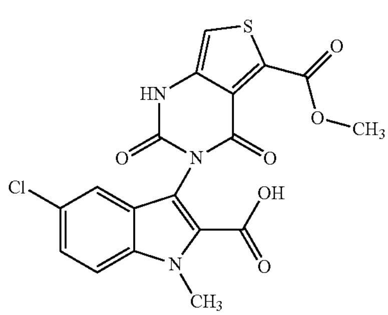 [SMILES: COC(=O)c1scc2[nH]c(=O)n(-c3c(C(=O)O)n(C)c4ccc(Cl)cc34)c(=O)c12] | 433.8 |

-continued

| Compound No. | Structure | LCMS (M + H) |
|---|---|---|
| 149 | 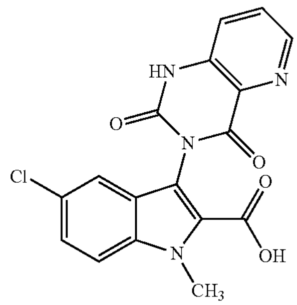 [SMILES: Cn1c(C(=O)O)c(-n2c(=O)[nH]c3cccnc3c2=O)c2cc(Cl)ccc21] | 370.8 |
| 150 | 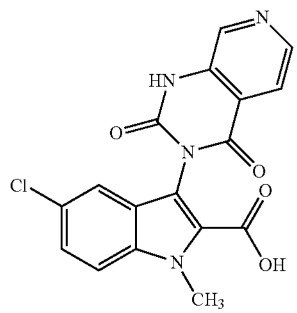 [SMILES: Cn1c(C(=O)O)c(-n2c(=O)[nH]c3cnccc3c2=O)c2cc(Cl)ccc21] | 370.8 |
| 151 | 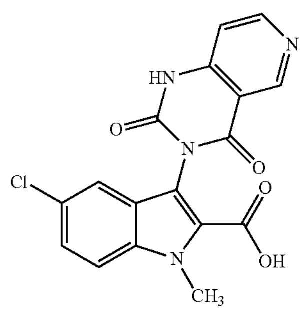 [SMILES: Cn1c(C(=O)O)c(-n2c(=O)[nH]c3ccncc3c2=O)c2cc(Cl)ccc21] | 370.8 |
| 152 | 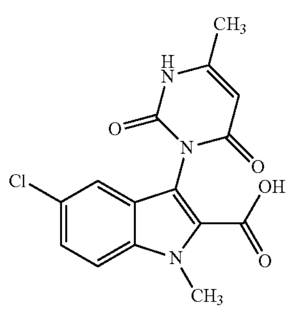 | 333.7 |
| 153 | 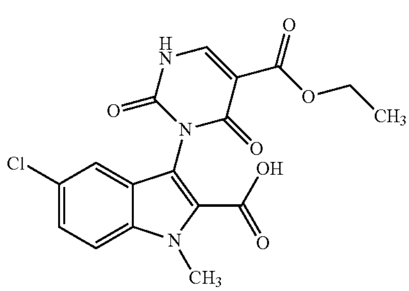 [SMILES: CCOC(=O)c1c[nH]c(=O)n(-c2c(C(=O)O)n(C)c3ccc(Cl)cc23)c1=O] | 391.8 |

-continued
| Compound No. | Structure | LCMS (M + H) |
|---|---|---|
| 154 | 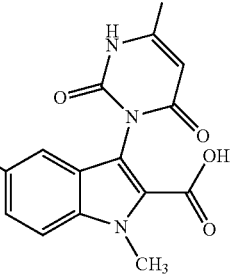 | 363.8 |
| 155 | 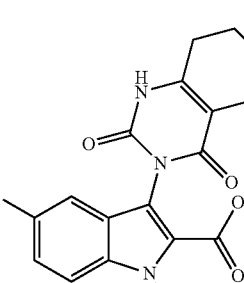 | 373.8 |
| 156 | 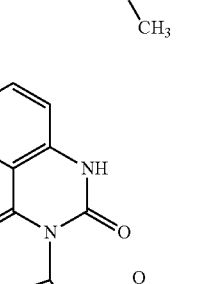 | 576.9 |
| 157 | 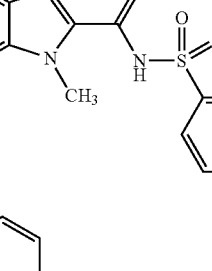 | 538.9 |

-continued
| Compound No. | Structure | LCMS (M + H) |
|---|---|---|
| 158 | 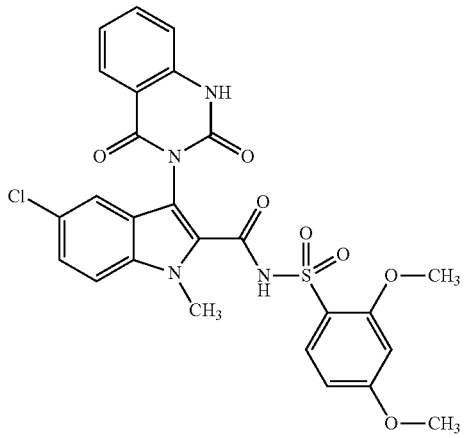 [SMILES: COc1ccc(S(=O)(=O)NC(=O)c2c(-n3c(=O)[nH]c4ccccc4c3=O)c3cc(Cl)ccc3n2C)c(OC)c1] | 568.9 |
| 159 | 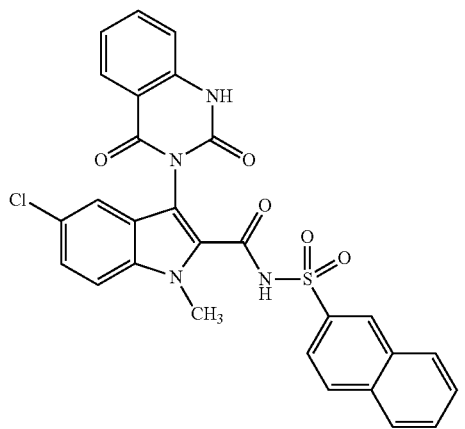 [SMILES: Cn1c(C(=O)NS(=O)(=O)c2ccc3ccccc3c2)c(-n2c(=O)[nH]c3ccccc3c2=O)c2cc(Cl)ccc21] | 559.0 |
| 160 | 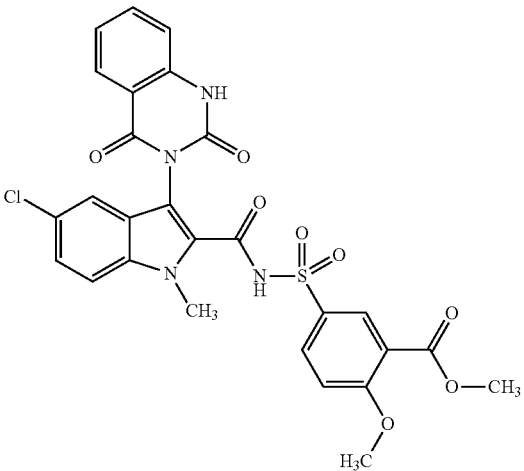 [SMILES: COC(=O)c1cc(S(=O)(=O)NC(=O)c2c(-n3c(=O)[nH]c4ccccc4c3=O)c3cc(Cl)ccc3n2C)ccc1OC] | 597.0 |

-continued

| Compound No. | Structure | LCMS (M + H) |
|---|---|---|
| 161 | 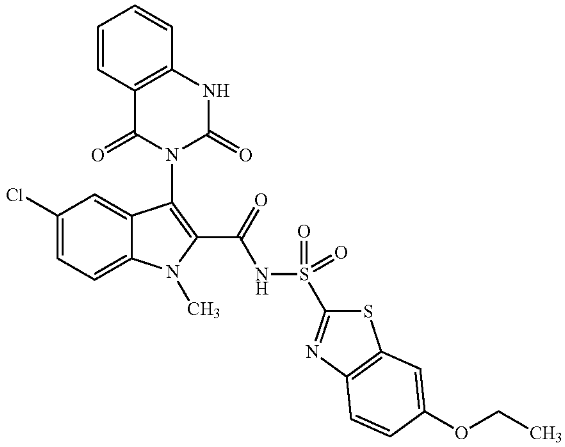 [SMILES: CCOc1ccc2nc(S(=O)(=O)NC(=O)c3c(-n4c(=O)[nH]c5ccccc5c4=O)c4cc(Cl)ccc4n3C)sc2c1] | 610.1 |
| 162 | 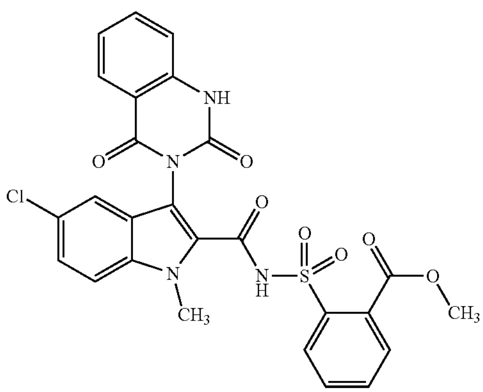 [SMILES: COC(=O)c1ccccc1S(=O)(=O)NC(=O)c1c(-n2c(=O)[nH]c3ccccc3c2=O)c2cc(Cl)ccc2n1C] | 566.9 |
| 163 | 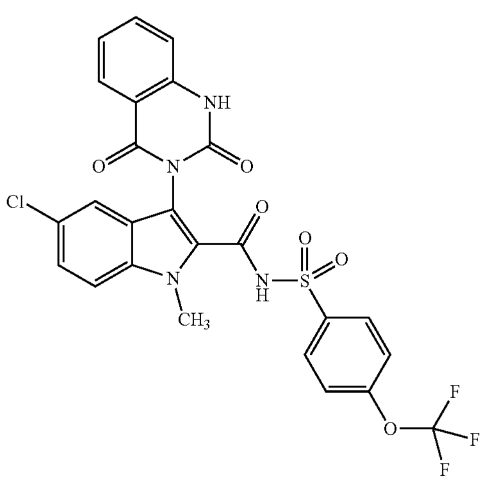 [SMILES: Cn1c(C(=O)NS(=O)(=O)c2ccc(OC(F)(F)F)cc2)c(-n2c(=O)[nH]c3ccccc3c2=O)c2cc(Cl)ccc21] | 592.9 |

-continued
| Compound No. | Structure | LCMS (M + H) |
|---|---|---|
| 164 | 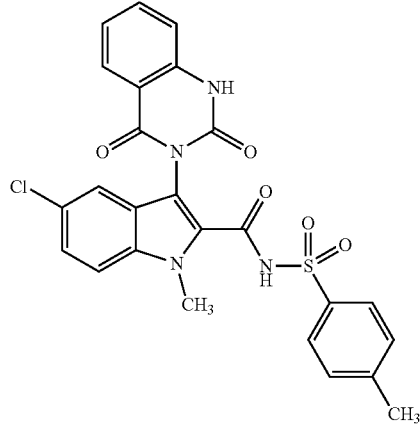 [SMILES: Cc1ccc(S(=O)(=O)NC(=O)c2c(-n3c(=O)[nH]c4ccccc4c3=O)c3cc(Cl)ccc3n2C)cc1] | 522.9 |
| 165 | 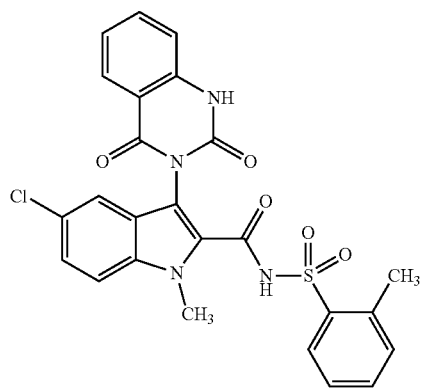 [SMILES: Cc1ccccc1S(=O)(=O)NC(=O)c1c(-n2c(=O)[nH]c3ccccc3c2=O)c2cc(Cl)ccc2n1C] | 522.9 |
| 166 | 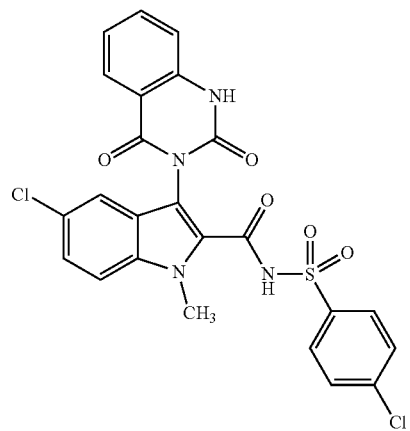 [SMILES: Cn1c(C(=O)NS(=O)(=O)c2ccc(Cl)cc2)c(-n2c(=O)[nH]c3ccccc3c2=O)c2cc(Cl)ccc21] | 543.4 |

-continued
| Compound No. | Structure | LCMS (M + H) |
|---|---|---|
| 167 | 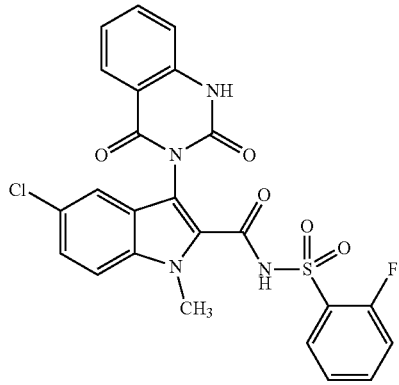 [SMILES: Cn1c(C(=O)NS(=O)(=O)c2ccccc2F)c(-n2c(=O)[nH]c3ccccc3c2=O)c2cc(Cl)ccc21] | 526.9 |
| 168 | 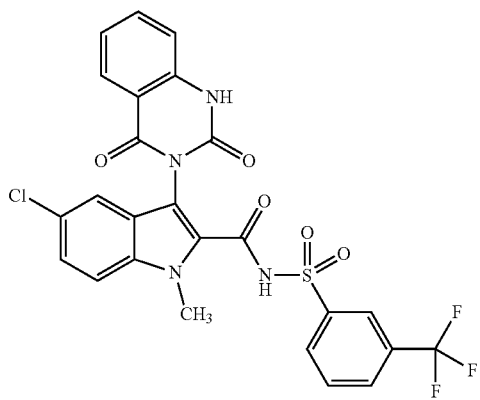 [SMILES: Cn1c(C(=O)NS(=O)(=O)c2cccc(C(F)(F)F)c2)c(-n2c(=O)[nH]c3ccccc3c2=O)c2cc(Cl)ccc21] | 576.9 |
| 169 | 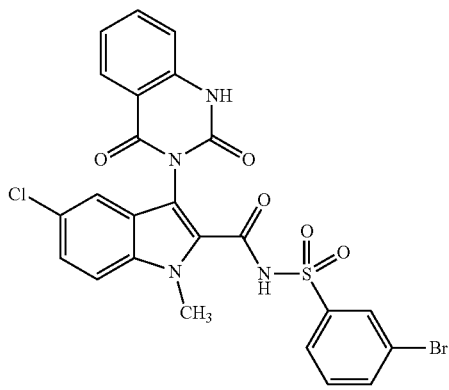 [SMILES: Cn1c(C(=O)NS(=O)(=O)c2cccc(Br)c2)c(-n2c(=O)[nH]c3ccccc3c2=O)c2cc(Cl)ccc21] | 587.8 |

| Compound No. | Structure | LCMS (M + H) |
|---|---|---|
| 170 | 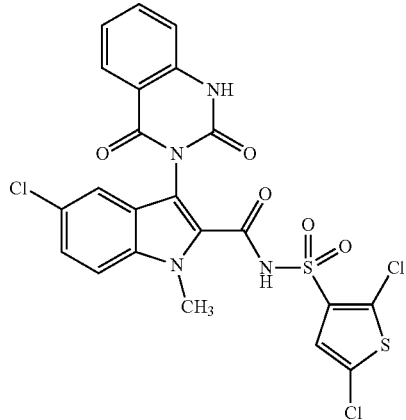 [SMILES: Cn1c(C(=O)NS(=O)(=O)c2cc(Cl)sc2Cl)c(-n2c(=O)[nH]c3ccccc3c2=O)c2cc(Cl)ccc21] | 583.9 |
| 171 | 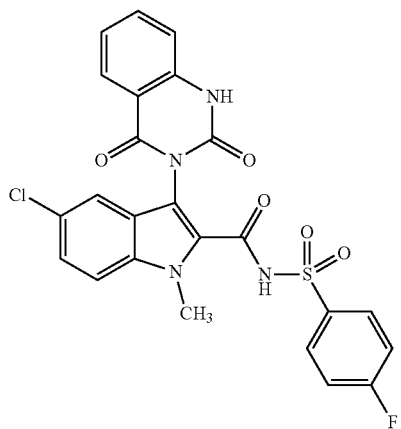 [SMILES: Cn1c(C(=O)NS(=O)(=O)c2ccc(F)cc2)c(-n2c(=O)[nH]c3ccccc3c2=O)c2cc(Cl)ccc21] | 526.9 |
| 172 | 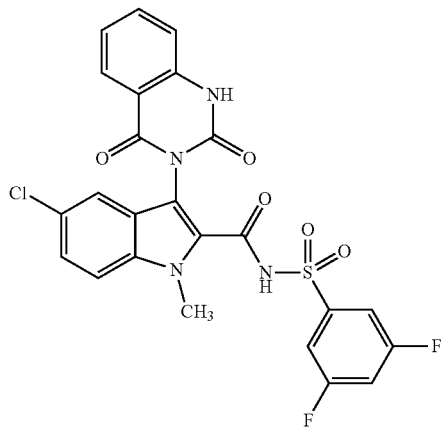 [SMILES: Cn1c(C(=O)NS(=O)(=O)c2cc(F)cc(F)c2)c(-n2c(=O)[nH]c3ccccc3c2=O)c2cc(Cl)ccc21] | 544.9 |

-continued
| Compound No. | Structure | LCMS (M + H) |
|---|---|---|
| 173 | 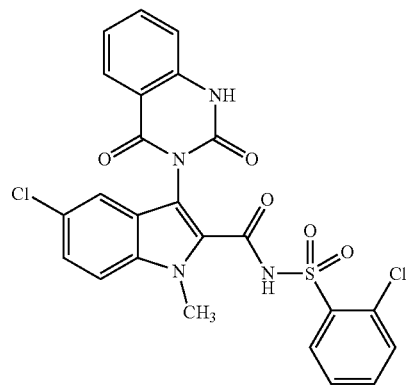 [SMILES: Cn1c(C(=O)NS(=O)(=O)c2ccccc2Cl)c(-n2c(=O)[nH]c3ccccc3c2=O)c2cc(Cl)ccc21] | 543.4 |
| 174 | 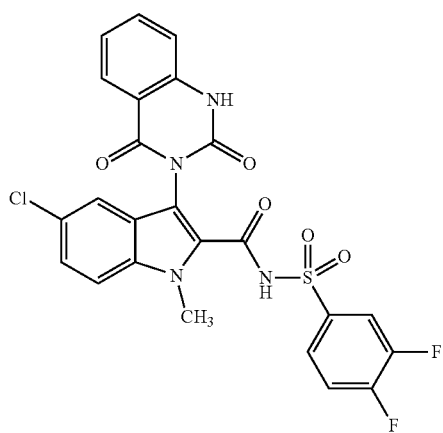 [SMILES: Cn1c(C(=O)NS(=O)(=O)c2ccc(F)c(F)c2)c(-n2c(=O)[nH]c3ccccc3c2=O)c2cc(Cl)ccc21] | 544.9 |
| 175 | 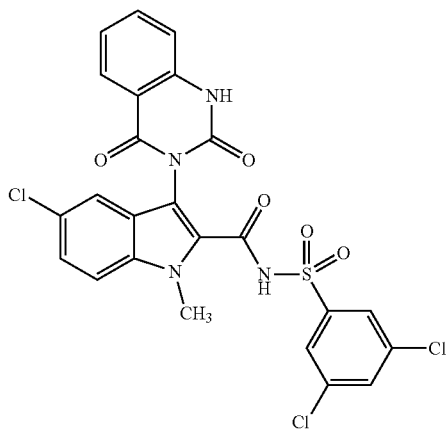 [SMILES: Cn1c(C(=O)NS(=O)(=O)c2cc(Cl)cc(Cl)c2)c(-n2c(=O)[nH]c3ccccc3c2=O)c2cc(Cl)ccc21] | 577.8 |

-continued
| Compound No. | Structure | LCMS (M + H) |
|---|---|---|
| 176 | 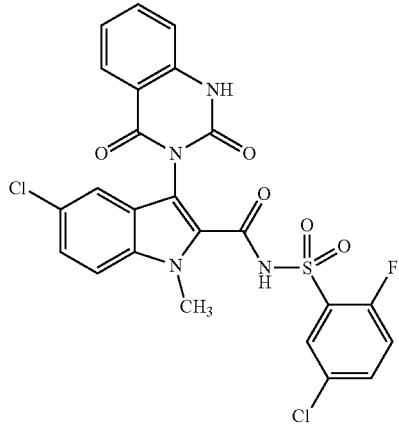 [SMILES: Cn1c(C(=O)NS(=O)(=O)c2cc(Cl)ccc2F)c(-n2c(=O)[nH]c3ccccc3c2=O)c2cc(Cl)ccc21] | 561.4 |
| 177 | 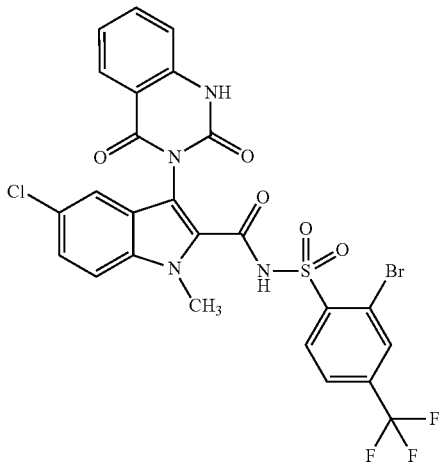 [SMILES: Cn1c(C(=O)NS(=O)(=O)c2ccc(C(F)(F)F)cc2Br)c(-n2c(=O)[nH]c3ccccc3c2=O)c2cc(Cl)ccc21] | 655.8 |
| 178 | 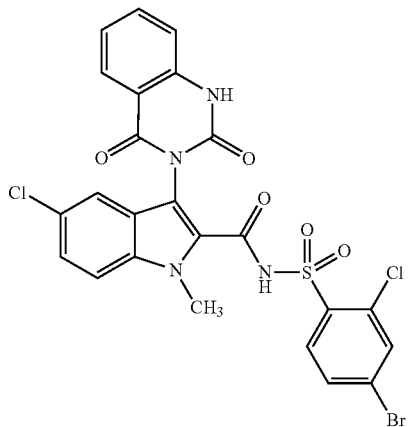 [SMILES: Cn1c(C(=O)NS(=O)(=O)c2ccc(Br)cc2Cl)c(-n2c(=O)[nH]c3ccccc3c2=O)c2cc(Cl)ccc21] | 622.3 |

|Compound No.|Structure|LCMS (M + H)|
|---|---|---|
| 179 | 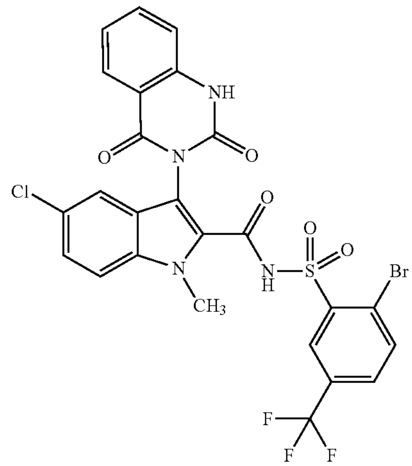 [SMILES: Cn1c(C(=O)NS(=O)(=O)c2cc(C(F)(F)F)ccc2Br)c(-n2c(=O)[nH]c3ccccc3c2=O)c2cc(Cl)ccc21] | 655.8 |
| 180 | 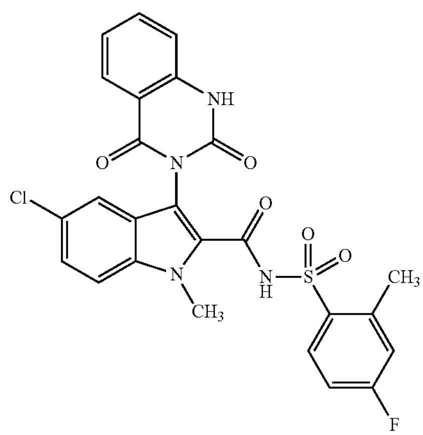 [SMILES: Cc1cc(F)ccc1S(=O)(=O)NC(=O)c1c(-n2c(=O)[nH]c3ccccc3c2=O)c2cc(Cl)ccc2n1C] | 540.9 |
| 181 | 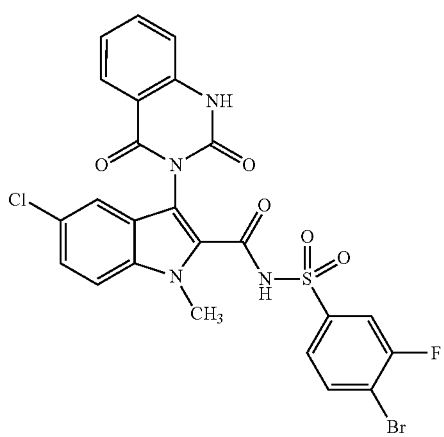 [SMILES: Cn1c(C(=O)NS(=O)(=O)c2ccc(Br)c(F)c2)c(-n2c(=O)[nH]c3ccccc3c2=O)c2cc(Cl)ccc21] | 605.8 |

-continued
| Compound No. | Structure | LCMS (M + H) |
|---|---|---|
| 182 | 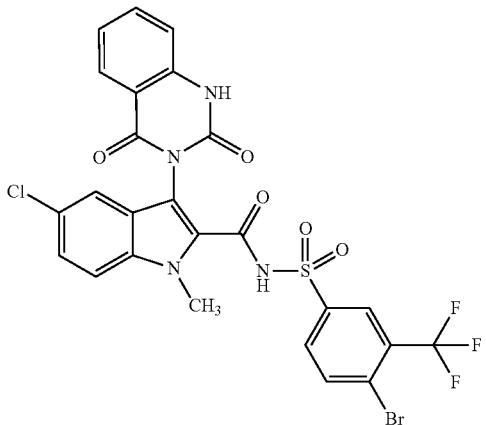 [SMILES: Cn1c(C(=O)NS(=O)(=O)c2ccc(Br)c(C(F)(F)F)c2)c(-n2c(=O)[nH]c3ccccc3c2=O)c2cc(Cl)ccc21] | 655.8 |
| 183 | 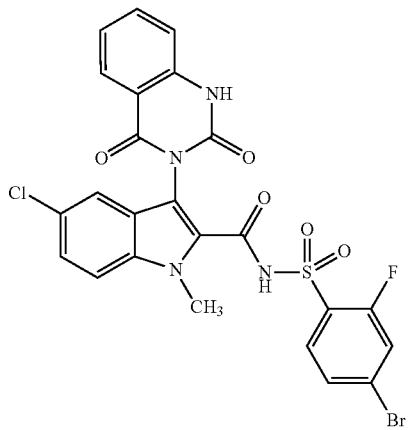 [SMILES: Cn1c(C(=O)NS(=O)(=O)c2ccc(Br)cc2F)c(-n2c(=O)[nH]c3ccccc3c2=O)c2cc(Cl)ccc21] | 605.8 |
| 184 | 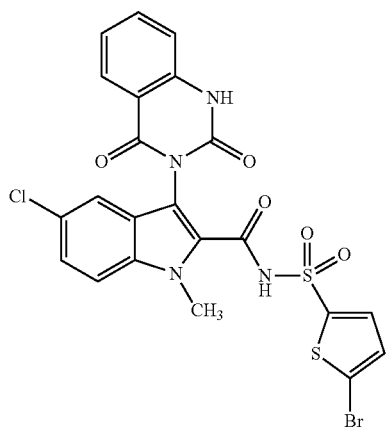 [SMILES: Cn1c(C(=O)NS(=O)(=O)c2ccc(Br)s2)c(-n2c(=O)[nH]c3ccccc3c2=O)c2cc(Cl)ccc21] | 593.9 |

-continued
| Compound No. | Structure | LCMS (M + H) |
|---|---|---|
| 185 | 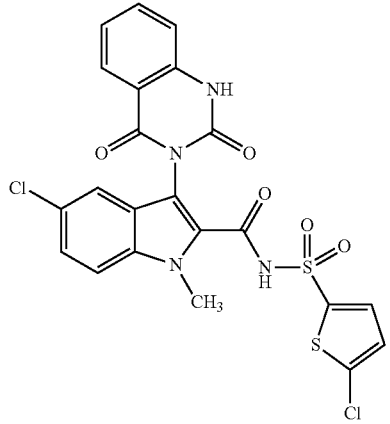 | 549.4 |
| 186 | 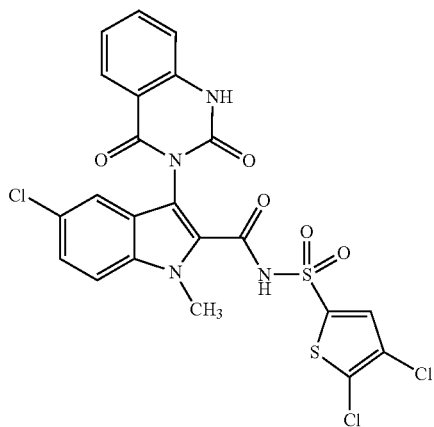 [SMILES: Cn1c(C(=O)NS(=O)(=O)c2cc(Cl)c(Cl)s2)c(-n2c(=O)[nH]c3ccccc3c2=O)c2cc(Cl)ccc21] | 583.9 |
| 187 | 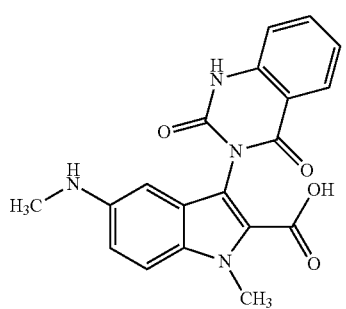 [SMILES: CNc1ccc2c(c1)c(-n1c(=O)[nH]c3ccccc3c1=O)c(C(=O)O)n2C] | 364.4 |

| Compound No. | Structure | LCMS (M + H) |
|---|---|---|
| 188 | 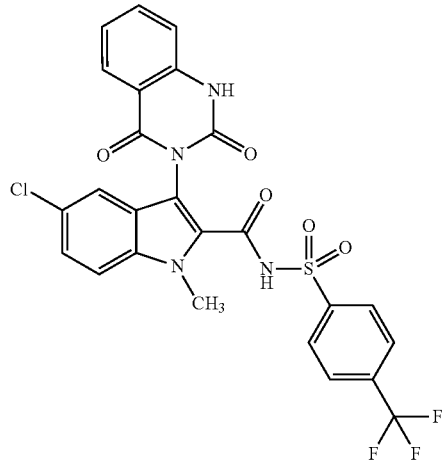 [SMILES: Cn1c(C(=O)NS(=O)(=O)c2ccc(C(F)(F)F)cc2)c(-n2c(=O)[nH]c3ccccc3c2=O)c2cc(Cl)ccc21] | 576.9 |
| 189 | 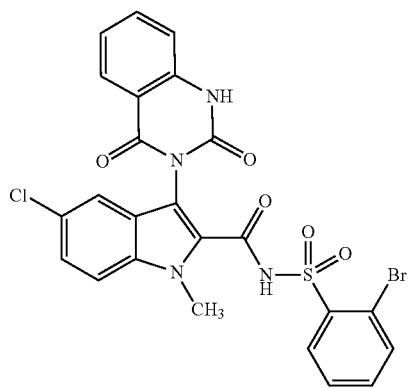 [SMILES: Cn1c(C(=O)NS(=O)(=O)c2ccccc2Br)c(-n2c(=O)[nH]c3ccccc3c2=O)c2cc(Cl)ccc21] | 587.8 |
| 190 | 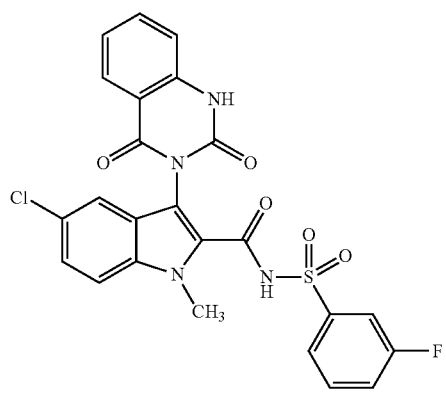 [SMILES: Cn1c(C(=O)NS(=O)(=O)c2cccc(F)c2)c(-n2c(=O)[nH]c3ccccc3c2=O)c2cc(Cl)ccc21] | 526.9 |

-continued

| Compound No. | Structure | LCMS (M + H) |
|---|---|---|
| 191 | 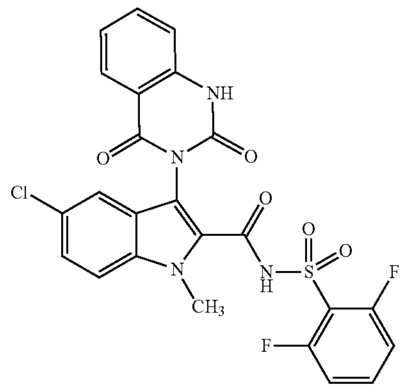 [SMILES: Cn1c(C(=O)NS(=O)(=O)c2c(F)cccc2F)c(-n2c(=O)[nH]c3ccccc3c2=O)c2cc(Cl)ccc21] | 544.9 |
| 192 | 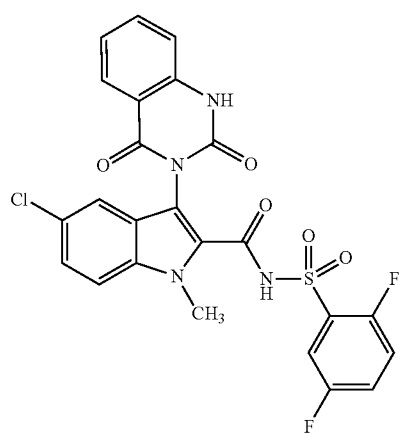 [SMILES: Cn1c(C(=O)NS(=O)(=O)c2cc(F)ccc2F)c(-n2c(=O)[nH]c3ccccc3c2=O)c2cc(Cl)ccc21] | 544.9 |
| 193 | 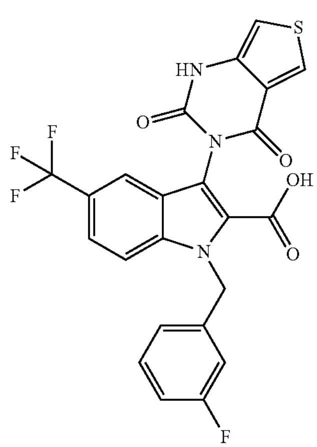 [SMILES: O=C(O)c1c(-n2c(=O)[nH]c3cscc3c2=O)c2cc(C(F)(F)F)ccc2n1Cc1cccc(F)c1] | 503.4 |

-continued
| Compound No. | Structure | LCMS (M + H) |
|---|---|---|
| 194 | 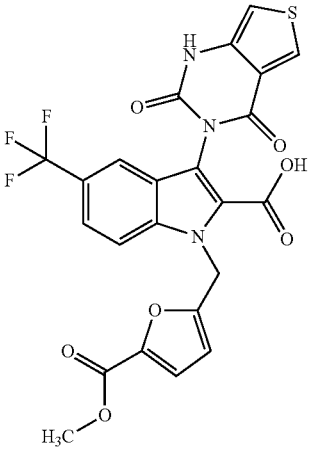 [SMILES: COC(=O)c1ccc(Cn2c(C(=O)O)c(-n3c(=O)[nH]c4cscc4c3=O)c3cc(C(F)(F)F)ccc32)o1] | 533.4 |
| 195 | 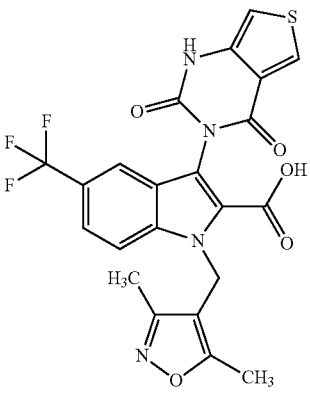 [SMILES: Cc1noc(C)c1Cn1c(C(=O)O)c(-n2c(=O)[nH]c3cscc3c2=O)c2cc(C(F)(F)F)ccc21] | 504.4 |
| 196 | 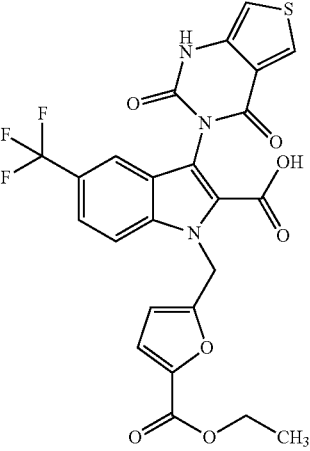 [SMILES: CCOC(=O)c1ccc(Cn2c(C(=O)O)c(-n3c(=O)[nH]c4cscc4c3=O)c3cc(C(F)(F)F)ccc32)o1] | 547.5 |

| Compound No. | Structure | LCMS (M + H) |
|---|---|---|
| 197 | 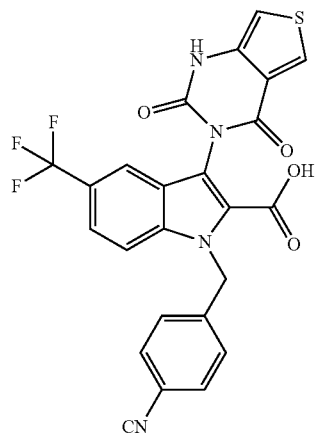 | 510.5 |
| 198 | 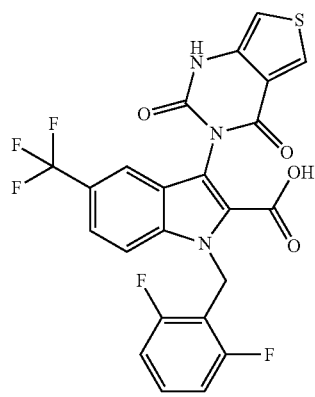 [SMILES: O=C(O)c1c(-n2c(=O)[nH]c3cscc3c2=O)c2cc(C(F)(F)F)ccc2n1Cc1c(F)cccc1F] | 521.4 |
| 199 | 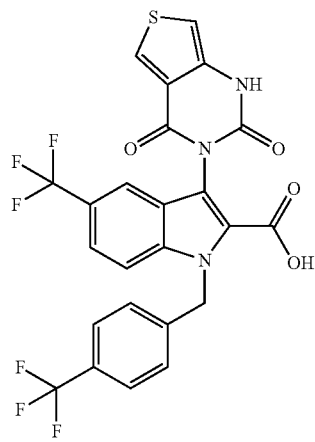 [SMILES: O=C(O)c1c(-n2c(=O)[nH]c3cscc3c2=O)c2cc(C(F)(F)F)ccc2n1Cc1ccc(C(F)(F)F)cc1] | 553.4 |

-continued
| Compound No. | Structure | LCMS (M + H) |
|---|---|---|
| 200 | 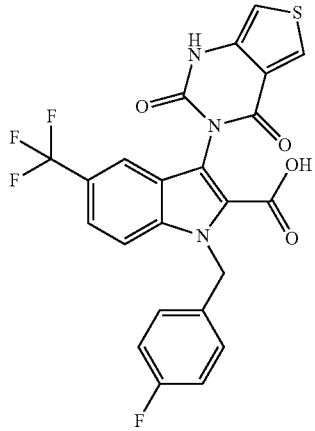 [SMILES: O=C(O)c1c(-n2c(=O)[nH]c3cscc3c2=O)c2cc(C(F)(F)F)ccc2n1Cc1ccc(F)cc1] | 503.4 |
| 201 | 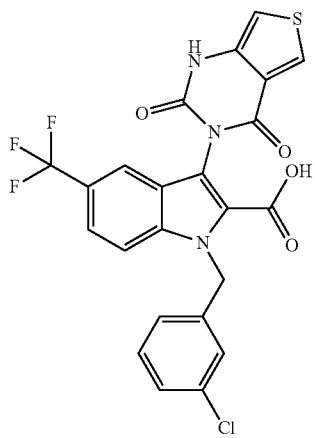 [SMILES: O=C(O)c1c(-n2c(=O)[nH]c3cscc3c2=O)c2cc(C(F)(F)F)ccc2n1Cc1cccc(Cl)c1] | 519.9 |
| 202 | 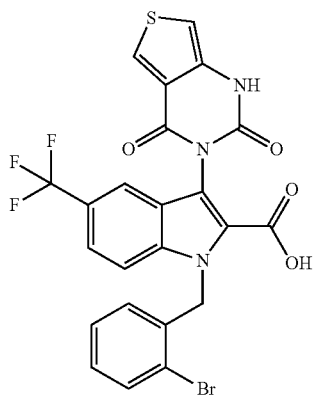 | 564.3 |

-continued
| Compound No. | Structure | LCMS (M + H) |
|---|---|---|
| 203 | 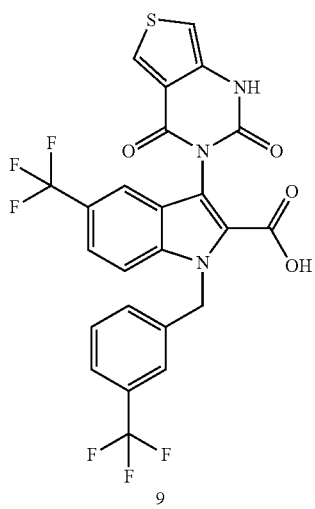 | 553.4 |
| 204 | 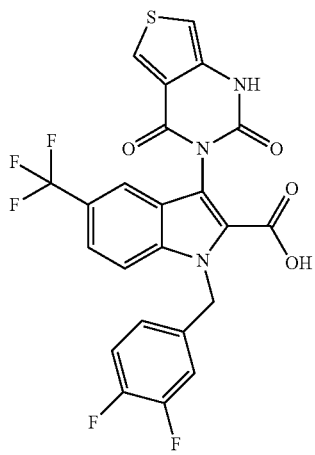 [SMILES: O=C(O)c1c(-n2c(=O)[nH]c3cscc3c2=O)c2cc(C(F)(F)F)ccc2n1Cc1ccc(F)c(F)c1] | 521.4 |
| 205 | 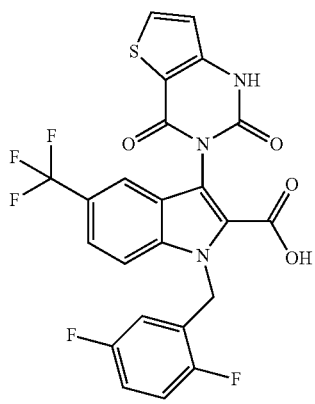 [SMILES: O=C(O)c1c(-n2c(=O)[nH]c3ccsc3c2=O)c2cc(C(F)(F)F)ccc2n1Cc1cc(F)ccc1F] | 521.4 |

| Compound No. | Structure | LCMS (M + H) |
|---|---|---|
| 206 | 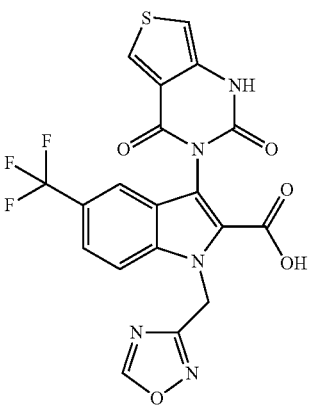 [SMILES: O=C(O)c1c(-n2c(=O)[nH]c3cscc3c2=O)c2cc(C(F)(F)F)ccc2n1Cc1ncon1] | 477.4 |
| 207 | 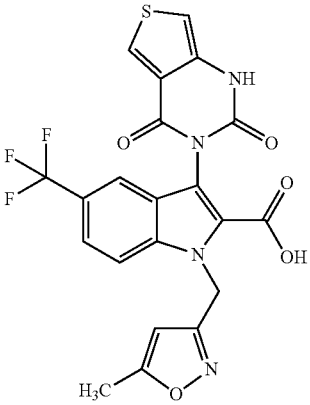 [SMILES: Cc1cc(Cn2c(C(=O)O)c(-n3c(=O)[nH]c4cscc4c3=O)c3cc(C(F)(F)F)ccc32)no1] | 490.4 |
| 208 | 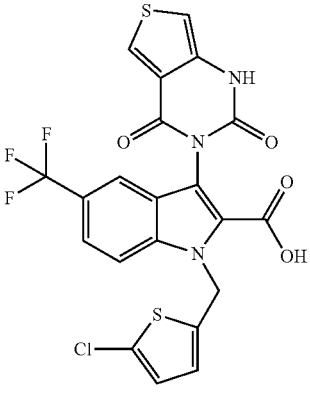 [SMILES: O=C(O)c1c(-n2c(=O)[nH]c3cscc3c2=O)c2cc(C(F)(F)F)ccc2n1Cc1ccc(Cl)s1] | 525.9 |

-continued
| Compound No. | Structure | LCMS (M + H) |
|---|---|---|
| 209 | 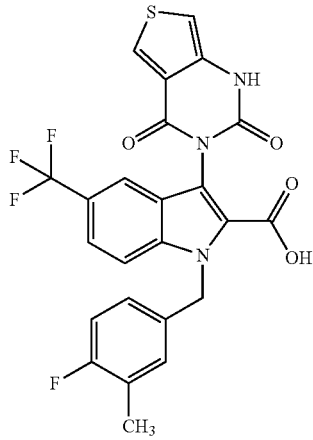 [SMILES: Cc1cc(Cn2c(C(=O)O)c(-n3c(=O)[nH]c4cscc4c3=O)c3cc(C(F)(F)F)ccc32)ccc1F] | 517.5 |
| 210 | 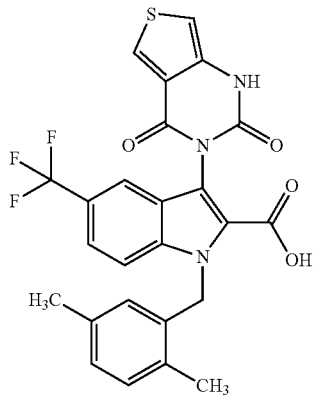 [SMILES: Cc1ccc(C)c(Cn2c(C(=O)O)c(-n3c(=O)[nH]c4cscc4c3=O)c3cc(C(F)(F)F)ccc32)c1] | 513.5 |
| 211 | 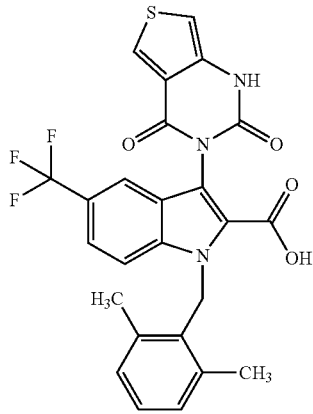 [SMILES: Cc1cccc(C)c1Cn1c(C(=O)O)c(-n2c(=O)[nH]c3cscc3c2=O)c2cc(C(F)(F)F)ccc21] | 513.5 |

-continued

| Compound No. | Structure | LCMS (M + H) |
|---|---|---|
| 212 | 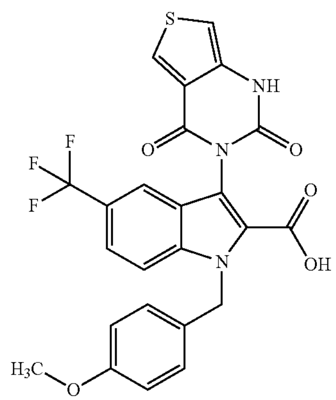 [SMILES: COc1ccc(Cn2c(C(=O)O)c(-n3c(=O)[nH]c4cscc4c3=O)c3cc(C(F)(F)F)ccc32)cc1] | 515.5 |
| 213 | 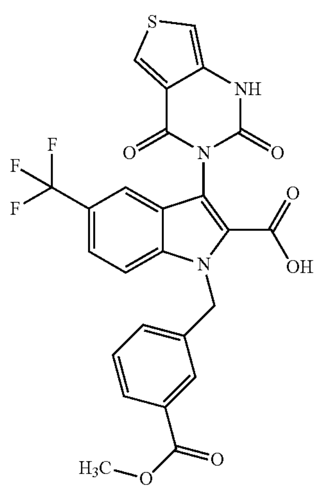 [SMILES: COC(=O)c1cccc(Cn2c(C(=O)O)c(-n3c(=O)[nH]c4cscc4c3=O)c3cc(C(F)(F)F)ccc32)c1] | 543.5 |
| 214 | 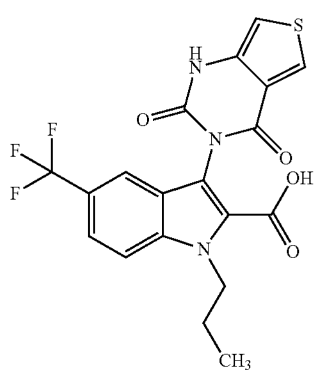 | 437.4 |

-continued

| Compound No. | Structure | LCMS (M + H) |
|---|---|---|
| 215 | 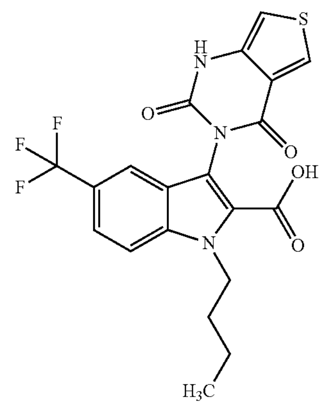 [SMILES: CCCCn1c(C(=O)O)c(-n2c(=O)[nH]c3cscc3c2=O)c2cc(C(F)(F)F)ccc21] | 451.4 |
| 216 | 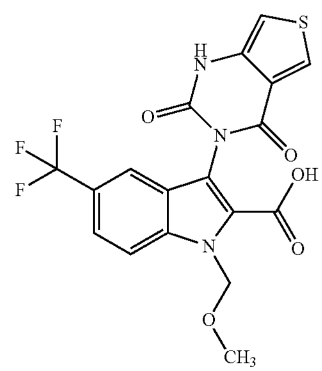 [SMILES: COCn1c(C(=O)O)c(-n2c(=O)[nH]c3cscc3c2=O)c2cc(C(F)(F)F)ccc21] | 439.4 |
| 217 | 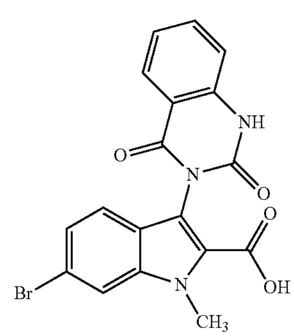 [SMILES: Cn1c(C(=O)O)c(-n2c(=O)[nH]c3ccccc3c2=O)c2ccc(Br)cc21] | 414.2 |
| 218 | 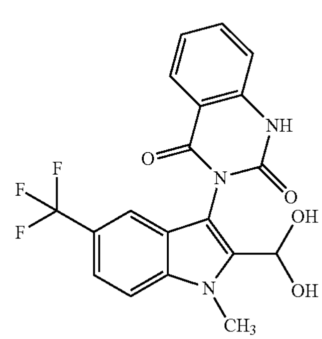 [SMILES: Cn1c(C(O)O)c(-n2c(=O)[nH]c3ccccc3c2=O)c2cc(C(F)(F)F)ccc21] | 403.3 |

-continued

| Compound No. | Structure | LCMS (M + H) |
|---|---|---|
| 219 | 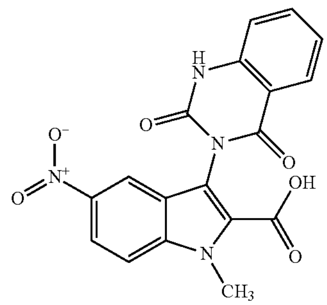 [SMILES: Cn1c(C(=O)O)c(-n2c(=O)[nH]c3ccccc3c2=O)c2cc([N+](=O)[O-])ccc21] | 380.3 |
| 220 | 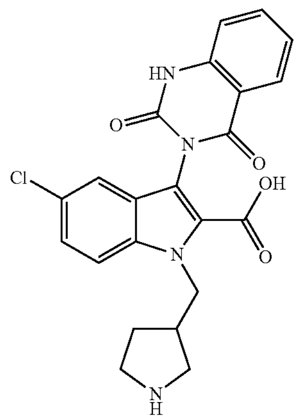 [SMILES: O=C(O)c1c(-n2c(=O)[nH]c3ccccc3c2=O)c2cc(Cl)ccc2n1CC1CCNC1] | 438.9 |
| 221 | 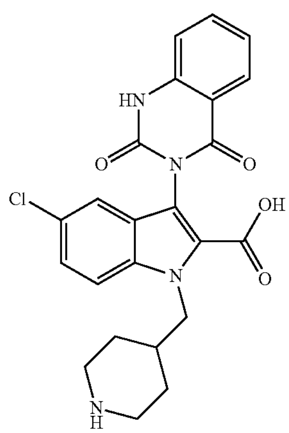 [SMILES: O=C(O)c1c(-n2c(=O)[nH]c3ccccc3c2=O)c2cc(Cl)ccc2n1CC1CCNCC1] | 452.9 |
| 222 | 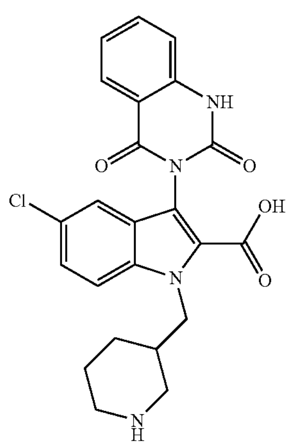 [SMILES: O=C(O)c1c(-n2c(=O)[nH]c3ccccc3c2=O)c2cc(Cl)ccc2n1CC1CCCNC1] | 452.9 |

| Compound No. | Structure | LCMS (M + H) |
|---|---|---|
| 223 | 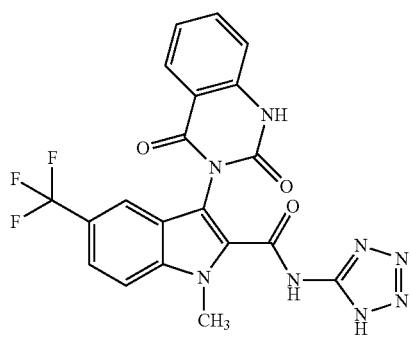 [SMILES: Cn1c(C(=O)Nc2nnn[nH]2)c(-n2c(=O)[nH]c3ccccc3c2=O)c2cc(C(F)(F)F)ccc21] | 470.4 |
| 224 | 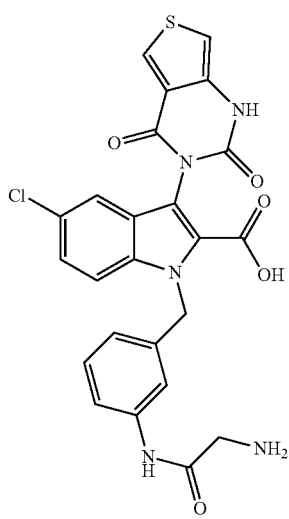 [SMILES: NCC(=O)Nc1cccc(Cn2c(C(=O)O)c(-n3c(=O)[nH]c4cscc4c3=O)c3cc(Cl)ccc32)c1] | 523.9 |
| 225 | 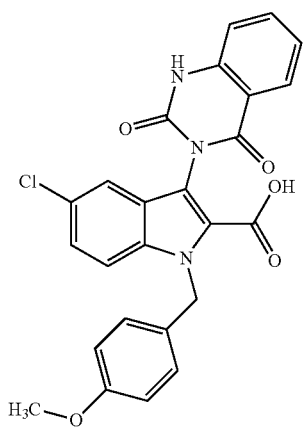 [SMILES: COc1ccc(Cn2c(C(=O)O)c(-n3c(=O)[nH]c4ccccc4c3=O)c3cc(Cl)ccc32)cc1] | 475.9 |

| Compound No. | Structure | LCMS (M + H) |
|---|---|---|
| 226 | 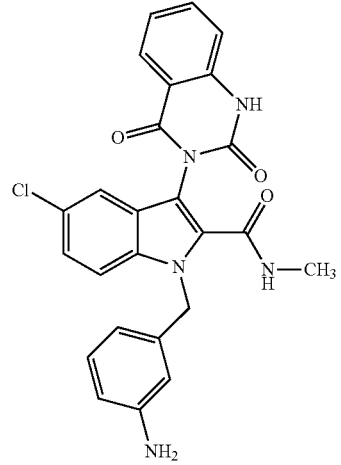 [SMILES: CNC(=O)c1c(-n2c(=O)[nH]c3ccccc3c2=O)c2cc(Cl)ccc2n1Cc1cccc(N)c1] | 473.9 |
| 227 | 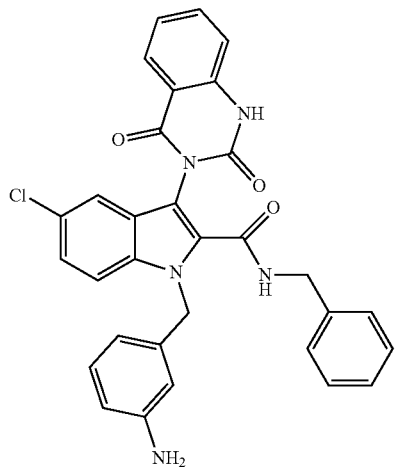 [SMILES: Nc1cccc(Cn2c(C(=O)NCc3ccccc3)c(-n3c(=O)[nH]c4ccccc4c3=O)c3cc(Cl)ccc32)c1] | 550.0 |
| 228 | 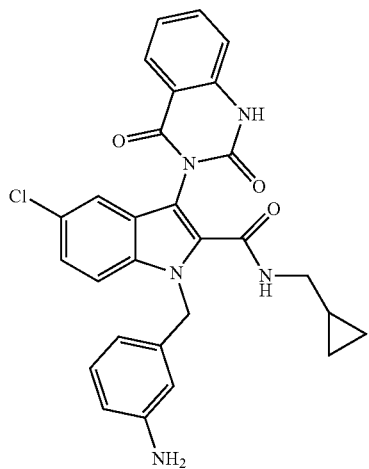 [SMILES: Nc1cccc(Cn2c(C(=O)NCC3CC3)c(-n3c(=O)[nH]c4ccccc4c3=O)c3cc(Cl)ccc32)c1] | 513.9 |

| Compound No. | Structure | LCMS (M + H) |
|---|---|---|
| 229 | 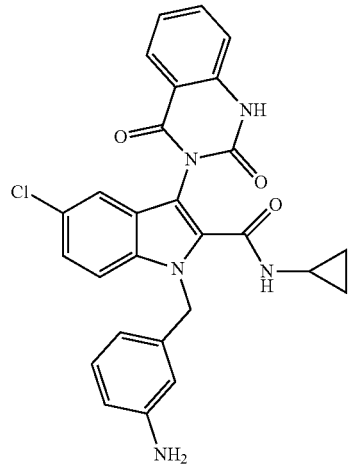 [SMILES: Nc1cccc(Cn2c(C(=O)NC3CC3)c(-n3c(=O)[nH]c4ccccc4c3=O)c3cc(Cl)ccc32)c1] | 499.9 |
| 230 | 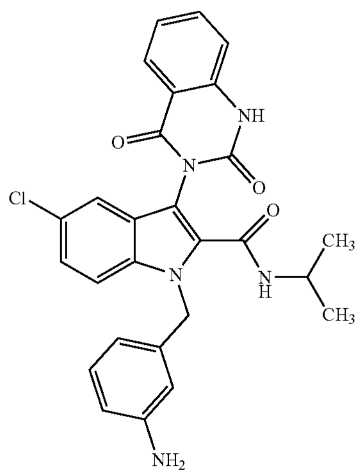 [SMILES: CC(C)NC(=O)c1c(-n2c(=O)[nH]c3ccccc3c2=O)c2cc(Cl)ccc2n1Cc1cccc(N)c1] | 501.9 |
| 231 | 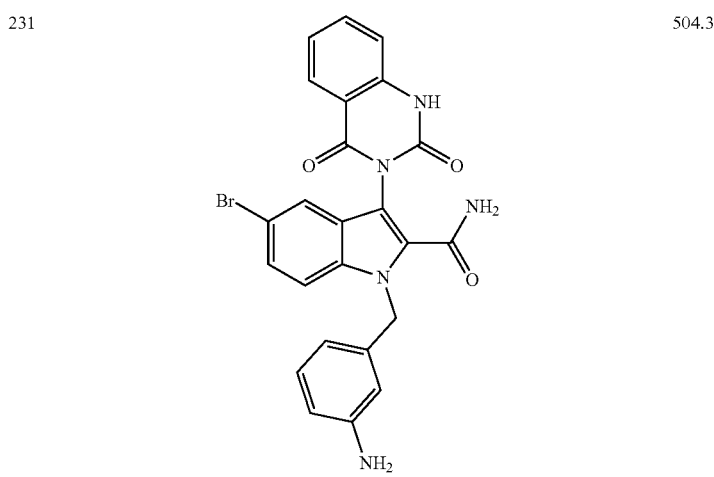 | 504.3 |

-continued
| Compound No. | Structure | LCMS (M + H) |
|---|---|---|
| 232 | 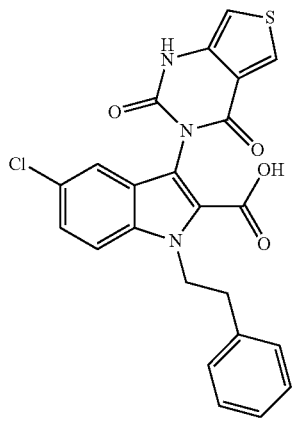 [SMILES: O=C(O)c1c(-n2c(=O)[nH]c3cscc3c2=O)c2cc(Cl)ccc2n1CCc1ccccc1] | 465.9 |
| 233 | 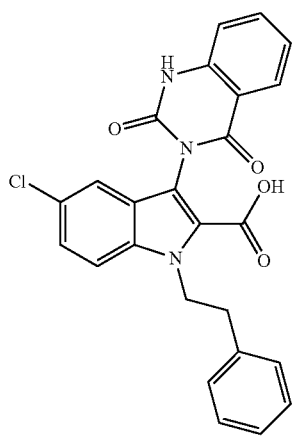 [SMILES: O=C(O)c1c(-n2c(=O)[nH]c3ccccc3c2=O)c2cc(Cl)ccc2n1CCc1ccccc1] | 459.9 |
| 234 | 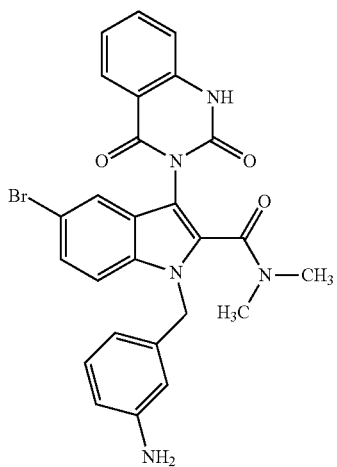 [SMILES: CN(C)C(=O)c1c(-n2c(=O)[nH]c3ccccc3c2=O)c2cc(Br)ccc2n1Cc1cccc(N)c1] | 532.4 |

-continued
| Compound No. | Structure | LCMS (M + H) |
|---|---|---|
| 235 | 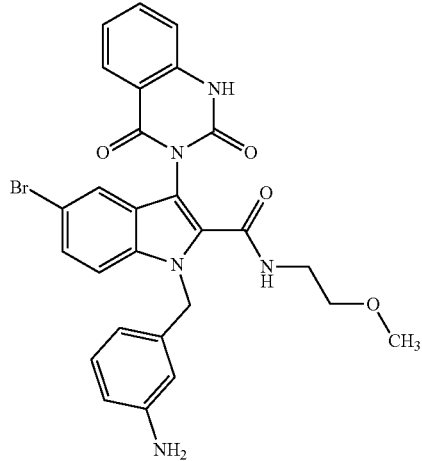 [SMILES: COCCNC(=O)c1c(-n2c(=O)[nH]c3ccccc3c2=O)c2cc(Br)ccc2n1Cc1cccc(N)c1] | 562.4 |
| 236 | 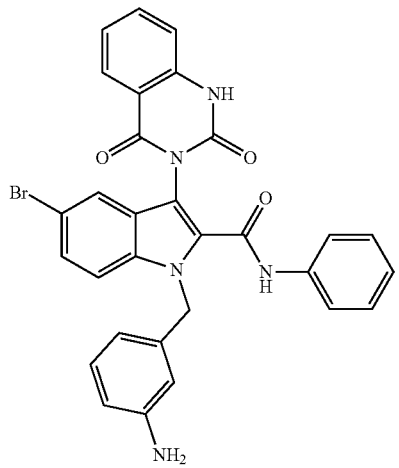 [SMILES: Nc1cccc(Cn2c(C(=O)Nc3ccccc3)c(-n3c(=O)[nH]c4ccccc4c3=O)c3cc(Br)ccc32)c1] | 580.4 |
| 237 | 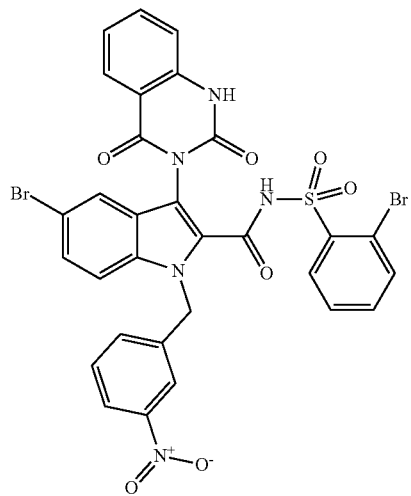 [SMILES: O=C(NS(=O)(=O)c1ccccc1Br)c1c(-n2c(=O)[nH]c3ccccc3c2=O)c2cc(Br)ccc2n1Cc1cccc([N+](=O)[O-])c1] | 753.4 |

-continued

| Compound No. | Structure | LCMS (M + H) |
|---|---|---|
| 238 | 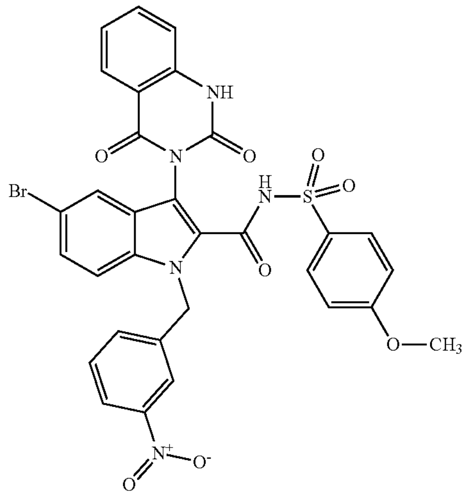 [SMILES: COc1ccc(S(=O)(=O)NC(=O)c2c(-n3c(=O)[nH]c4ccccc4c3=O)c3cc(Br)ccc3n2Cc2cccc([N+](=O)[O-])c2)cc1] | 704.5 |
| 239 | 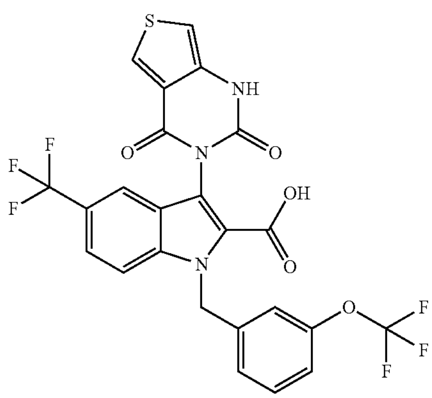 [SMILES: O=C(O)c1c(-n2c(=O)[nH]c3cscc3c2=O)c2cc(C(F)(F)F)ccc2n1Cc1cccc(OC(F)(F)F)c1] | 569.4 |
| 240 | 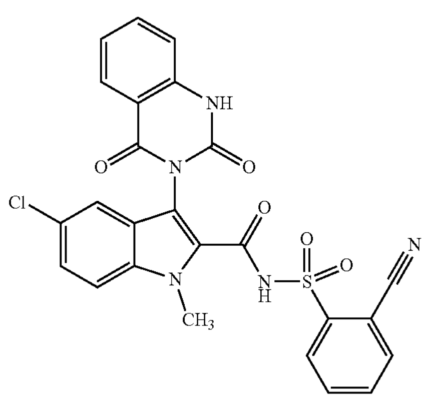 [SMILES: Cn1c(C(=O)NS(=O)(=O)c2ccccc2C#N)c(-n2c(=O)[nH]c3ccccc3c2=O)c2cc(Cl)ccc21] | 533.9 |

-continued
| Compound No. | Structure | LCMS (M + H) |
|---|---|---|
| 241 | 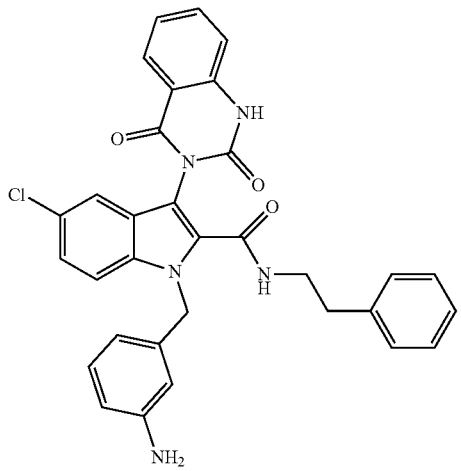 [SMILES: Nc1cccc(Cn2c(C(=O)NCCc3ccccc3)c(-n3c(=O)[nH]c4ccccc4c3=O)c3cc(Cl)ccc32)c1] | 564.0 |
| 242 | 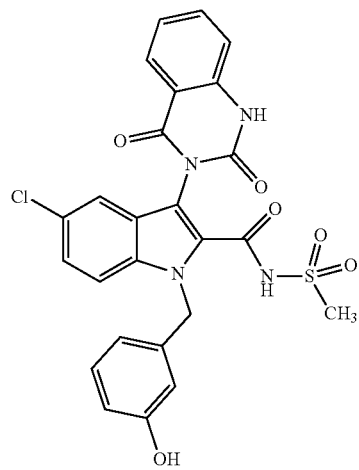 [SMILES: CS(=O)(=O)NC(=O)c1c(-n2c(=O)[nH]c3ccccc3c2=O)c2cc(Cl)ccc2n1Cc1cccc(O)c1] | 538.9 |
| 243 | 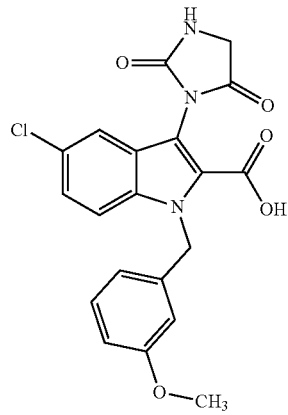 [SMILES: COc1cccc(Cn2c(C(=O)O)c(N3C(=O)CNC3=O)c3cc(Cl)ccc32)c1] | 413.8 |

-continued
| Compound No. | Structure | LCMS (M + H) |
|---|---|---|
| 244 | 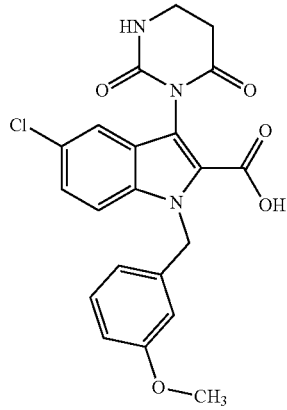 [SMILES: COc1cccc(Cn2c(C(=O)O)c(N3C(=O)CCNC3=O)c3cc(Cl)ccc32)c1] | 427.8 |
| 245 | 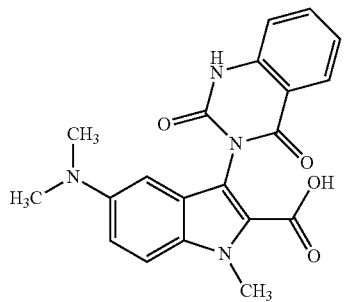 [SMILES: CN(C)c1ccc2c(c1)c(-n1c(=O)[nH]c3ccccc3c1=O)c(C(=O)O)n2C] | 378.4 |
| 246 | 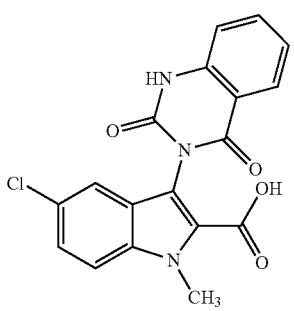 [SMILES: Cn1c(C(=O)O)c(-n2c(=O)[nH]c3ccccc3c2=O)c2cc(Cl)ccc21] | 369.8 |
| 247 | 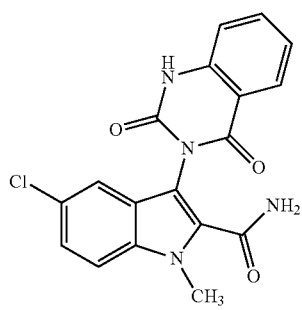 [SMILES: Cn1c(C(N)=O)c(-n2c(=O)[nH]c3ccccc3c2=O)c2cc(Cl)ccc21] | 368.8 |

-continued

| Compound No. | Structure | LCMS (M + H) |
|---|---|---|
| 248 | 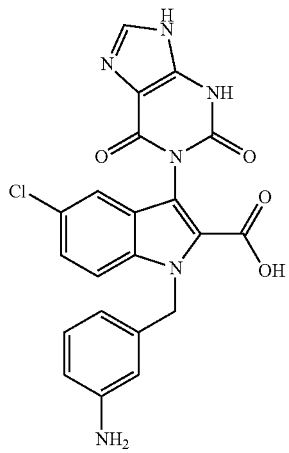 [SMILES: Nc1cccc(Cn2c(C(=O)O)c(-n3c(=O)[nH]c4[nH]cnc4c3=O)c3cc(Cl)ccc32)c1] | 450.8 |
| 249 | 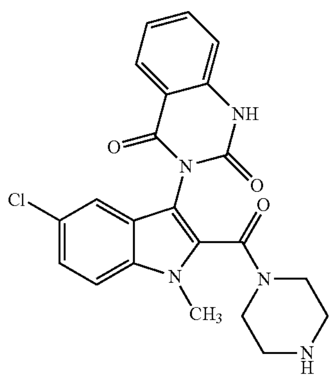 [SMILES: Cn1c(C(=O)N2CCNCC2)c(-n2c(=O)[nH]c3ccccc3c2=O)c2cc(Cl)ccc21] | 437.9 |
| 250 | 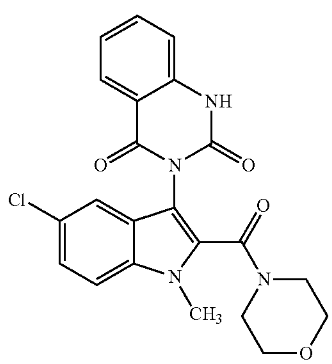 [SMILES: Cn1c(C(=O)N2CCOCC2)c(-n2c(=O)[nH]c3ccccc3c2=O)c2cc(Cl)ccc21] | 438.9 |
| 251 | 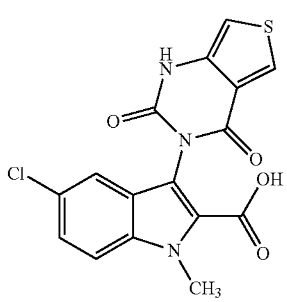 [SMILES: Cn1c(C(=O)O)c(-n2c(=O)[nH]c3cscc3c2=O)c2cc(Cl)ccc21] | 375.8 |

-continued
| Compound No. | Structure | LCMS (M + H) |
|---|---|---|
| 252 | 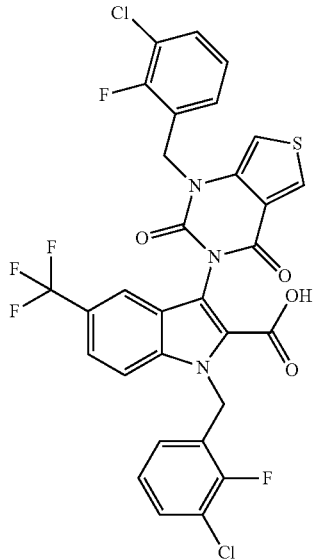 [SMILES: O=C(O)c1c(-n2c(=O)c3cscc3n(Cc3cccc(Cl)c3F)c2=O)c2cc(C(F)(F)F)ccc2n1Cc1cccc(Cl)c1F] | 680.4 |
| 253 | 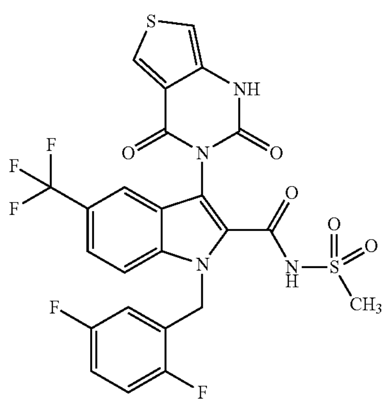 [SMILES: CS(=O)(=O)NC(=O)c1c(-n2c(=O)[nH]c3cscc3c2=O)c2cc(C(F)(F)F)ccc2n1Cc1cc(F)ccc1F] | 598.5 |
| 254 | 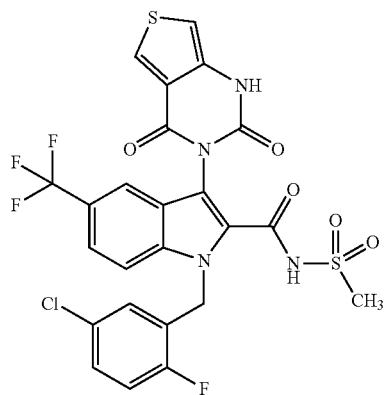 [SMILES: CS(=O)(=O)NC(=O)c1c(-n2c(=O)[nH]c3cscc3c2=O)c2cc(C(F)(F)F)ccc2n1Cc1cc(Cl)ccc1F] | 614.9 |

-continued
| Compound No. | Structure | LCMS (M + H) |
|---|---|---|
| 255 | 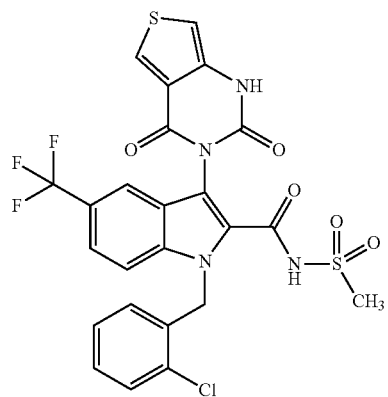 [SMILES: CS(=O)(=O)NC(=O)c1c(-n2c(=O)[nH]c3cscc3c2=O)c2cc(C(F)(F)F)ccc2n1Cc1ccccc1Cl] | 596.9 |
| 256 | 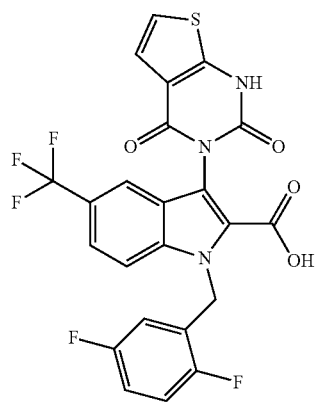 [SMILES: O=C(O)c1c(-n2c(=O)[nH]c3sccc3c2=O)c2cc(C(F)(F)F)ccc2n1Cc1cc(F)ccc1F] | 521.4 |
| 257 | 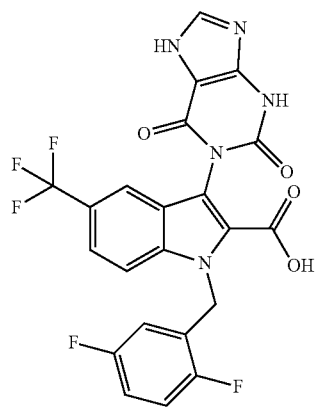 [SMILES: O=C(O)c1c(-n2c(=O)[nH]c3nc[nH]c3c2=O)c2cc(C(F)(F)F)ccc2n1Cc1cc(F)ccc1F] | 505.4 |

-continued
| Compound No. | Structure | LCMS (M + H) |
|---|---|---|
| 258 | 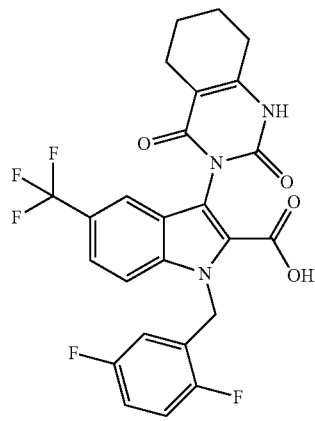 [SMILES: O=C(O)c1c(-n2c(=O)[nH]c3c(c2=O)CCCC3)c2cc(C(F)(F)F)ccc2n1Cc1cc(F)ccc1F] | 519.4 |
| 259 | 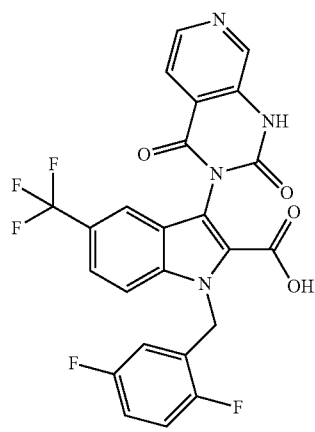 [SMILES: O=C(O)c1c(-n2c(=O)[nH]c3cnccc3c2=O)c2cc(C(F)(F)F)ccc2n1Cc1cc(F)ccc1F] | 516.4 |
| 260 | 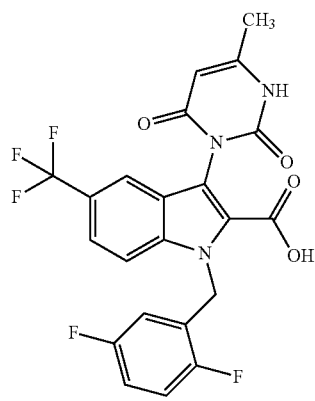 [SMILES: Cc1cc(=O)n(-c2c(C(=O)O)n(Cc3cc(F)ccc3F)c3ccc(C(F)(F)F)cc23)c(=O)[nH]1] | 479.4 |

-continued
| Compound No. | Structure | LCMS (M + H) |
|---|---|---|
| 261 | 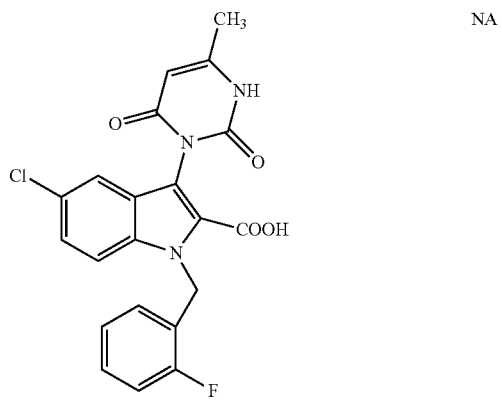 | NA |
| 262 | 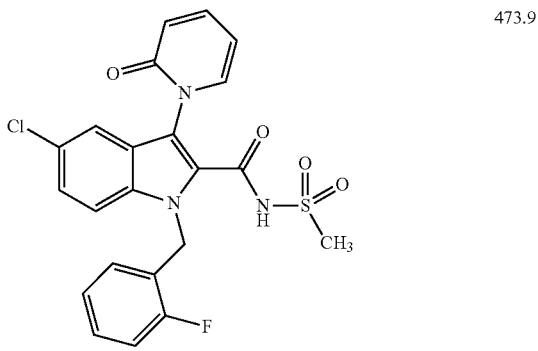 | 473.9 |
| 263 | 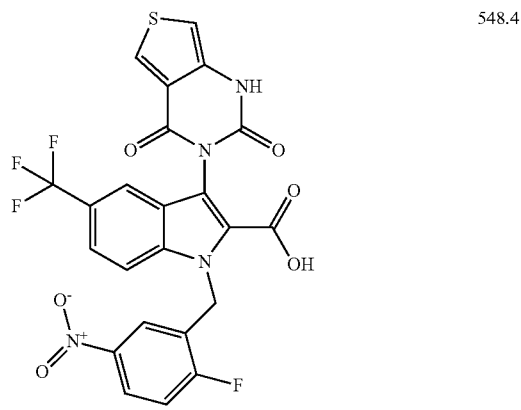 | 548.4 |

| Compound No. | Structure | LCMS (M + H) |
|---|---|---|
| 264 | 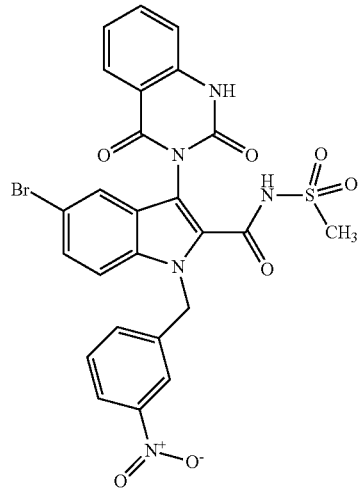 [SMILES: CS(=O)(=O)NC(=O)c1c(-n2c(=O)[nH]c3ccccc3c2=O)c2cc(Br)ccc2n1Cc1cccc([N+](=O)[O-])c1] | 612.4 |
| 265 | 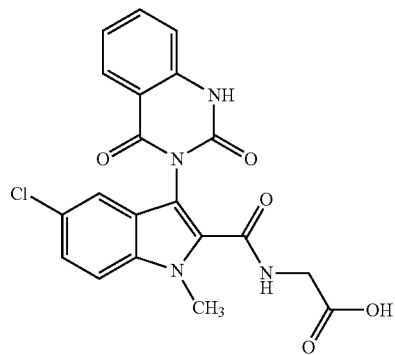 [SMILES: Cn1c(C(=O)NCC(=O)O)c(-n2c(=O)[nH]c3ccccc3c2=O)c2cc(Cl)ccc21] | 426.8 |
| 266 | 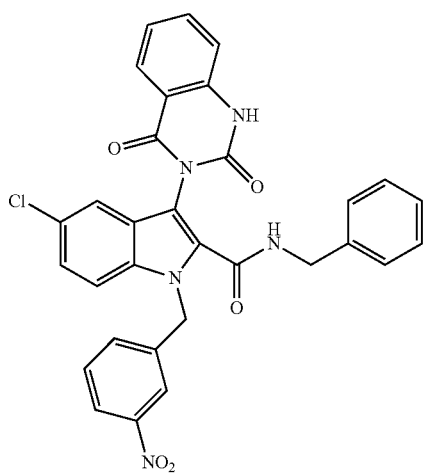 [SMILES: O=C(NCc1ccccc1)c1c(-n2c(=O)[nH]c3ccccc3c2=O)c2cc(Cl)ccc2n1Cc1cccc([N+](=O)[O-])c1] | 550.3 |

| Compound No. | Structure | LCMS (M + H) |
|---|---|---|
| 267 | 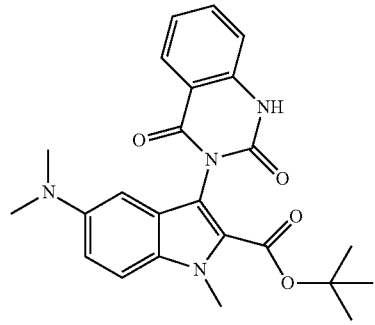 [SMILES: CN(C)c1ccc2c(c1)c(-n1c(=O)[nH]c3ccccc3c1=O)c(C(=O)OC(C)(C)C)n2C] | 435.2 |
| 268 | 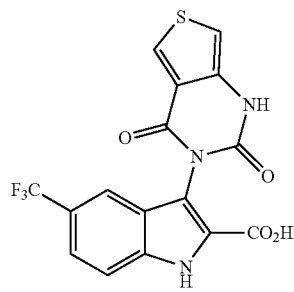 [SMILES: O=C(O)c1[nH]c2ccc(C(F)(F)F)cc2c1-n1c(=O)[nH]c2cscc2c1=O] | 396.2 |
| 269 | 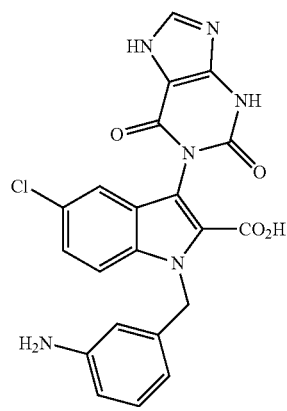 [SMILES: Nc1cccc(Cn2c(C(=O)O)c(-n3c(=O)[nH]c4nc[nH]c4c3=O)c3cc(Cl)ccc32)c1] | 451.2 |
| 270 | 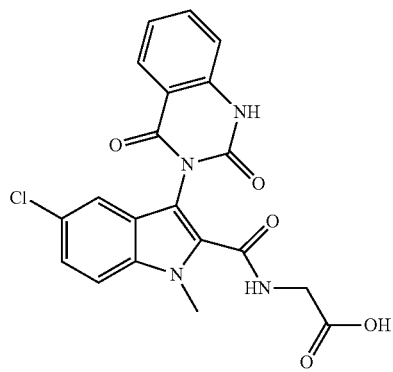 [SMILES: Cn1c(C(=O)NCC(=O)O)c(-n2c(=O)[nH]c3ccccc3c2=O)c2cc(Cl)ccc21] | 427.2 |

-continued
| Compound No. | Structure | LCMS (M + H) |
|---|---|---|
| 271 | 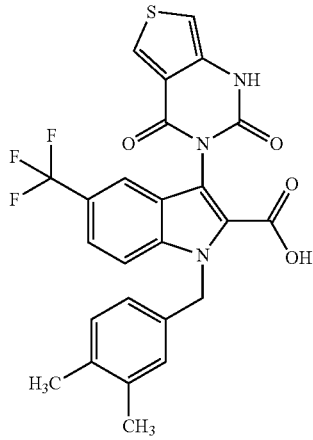 [SMILES: Cc1ccc(Cn2c(C(=O)O)c(-n3c(=O)[nH]c4cscc4c3=O)c3cc(C(F)(F)F)ccc32)cc1C] | 513.5 |
| 272 | 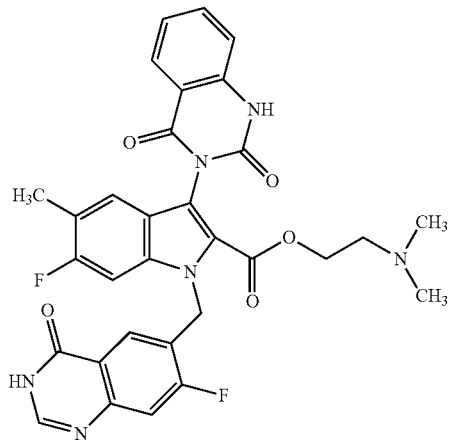 [SMILES: Cc1cc2c(-n3c(=O)[nH]c4ccccc4c3=O)c(C(=O)OCCN(C)C)n(Cc3cc4c(=O)[nH]cnc4cc3F)c2cc1F] | NA |
| 273 | 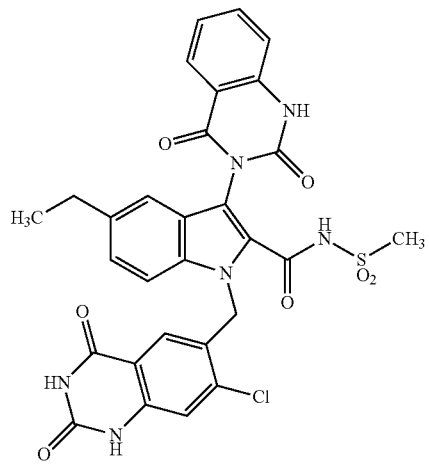 [SMILES: CCc1ccc2c(c1)c(-n1c(=O)[nH]c3ccccc3c1=O)c(C(=O)NS(C)(=O)=O)n2Cc1cc2c(=O)[nH]c(=O)[nH]c2cc1Cl] | NA |

| Compound No. | Structure | LCMS (M + H) |
|---|---|---|
| 274 | 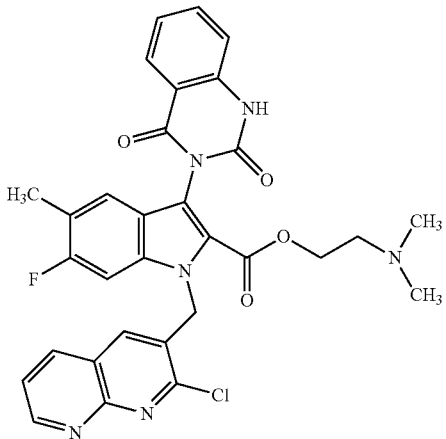 [SMILES: Cc1cc2c(-n3c(=O)[nH]c4ccccc4c3=O)c(C(=O)OCCN(C)C)n(Cc3cc4cccnc4nc3Cl)c2cc1F] | NA |
| 275 | 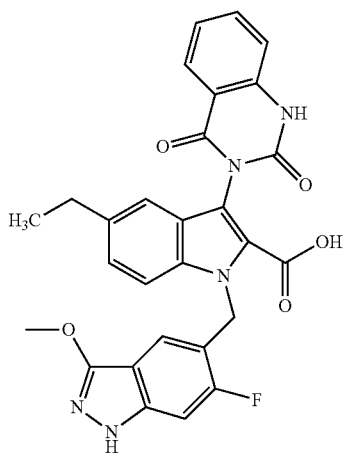 [SMILES: CCc1ccc2c(c1)c(-n1c(=O)[nH]c3ccccc3c1=O)c(C(=O)O)n2Cc1cc2c(OC)n[nH]c2cc1F] | NA |
| 276 | 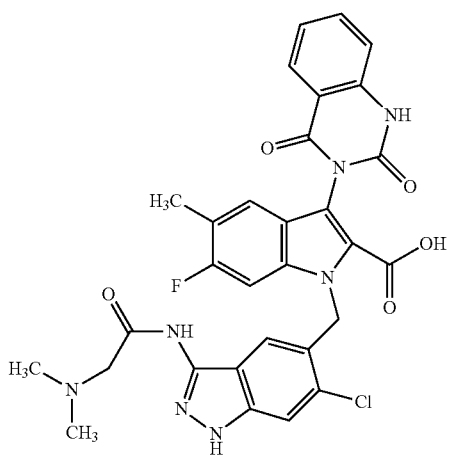 [SMILES: Cc1cc2c(-n3c(=O)[nH]c4ccccc4c3=O)c(C(=O)O)n(Cc3cc4c(NC(=O)CN(C)C)n[nH]c4cc3Cl)c2cc1F] | NA |

| Compound No. | Structure | LCMS (M + H) |
|---|---|---|
| 277 | 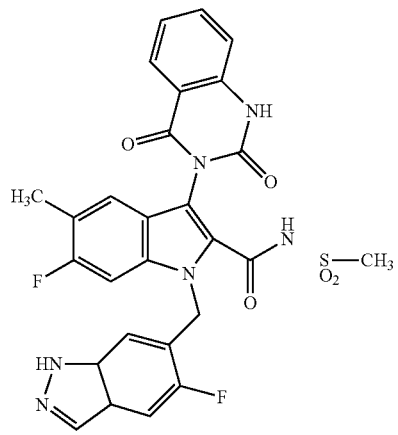 | NA |
| 278 | 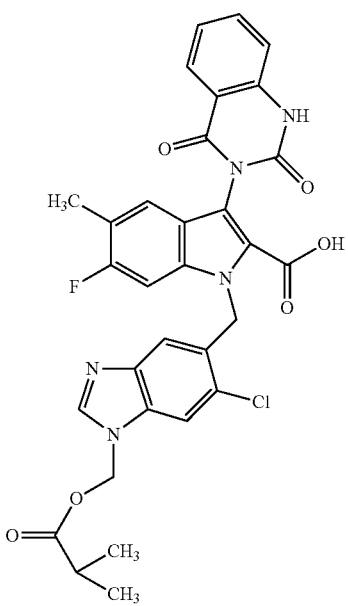 [SMILES: Cc1cc2c(-n3c(=O)[nH]c4ccccc4c3=O)c(C(=O)O)n(Cc3cc4ncn(COC(=O)C(C)C)c4cc3Cl)c2cc1F] | NA |
| 279 | 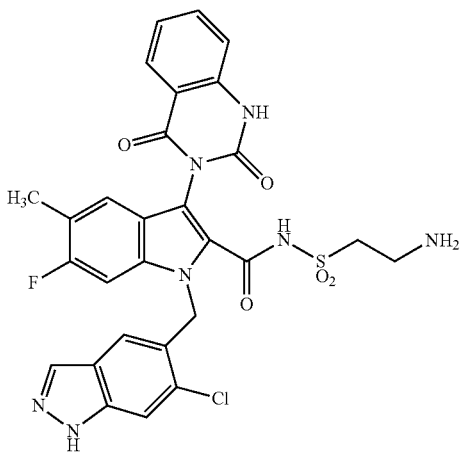 [SMILES: Cc1cc2c(-n3c(=O)[nH]c4ccccc4c3=O)c(C(=O)NS(=O)(=O)CCN)n(Cc3cc4cn[nH]c4cc3Cl)c2cc1F] | NA |

| Compound No. | Structure | LCMS (M + H) |
|---|---|---|
| 280 | 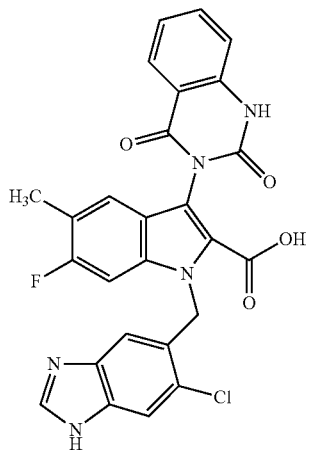 [SMILES: Cc1cc2c(-n3c(=O)[nH]c4ccccc4c3=O)c(C(=O)O)n(Cc3cc4nc[nH]c4cc3Cl)c2cc1F] | NA |
| 281 | 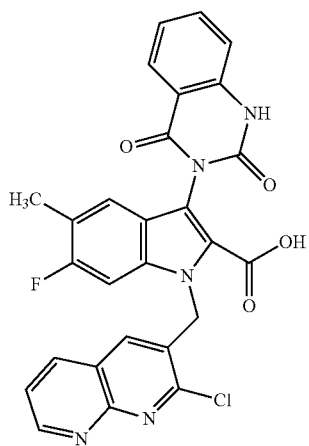 [SMILES: Cc1cc2c(-n3c(=O)[nH]c4ccccc4c3=O)c(C(=O)O)n(Cc3cc4cccnc4nc3Cl)c2cc1F] | NA |
| 282 | 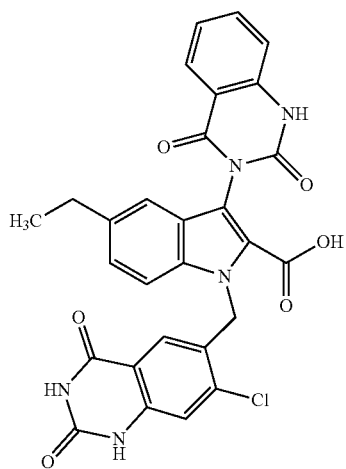 [SMILES: CCc1ccc2c(c1)c(-n1c(=O)[nH]c3ccccc3c1=O)c(C(=O)O)n2Cc1cc2c(=O)[nH]c(=O)[nH]c2cc1Cl] | NA |

-continued

| Compound No. | Structure | LCMS (M + H) |
|---|---|---|
| 283 | 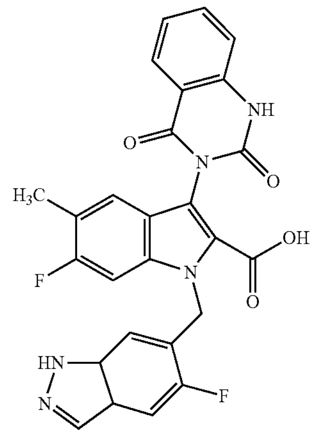 [SMILES: Cc1cc2c(-n3c(=O)[nH]c4ccccc4c3=O)c(C(=O)O)n(CC3=CC4NN=CC4C=C3F)c2cc1F] | NA |
| 284 | 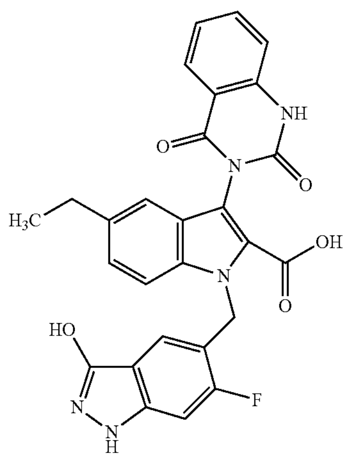 [SMILES: CCc1ccc2c(c1)c(-n1c(=O)[nH]c3ccccc3c1=O)c(C(=O)O)n2Cc1cc2c(O)n[nH]c2cc1F] | NA |
| 285 | 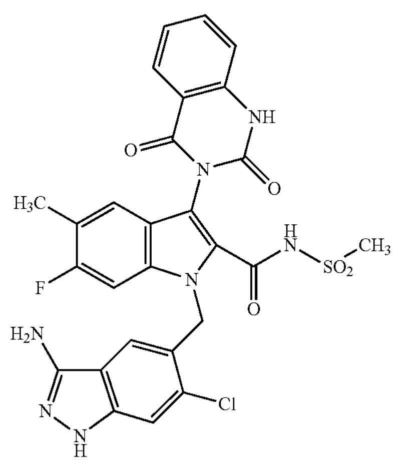 [SMILES: Cc1cc2c(-n3c(=O)[nH]c4ccccc4c3=O)c(C(=O)NS(C)(=O)=O)n(Cc3cc4c(N)n[nH]c4cc3Cl)c2cc1F] | NA |

NA = not available and pharmaceutically acceptable salts, solvates, esters and prodrugs thereof.

Methods for Making the 3-Heterocyclic Substituted Indole Derivatives

Methods useful for making the 3-Heterocyclic Substituted Indole Derivatives are set forth below in Schemes 1-8 and in the Examples section. Examples of commonly known methodologies useful for the synthesis of indoles are set forth, for example, in G. R. Humphrey and J. T. Kuethe, *Chemical Reviews* 106:2875-2911, 2006.

Scheme 1 sets forth a method for making compounds of formula A-4, which are useful intermediates for making the 3-Heterocyclic Substituted Indole Derivatives.

Scheme 1

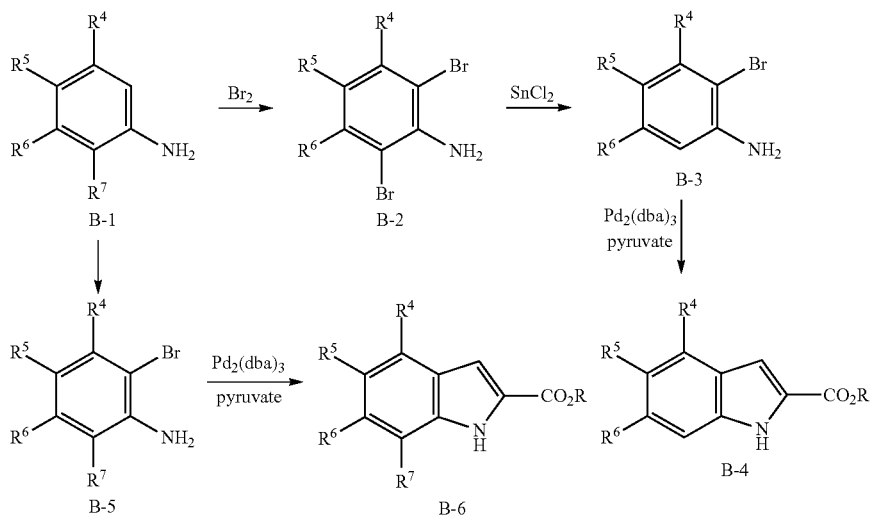

Scheme 2 wherein $R^4$, $R^5$, $R^6$ and $R^7$ are defined above for the compounds of formulas (I) and (II) and R is ethyl.

An aniline compound of formula A-1 can be converted to an indole compound of formula A-4 using the method outlined in Scheme 3, which is described in Nazare et al., *Angew. Chem.*, 116:4626-4629 (2004). Alternatively, the compounds of formula A-4 can be obtained from the compounds of formula A-1 using various indole syntheses that are well-known to those skilled in the art of organic synthesis, such as the Fischer indole synthesis.

Scheme 2 shows methods useful for making compounds of formulas B-4 and B-6, which are useful intermediates for making the 3-Heterocyclic Substituted Indole Derivatives.

-continued

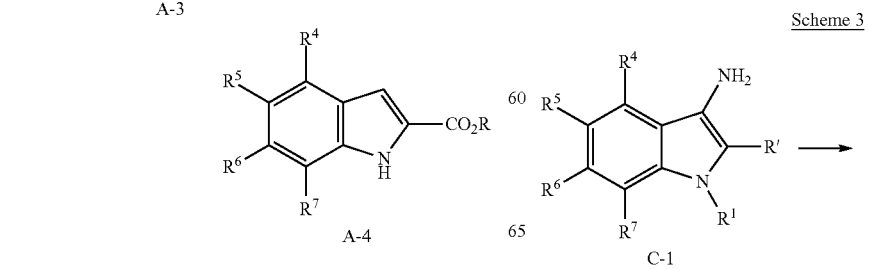

wherein $R^4$, $R^5$, $R^6$ and $R^7$ are defined above for the compounds of formulas (I) and (II) and R is ethyl.

A substituted aniline of formula B-1, wherein $R^7$ is H, can be di-brominated using bromine to provide the compounds of formula B-2. Selective de-bromination using tin(II) chloride provides the corresponding monobromo compounds of formula B-3, which can then undergo palladium-catalyzed cyclization in the presence of pyruvate to provide the compounds of formula B-4, wherein $R^7$ is H. Alternatively, a compound of formula B-1, wherein $R^7$ is other than H, can be monobrominated using bromine to provide the compounds of formula B-5. A compound of formula B-5 can then undergo palladium-catalyzed cyclization in the presence of pyruvate to provide the compounds of formula B-6, wherein $R^7$ is other than H.

Scheme 3 shows methods useful for making compounds of formula C-5, which are useful intermediates for making the 3-Heterocyclic Substituted Indole Derivatives.

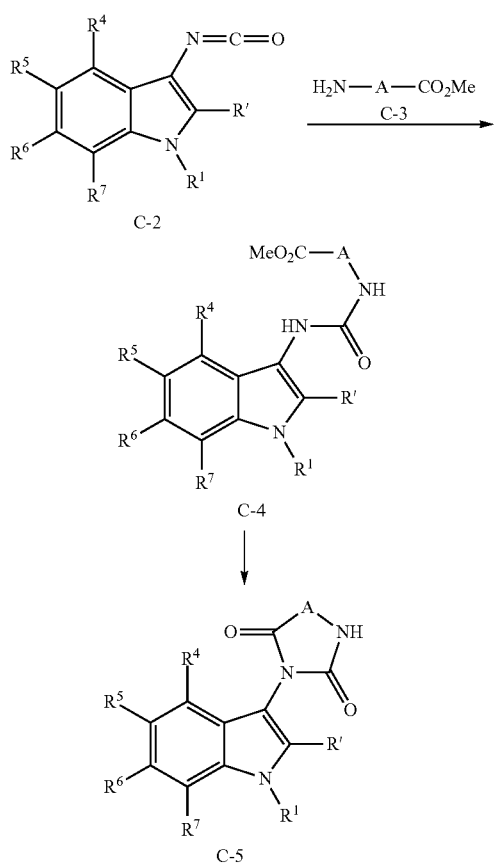

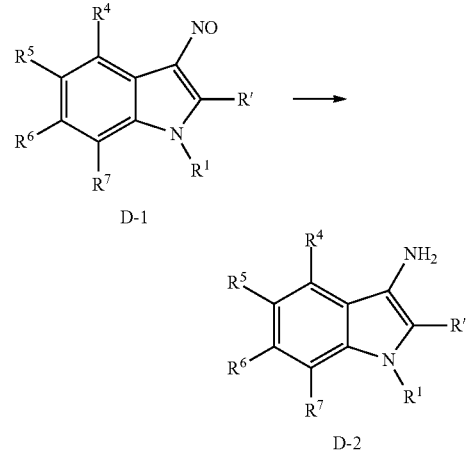

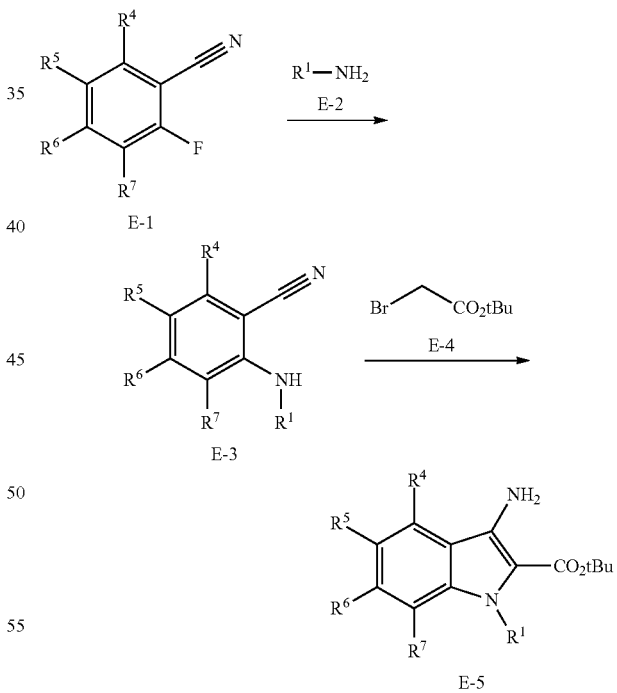

wherein $R^1$, $R^4$, $R^5$, $R^6$ and $R^7$ are defined above for the compounds of formulas (I) and (II) and R' is —C(O)O-alkyl.

Compounds of either formula A-4, B-4, or B-6 can be converted into compounds of formula D-1 by treatment with sodium nitrite (NaNO$_2$). Compounds of formula D-1 can be converted into compounds of formula D-2 by treatment with sodium hydrosulfite (Na$_2$S$_2$O$_4$).

Scheme 5 shows methods useful for making compounds of formula E-5, which are useful intermediates for making the 3-Heterocyclic Substituted Indole Derivatives.

wherein $R^1$, $R^4$, $R^5$, $R^6$ and $R^7$ are defined above for the compounds of formulas (I) and (II); A is alkylene, cycloalkylene, heterocycloalklene, arylene or heteroarylene; R' is —C(O)O-alkyl.

3-Amino indole compounds of formula C-1 can be converted into compounds of formula C-2 using triphosgene in the presence of a base, such as triethylamine. The compounds of formula C-2 can then be reacted with a compound of formula C-3 to provide the urea compounds of formula C-4. The compounds of formula C-4 can be converted into compounds of formula C-5 via a base-catalyzed ring closure using as base such as potassium tert-butoxide.

Scheme 4 shows methods useful for making compounds of formula C-5, which are useful intermediates for making the 3-Heterocyclic Substituted Indole Derivatives.

Scheme 4

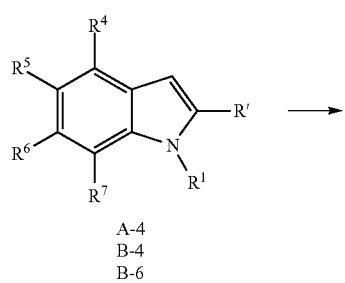

A-4
B-4
B-6 wherein $R^1$, $R^4$, $R^5$, $R^6$ and $R^7$ are defined above for the compounds of formulas (I) and (II).

Fluorophenyl compounds of formula E-1 can be reacted with an amine of formula E-2 in the presence of a base, such as diisopropylethylamine, to provide the aminophenyl compounds of formula E-3. The compounds of formula E-3 can then be reacted with ten-butyl bromoacetate (E-4) in the presence of a base, such as potassium tert-butoxide, to provide the 2-carboethoxy indole compounds of formula E-5.

Scheme 6 shows methods useful for making compounds of formula F-4, which correspond to the 3-Heterocyclic Substituted Indole Derivatives of formula (I), wherein $R^2$ is —C(O)N($R^9$)S(O)$_2$—$R^{11}$.

Scheme 6

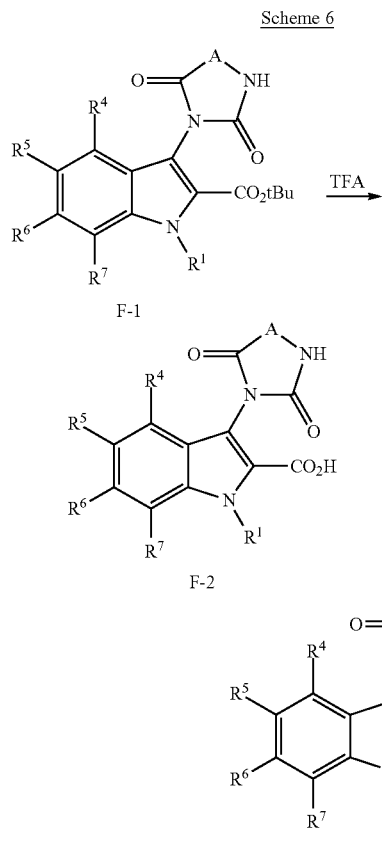

wherein $R^1$, $R^4$, $R^5$, $R^6$, $R^7$ and $R^{11}$ are defined above for the compounds of formula (I), and A is alkylene, cycloalkylene, heterocycloalklene, arylene or heteroarylene.

The compounds of formula F-1 can be treated with trifluoroacetic acid to provide the compounds of formula F-2. Compounds of formula F-2 can then be reacted with a compound of formula F-3 in the presence of a base, such as 1,8-diazabicyclo[5.4.0]undec-7-ene (DBU), to provide the compounds of formula F-4.

Scheme 7 shows a method useful for making compounds of formula J, which correspond to the compounds of formula (II), wherein $R^2$ is an amide.

Scheme 7

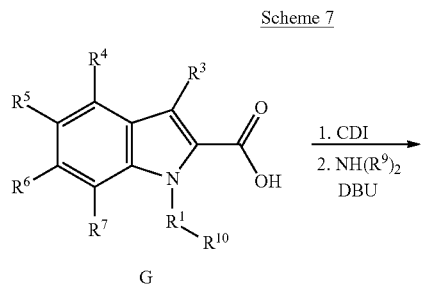

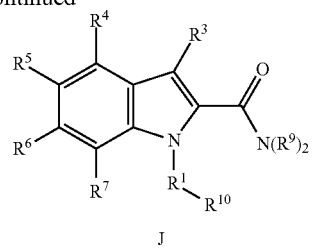

wherein $R^1$, $R^3$, $R^4$, $R^5$, $R^6$, $R^7$, $R^9$ and $R^{10}$ are defined above for the compounds of formulas (I) and (II).

A 2-carboxy indole compound of formula G can be coupled with an amine of formula NH($R^9$)$_2$ in the presence of carbonyldiimidazole (CDI) and 1,8-diazabicyclo[5.4.0]undec-7-ene (DBU) to provide the compounds of formula J, which correspond to the Compounds of Formula (I) wherein $R^2$ is —C(O)N($R^9$)$_2$.

Scheme 8 shows a method useful for making the Compounds of Formula (I), wherein $R^2$ is:

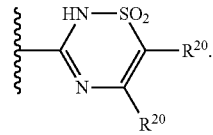

Scheme 8

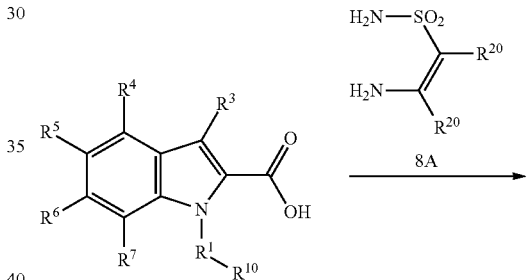

wherein $R^1$, $R^3$, $R^4$, $R^5$, $R^6$, $R^7$, $R^{10}$ and $R^{20}$ are defined above for the compounds of formulas (I) and (II).

A 2-carboxy indole compound of formula G can be reacted with a compound of formula 8A to provide the compounds of formula K, which correspond to the 3-Heterocyclic Substituted Indole Derivatives wherein $R^2$ is:

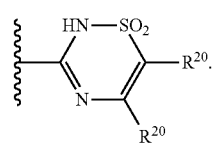

The starting material and reagents depicted in Schemes 1-8 are either available from commercial suppliers such as Sigma-Aldrich (St. Louis, Mo.) and Acros Organics Co. (Fair Lawn, N.J.), or can be prepared using methods well-known to those of skill in the art of organic synthesis.

One skilled in the art will recognize that the synthesis of 3-Heterocyclic Substituted Indole Derivatives may require the need for the protection of certain functional groups (i.e., derivatization for the purpose of chemical compatibility with a particular reaction condition). Suitable protecting groups for the various functional groups of the 3-Heterocyclic Substituted Indole Derivatives and methods for their installation and removal may be found in Greene et al., *Protective Groups in Organic Synthesis*, Wiley-Interscience, New York, (1999).

One skilled in the art will recognize that one route will be optimal depending on the choice of appendage substituents. Additionally, one skilled in the art will recognize that in some cases the order of steps has to be controlled to avoid functional group incompatibilities. One skilled in the art will recognize that a more convergent route (i.e. non-linear or preassembly of certain portions of the molecule) is a more efficient method of assembly of the target compounds. Methods suitable for the preparation of 3-Heterocyclic Substituted Indole Derivatives are set forth above in Schemes 1-8.

One skilled in the art will recognize that the synthesis of the 3-Heterocyclic Substituted Indole Derivatives may require the construction of an amide bond. Methods include but are not limited to the use of a reactive carboxy derivative (e.g. acid halide, or ester at elevated temperatures) or the use of an acid with a coupling reagent (e.g. DECI, DCC) with an amine at 0° C. to 100° C. Suitable solvents for the reaction are halogenated hydrocarbons, ethereal solvents, dimethyl formamide and the like. The reaction can be conducted under pressure or in a sealed vessel.

The starting materials and the intermediates prepared using the methods set forth in Schemes 1-8 may be isolated and purified if desired using conventional techniques, including but not limited to filtration, distillation, crystallization, chromatography and the like. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column. Altech platinum C18, 3 micron, 33 mm×7 mm ID; gradient flow: 0 min—10% CH$_3$CN, 5 min—95% CH$_3$CN, 5-7 min—95% CH$_3$CN, 7 min—stop. The retention time and observed parent ion are given. Flash column chromatography was performed using pre-packed normal phase silica from Biotage, Inc. or bulk silica from Fisher Scientific.

Example 1

Preparation of Compound 30

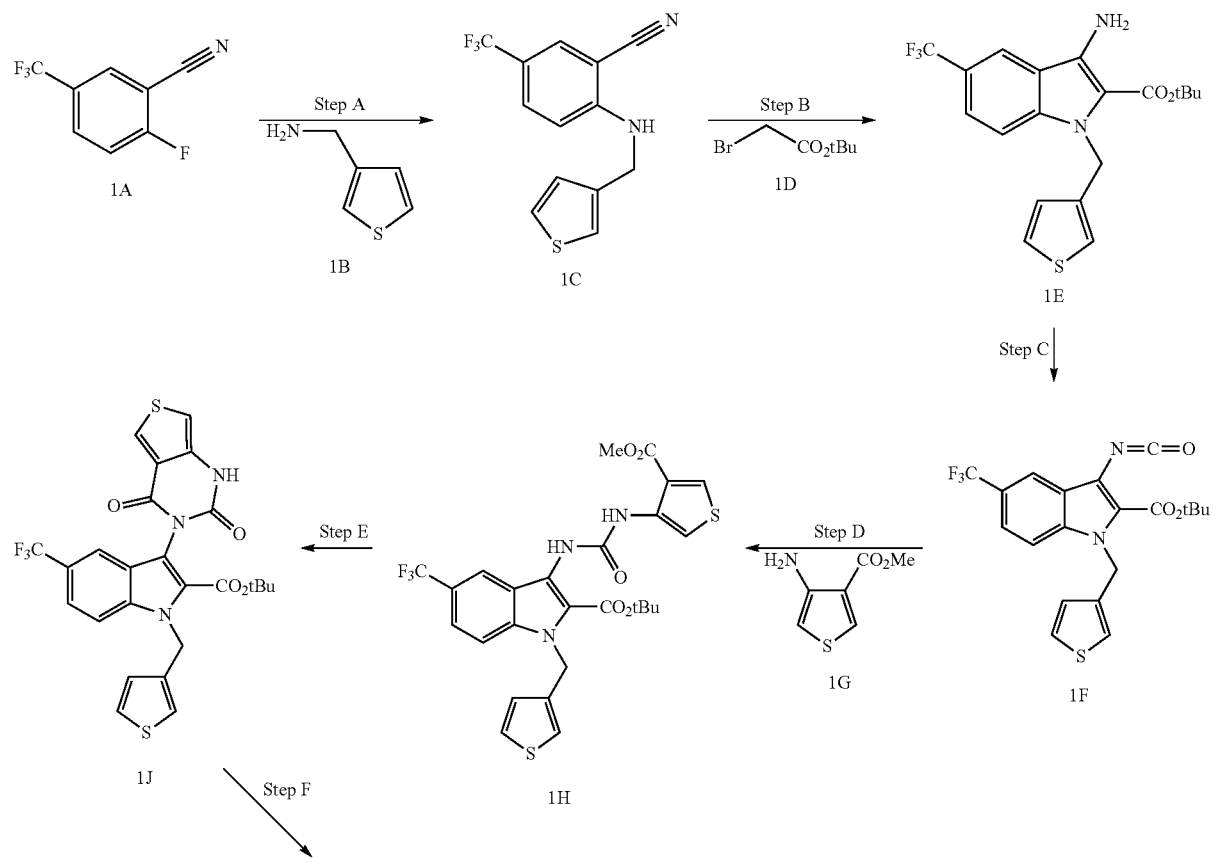

-continued

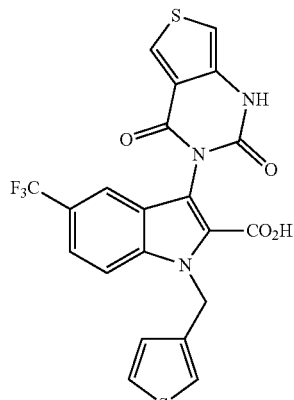

30

Step A—Synthesis of Compound 1C

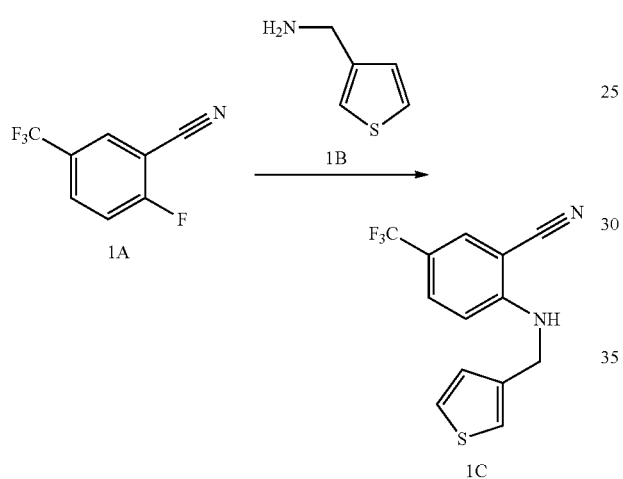

To a solution of 2-fluoro-5-trifluoromethylbenzonitrile 1A (1.11 g, 5.87 mmol) and 3-(aminomethyl)thiophene 1B (1.0 g, 8.85 mmol) in trifluoromethylbenzene (10 mL) was added diisopropylethylamine (2.3 g, 17.8 mmol). The reaction mixture was heated in a microwave reactor at 160° C. for 30 minutes. Ethyl acetate (100 mL) was added and the organic layer was washed with 1 N hydrochloric acid and brine. The organic layer was dried over sodium sulfate. The organic solvent was evaporated under reduced pressure to provide 2-[(thiophen-3-yl-methyl)amino]-5-trifluoromethylbenzonitrile 1C (1.42 g, 5.04 mmol) which was used in the next step without further purification.

Step B—Synthesis of Compound 1E

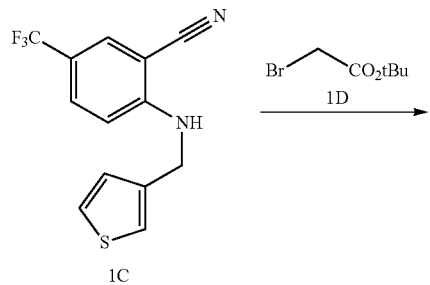

To a solution of 2-[(thiophen-3-yl-methyl)amino]-5-trifluoromethylbenzonitrile 1C (1.42 g, 5.04 mmol) in anhydrous tetrahydrofuran (THF) (10 mL) and anhydrous N,N-dimethylformamide (DMF) (10 mL) at 0° C. was added potassium tert-butoxide (1.13 g, 10.1 mmol). The reaction mixture was stirred at 0° C. for 5 minutes and tert-butyl bromoacetate 1D (1.47 g, 7.54 mmol) was added. The reaction mixture was stirred at room temperature overnight. Ethyl acetate (100 mL) was added and the organic layer was washed with 1 N hydrochloric acid and brine. The organic layer was dried over sodium sulfate. The organic solvent was evaporated under reduced pressure. The crude product was purified by flash column chromatography to provide 3-amino-1-thiophen-3-yl-methyl-5-trifluoromethyl-1H-indole-2-carboxylic acid tert-butyl ester 1E (1.74 g, 4.39 mmol).

Step C—Synthesis of Compound 1F

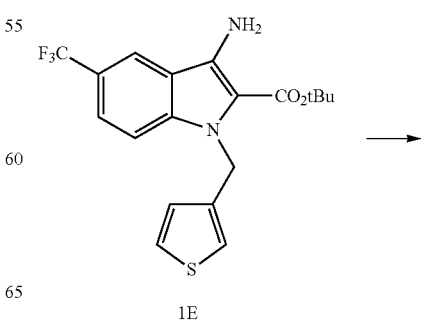

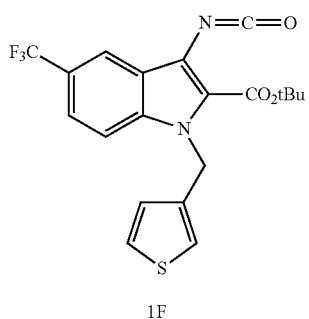

1F

To a solution of 3-amino-1-thiophen-3-yl-methyl-5-trifluoromethyl-1H-indole-2-carboxylic acid tert-butyl ester 1E (1.74 g, 4.39 mmol) in anhydrous toluene (50 mL) was added triphosgene (0.44 g, 1.48 mmol) and triethylamine (0.89 g, 8.81 mmol). The reaction mixture was heated at reflux for 3 hours. Toluene (50 mL) was added and the organic layer was washed with water and brine. The organic layer was dried over sodium sulfate. The organic solvent was evaporated under reduced pressure to provide 3-isocyanato-1-thiophen-3-yl-methyl-5-trifluoromethyl-1H-indole-2-carboxylic acid tert-butyl ester 1F which was used in the next step without further purification.

Step D—Synthesis of Compound 1H

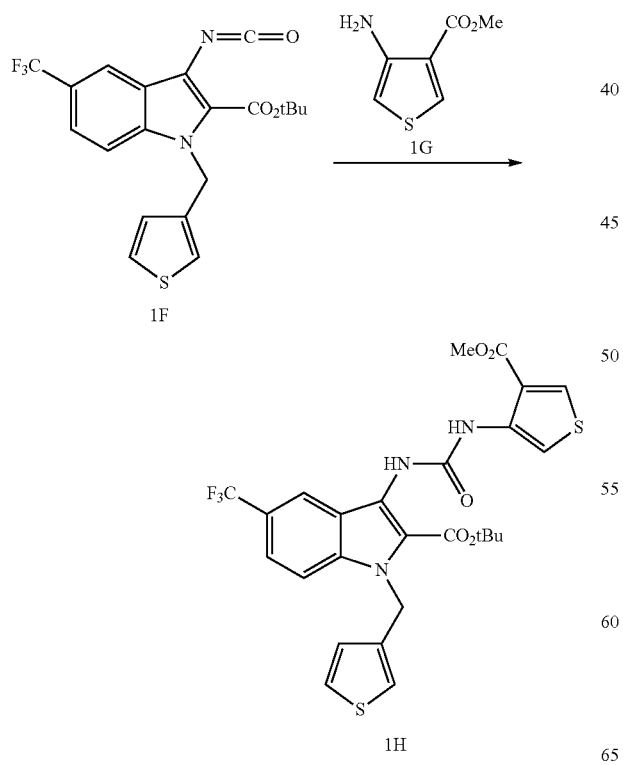

To a solution of 3-isocyanato-1-thiophen-3-yl-methyl-5-trifluoromethyl-1H-indole-2-carboxylic acid tert-butyl ester 1F (~4.39 mmol) in trifluoromethylbenzene (10 mL) was added 4-aminothiophene-3-carboxylic acid methyl ester 1G (1.38 g, 8.79 mmol). The reaction mixture was heated in a microwave reactor at 150° C. for 20 minutes. Ethyl acetate (100 mL) was added and the organic layer was washed with 1 N hydrochloric acid and brine. The organic layer was dried over sodium sulfate. The organic solvent was evaporated under reduced pressure. The crude product was purified by flash column chromatography to provide 3-[3-(4-methoxycarbonyl-thiophen-3-yl)-ureido]-1-thiophen-3-yl-methyl-5-trifluoromethyl-1H-indole-2-carboxylic acid tert-butyl ester 1H (1.50 g, 2.59 mmol).

Step E—Synthesis of Compound 1J

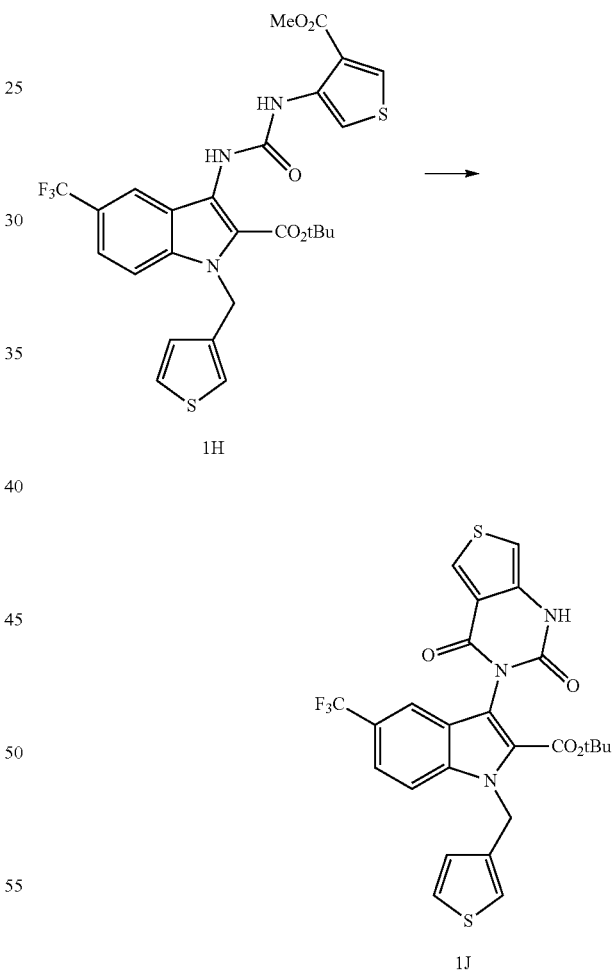

To a solution of 3-[3-(4-methoxycarbonyl-thiophen-3-yl)-ureido]-1-thiophen-3-yl-methyl-5-trifluoromethyl-1H-indole-2-carboxylic acid tert-butyl ester 1H (1.50 g, 2.59 mmol) in anhydrous methanol (10 mL) was added a 0.5 M solution of sodium methoxide (7.8 mL, 3.90 mmol). The reaction mixture was heated in a microwave reactor at 100° C.

for 20 minutes. Ethyl acetate (100 mL) was added and the organic layer was washed with 1 N hydrochloric acid and brine. The organic layer was dried over sodium sulfate. The organic solvent was evaporated under reduced pressure to provide 3-(2,4-dioxo-1,2-dihydro-4H-thieno[3,4-d]pyrimidin-3-yl)-1-thiophen-3-yl-methyl-5-trifluoromethyl-1H-indole-2-carboxylic acid tert-butyl ester 1J which was used in the next step without further purification.

Step F—Synthesis of Compound 30

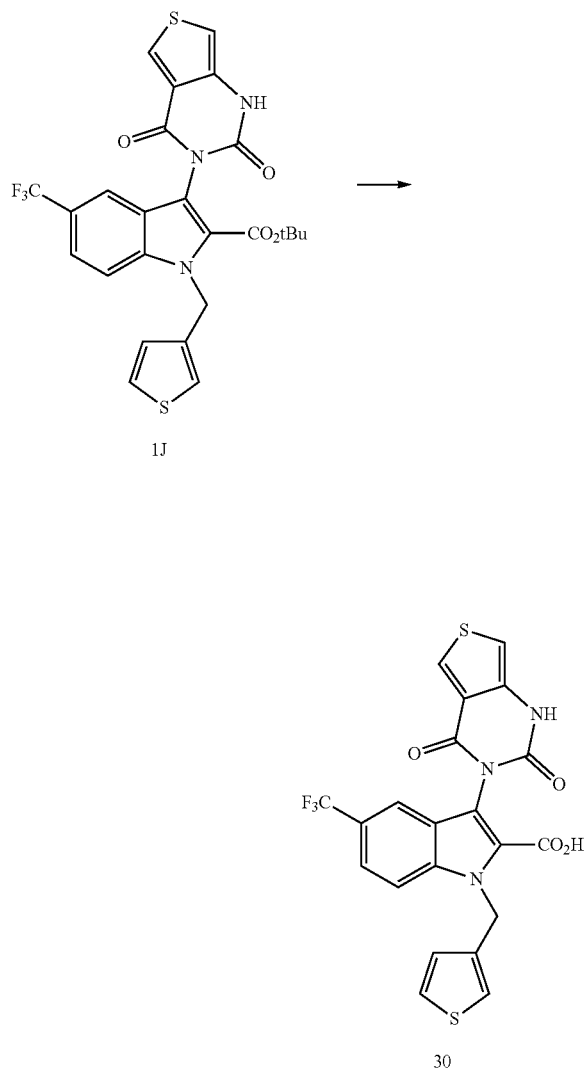

1J

30

To a sample of 3-(2,4-dioxo-1,2-dihydro-4H-thieno[3,4-d]pyrimidin-3-yl)-1-thiophen-3-yl-methyl-5-trifluoromethyl-1H-indole-2-carboxylic acid tert-butyl ester 1J (~2.59 mmol) was added a 30% v/v solution of trifluoroacetic acid in dichloromethane (20 mL). The reaction mixture was stirred at room temperature for 3 hours. The organic solvent was evaporated under reduced pressure. A sample of the crude product (60 mg) was purified by RP-HPLC to provide compound 30 (34 mg, 0.069 mmol).

Example 2

Preparation of Compound 98

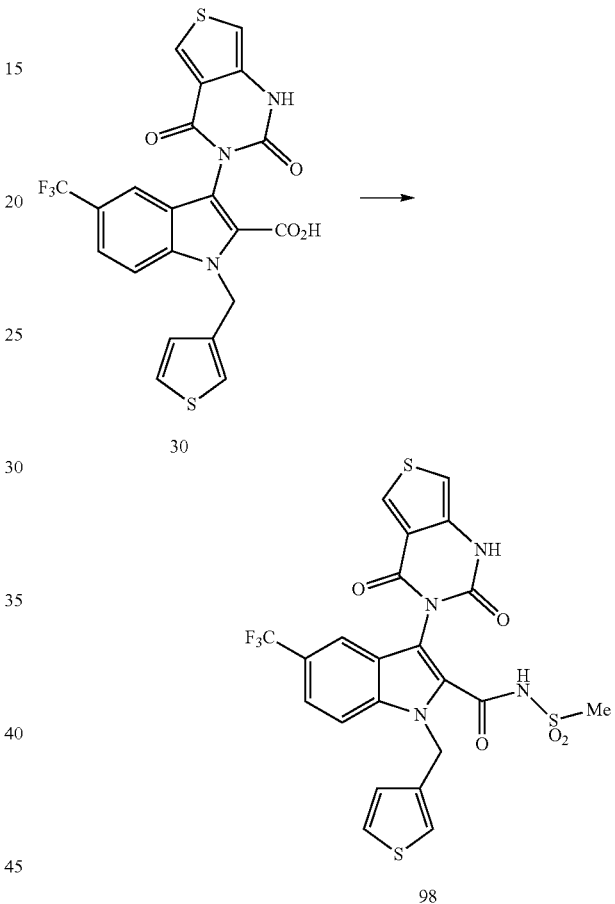

30

98

To a solution of compound 30 (0.20 g, 0.41 mmol) in anhydrous THF (3 mL) and anhydrous DMF (1 mL) was added N,N'-carbonyldiimidazole (66 mg, 0.41 mmol). The reaction mixture was heated at 80° C. overnight. The reaction mixture was allowed to cool to room temperature and methanesulfonamide (39 mg, 0.41 mmol) was added. The reaction mixture was stirred at room temperature for 5 minutes and 1,8-diazabicyclo[5.4.0]undec-7-ene (DBU) (62 mg, 0.41 mmol) was added. The reaction mixture was stirred at room temperature overnight. Ethyl acetate (50 mL) was added and the organic layer was washed with 1 N hydrochloric acid and brine. The organic layer was dried over sodium sulfate. The organic solvent was evaporated under reduced pressure. The crude product was purified by RP-HPLC to provide compound 98 (0.156 g, 0.27 mmol).

Example 3

Preparation of Compound 266

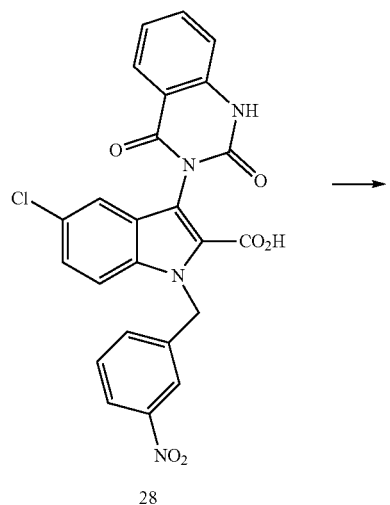

28

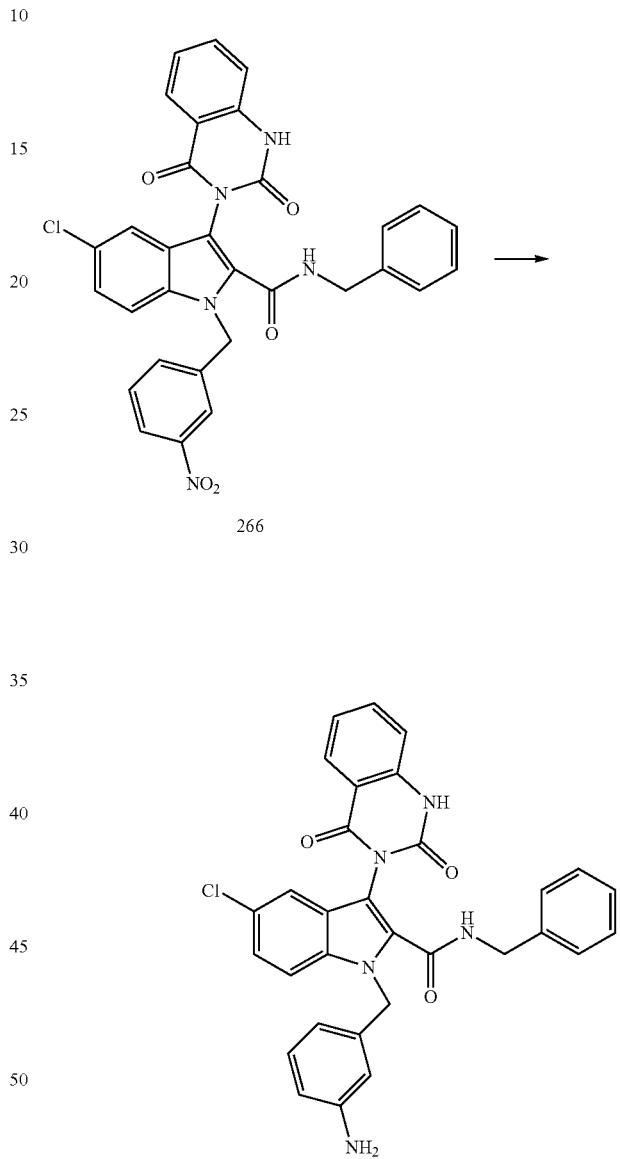

266

To a solution of 5-chloro-3-(2,4-dioxo-1,4-dihydro-2H-quinazolin-3-yl)-1-(3-nitrobenzyl)-1H-indole-2-carboxylic acid 28 (30 mg, 0.061 mmol) in DMF (2 mL) was added benzylamine (13 mg, 0.12 mmol), O-(7-azabenzotriazol-1-yl)-N,N,N',N'-tetramethyluronium hexafluoro-phosphate (HATU) (46 mg, 0.12 mmol) and diisopropylethylamine (16 mg, 0.12 mmol). The reaction mixture was stirred at room temperature overnight. Ethyl acetate (50 mL) was added and the organic layer was washed with 1 N hydrochloric acid and brine. The organic layer was dried over sodium sulfate. The organic solvent was evaporated under reduced pressure. The crude product was purified by RP-HPLC to provide compound 266 (19 mg, 0.033 mmol).

Example 4

Preparation of Compound 127

To a solution of compound 266 (19 mg, 0.033 mmol) in ethanol (3 mL) was added stannous chloride dihydrate (30 mg, 0.13 mmol). The reaction mixture was heated in a microwave reactor at 120° C. for 20 minutes. The solvent was evaporated under reduced pressure. The crude product was purified by RP-HPLC to provide compound 127 (12 mg, 0.022 mmol).

Example 5
Preparation of Compound 65
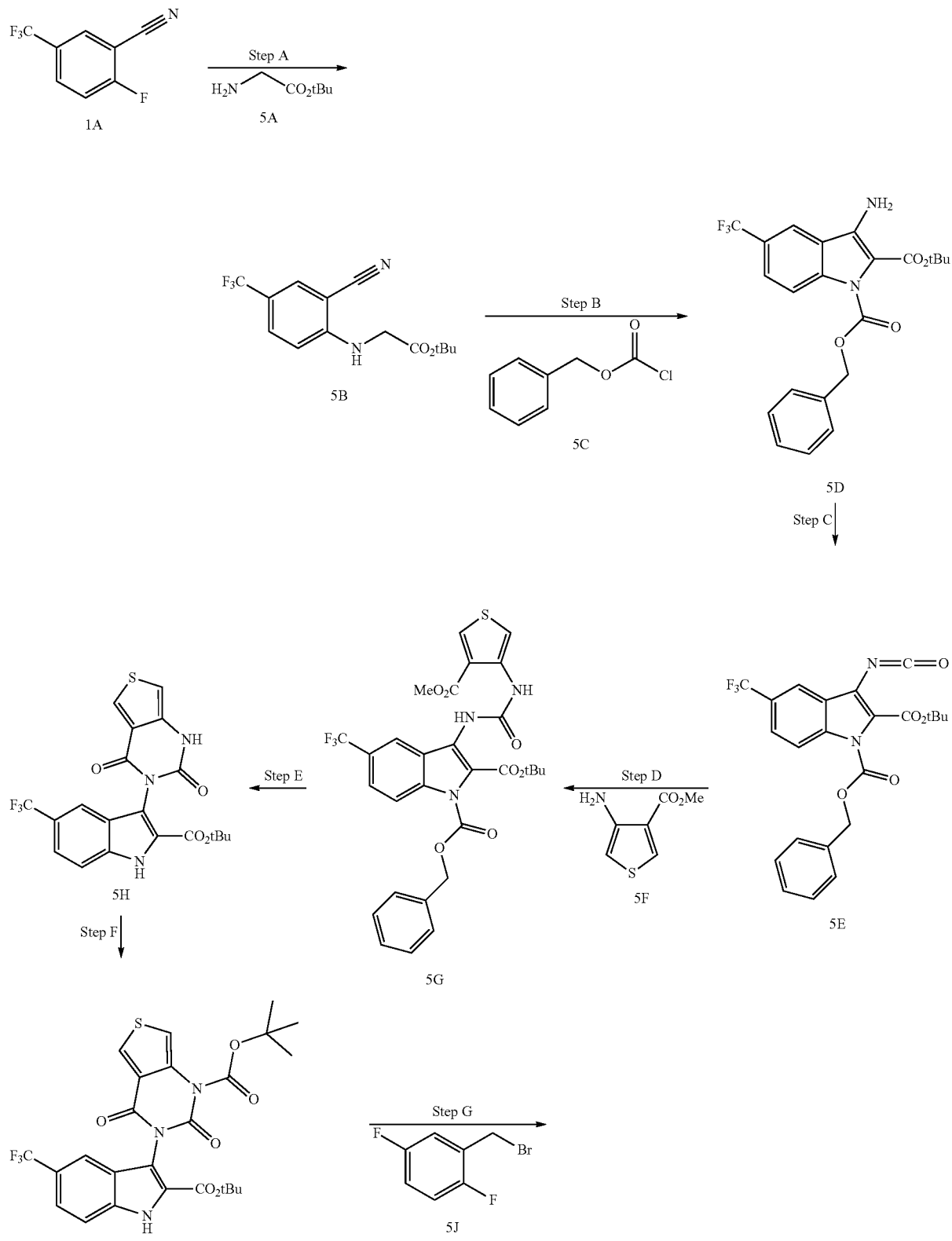

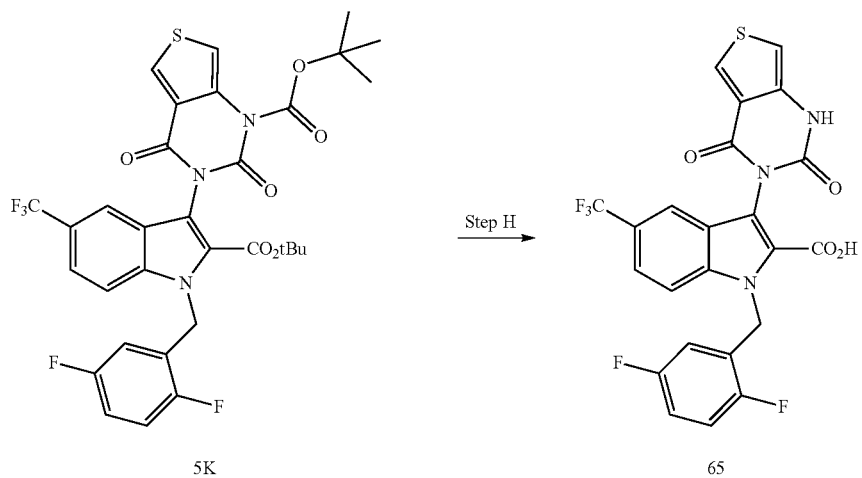 [SMILES: CC(C)(C)OC(=O)c1c(-n2c(=O)c3cscc3n(C(=O)OC(C)(C)C)c2=O)c2cc(C(F)(F)F)ccc2n1Cc1cc(F)ccc1F ; O=C(O)c1c(-n2c(=O)[nH]c3cscc3c2=O)c2cc(C(F)(F)F)ccc2n1Cc1cc(F)ccc1F]

5K

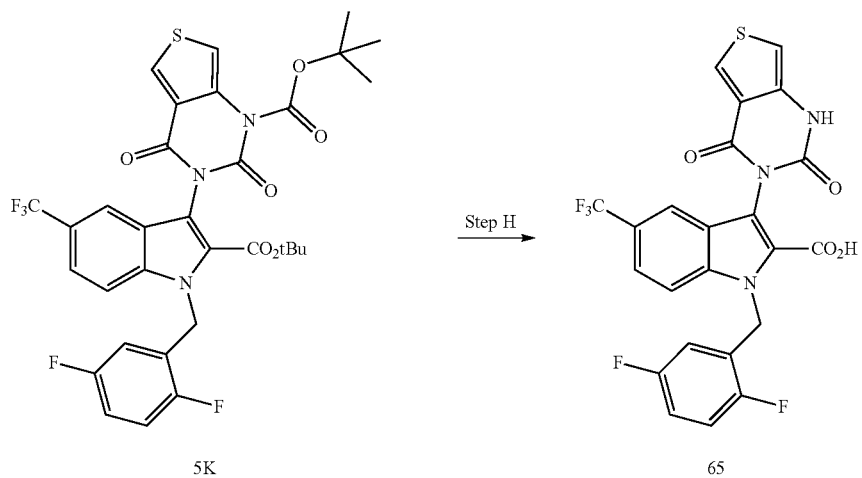 [SMILES: CC(C)(C)OC(=O)c1c(-n2c(=O)c3cscc3n(C(=O)OC(C)(C)C)c2=O)c2cc(C(F)(F)F)ccc2n1Cc1cc(F)ccc1F ; O=C(O)c1c(-n2c(=O)[nH]c3cscc3c2=O)c2cc(C(F)(F)F)ccc2n1Cc1cc(F)ccc1F]

65

Step A—Synthesis of Compound 5B

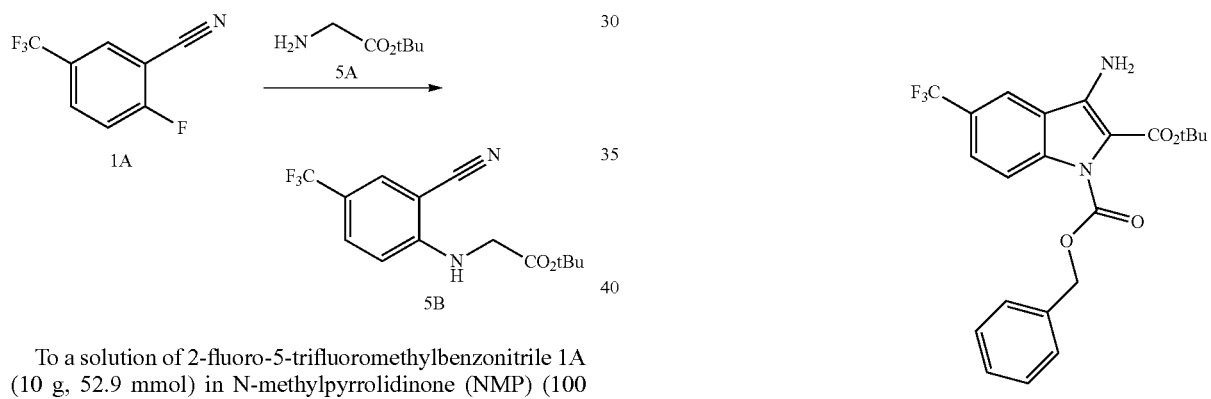

To a solution of 2-fluoro-5-trifluoromethylbenzonitrile 1A (10 g, 52.9 mmol) in N-methylpyrrolidinone (NMP) (100 mL) was added glycine tert-butyl ester 5A (13.8 g, 105 mmol) and diisopropylethylamine (20 g, 155 mmol). The reaction mixture was heated at 110° C. for 4 hours. Ethyl acetate (500 mL) was added and the organic layer was washed with water and brine. The organic layer was dried over sodium sulfate. The organic solvent was evaporated under reduced pressure. The crude product was purified by flash column chromatography to provide (2-cyano-4-trifluoromethylphenylamino) acetic acid tert-butyl ester 5B (15.2 g, 50.7 mmol).

Step B—Synthesis of Compound 5D

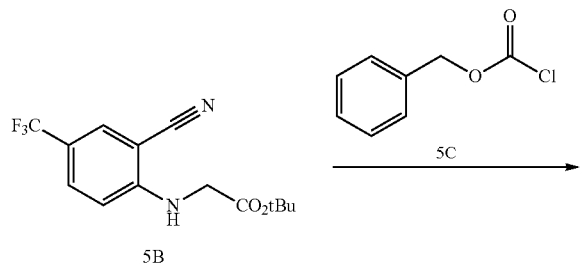

-continued

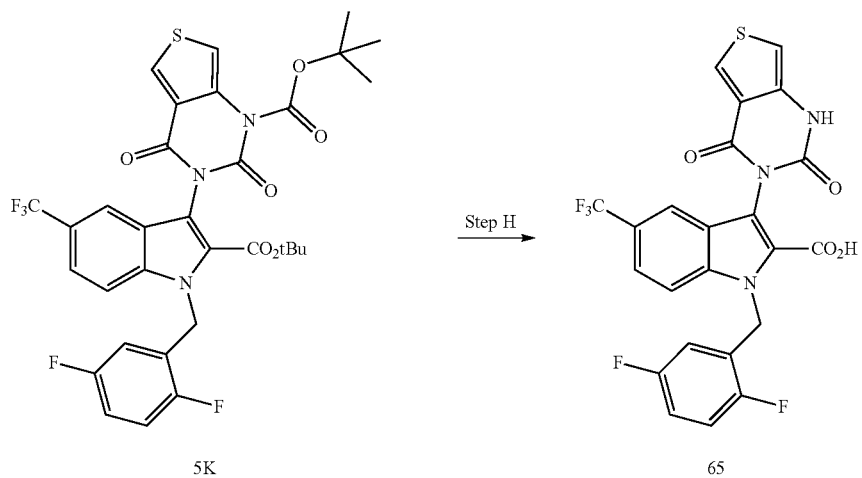 [SMILES: CC(C)(C)OC(=O)c1c(-n2c(=O)c3cscc3n(C(=O)OC(C)(C)C)c2=O)c2cc(C(F)(F)F)ccc2n1Cc1cc(F)ccc1F ; O=C(O)c1c(-n2c(=O)[nH]c3cscc3c2=O)c2cc(C(F)(F)F)ccc2n1Cc1cc(F)ccc1F]

5D

To a solution of (2-cyano-4-trifluoromethylphenylamino) acetic acid tert-butyl ester 5B (11.7 g, 39.0 mmol) in anhydrous THF (60 mL) and anhydrous DMF (60 mL) at 0° C. was added potassium tert-butoxide (8.74 g, 78.0 mmol). The reaction mixture was stirred at 0° C. for 5 minutes and benzyl chloroformate 5C (10 g, 58.7 mmol) was added. The reaction mixture was stirred at room temperature for 4 hours. Ethyl acetate (500 mL) was added and the organic layer was washed with water and brine. The organic layer was dried over sodium sulfate. The organic solvent was evaporated under reduced pressure. The crude product was purified by flash column chromatography to provide 3-amino-1-benzyloxycarbonyl-5-trifluoromethylindole-2-carboxylic acid tert-butyl ester 5D (5.96 g, 13.7 mmol).

Step C—Synthesis of Compound 5F

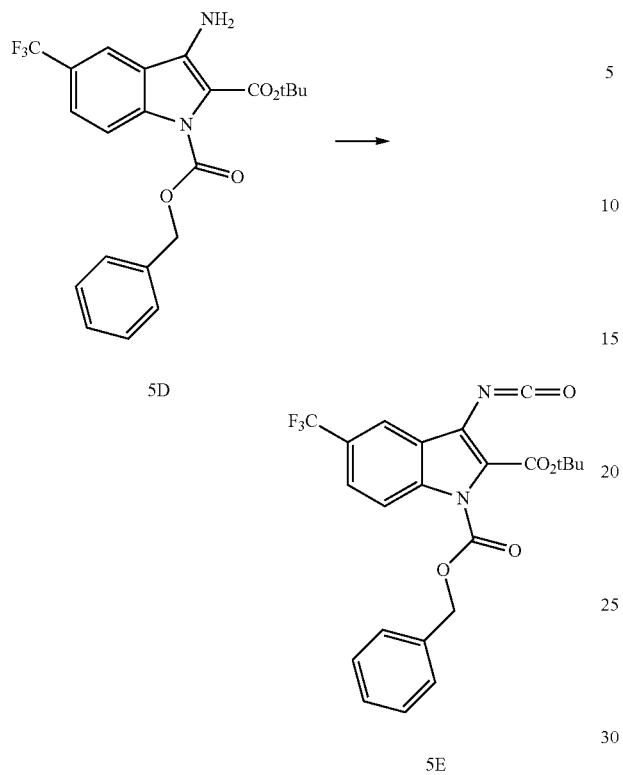

To a solution of 3-amino-1-benzyloxycarbonyl-5-trifluoromethylindole-2-carboxylic acid tert-butyl ester 5D (1.78 g, 4.10 mmol) in anhydrous toluene (40 mL) was added triphosgene (0.42 g, 1.41 mmol) and triethylamine (0.83 g, 8.22 mmol). The reaction mixture was heated under reflux for 2 hours. Toluene (50 mL) was added and the organic layer was washed with water and brine. The organic layer was dried over sodium sulfate. The organic solvent was evaporated under reduced pressure to provide 1-benzyloxycarbonyl-3-isocyanato-5-trifluoromethylindole-2-carboxylic acid tert-butyl ester 5E which was used in the next step without further purification.

Step D—Synthesis of Compound 5G

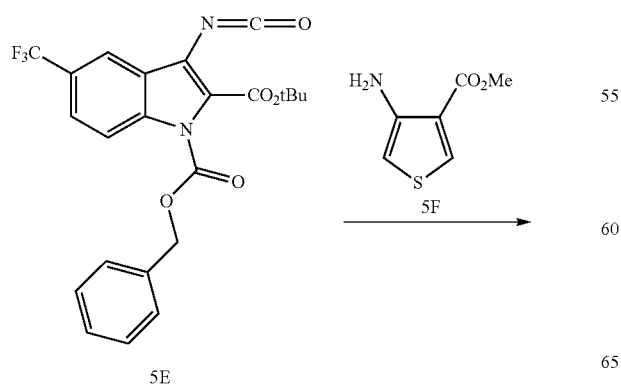

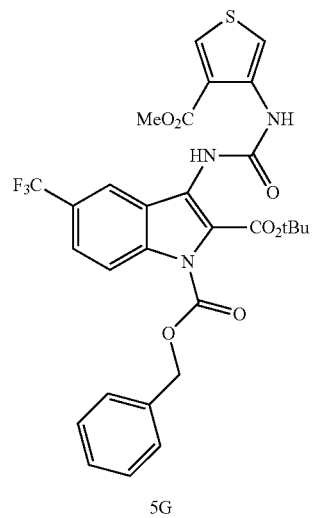

To a solution of 1-benzyloxycarbonyl-3-isocyanato-5-trifluoromethylindole-2-carboxylic acid tert-butyl ester 5E (~4.10 mmol) in trifluoromethylbenzene (10 mL) was added 4-aminothiophene-3-carboxylic acid methyl ester 5F (1.30 g, 8.28 mmol). The reaction mixture was heated in a microwave reactor at 150° C. for 30 minutes. Ethyl acetate (100 mL) was added and the organic layer was washed with 1 N hydrochloric acid and brine. The organic layer was dried over sodium sulfate. The organic solvent was evaporated under reduced pressure. The crude product was purified by flash column chromatography to provide 1-benzyloxycarbonyl-3-[3-(4-methoxycarbonylthiophen-3-yl)-ureido]-5-trifluoromethyl-1H-indole-2-carboxylic acid tert-butyl ester 5G (1.89 g, 3.06 mmol).

Step E—Synthesis of Compound 5H

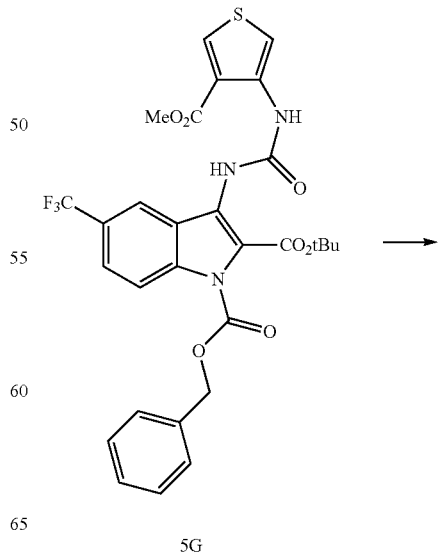

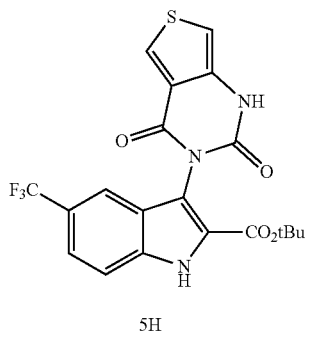

5H

To a solution of 1-benzyloxycarbonyl-3-[3-(4-methoxycarbonylthiophen-3-yl)-ureido]-5-trifluoromethyl-1H-indole-2-carboxylic acid tert-butyl ester 5G (5.29 g, 8.57 mmol) in anhydrous methanol (50 mL) was added a 0.5 M solution of sodium methoxide (25 mL, 12.5 mmol). The reaction mixture was heated in a microwave reactor at 100° C. for 10 minutes. Ethyl acetate (500 mL) was added and the organic layer was washed with 1 N hydrochloric acid and brine. The organic layer was dried over sodium sulfate. The organic solvent was evaporated under reduced pressure. The crude product was purified by flash column chromatography to provide 3-(2,4-dioxo-1,2-dihydro-4H-thieno[3,4-d]pyrimidin-3-yl)-5-trifluoromethyl-1H-indole-2-carboxylic acid tert-butyl ester 5H (3.36 g, 7.45 mmol).

Step F—Synthesis of Compound 5I

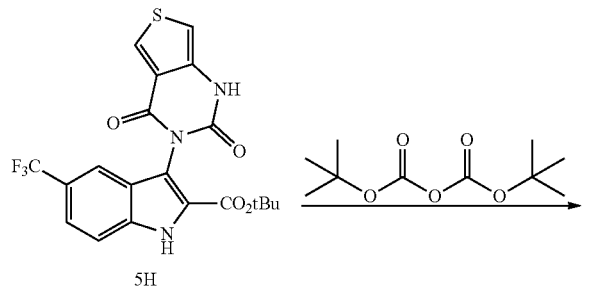

5H

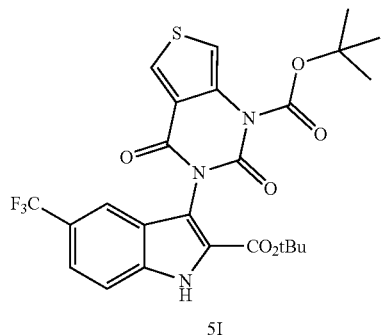

5I

To a solution of 3-(2,4-dioxo-1,2-dihydro-4H-thieno[3,4-d]pyrimidin-3-yl)-5-trifluoromethyl-1H-indole-2-carboxylic acid tert-butyl ester 5H (3.30 g, 7.32 mmol) in anhydrous 1,4-dioxane (120 mL) was added di-tert-butyl dicarbonate (1.60 g, 7.34 mmol) and 4-dimethylaminopyridine (89 mg, 0.73 mmol). The reaction mixture was stirred at room temperature for 2 hours. Ethyl acetate (500 mL) was added and the organic layer was washed with 1 N hydrochloric acid and brine. The organic layer was dried over sodium sulfate. The organic solvent was evaporated under reduced pressure. The crude product was purified by flash column chromatography to provide 3-(1-tert-butoxycarbonyl-2,4-dioxo-1,2-dihydro-4H-thieno[3,4-d]pyrimidin-3-yl)-5-trifluoromethyl-1H-indole-2-carboxylic acid tert-butyl ester 5I (2.85 g, 5.17 mmol).

Step G—Synthesis of Compound 5K

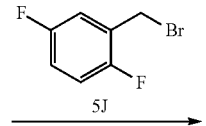

5I

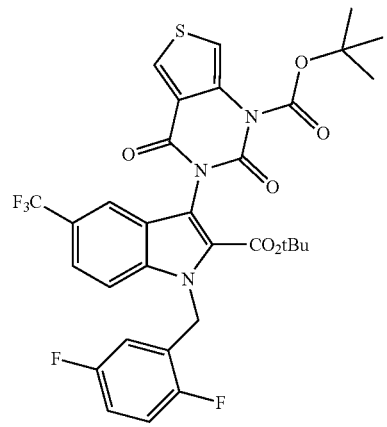

5K

To a solution of 3-(1-tert-butoxycarbonyl-2,4-dioxo-1,2-dihydro-4H-thieno[3,4-d]pyrimidin-3-yl)-5-trifluoromethyl-1H-indole-2-carboxylic acid tert-butyl ester 5I (30 mg, 0.054 mmol) in anhydrous THF (1 mL) and anhydrous DMF (1 mL) was added potassium tert-butoxide (9 mg, 0.080 mmol) and 2,5-difluorobenzyl bromide 5J (14.6 mg, 0.071 mmol). The reaction mixture was stirred at room temperature for 3 hours. Ethyl acetate (50 mL) was added and the organic layer was washed with saturated ammonium chloride solution and brine. The organic layer was dried over sodium sulfate. The organic solvent was removed under reduced pressure to provide 3-(1-tert-butoxycarbonyl-2,4-dioxo-1,2-dihydro-4H-thieno[3,4-d]pyrimidin-3-yl)-1-(2,5-difluorobenzyl)-5-trifluoromethyl-1H-indole-2-carboxylic acid tert-butyl ester 5K which was used in the next step without further purification.

Step H—Synthesis of Compound 65

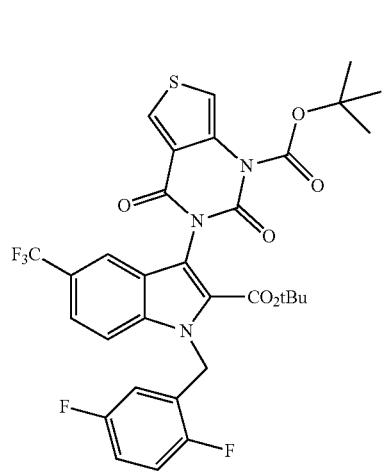

5K

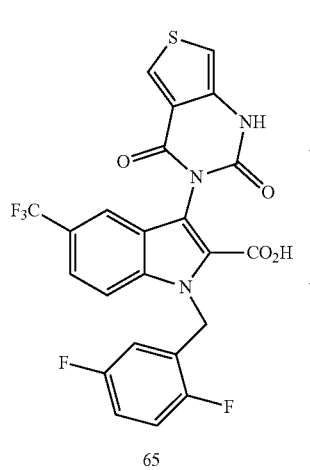

65

To a sample of 3-(1-tert-butoxycarbonyl-2,4-dioxo-1,2-dihydro-4H-thieno[3,4-d]pyrimidin-3-yl)-1-(2,5-difluorobenzyl)-5-trifluoromethyl-1H-indole-2-carboxylic acid tert-butyl ester 5K (~0.054 mmol) was added a 20% v/v solution of trifluoroacetic acid in dichloromethane (5 mL). The reaction mixture was stirred at room temperature for 3 hours. The organic solvent was evaporated under reduced pressure. The crude product was purified by RP-HPLC to yield to provide compound 65 (17 mg, 0.033 mmol).

Example 6

Preparation of Compound 39

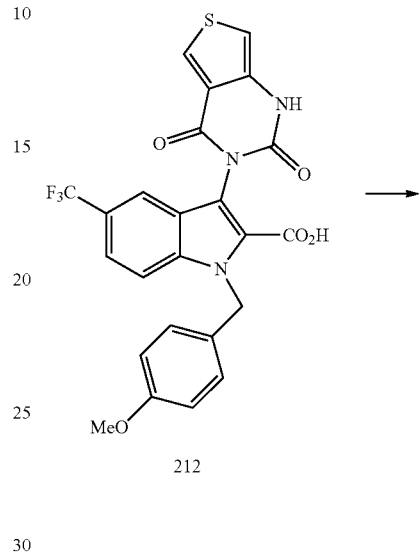

212

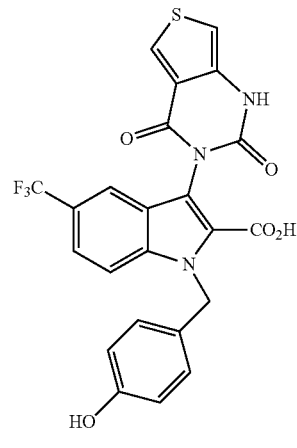

39

To a solution of 3-(2,4-dioxo-1,2-dihydro-4H-thieno[3,4-d]pyrimidin-3-yl)-1-(4-methoxybenzyl)-5-trifluoromethyl-1H-indole-2-carboxylic acid 212 (14.2 mg, 0.027 mmol) in anhydrous dichloromethane (2 mL) was added a 1 M solution of boron tribromide in dichloromethane (0.11 mL, 0.11 mmol). The reaction mixture was stirred at room temperature for 10 minutes. Saturated sodium bicarbonate solution (2 mL) was added. Ethyl acetate (50 mL) was added and the organic layer was washed with 1 N hydrochloric acid and brine. The organic layer was dried over sodium sulfate. The organic solvent was evaporated under reduced pressure. The crude product was purified by RP-HPLC to provide compound 39 (9.8 mg, 0.019 mmol).

Example 7

Preparation of Compound 267

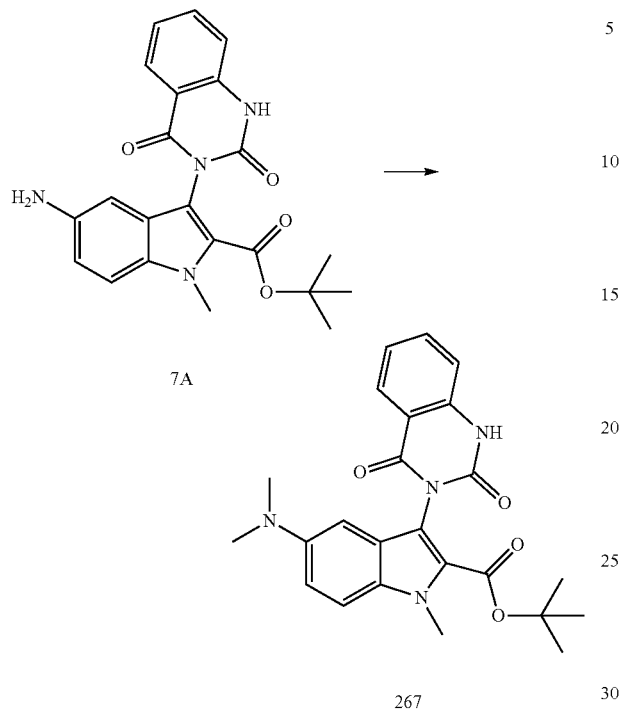

To a solution of 5-amino-3-(2,4-dioxo-1,4-dihydro-2H-quinazolin-3-yl)-1-methyl-1H-indole-2-carboxylic acid tert-butyl ester 7A (56 mg, 0.138 mmol) in methanol (2.7 mL) and acetic acid (0.3 mL) was added MP-cyanoborohydride resin (2.42 mmol/g, 85 mg, 0.206 mmol) and aqueous formaldehyde solution (37% w/w, 112 mg, 1.38 mmol). The reaction mixture was stirred at room temperature overnight. The resin was removed by filtration. The solvent was evaporated under reduced pressure. The crude product was purified by RP-HPLC to provide compound 267 (36.4 mg, 0.084 mmol).

Example 8

Preparation of Compound 8

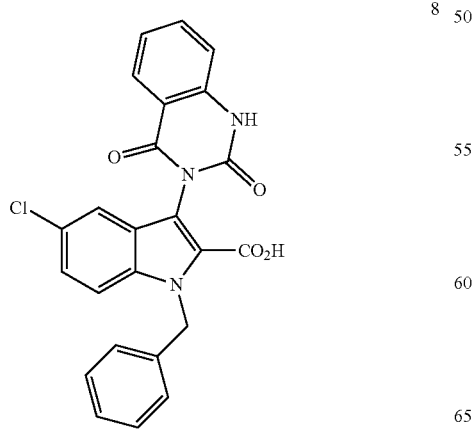

Compound 8 was prepared using the method described in Example 1 and using 5-chloro-2-fluorobenzonitrile and benzylamine in Step A (and methyl anthranilate in Step D.

Example 9

Preparation of Compound 129

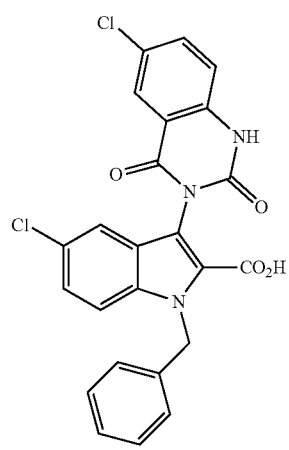

Compound 129 was prepared using the method described in Example 1 and using 5-chloro-2-fluorobenzonitrile and benzylamine in Step A and methyl 2-amino-5-chlorobenzoate in Step D.

Example 10

Preparation of Compound 130

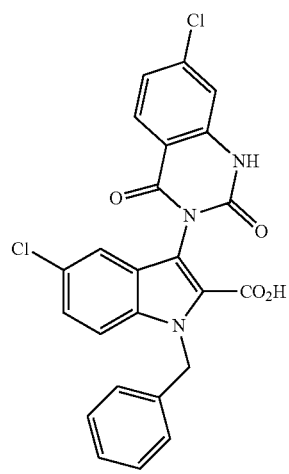

Compound 130 was prepared using the method described in Example 1 and using 5-chloro-2-fluorobenzonitrile and benzylamine in Step A and methyl 2-amino-4-chlorobenzoate in Step D.

Example 11

Preparation of Compound 13

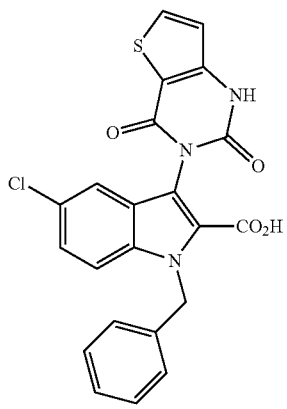

Compound 13 was prepared using the method described in Example 1 and using 5-chloro-2-fluorobenzonitrile and benzylamine in Step A and 3-aminothiophene-2-carboxylic acid methyl ester in Step D.

Example 12

Preparation of Compound 131

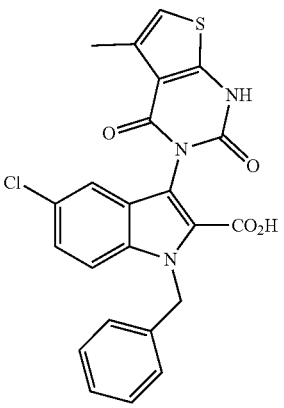

Compound 131 was prepared using the method described in Example 1 and using 5-chloro-2-fluorobenzonitrile and benzylamine in Step A and 2-amino-4-methylthiophene-3-carboxylic acid methyl ester in Step D.

Example 13

Preparation of Compound 12

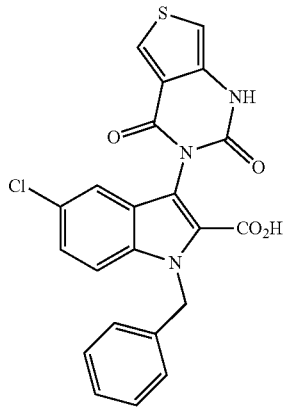

Compound 12 was prepared using the method described in Example 1 and using 5-chloro-2-fluorobenzonitrile and benzylamine in Step A and 4-aminothiophene-3-carboxylic acid methyl ester in Step D.

Example 14

Preparation of Compound 132

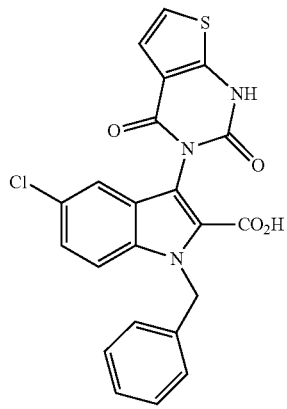

Compound 132 was prepared using the method described in Example 1 and using 5-chloro-2-fluorobenzonitrile and benzylamine in Step A and 2-aminothiophene-3-carboxylic acid methyl ester in Step D.

Example 15

Preparation of Compound 133

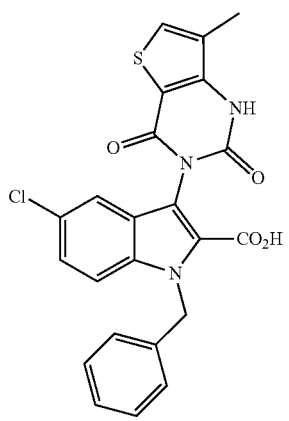
133

Compound 133 was prepared using the method described in Example 1 and using 5-chloro-2-fluorobenzonitrile and benzylamine in Step A and 3-amino-4-methylthiophene-2-carboxylic acid methyl ester in Step D.

Example 16

Preparation of Compound 134

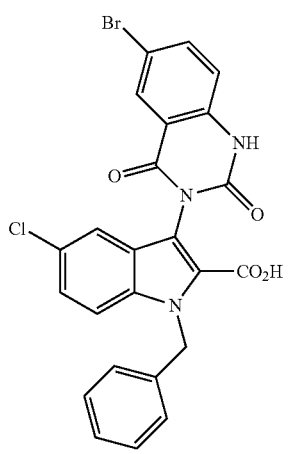
134

Compound 134 was prepared using the method described in Example 1 and using 5-chloro-2-fluorobenzonitrile and benzylamine in Step A and methyl 2-amino-5-bromobenzoate in Step D.

Example 17

Preparation of Compound 135

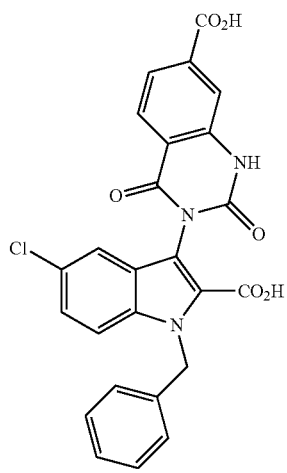
135

Compound 135 was prepared using the method described in Example 1 and using 5-chloro-2-fluorobenzonitrile and benzylamine in Step A and dimethyl aminoterephthalate in Step D.

Example 18

Preparation of Compound 136

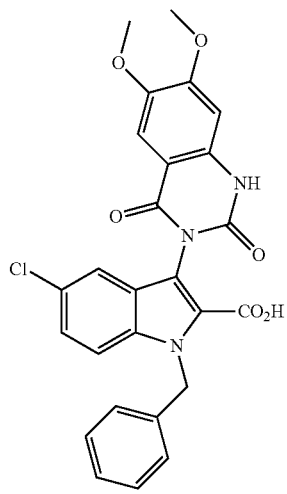
136

Compound 136 was prepared using the method described in Example 1 and using 5-chloro-2-fluorobenzonitrile and benzylamine in Step A and methyl 2-amino-4,5-dimethoxybenzoate in Step D.

Example 19

Preparation of Compound 137

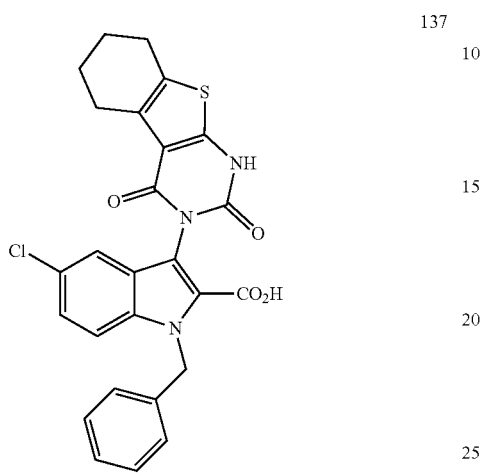

137

Compound 137 was prepared using the method described in Example 1 and using 5-chloro-2-fluorobenzonitrile and benzylamine in Step A and 2-amino-4,5,6,7-tetrahydrobenzo[b]thiophene-3-carboxylic acid methyl ester in Step D.

Example 20

Preparation of Compound 51

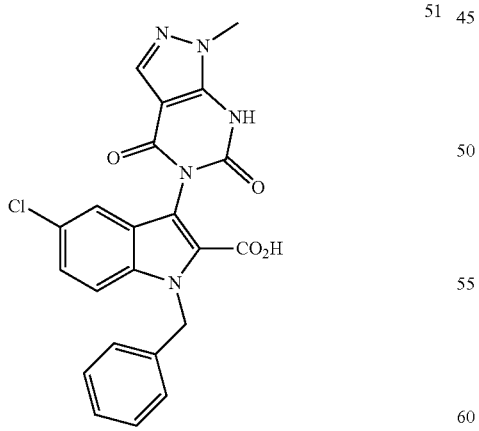

51

Compound 51 was prepared using the method described in Example 1 and using 5-chloro-2-fluorobenzonitrile and benzylamine in Step A and 5-amino-1-methyl-1H-pyrazole-4-carboxylic acid ethyl ester in Step D.

Example 21

Preparation of Compound 138

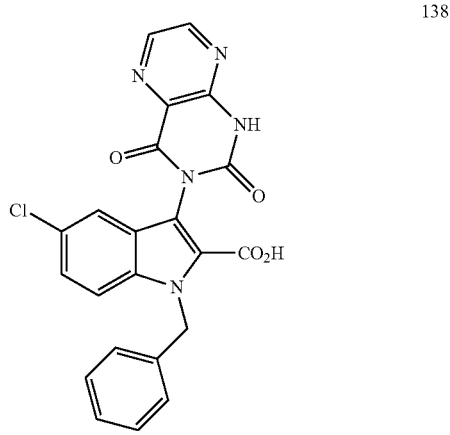 [SMILES: O=C(O)c1c(-n2c(=O)[nH]c3nccnc3c2=O)c2cc(Cl)ccc2n1Cc1ccccc1]

138

Compound 138 was prepared using the method described in Example 1 and using 5-chloro-2-fluorobenzonitrile and benzylamine in Step A and 3-aminopyrazine-2-carboxylic acid methyl ester in Step D.

Example 22

Preparation of Compound 139

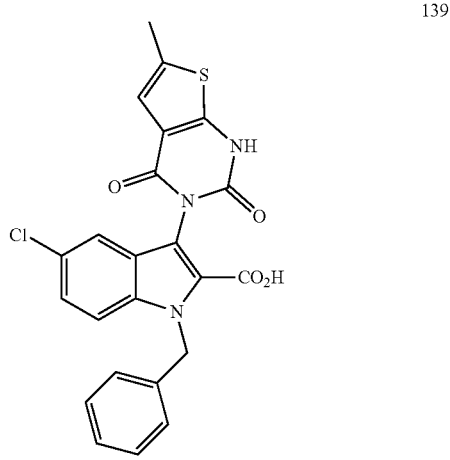 [SMILES: Cc1cc2c(=O)n(-c3c(C(=O)O)n(Cc4ccccc4)c4ccc(Cl)cc34)c(=O)[nH]c2s1]

139

Compound 139 was prepared using the method described in Example 1 and using 5-chloro-2-fluorobenzonitrile and benzylamine in Step A and 2-amino-5-methylthiophene-3-carboxylic acid methyl ester in Step D.

Example 23

Preparation of Compound 140

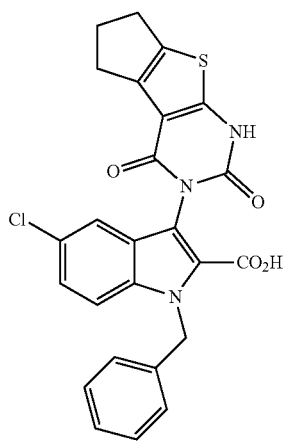

140

Compound 140 was prepared using the method described in Example 1 and using 5-chloro-2-fluorobenzonitrile and benzylamine in Step A and 2-amino-5,6-dihydro-4H-cyclopenta[b]thiophene-3-carboxylic acid methyl ester in Step D.

Example 24

Preparation of Compound 141

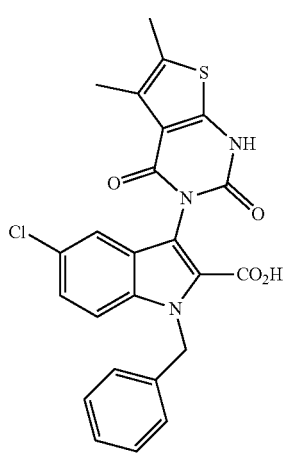

141

Compound 141 was prepared using the method described in Example 1 and using 5-chloro-2-fluorobenzonitrile and benzylamine in Step A and 2-amino-4,5-dimethylthiophene-3-carboxylic acid methyl ester in Step D.

Example 25

Preparation of Compound 142

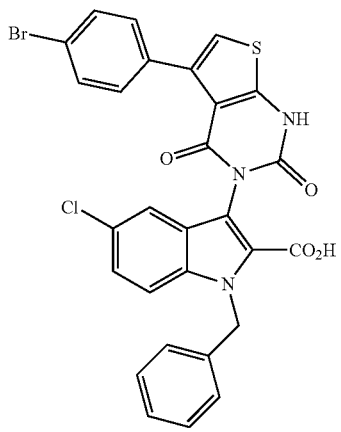

142

Compound 142 was prepared using the method described in Example 1 and using 5-chloro-2-fluorobenzonitrile and benzylamine in Step A and 2-amino-4-(4-bromophenyl)thiophene-3-carboxylic acid methyl ester in Step D.

Example 26

Preparation of Compound 143

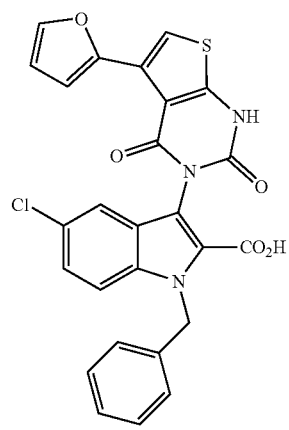

143

Compound 143 was prepared using the method described in Example 1 and using 5-chloro-2-fluorobenzonitrile and benzylamine in Step A and 2-amino-4-furan-2-yl-thiophene-3-carboxylic acid methyl ester in Step D.

Example 27

Preparation of Compound 144

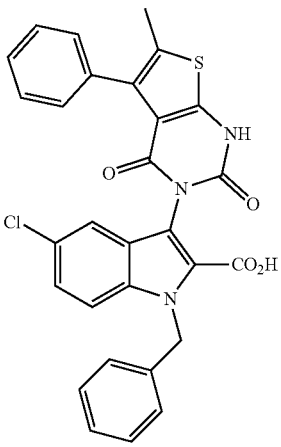

144

Compound 144 was prepared using the method described in Example 1 and using 5-chloro-2-fluorobenzonitrile and benzylamine in Step A and 2-amino-5-methyl-4-phenylthiophene-3-carboxylic acid methyl ester in Step D.

Example 28

Preparation of Compound 145

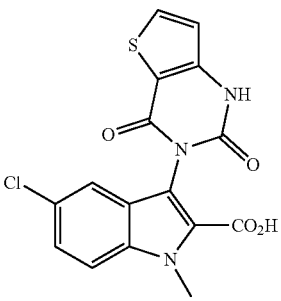

145

Compound 145 was prepared using the method described in Example 1 and using 5-chloro-2-fluorobenzonitrile and methylamine in Step A and 3-amino-thiophene-2-carboxylic acid methyl ester in Step D.

Example 29

Preparation of Compound 146

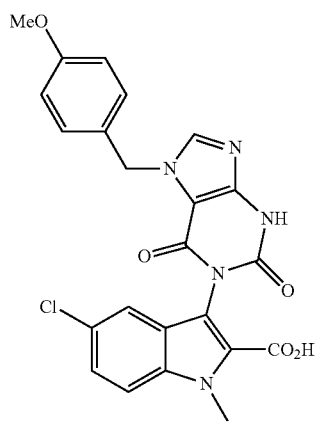

146

Compound 146 was prepared using the method described in Example 1 and using 5-chloro-2-fluorobenzonitrile and methylamine in Step A and 5-amino-3-(4-methoxybenzyl)-3H-imidazole-4-carboxylic acid methyl ester in Step D.

Example 30

Preparation of Compound 1

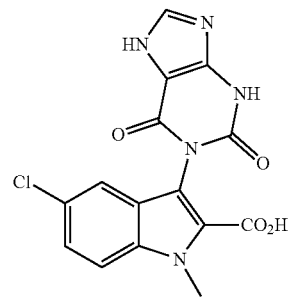

1

Compound 1 using the method described in Step F wherein trifluoroacetic acid was used in a microwave reactor at 120° C. for 30 minutes.

Example 31

Preparation of Compound 147

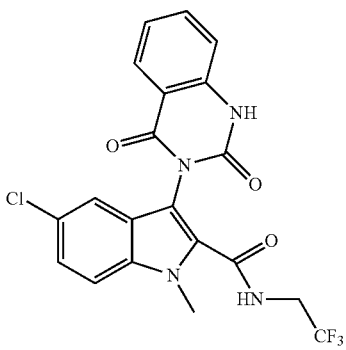

147

Compound 147 was prepared from compound 138 using the method described in Example 3, wherein 2,2,2-trifluoroethylamine was used.

Example 32

Preparation of Compound 148

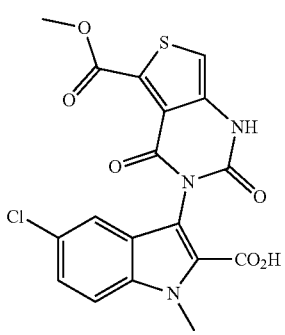

148

Compound 148 was prepared using the method described in Example 1 and using 5-chloro-2-fluorobenzonitrile and methylamine in Step A and 4-aminothiophene-2,3-dicarboxylic acid dimethyl ester in Step D.

Example 33

Preparation of Compound 149

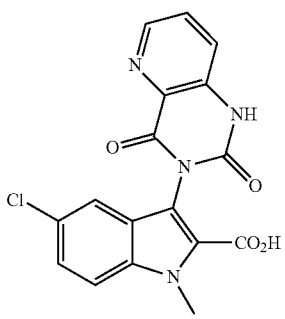

149

Compound 149 was prepared using the method described in Example 1 and using 5-chloro-2-fluorobenzonitrile and methylamine in Step A and 3-amino-pyridine-2-carboxylic acid methyl ester in Step D.

Example 34

Preparation of Compound 150

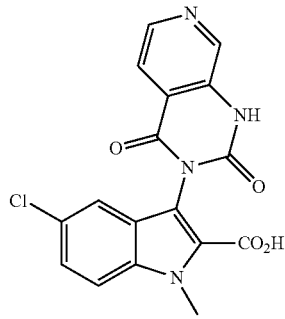

150

Compound 150 was prepared using the method described in Example 1 and using 5-chloro-2-fluorobenzonitrile and methylamine in Step A and 3-aminoisonicotinic acid methyl ester in Step D.

Example 35

Preparation of Compound 151

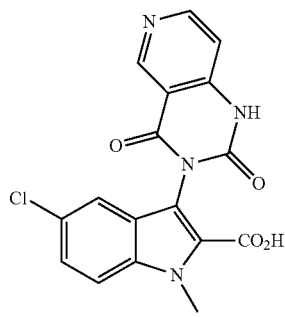

151

Compound 151 was prepared using the method described in Example 1 and using 5-chloro-2-fluorobenzonitrile and methylamine in Step A and 4-aminonicotinic acid methyl ester in Step D.

Example 36

Preparation of Compound 152

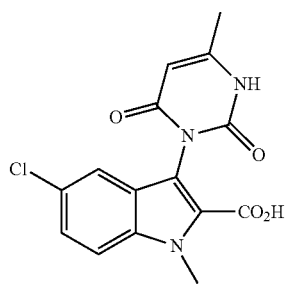

152

Compound 152 was prepared using the method described in Example 1 and using 5-chloro-2-fluorobenzonitrile and methylamine in Step A and methyl 3-aminocrotonate in Step D.

Example 37

Preparation of Compound 153

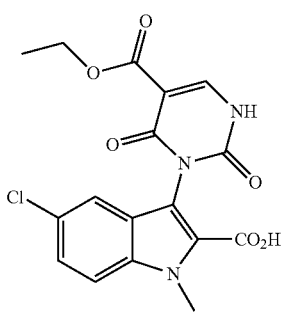

153

Compound 153 was prepared using the method described in Example 1 and using 5-chloro-2-fluorobenzonitrile and methylamine in Step A and diethyl aminomethylenemalonate in Step D.

Example 38

Preparation of Compound 154

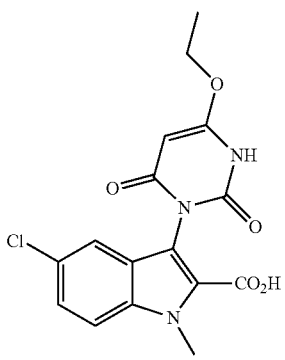

154

Compound 154 was prepared using the method described in Example 1 and using 5-chloro-2-fluorobenzonitrile and methylamine in Step A and ethyl 3-amino-3-ethoxyacrylate in Step D.

Example 39

Preparation of Compound 155

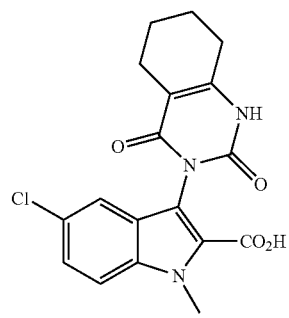

155

Compound 155 was prepared using the method described in Example 1 and using 5-chloro-2-fluorobenzonitrile and methylamine in Step A and 2-aminocyclohex-1-enecarboxylic acid methyl ester in Step D.

Example 40

Preparation of Compound 74

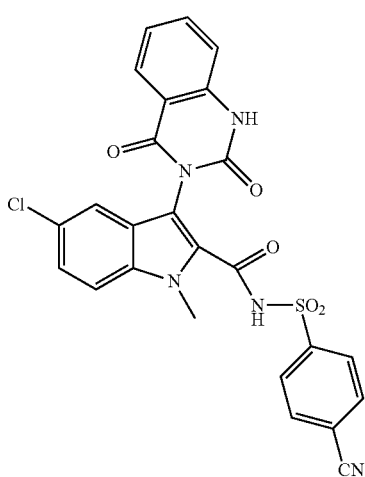

74

Compound 74 was prepared from compound 138 using the method described in Example 2, wherein 4-cyanobenzenesulfonamide was used.

Example 41

Preparation of Compound 156

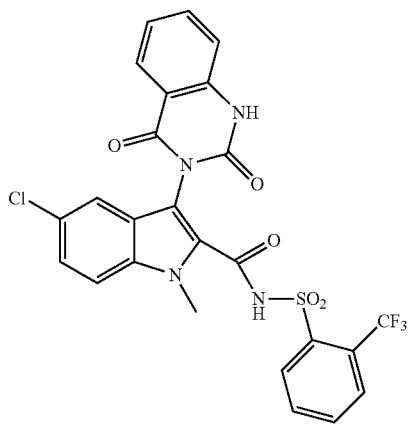

Compound 156 was prepared from compound 138 using the method described in Example 2, wherein 2-trifluoromethylbenzenesulfonamide was used.

Example 42

Preparation of Compound 157

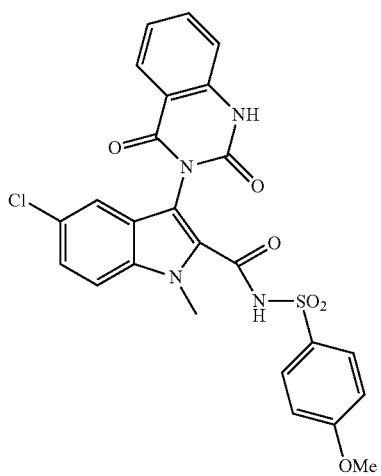

Compound 157 was prepared from compound 138 using the method described in Example 2, wherein 4-methoxybenzenesulfonamide was used.

Example 43

Preparation of Compound 158

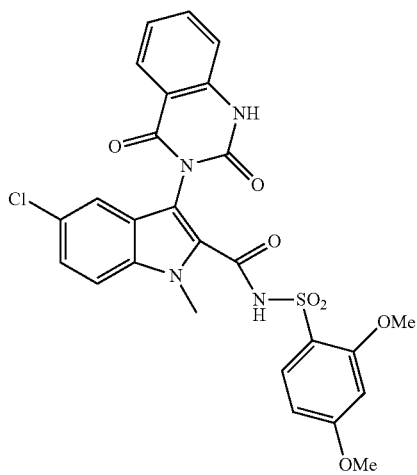

Compound 158 was prepared from compound 138 using the method described in Example 2, wherein 2,4-dimethoxybenzenesulfonamide was used.

Example 44

Preparation of Compound 159

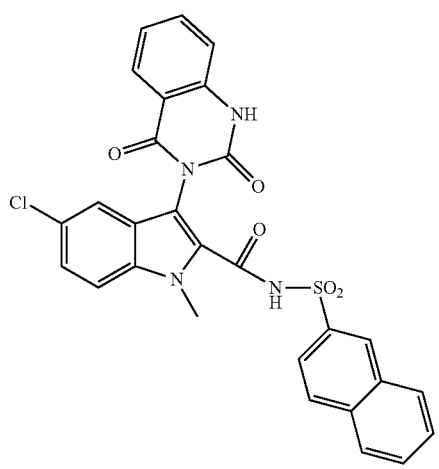

Compound 159 was prepared from compound 138 using the method described in Example 2, wherein naphthalene-2-sulfonamide was used.

Example 45

Preparation of Compound 160

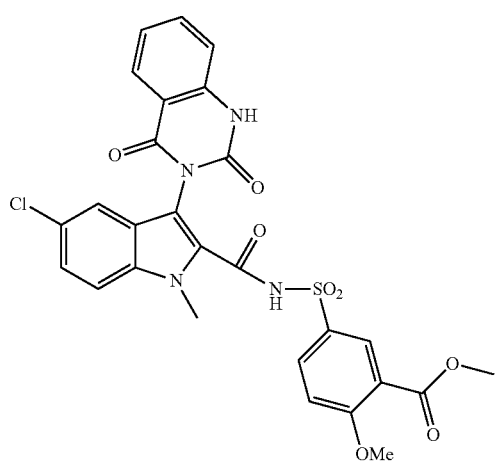

160

Compound 160 was prepared from compound 138 using the method described in Example 2, wherein 4-methoxy-3-methoxycarbonylbenzenesulfonamide was used.

Example 46

Preparation of Compound 161

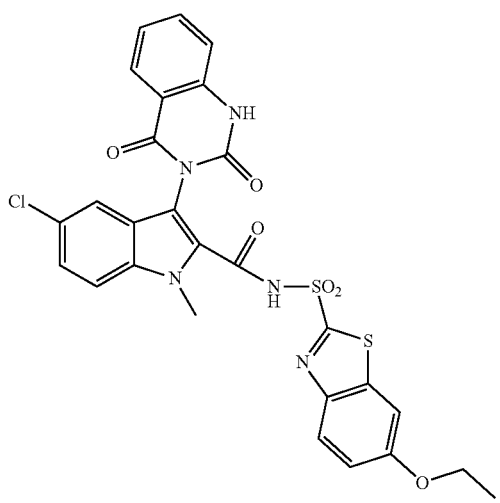

161

Compound 161 was prepared from compound 138 using the method described in Example 2, wherein 6-ethoxybenzothiazole-2-sulfonamide was used.

Example 47

Preparation of Compound 162

162

Compound 162 was prepared from compound 138 using the method described in Example 2, wherein 2-methoxycarbonylbenzenesulfonamide was used.

Example 48

Preparation of Compound 163

163

Compound 163 was prepared from compound 138 using the method described in Example 2, wherein 4-trifluoromethoxybenzenesulfonamide was used.

Example 49

Preparation of Compound 164

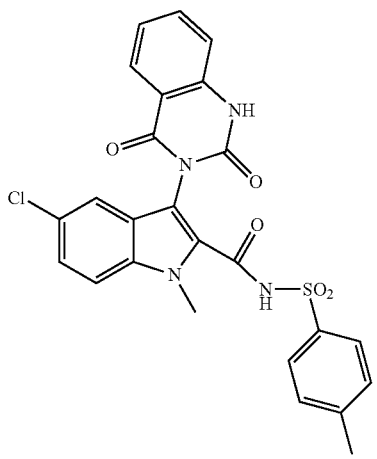

164

Compound 164 was prepared from compound 138 using the method described in Example 2, wherein 4-methylbenzenesulfonamide was used.

Example 50

Preparation of Compound 165

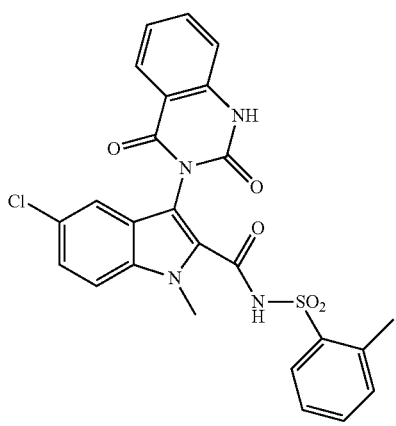

165

Compound 165 was prepared from compound 138 using the method described in Example 2, wherein 2-methylbenzenesulfonamide was used.

Example 51

Preparation of Compound 166

166

Compound 166 was prepared from compound 138 using the method described in Example 2, wherein 4-chlorobenzenesulfonamide was used.

Example 52

Preparation of Compound 167

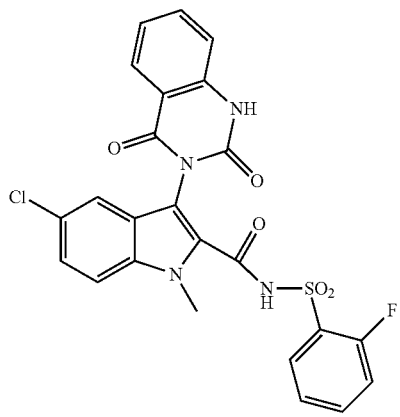

167

Compound 167 was prepared from compound 138 using the method described in Example 2, wherein 2-fluorobenzenesulfonamide was used.

Example 53

Preparation of Compound 168

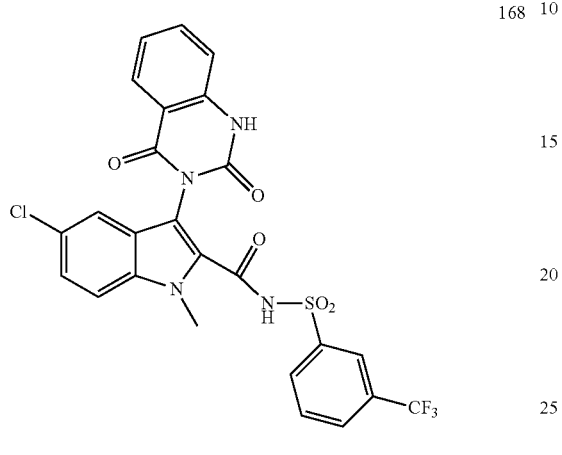

168

Compound 168 was prepared from compound 138 using the method described in Example 2, wherein 3-trifluoromethylbenzenesulfonamide was used.

Example 54

Preparation of Compound 169

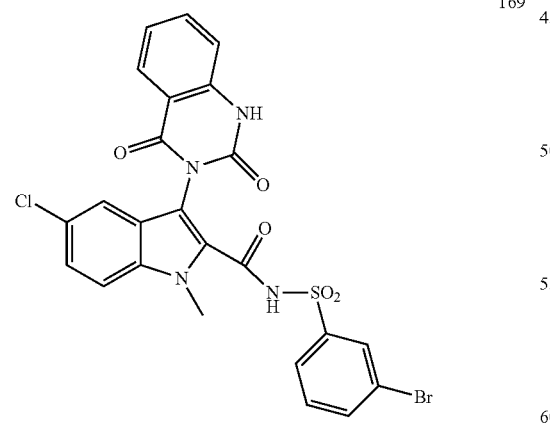

169

Compound 169 was prepared from compound 138 using the method described in Example 2, wherein 3-bromomethylbenzenesulfonamide was used.

Example 55

Preparation of Compound 170

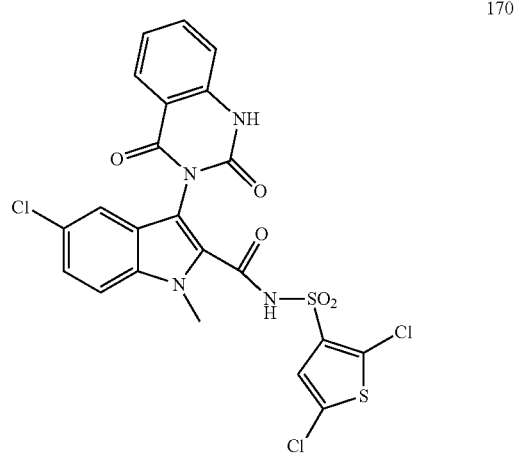 [SMILES: Cn1c(C(=O)NS(=O)(=O)c2cc(Cl)sc2Cl)c(-n2c(=O)[nH]c3ccccc3c2=O)c2cc(Cl)ccc21]

170

Compound 170 was prepared from compound 138 using the method described in Example 2, wherein 2,5-dichlorothiophene-3-sulfonamide was used.

Example 56

Preparation of Compound 171

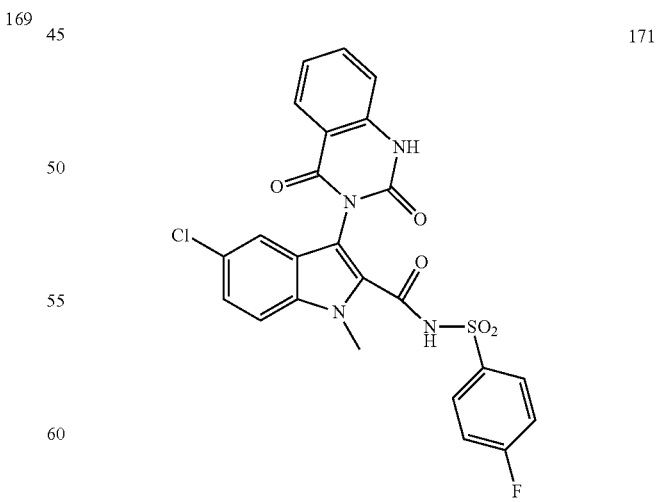

171

Compound 171 was prepared from compound 138 using the method described in Example 2, wherein 4-fluorobenzenesulfonamide was used.

Example 57

Preparation of Compound 172

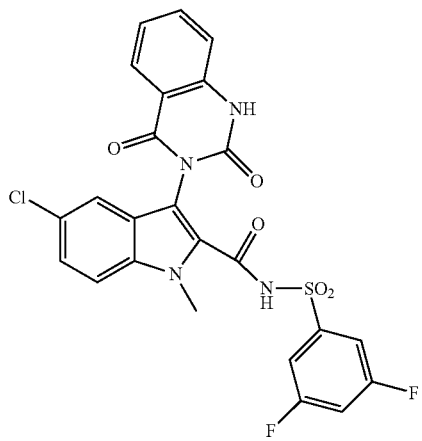

172

Compound 172 was prepared from compound 138 using the method described in Example 2, wherein 3,5-difluorobenzenesulfonamide was used.

Example 58

Preparation of Compound 173

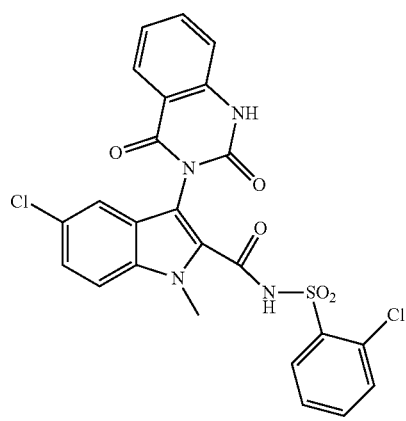

173

Compound 173 was prepared from compound 138 using the method described in Example 2, wherein 2-chlorobenzenesulfonamide was used.

Example 59

Preparation of Compound 174

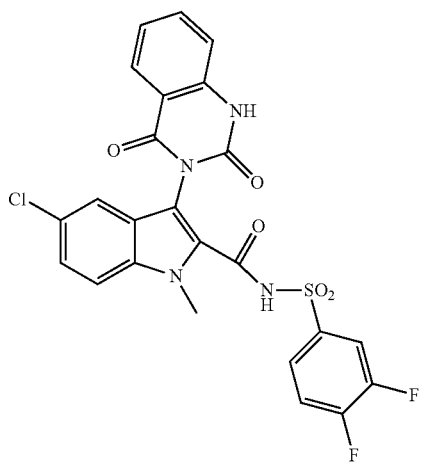

174

Compound 174 was prepared from compound 138 using the method described in Example 2, wherein 3,4-difluorobenzenesulfonamide was used.

Example 60

Preparation of Compound 175

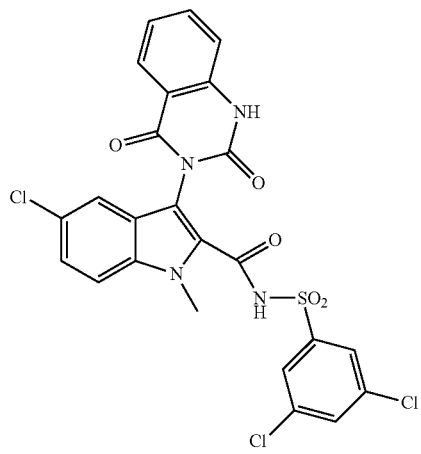

175

Compound 175 was prepared from compound 138 using the method described in Example 2, wherein 3,5-dichlorobenzenesulfonamide was used.

Example 61

Preparation of Compound 176

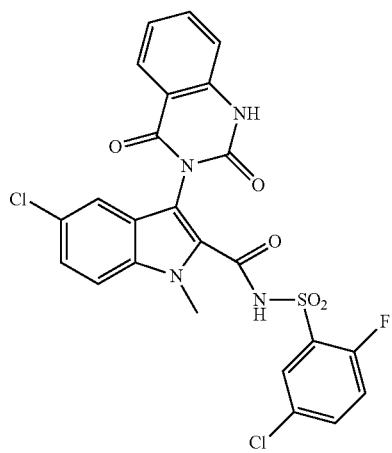

176

Compound 176 was prepared from compound 138 using the method described in Example 2, wherein 5-chloro-2-fluorobenzenesulfonamide was used.

Example 62

Preparation of Compound 177

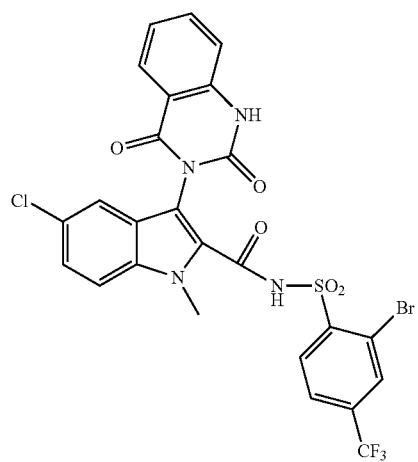

177

Compound 177 was prepared from compound 138 using the method described in Example 2, wherein 2-bromo-4-trifluoromethylbenzenesulfonamide was used.

Example 63

Preparation of Compound 178

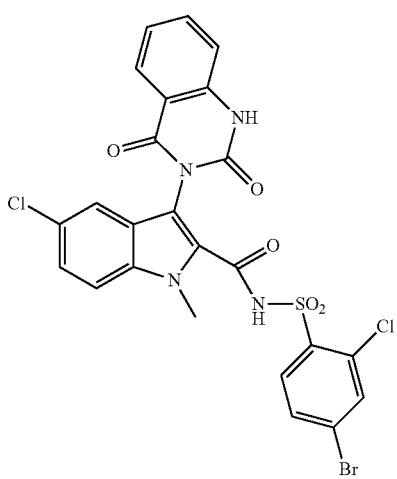

178

Compound 178 was prepared from compound 138 using the method described in Example 2, wherein 4-bromo-2-chlorobenzenesulfonamide was used.

Example 64

Preparation of Compound 179

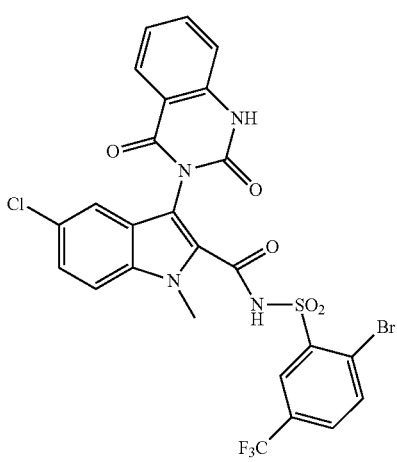

179

Compound 179 was prepared from compound 138 using the method described in Example 2, wherein 2-bromo-5-trifluoromethylbenzenesulfonamide was used.

Example 65

Preparation of Compound 180

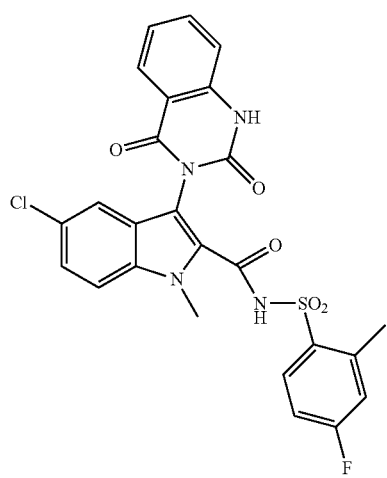

180

Compound 180 was prepared from compound 138 using the method described in Example 2, wherein 4-fluoro-2-methylbenzenesulfonamide was used.

Example 66

Preparation of Compound 181

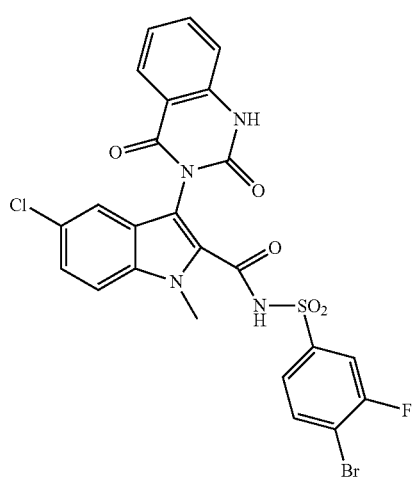

181

Compound 181 was prepared from compound 138 using the method described in Example 2, wherein 4-bromo-3-fluorobenzenesulfonamide was used.

Example 67

Preparation of Compound 182

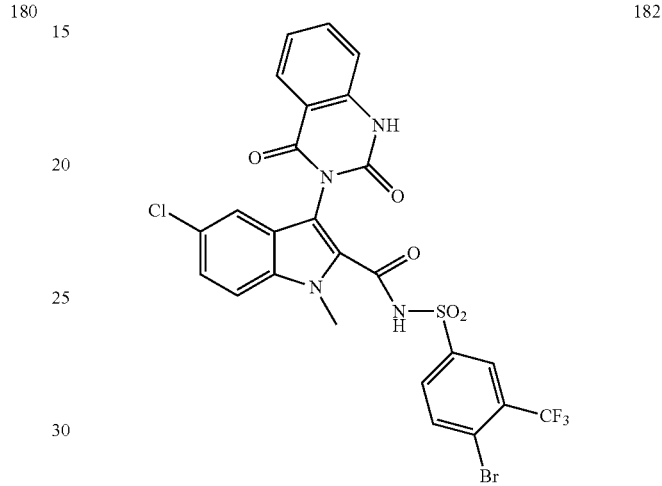

182

Compound 182 was prepared from compound 138 using the method described in Example 2, wherein 4-bromo-3-trifluoromethylbenzenesulfonamide was used.

Example 68

Preparation of Compound 183

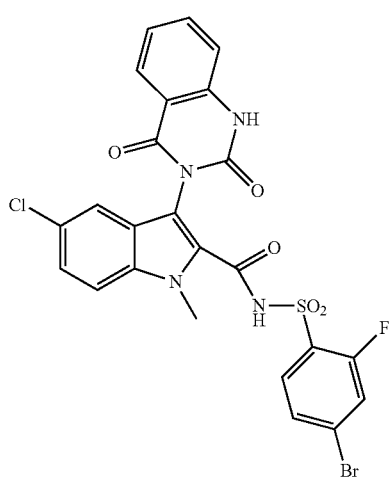

183

Compound 183 was prepared from compound 138 using the method described in Example 2, wherein 4-bromo-2-fluorobenzenesulfonamide was used.

Example 69

Preparation of Compound 184

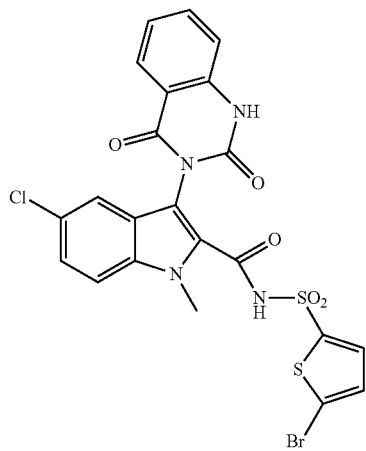

184

Compound 184 was prepared from compound 138 using the method described in Example 2, wherein 5-bromothiophene-2-sulfonamide was used.

Example 70

Preparation of Compound 185

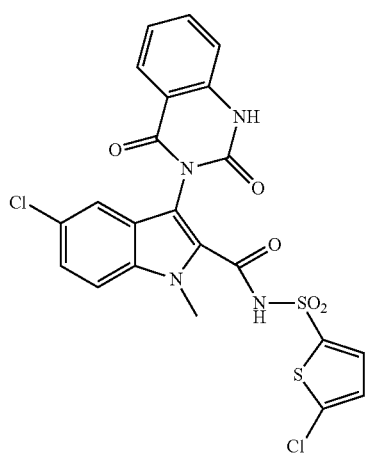

185

Compound 185 was prepared from compound 138 using the method described in Example 2, wherein 5-chlorothiophene-2-sulfonamide was used.

Example 71

Preparation of Compound 186

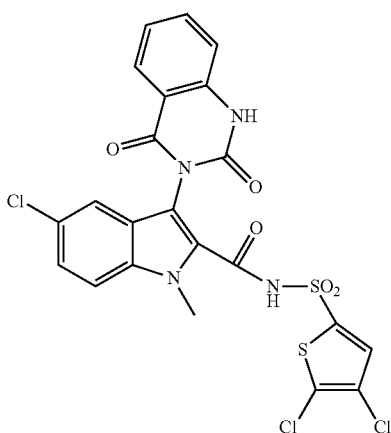

186

Compound 186 was prepared from compound 138 using the method described in Example 2, wherein 4,5-dichlorothiophene-2-sulfonamide was used.

Example 72

Preparation of Compound 188

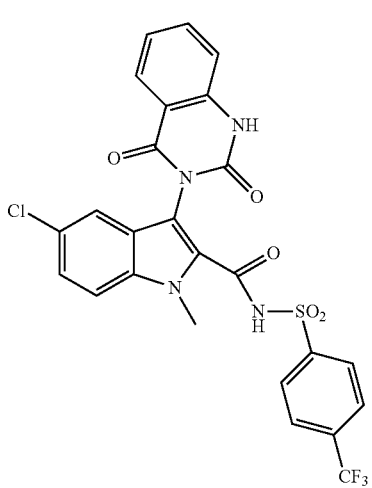

188

Compound 188 was prepared from compound 138 using the method described in Example 2, wherein 4-trifluoromethylbenzenesulfonamide was used.

Example 73

Preparation of Compound 189

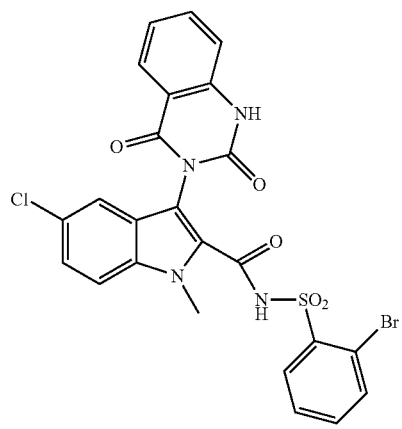

189

Compound 189 was prepared from compound 138 using the method described in Example 2, wherein 2-bromobenzenesulfonamide was used.

Example 74

Preparation of Compound 190

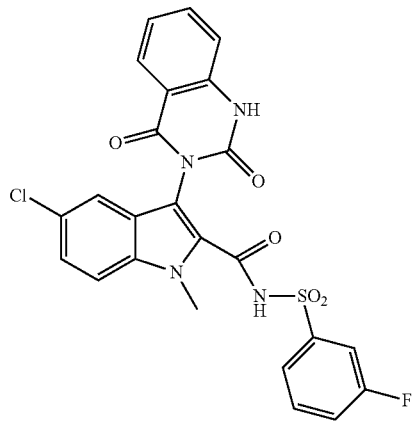

190

Compound 190 was prepared from compound 138 using the method described in Example 2, wherein 3-fluorobenzenesulfonamide was used.

Example 75

Preparation of Compound 191

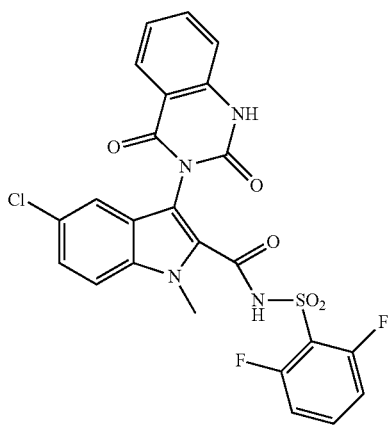

191

Compound 191 was prepared from compound 138 using the method described in Example 2, wherein 2,6-difluorobenzenesulfonamide was used.

Example 76

Preparation of Compound 192

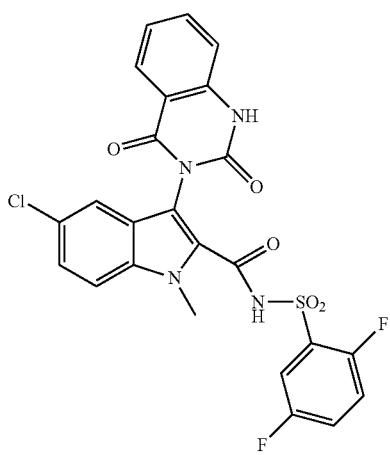

192

Compound 192 was prepared from compound 138 using the method described in Example 2, wherein 2,5-difluorobenzenesulfonamide was used.

Example 77

Preparation of Compound 47

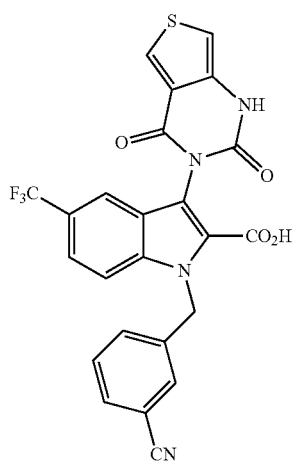

47

Compound 47 was prepared using the method described in Example 5, wherein 2-fluoro-5-trifluoromethylbenzonitrile was used in Step A, 4-aminothiophene-3-carboxylic acid methyl ester was used in Step D, and 3-cyanobenzyl bromide was used in Step G.

Example 78

Preparation of Compound 41

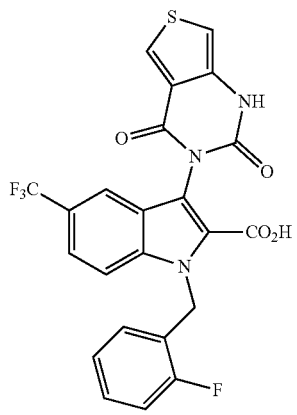

41

Compound 41 was prepared using the method described in Example 5, wherein 2-fluoro-5-trifluoromethylbenzonitrile was used in Step A, 4-aminothiophene-3-carboxylic acid methyl ester was used in Step D, and 2-fluorobenzyl bromide was used in Step G.

Example 79

Preparation of Compound 57

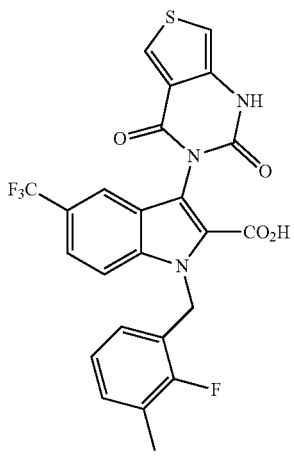

57

Compound 57 was prepared using the method described in Example 5, wherein 2-fluoro-5-trifluoromethylbenzonitrile was used in Step A, 4-aminothiophene-3-carboxylic acid methyl ester was used in Step D, and 2-fluoro-3-methylbenzyl bromide was used in Step G.

Example 80

Preparation of Compound 81

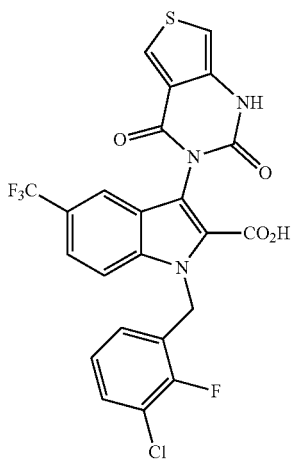

81

Compound 81 was prepared using the method described in Example 5, wherein 2-fluoro-5-trifluoromethylbenzonitrile was used in Step A, 4-aminothiophene-3-carboxylic acid methyl ester was used in Step D, and 3-chloro-2-fluorobenzyl bromide was used in Step G.

Example 81

Preparation of Compound 193

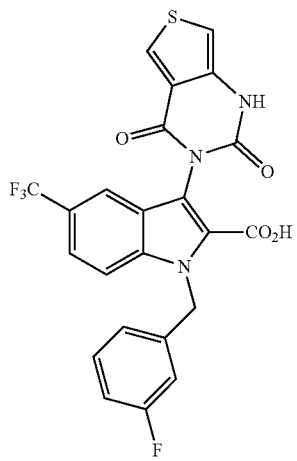

193

Compound 193 was prepared using the method described in Example 5, wherein 2-fluoro-5-trifluoromethylbenzonitrile was used in Step A, 4-aminothiophene-3-carboxylic acid methyl ester was used in Step D, and 3-fluorobenzyl bromide was used in Step G.

Example 82

Preparation of Compound 68

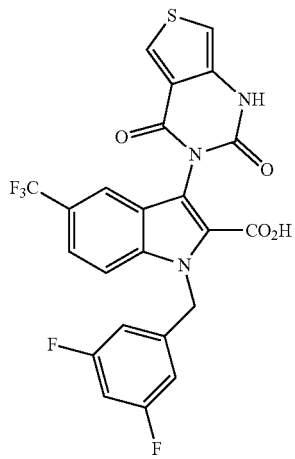

68

Compound 68 was prepared using the method described in Example 5, wherein 2-fluoro-5-trifluoromethylbenzonitrile was used in Step A, 4-aminothiophene-3-carboxylic acid methyl ester was used in Step D, and 3,5-difluorobenzyl bromide was used in Step G.

Example 83

Preparation of Compound 194

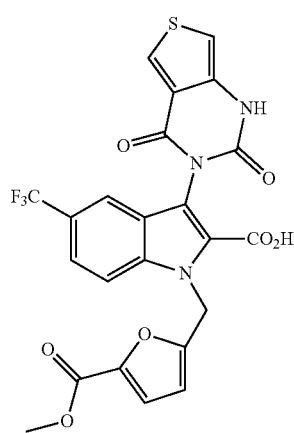

194

Compound 194 was prepared using the method described in Example 5, wherein 2-fluoro-5-trifluoromethylbenzonitrile was used in Step A, 4-aminothiophene-3-carboxylic acid methyl ester was used in Step D, and 5-methoxycarbonyl-furan-2-yl-methyl bromide was used in Step G.

Example 84

Preparation of Compound 48

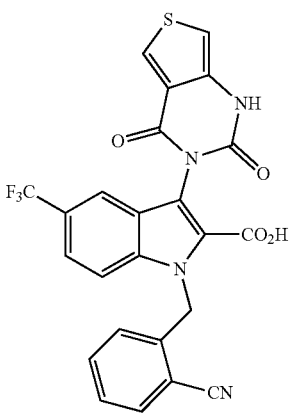

48

Compound 48 was prepared using the method described in Example 5, wherein 2-fluoro-5-trifluoromethylbenzonitrile

Example 85

Preparation of Compound 43

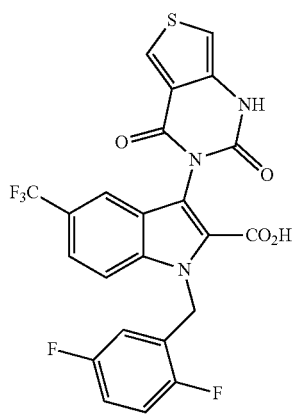

Compound 43 was prepared using the method described in Example 5, wherein 2-fluoro-5-trifluoromethylbenzonitrile was used in Step A, 4-aminothiophene-3-carboxylic acid methyl ester was used in Step D, and 2,5-difluorobenzyl bromide was used in Step G.

Example 86

Preparation of Compound 75

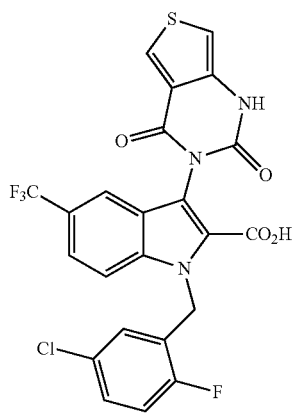

Compound 75 was prepared using the method described in Example 5, wherein 2-fluoro-5-trifluoromethylbenzonitrile was used in Step A, 4-aminothiophene-3-carboxylic acid methyl ester was used in Step D, and 2-cyanobenzyl bromide was used in Step G.

Example 87

Preparation of Compound 195

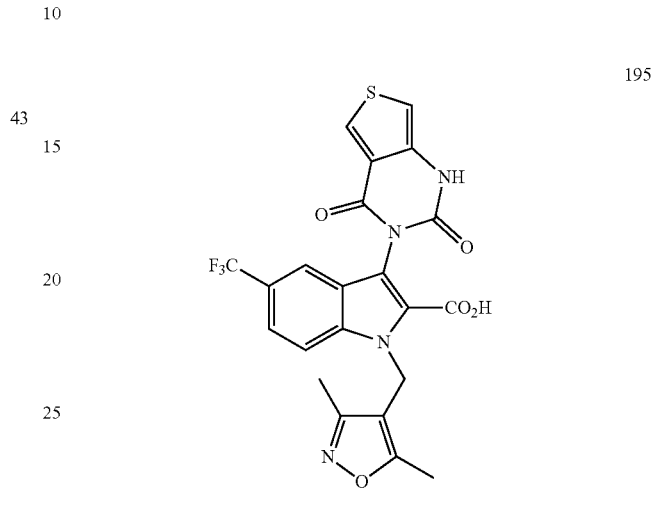

Compound 195 was prepared using the method described in Example 5, wherein 2-fluoro-5-trifluoromethylbenzonitrile was used in Step A, 4-aminothiophene-3-carboxylic acid methyl ester was used in Step D, and 5-chloro-2-fluorobenzyl bromide was used in Step G.

Example 88

Preparation of Compound 196

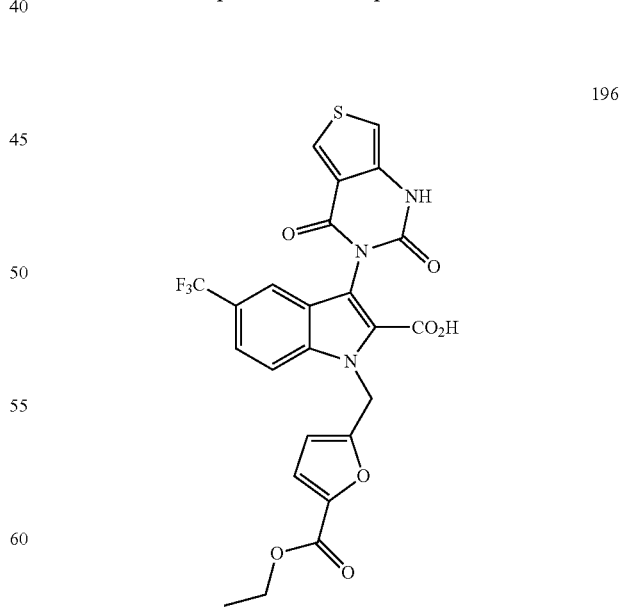

Compound 196 was prepared using the method described in Example 5, wherein 2-fluoro-5-trifluoromethylbenzonitrile was used in Step A, 4-aminothiophene-3-carboxylic acid methyl ester was used in Step D, and 5-ethoxycarbonyl-furan-2-yl-methyl bromide was used in Step G.

Example 89

Preparation of Compound 60

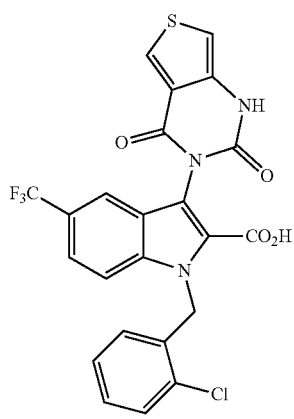

60

Compound 196 was prepared using the method described in Example 5, wherein 2-fluoro-5-trifluoromethylbenzonitrile was used in Step A, 4-aminothiophene-3-carboxylic acid methyl ester was used in Step D, and 2-chlorobenzyl bromide was used in Step G.

Example 90

Preparation of Compound 96

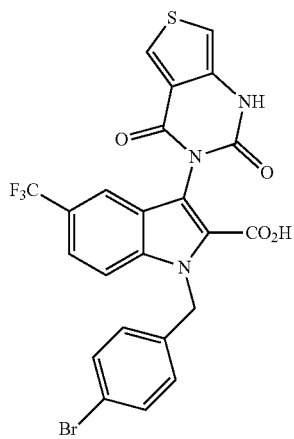

96

Compound 96 was prepared using the method described in Example 5, wherein 2-fluoro-5-trifluoromethylbenzonitrile was used in Step A, 4-aminothiophene-3-carboxylic acid methyl ester was used in Step D, and 4-bromobenzyl bromide was used in Step G.

Example 91

Preparation of Compound 34

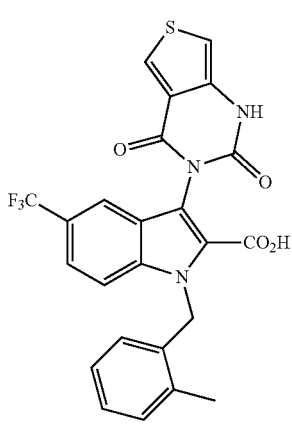

34

Compound 34 was prepared using the method described in Example 5, wherein 2-fluoro-5-trifluoromethylbenzonitrile was used in Step A, 4-aminothiophene-3-carboxylic acid methyl ester was used in Step D, and 2-methylbenzyl bromide was used in Step G.

Example 92

Preparation of Compound 51

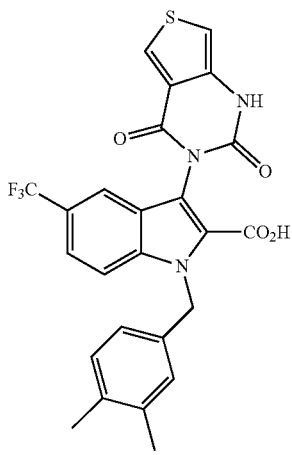

51

Compound 51 was prepared using the method described in Example 5, wherein 2-fluoro-5-trifluoromethylbenzonitrile

307 was used in Step A, 4-aminothiophene-3-carboxylic acid methyl ester was used in Step D, and 3,4-dimethylbenzyl bromide was used in Step G.

Example 93

Preparation of Compound 93

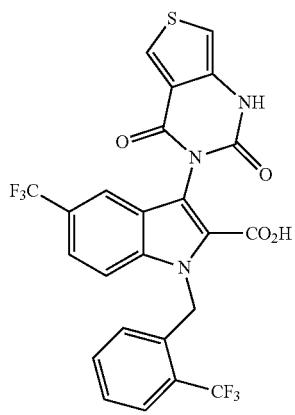

93

Compound 93 was prepared using the method described in Example 5, wherein 2-fluoro-5-trifluoromethylbenzonitrile was used in Step A, 4-aminothiophene-3-carboxylic acid methyl ester was used in Step D, and 2-trifluoromethylbenzyl bromide was used in Step G.

Example 94

Preparation of Compound 197

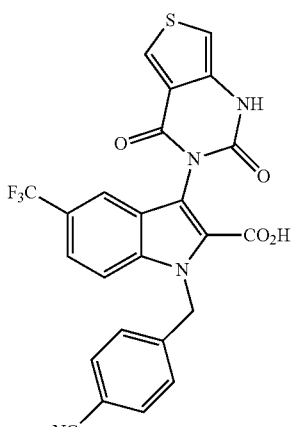

197

Compound 197 was prepared using the method described in Example 5, wherein 2-fluoro-5-trifluoromethylbenzoni-

308 trile was used in Step A, 4-aminothiophene-3-carboxylic acid methyl ester was used in Step D, and 4-cyanobenzyl bromide was used in Step G.

Example 95

Preparation of Compound 198

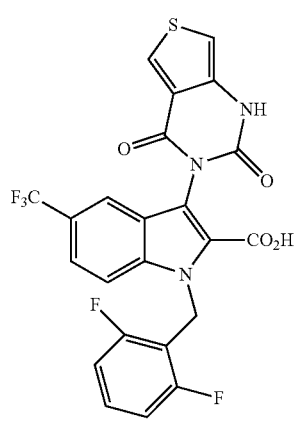

198

Compound 198 was prepared using the method described in Example 5, wherein 2-fluoro-5-trifluoromethylbenzonitrile was used in Step A, 4-aminothiophene-3-carboxylic acid methyl ester was used in Step D, and 2,6-difluorobenzyl bromide was used in Step G.

Example 96

Preparation of Compound 67

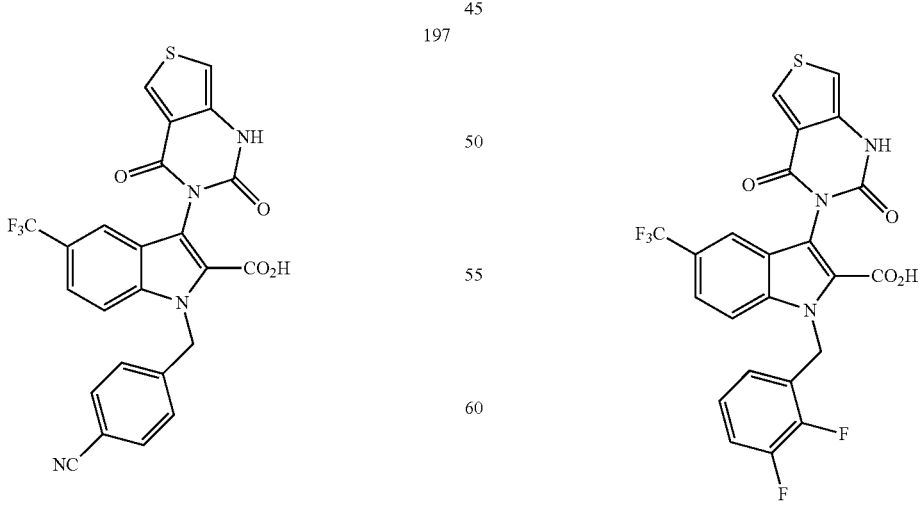

67

Compound 67 was prepared using the method described in Example 5, wherein 2-fluoro-5-trifluoromethylbenzonitrile was used in Step A, 4-aminothiophene-3-carboxylic acid methyl ester was used in Step D, and 2,3-difluorobenzyl bromide was used in Step G.

Example 97

Preparation of Compound 77

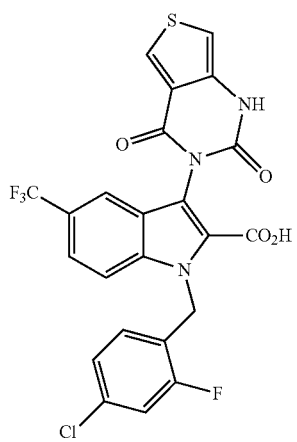

Compound 77 was prepared using the method described in Example 5, wherein 2-fluoro-5-trifluoromethylbenzonitrile was used in Step A, 4-aminothiophene-3-carboxylic acid methyl ester was used in Step D, and 4-chloro-2-fluorobenzyl bromide was used in Step G.

Example 98

Preparation of Compound 61

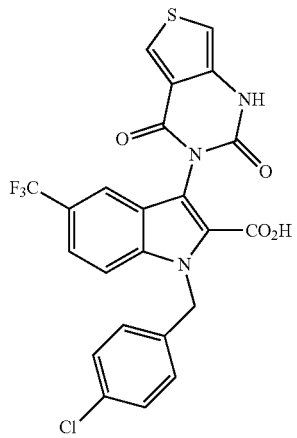

Compound 77 was prepared using the method described in Example 5, wherein 2-fluoro-5-trifluoromethylbenzonitrile was used in Step A, 4-aminothiophene-3-carboxylic acid methyl ester was used in Step D, and 4-chlorobenzyl bromide was used in Step G.

Example 99

Preparation of Compound 33

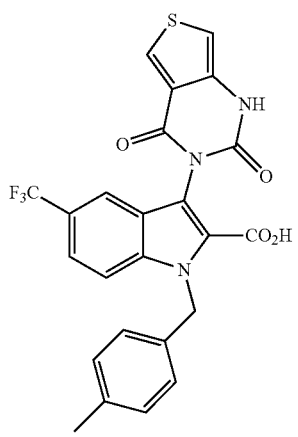

Compound 33 was prepared using the method described in Example 5, wherein 2-fluoro-5-trifluoromethylbenzonitrile was used in Step A, 4-aminothiophene-3-carboxylic acid methyl ester was used in Step D, and 4-methylbenzyl bromide was used in Step G.

Example 100

Preparation of Compound 199

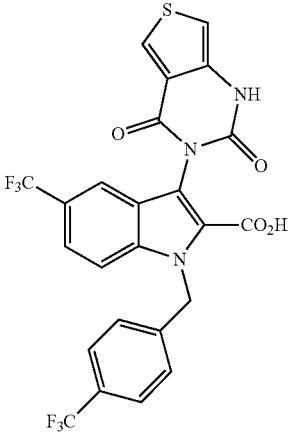

Compound 199 was prepared using the method described in Example 5, wherein 2-fluoro-5-trifluoromethylbenzonitrile was used in Step A, 4-aminothiophene-3-carboxylic acid methyl ester was used in Step D, and 4-trifluoromethylbenzyl bromide was used in Step G.

Example 101

Preparation of Compound 200

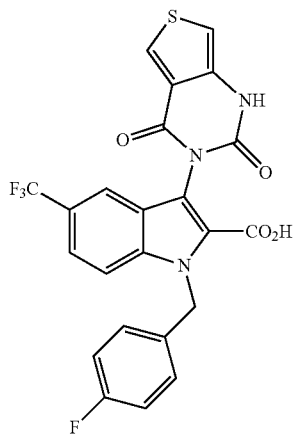

Compound 200 was prepared using the method described in Example 5, wherein 2-fluoro-5-trifluoromethylbenzonitrile was used in Step A, 4-aminothiophene-3-carboxylic acid methyl ester was used in Step D, and 4-fluorobenzyl bromide was used in Step G.

Example 102

Preparation of Compound 201

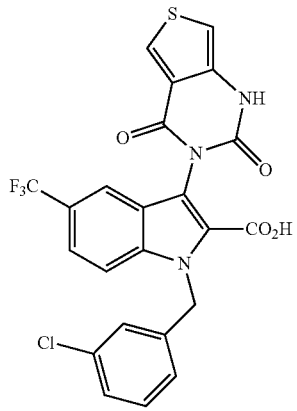

Compound 201 was prepared using the method described in Example 5, wherein 2-fluoro-5-trifluoromethylbenzonitrile was used in Step A, 4-aminothiophene-3-carboxylic acid methyl ester was used in Step D, and 4,3-chlorobenzyl bromide was used in Step G.

Example 103

Preparation of Compound 202

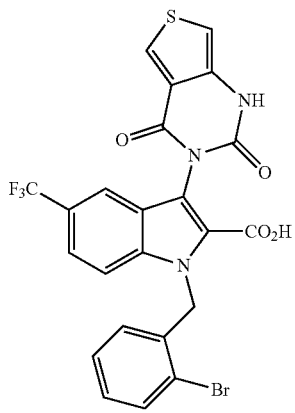

Compound 202 was prepared using the method described in Example 5, wherein 2-fluoro-5-trifluoromethylbenzonitrile was used in Step A, 4-aminothiophene-3-carboxylic acid methyl ester was used in Step D, and 2-bromobenzyl bromide was used in Step G.

Example 104

Preparation of Compound 35

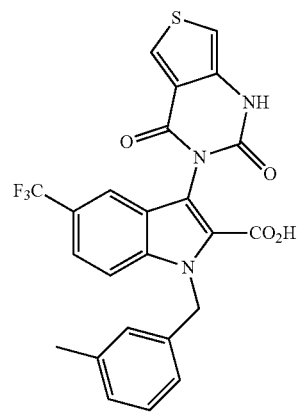

Compound 35 was prepared using the method described in Example 5, wherein 2-fluoro-5-trifluoromethylbenzonitrile was used in Step A, 4-aminothiophene-3-carboxylic acid methyl ester was used in Step D, and 3-methylbenzyl bromide was used in Step G.

Example 105

Preparation of Compound 203

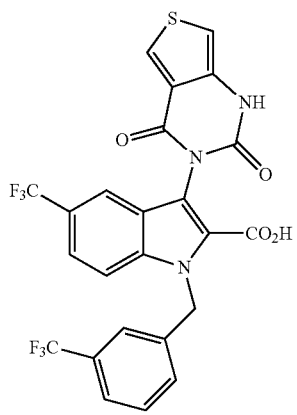

203

Compound 203 was prepared using the method described in Example 5, wherein 2-fluoro-5-trifluoromethylbenzonitrile was used in Step A, 4-aminothiophene-3-carboxylic acid methyl ester was used in Step D, and 3-trifluoromethylbenzyl bromide was used in Step G.

Example 106

Preparation of Compound 52

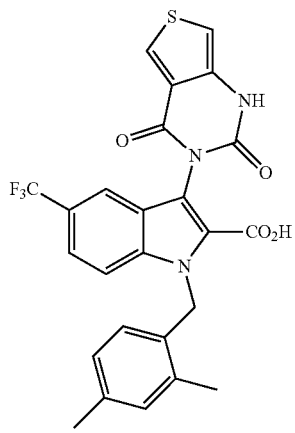

52

Compound 52 was prepared using the method described in Example 5, wherein 2-fluoro-5-trifluoromethylbenzonitrile was used in Step A, 4-aminothiophene-3-carboxylic acid methyl ester was used in Step D, and 2,4-dimethylbenzyl bromide was used in Step G.

Example 107

Preparation of Compound 26

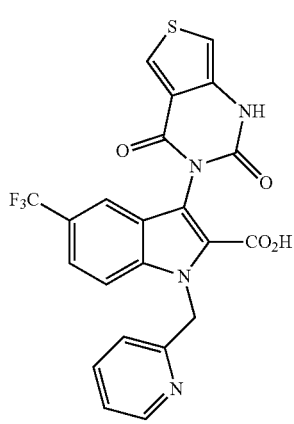

26

Compound 26 was prepared using the method described in Example 5, wherein 2-fluoro-5-trifluoromethylbenzonitrile was used in Step A, 4-aminothiophene-3-carboxylic acid methyl ester was used in Step D, and pyridin-2-yl-methyl bromide was used in Step G.

Example 108

Preparation of Compound 27

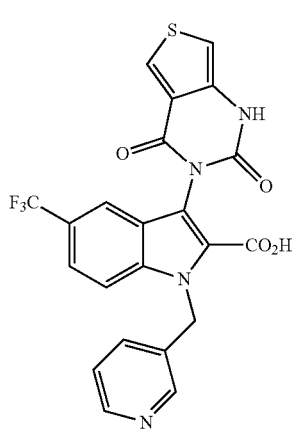

27

Compound 27 was prepared using the method described in Example 5, wherein 2-fluoro-5-trifluoromethylbenzonitrile was used in Step A, 4-aminothiophene-3-carboxylic acid methyl ester was used in Step D, and pyridin-3-yl-methyl bromide was used in Step G.

Example 109

Preparation of Compound 76

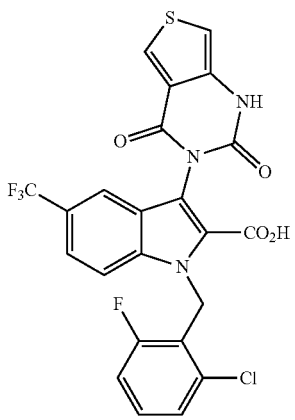

76

Compound 76 was prepared using the method described in Example 5, wherein 2-fluoro-5-trifluoromethylbenzonitrile was used in Step A, 4-aminothiophene-3-carboxylic acid methyl ester was used in Step D, and 2-chloro-6-fluorobenzyl bromide was used in Step G.

Example 110

Preparation of Compound 204

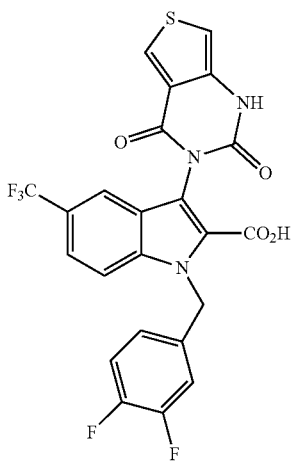

204

Compound 204 was prepared using the method described in Example 5, wherein 2-fluoro-5-trifluoromethylbenzonitrile was used in Step A, 4-aminothiophene-3-carboxylic acid methyl ester was used in Step D, and 3,4-difluorobenzyl bromide was used in Step G.

Example 111

Preparation of Compound 78

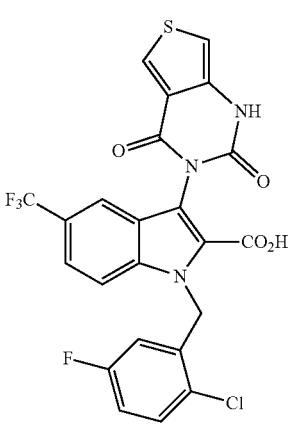

78

Compound 78 was prepared using the method described in Example 5, wherein 2-fluoro-5-trifluoromethylbenzonitrile was used in Step A, 4-aminothiophene-3-carboxylic acid methyl ester was used in Step D, and 2-chloro-5-fluorobenzyl bromide was used in Step G.

Example 112

Preparation of Compound 206

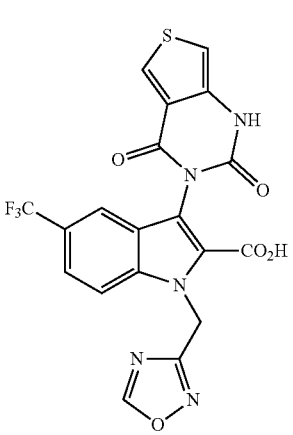

206

Compound 206 was prepared using the method described in Example 5, wherein 2-fluoro-5-trifluoromethylbenzoni- trile was used in Step A, 4-aminothiophene-3-carboxylic acid methyl ester was used in Step D, and [1,2,4]oxadiazol-3-yl-methyl bromide was used in Step G.

Example 113

Preparation of Compound 207

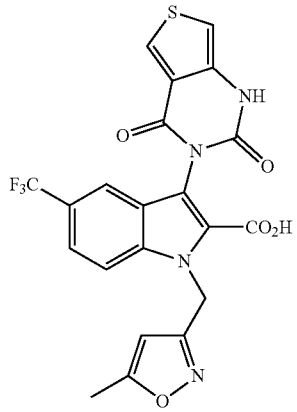

207

Compound 207 was prepared using the method described in Example 5, wherein 2-fluoro-5-trifluoromethylbenzonitrile was used in Step A, 4-aminothiophene-3-carboxylic acid methyl ester was used in Step D, and 5-methylisoxazol-3-yl-methyl bromide was used in Step G.

Example 114

Preparation of Compound 208

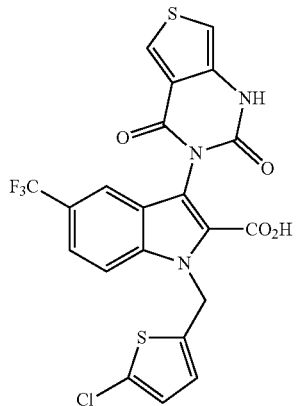

208

Compound 208 was prepared using the method described in Example 5, wherein 2-fluoro-5-trifluoromethylbenzonitrile was used in Step A, 4-aminothiophene-3-carboxylic acid methyl ester was used in Step D, and 5-chlorothiophen-2-yl-methyl bromide was used in Step G.

Example 115

Preparation of Compound 58

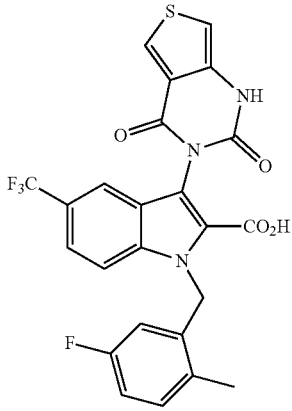

58

Compound 58 was prepared using the method described in Example 5, wherein 2-fluoro-5-trifluoromethylbenzonitrile was used in Step A, 4-aminothiophene-3-carboxylic acid methyl ester was used in Step D, and 5-fluoro-2-methylbenzyl bromide was used in Step G.

Example 116

Preparation of Compound 59

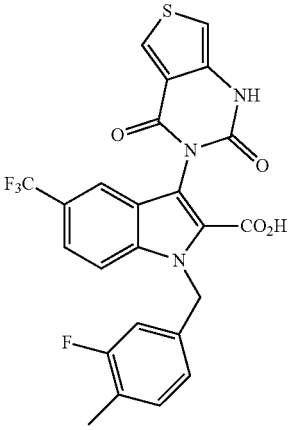

59

Compound 59 was prepared using the method described in Example 5, wherein 2-fluoro-5-trifluoromethylbenzonitrile was used in Step A, 4-aminothiophene-3-carboxylic acid methyl ester was used in Step D, and 3-fluoro-4-methylbenzyl bromide was used in Step G.

Example 117

Preparation of Compound 95

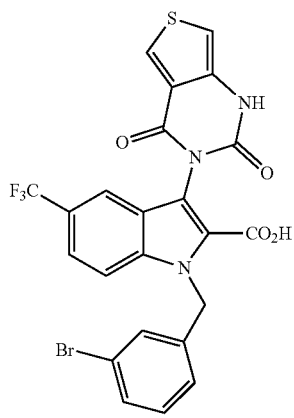

95

Compound 95 was prepared using the method described in Example 5, wherein 2-fluoro-5-trifluoromethylbenzonitrile was used in Step A, 4-aminothiophene-3-carboxylic acid methyl ester was used in Step D, and 3-bromobenzyl bromide was used in Step G.

Example 118

Preparation of Compound 79

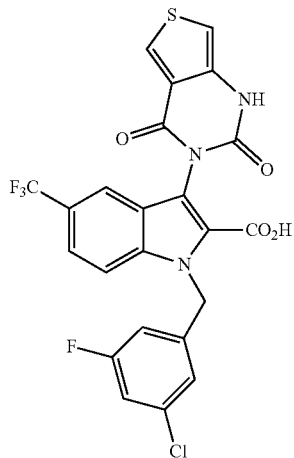

79

Compound 79 was prepared using the method described in Example 5, wherein 2-fluoro-5-trifluoromethylbenzonitrile was used in Step A, 4-aminothiophene-3-carboxylic acid methyl ester was used in Step D, and 3-chloro-5-fluorobenzyl bromide was used in Step G.

Example 119

Preparation of Compound 55

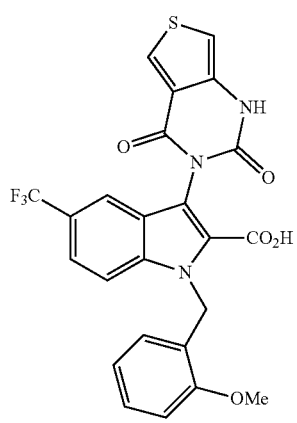

55

Compound 55 was prepared using the method described in Example 5, wherein 2-fluoro-5-trifluoromethylbenzonitrile was used in Step A, 4-aminothiophene-3-carboxylic acid methyl ester was used in Step D, and 2-methoxybenzyl chloride was used in the presence of sodium iodide in Step G.

Example 120

Preparation of Compound 80

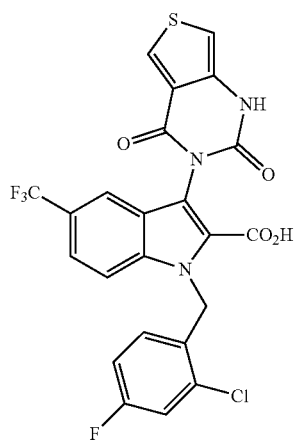

80

Compound 80 was prepared using the method described in Example 5, wherein 2-fluoro-5-trifluoromethylbenzonitrile was used in Step A, 4-aminothiophene-3-carboxylic acid methyl ester was used in Step D, and 2-chloro-4-fluorobenzyl bromide was used in Step G.

Example 121

Preparation of Compound 209

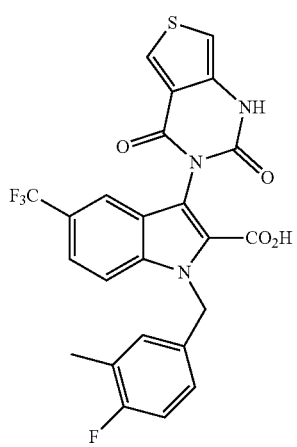

209

Compound 209 was prepared using the method described in Example 5, wherein 2-fluoro-5-trifluoromethylbenzonitrile was used in Step A, 4-aminothiophene-3-carboxylic acid methyl ester was used in Step D, and 4-fluoro-3-methylbenzyl bromide was used in Step G.

Example 122

Preparation of Compound 210

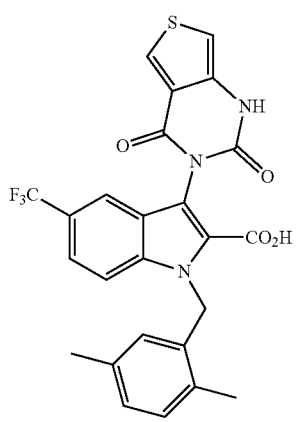

210

Compound 210 was prepared using the method described in Example 5, wherein 2-fluoro-5-trifluoromethylbenzonitrile was used in Step A, 4-aminothiophene-3-carboxylic acid methyl ester was used in Step D, and 2,5-dimethylbenzyl bromide was used in Step G.

Example 123

Preparation of Compound 211

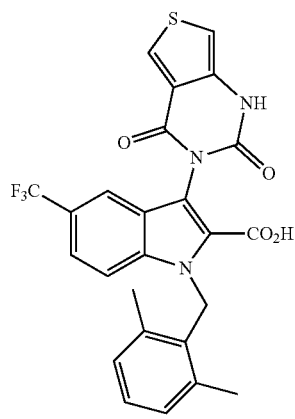

211

Compound 211 was prepared using the method described in Example 5, wherein 2-fluoro-5-trifluoromethylbenzonitrile was used in Step A, 4-aminothiophene-3-carboxylic acid methyl ester was used in Step D, and 2,6-dimethylbenzyl bromide was used in Step G.

Example 124

Preparation of Compound 71

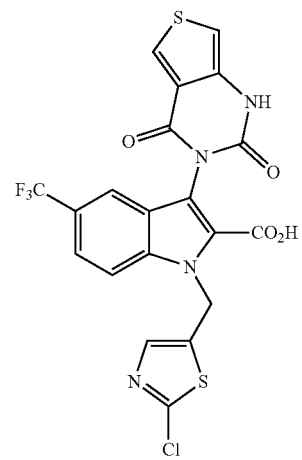

71

Compound 211 was prepared using the method described in Example 5, wherein 2-fluoro-5-trifluoromethylbenzonitrile was used in Step A, 4-aminothiophene-3-carboxylic acid methyl ester was used in Step D, and 2-chlorothiazol-5-yl-methyl bromide was used in Step G.

Example 125

Preparation of Compound 66

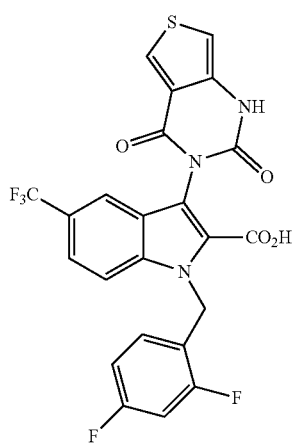

66

Compound 66 was prepared using the method described in Example 5, wherein 2-fluoro-5-trifluoromethylbenzonitrile was used in Step A, 4-aminothiophene-3-carboxylic acid methyl ester was used in Step D, and 2,4-difluorobenzyl bromide was used in Step G.

Example 126

Preparation of Compound 212

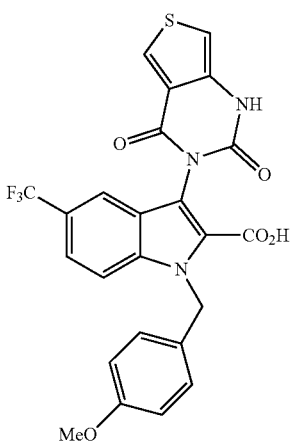

212

Compound 212 was prepared using the method described in Example 5, wherein 2-fluoro-5-trifluoromethylbenzoni-trile was used in Step A, 4-aminothiophene-3-carboxylic acid methyl ester was used in Step D, and 4-methoxybenzyl bromide was used in Step G.

Example 127

Preparation of Compound 5

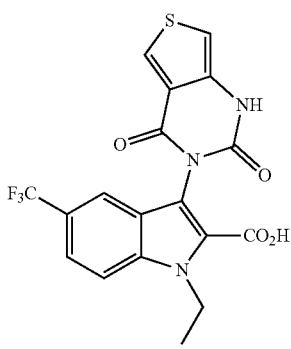

5

Compound 5 was prepared using the method described in Example 5, wherein 2-fluoro-5-trifluoromethylbenzonitrile was used in Step A, 4-aminothiophene-3-carboxylic acid methyl ester was used in Step D, and ethyl bromide was used in Step G.

Example 128

Preparation of Compound 7

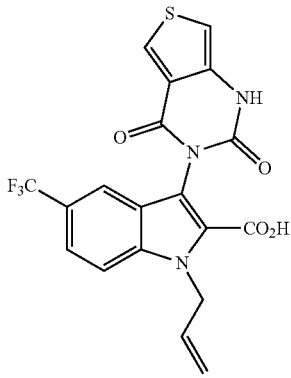

7

Compound 7 was prepared using the method described in Example 5, wherein 2-fluoro-5-trifluoromethylbenzonitrile was used in Step A, 4-aminothiophene-3-carboxylic acid methyl ester was used in Step D, and allyl bromide was used in Step G.

Example 129

Preparation of Compound 213

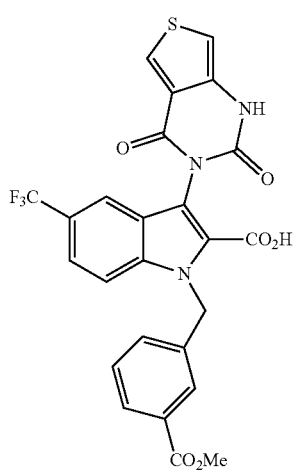

Compound 213 was prepared using the method described in Example 5, wherein 2-fluoro-5-trifluoromethylbenzonitrile was used in Step A, 4-aminothiophene-3-carboxylic acid methyl ester was used in Step D, and 3-methoxycarbonylbenzyl bromide was used in Step G.

Example 130

Preparation of Compound 44

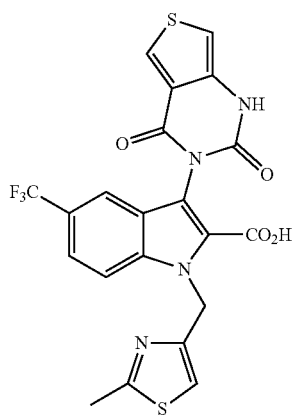

Compound 44 was prepared using the method described in Example 5, wherein 2-fluoro-5-trifluoromethylbenzonitrile was used in Step A, 4-aminothiophene-3-carboxylic acid methyl ester was used in Step D, and 2-methylthiazol-4-yl-methyl bromide was used in Step G.

Example 131

Preparation of Compound 22

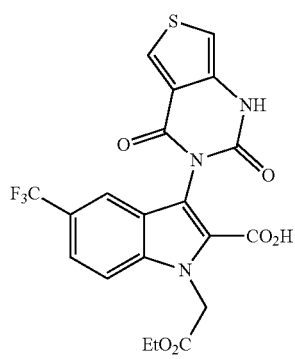

Compound 22 was prepared using the method described in Example 5, wherein 2-fluoro-5-trifluoromethylbenzonitrile was used in Step A, 4-aminothiophene-3-carboxylic acid methyl ester was used in Step D, and ethyl bromoacetate was used in Step G.

Example 132

Preparation of Compound 6

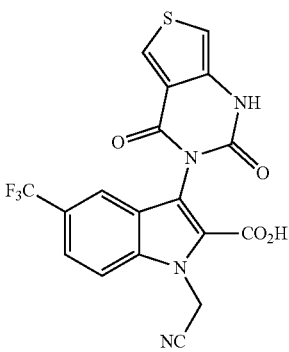

Compound 6 was prepared using the method described in Example 5, wherein 2-fluoro-5-trifluoromethylbenzonitrile was used in Step A, 4-aminothiophene-3-carboxylic acid methyl ester was used in Step D, and bromoacetonitrile was used in Step G.

Example 133

Preparation of Compound 3

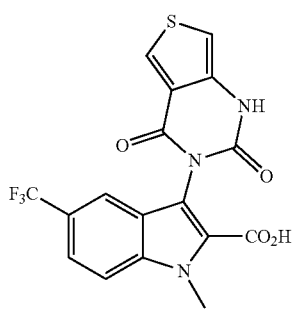

Compound 3 was prepared using the method described in Example 5, wherein 2-fluoro-5-trifluoromethylbenzonitrile was used in Step A, 4-aminothiophene-3-carboxylic acid methyl ester was used in Step D, and methyl iodide was used in Step G.

Example 134

Preparation of Compound 65

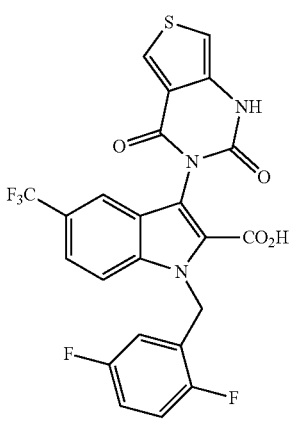

Compound 65 was prepared using the method described in Example 5, wherein 2-fluoro-5-trifluoromethylbenzonitrile was used in Step A, 4-aminothiophene-3-carboxylic acid methyl ester was used in Step D, and 2,5-difluorobenzyl bromide was used in Step G.

Example 135

Preparation of Compound 75

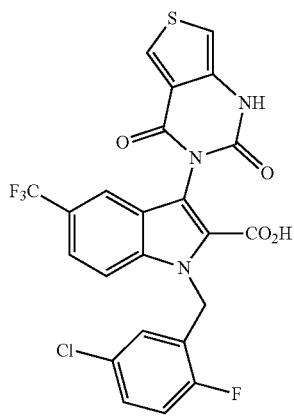

Compound 75 was prepared using the method described in Example 5, wherein 2-fluoro-5-trifluoromethylbenzonitrile was used in Step A, 4-aminothiophene-3-carboxylic acid methyl ester was used in Step D, and 5-chloro-2-fluorobenzyl bromide was used in Step G.

Example 136

Preparation of Compound 60

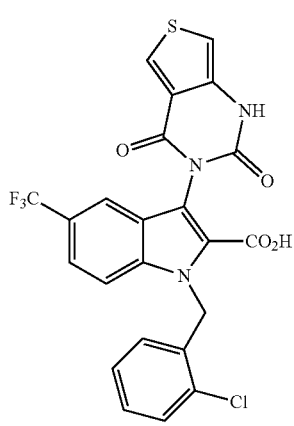

Compound 60 was prepared using the method described in Example 5, wherein 2-fluoro-5-trifluoromethylbenzonitrile was used in Step A, 4-aminothiophene-3-carboxylic acid methyl ester was used in Step D, and 2-chlorobenzyl bromide was used in Step G.

Example 137

Preparation of Compound 214

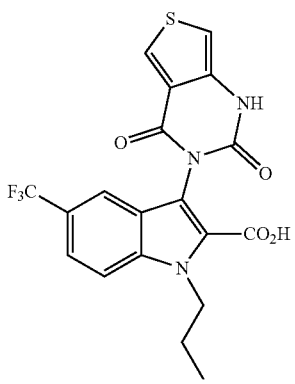

Compound 214 was prepared using the method described in Example 5, wherein 2-fluoro-5-trifluoromethylbenzonitrile was used in Step A, 4-aminothiophene-3-carboxylic acid methyl ester was used in Step D, and propyl bromide was used in Step G.

Example 138

Preparation of Compound 215

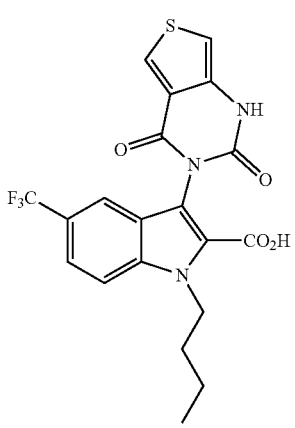

Compound 215 was prepared using the method described in Example 5, wherein 2-fluoro-5-trifluoromethylbenzonitrile was used in Step A, 4-aminothiophene-3-carboxylic acid methyl ester was used in Step D, and butyl bromide was used in Step G.

Example 139

Preparation of Compound 216

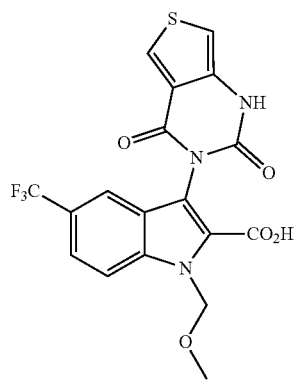

Compound 216 was prepared using the method described in Example 5, wherein 2-fluoro-5-trifluoromethylbenzonitrile was used in Step A, 4-aminothiophene-3-carboxylic acid methyl ester was used in Step D, and methoxymethyl chloride was used in Step G.

Example 140

Preparation of Compound 97

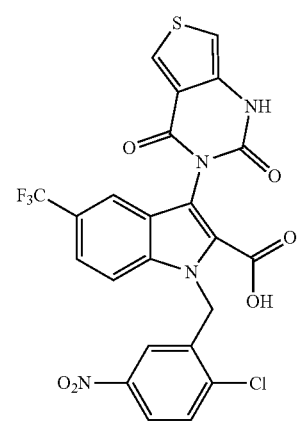

Compound 97 was prepared using the method described in Example 1, wherein 2-fluoro-5-trifluoromethylbenzonitrile and 2-chloro-5-nitrobenzylamine was used in Step A, and 4-aminothiophene-3-carboxylic acid methyl ester was used in Step D.

Example 141

Preparation of Compound 10

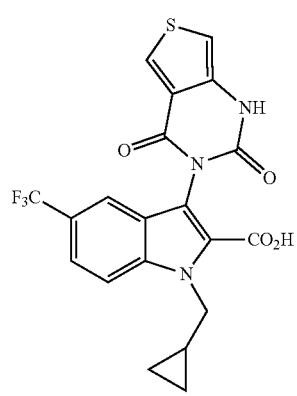

Compound 10 was prepared using the method described in Example 5, wherein 2-fluoro-5-trifluoromethylbenzonitrile was used in Step A, 4-aminothiophene-3-carboxylic acid methyl ester was used in Step D, and cyclopropylmethyl bromide was used in Step G.

Example 142

Preparation of Compound 54

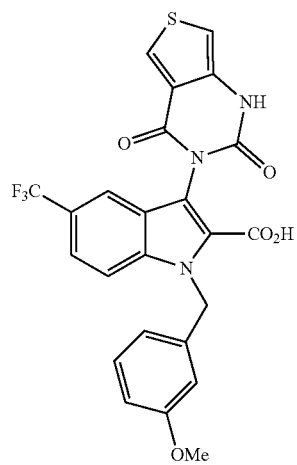

Compound 54 was prepared using the method described in Example 5, wherein 2-fluoro-5-trifluoromethylbenzonitrile was used in Step A, 4-aminothiophene-3-carboxylic acid methyl ester was used in Step D, and 3-methoxybenzyl bromide was used in Step G.

Example 143

Preparation of Compound 40

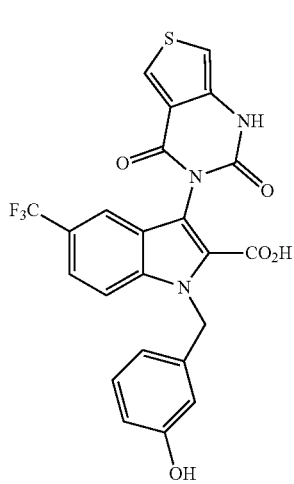

Compound 40 was prepared from compound 54 using the method described in Example 6.

Example 144

Preparation of Compound 104

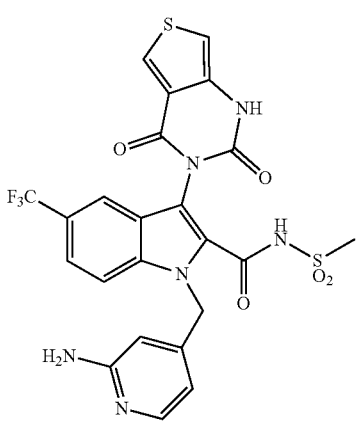

Compound 104 was prepared using the method described in Example 5, wherein 2-fluoro-5-trifluoromethylbenzonitrile was used in Step A, (wherein was used), 4-aminothiophene-3-carboxylic acid methyl ester was used in Step D, and 2-tert-butoxycarbonylaminopyridin-4-yl-methyl bromide was used in Step G

Example 145

Preparation of Compound 39

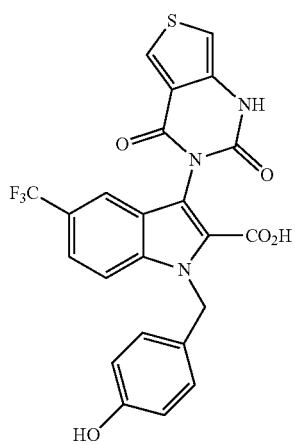

Compound 39 was prepared from compound 212 using the method described in Example 6.

Example 146

Preparation of Compound 101

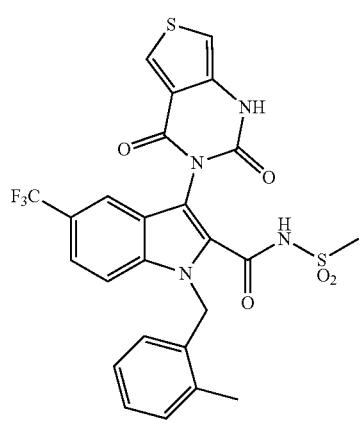

Compound 101 was prepared by reacting 34 with methanesulfonamide, using the method described in Example 2.

Example 147

Preparation of Compound 122

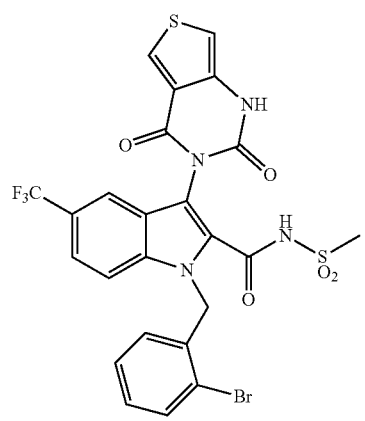

Compound 122 was prepared by reacting compound 202 with methanesulfonimide, using the method described in Example 2.

Example 148

Preparation of Compound 50

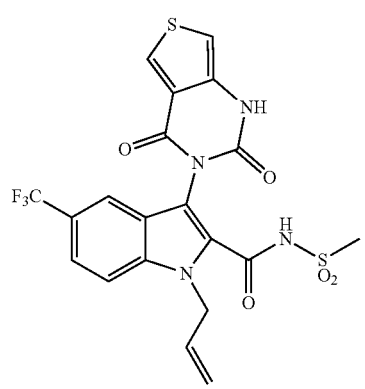

Compound 50 was prepared by reacting compound 7 with methanesulfonimide, using the method described in Example 2.

Example 149

Preparation of Compound 105

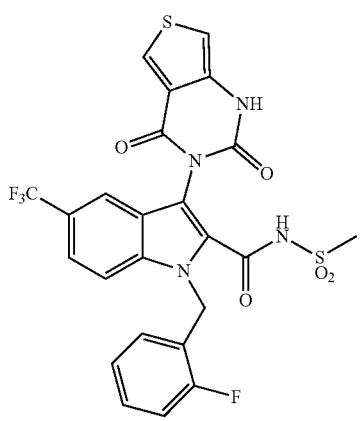

105

Compound 105 was prepared by reacting compound 41 with methanesulfonimide, using the method described in Example 2.

Example 150

Preparation of Compound 37

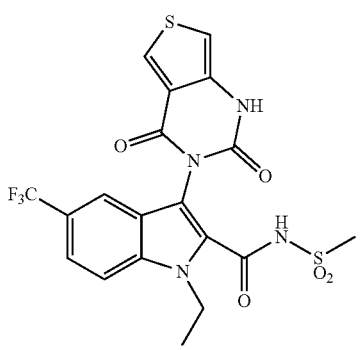

37

Compound 37 was prepared by reacting compound 127 with methanesulfonimide, using the method described in Example 2.

Example 151

Preparation of Compound 111

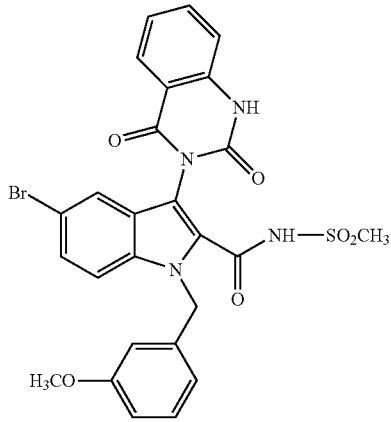

111

Compound 111 was prepared by first using the methods shown in Example 1, wherein 5-bromo-2-fluorobenzonitrile and 3-methoxybenzylamine were used in Step A, and methyl anthranilate was used in Step D. The product such obtained was then reacted with methanesulfonamide according to the method disclosed in Example 2 to provide compound 111.

Example 152

Preparation of Compound 4

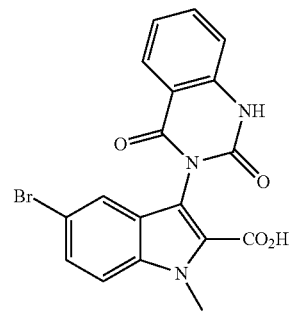

4

Compound 4 was prepared using the methods shown in Example 1, wherein 5-bromo-2-fluorobenzonitrile and methylamine were used in Step A, and methyl anthranilate was used in Step D.

Example 153

Preparation of Compound 217

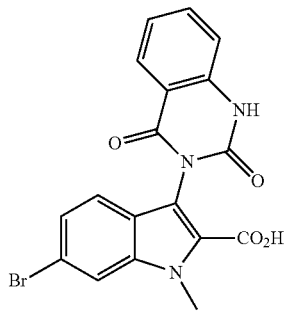

217

Compound 217 was prepared using the methods shown in Example 1, wherein 4-bromo-2-fluorobenzonitrile and methylamine were used in Step A, and methyl anthranilate was used in Step D.

Example 154

Preparation of Compound 218

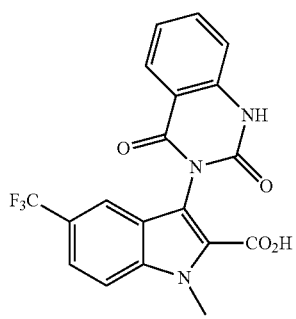
218

Compound 218 was prepared using the methods shown in Example 1, wherein 2-fluoro-5-trifluoromethylbenzonitrile and methylamine were used in Step A, and methyl anthranilate was used in Step D.

Example 155

Preparation of Compound 28

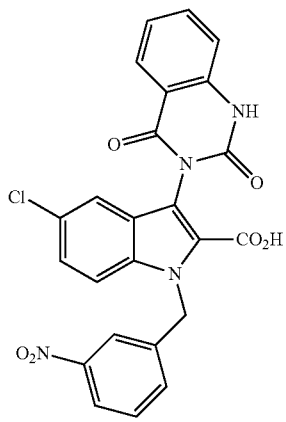
28

Compound 28 was prepared using the methods shown in Example 1, wherein 5-chloro-2-fluorobenzonitrile and methylamine were used in Step A, and methyl anthranilate was used in Step D.

Example 156

Preparation of Compound 14

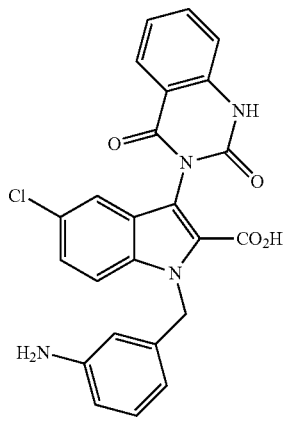
14

Compound 14 was prepared from compound 28 using the method described in Example 4.

Example 157

Preparation of Compound 219

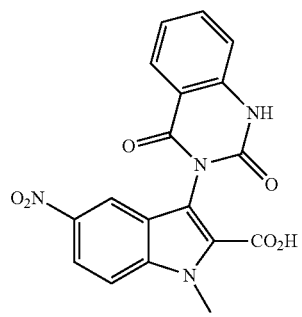
219

Compound 219 was prepared using the methods shown in Example 1, wherein 2-fluoro-5-nitrobenzonitrile and methylamine were used in Step A, and methyl anthranilate was used in Step D.

Example 158

Preparation of Compound 220

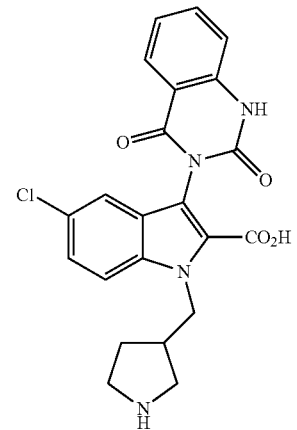
220

Compound 220 was prepared using the methods shown in Example 1, wherein 5-chloro-2-fluorobenzonitrile and 3-aminomethyl-1-tert-butoxycarbonylpyrrolidine were used in Step A, and methyl anthranilate was used in Step D.

Example 159

Preparation of Compound 221

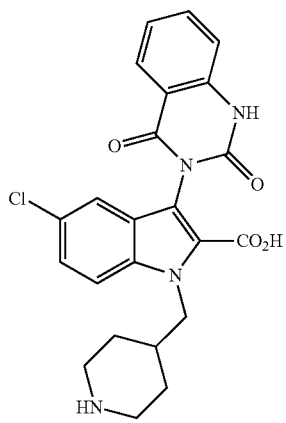

221

Compound 221 was prepared using the methods shown in Example 1, wherein 5-chloro-2-fluorobenzonitrile and 4-aminomethyl-1-tert-butoxycarbonylpiperidine were used in Step A, and methyl anthranilate was used in Step D.

Example 160

Preparation of Compound 222

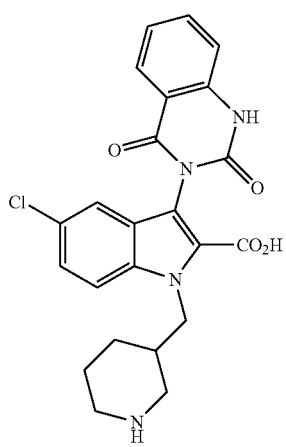

222

Compound 222 was prepared using the methods shown in Example 1, wherein 5-chloro-2-fluorobenzonitrile and 3-aminomethyl-1-tert-butoxycarbonylpiperidine were used in Step A, and methyl anthranilate was used in Step D.

Example 161

Preparation of Compound 16

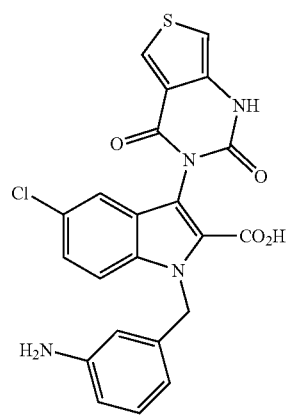

16

Compound 16 was prepared using the methods shown in Example 1, wherein 5-chloro-2-fluorobenzonitrile and 3-nitrobenzylamine were used in Step A, and 4-aminothiophene-3-carboxylic acid methyl ester was used in Step D.

Example 162

Preparation of Compound 49

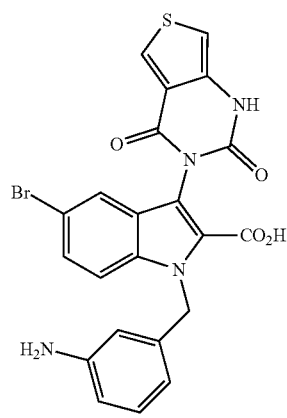

49

Compound 49 was prepared using the methods shown in Example 1, wherein 5-bromo-2-fluorobenzonitrile and 3-nitrobenzylamine were used in Step A, and 4-aminothiophene-3-carboxylic acid methyl ester was used in Step D.

Example 163

Preparation of Compound 42

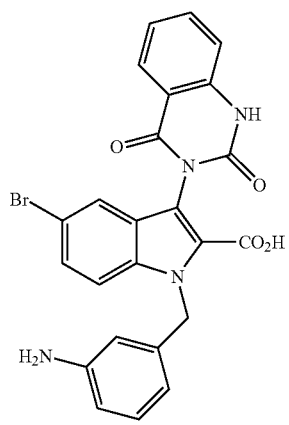

42

Compound 42 was prepared using the methods shown in Example 1, wherein 5-bromo-2-fluorobenzonitrile and 3-nitrobenzylamine were used in Step A, and methyl anthranilate was used in Step D.

Example 164

Preparation of Compound 32

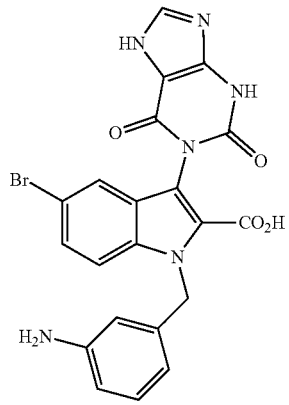

32

Compound 32 was prepared by first using methods shown in Example 1, wherein 5-bromo-2-fluorobenzonitrile and 3-nitrobenzylamine were used in Step A, Step B, Step C, 5-amino-3-(4-methoxybenzyl)-3H-imidazole-4-carboxylic acid methyl ester was used in Step D and trifluoroacetic acid was used in a microwave reactor at 120° C. for 30 minutes in Step F. This provided an intermediate nitro compound which was subsequently reduced using the method described in Example 4 to provide amino compound 32.

Example 165

Preparation of Compound 223

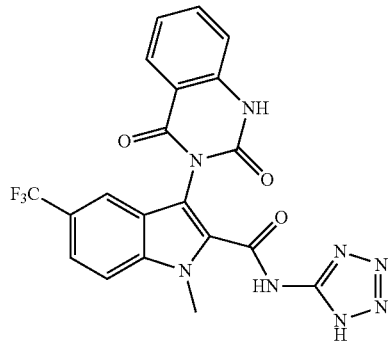

223

Compound 223 was prepared from compound 218 using the method described in Example 3, wherein 5-aminotetrazole was used.

Example 166

Preparation of Compound 92

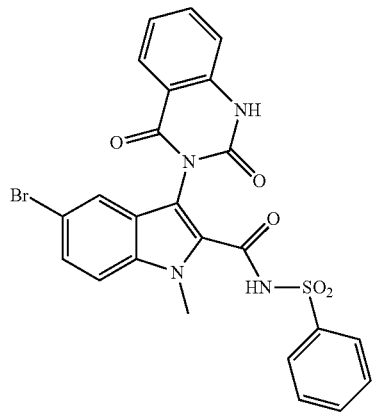

92

Compound 92 was prepared from compound 4 using the method described in Example 2, wherein benzenesulfonamide was used.

Example 167

Preparation of Compound 224

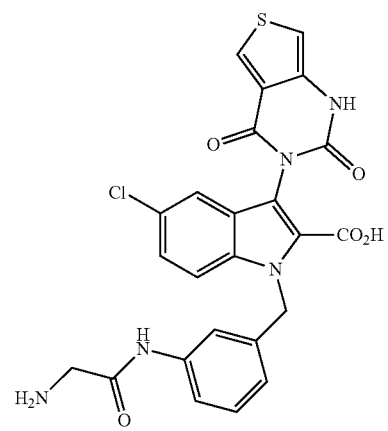

224

Compound 224 was prepared by first using the method described in Example 1 and using 5-chloro-2-fluorobenzonitrile and 3-nitrobenzylamine in Step A, and 4-aminothiophene-3-carboxylic acid methyl ester in Step D. This provided an intermediate benzylnitro compound which was subsequently reduced using the method described in Example 4 to provide an intermediate benzylamino. The resulting benzylamino intermediate was then reacted with tert-butoxycarbonylaminoacetic acid according to the method described in Example 3 to provide compound 224.

Example 168

Preparation of Compound 15

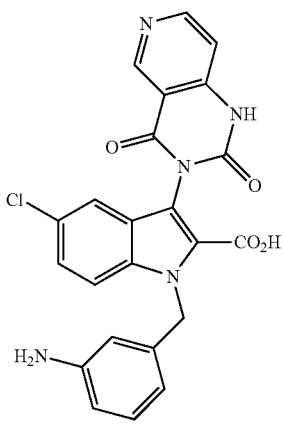

Compound 15 was prepared by first using the method described in Example 1 and using 5-chloro-2-fluorobenzonitrile and 3-nitrobenzylamine in Step A, and 4-aminonicotinic acid methyl ester in Step D. This provided an intermediate benzylnitro compound which was subsequently reduced using the method described in Example 4 to provide benzylamino compound 15.

Example 169

Preparation of Compound 225

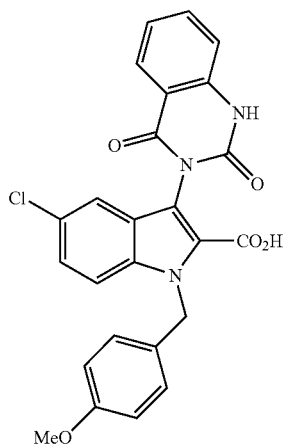

Compound 225 was prepared using the method described in Example 1 and using 5-chloro-2-fluorobenzonitrile and 4-methoxybenzylamine in Step A and methyl anthranilate in Step D.

Example 170

Preparation of Compound 45

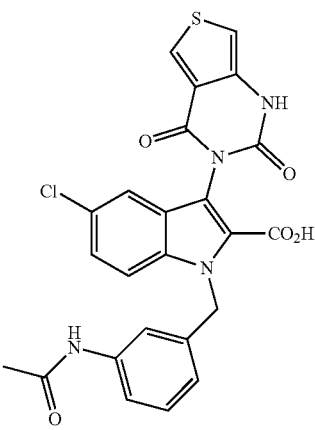

Compound 45 was prepared by first using the method described in Example 1 and using 5-chloro-2-fluorobenzonitrile and 3-nitrobenzylamine in Step A, and 4-aminothiophene-3-carboxylic acid methyl ester in Step D. This provided an intermediate benzylnitro compound which was subsequently reduced using the method described in Example 4 to provide an intermediate benzylamino. The resulting benzylamino intermediate was then reacted with acetic acid according to the method described in Example 3 to provide compound 45.

Example 171

Preparation of Compound 226

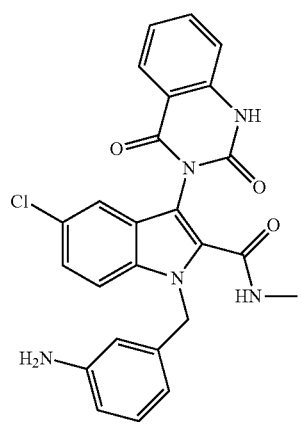

Compound 226 was prepared from 5-chloro-3-(2,4-dioxo-1,4-dihydro-2H-quinazolin-3-yl)-1-(3-nitrobenzyl)-1H-indole-2-carboxylic acid B155 using the method described in Example 3, (wherein methylamine was used) in Example 4.

Example 172

Preparation of Compound 227

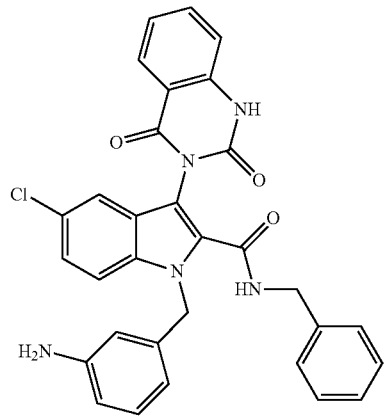

227

Compound 227 was prepared by first reacting compound 28 with methylamine using the method described in Example 3. This provided an intermediate amido compound which was then reduced using the method described in Example 4 to provide compound 229.

Example 173

Preparation of Compound 228

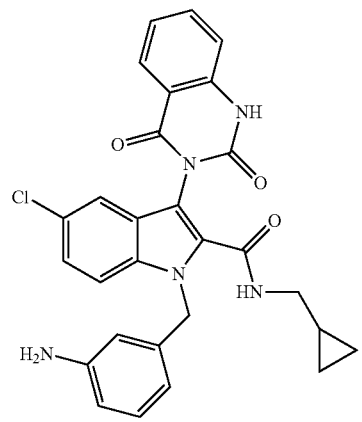

228

Compound 228 was prepared by first reacting compound 28 with cyclopropylmethylamine using the method described in Example 3. This provided an intermediate amido compound which was then reduced using the method described in Example 4 to provide compound 228.

Example 174

Preparation of Compound 229

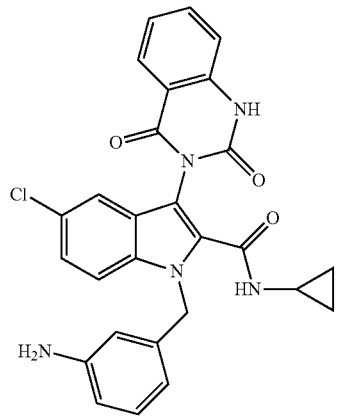

229

Compound 229 was prepared by first reacting compound 28 with cyclopropylamine using the method described in Example 3. This provided an intermediate amido compound which was then reduced using the method described in Example 4 to provide compound 229.

Example 175

Preparation of Compound 230

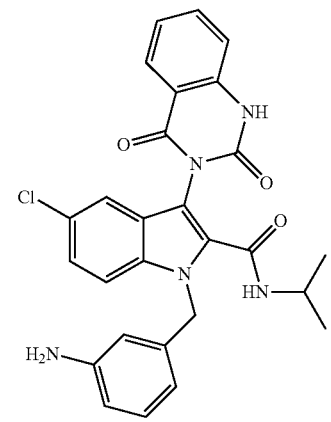

230

Compound 230 was prepared by first reacting compound 28 with isopropylamine using the method described in Example 3. This provided an intermediate amido compound which was then reduced using the method described in Example 4 to provide compound 230.

Example 176

Preparation of Compound 231

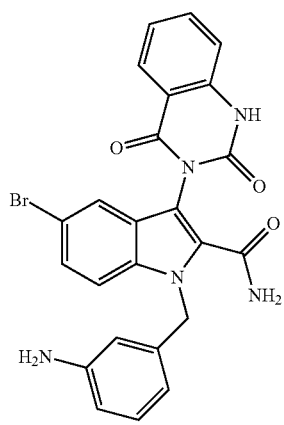

Compound 231 was prepared by first reacting compound 28 with ammonia using the method described in Example 3. This provided an intermediate amido compound which was then reduced using the method described in Example 4 to provide compound 231.

Example 177

Preparation of Compound 115

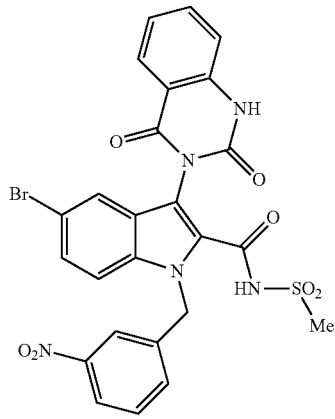

Compound 115 was prepared by first using methods shown in Example 1, wherein 5-bromo-2-fluorobenzonitrile and 3-nitrobenzylamine were used in Step A, and methyl anthranilate was used in Step D. This provided an intermediate compound which was then reacted with methanesulfonamide using the method described in Example 2 to provide compound 115.

Example 178

Preparation of Compound 106

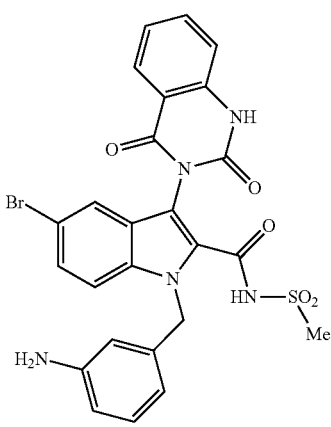

Compound 106 was prepared by reducing compound 115 using the method described in Example 4.

Example 179

Preparation of Compound 123

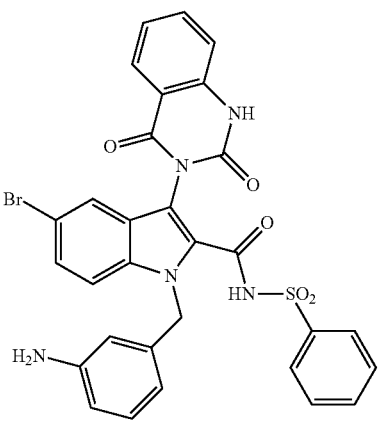

Compound 123 was prepared by first using the methods described in Example 1, 5-bromo-2-fluorobenzonitrile and 3-nitrobenzylamine were used in Step A, methyl anthranilate was used in Step D. This provided an intermediate compound which was then reacted with benzenesulfonamide according to the method described in Example 2. The compound such Example 180

Preparation of Compound 121

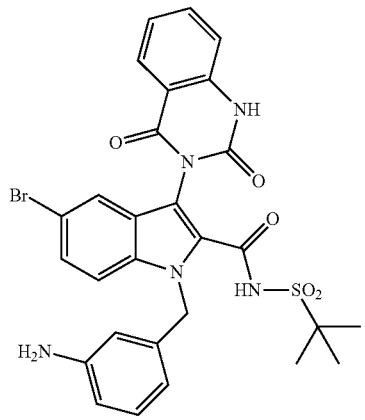
121

Compound 121 was prepared by first using the method described in Example 1 and using 5-bromo-2-fluorobenzonitrile and 3-nitrobenzylamine in Step A, and methyl anthranilate in Step D. This provided an intermediate an intermediate compound which was then reacted with tert-butanesulfonamide using the method described in Example 2. The resulting tert-butyl acyl sulfonamide compound was subsequently reduced using the method described in Example 4 to provide compound 121.

Example 181

Preparation of Compound 69

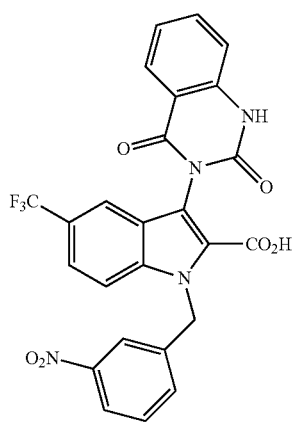
69

Compound 69 was prepared using the method described in Example 1 and using 2-fluoro-5-trifluoromethylbenzonitrile and 3-nitrobenzylamine in Step A and methyl anthranilate in Step D.

Example 182

Preparation of Compound 31

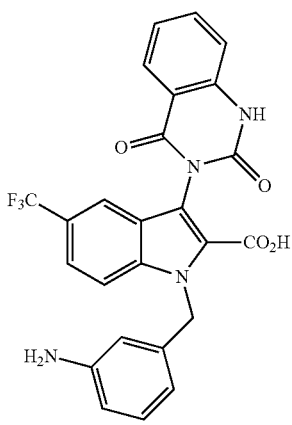
31

Compound 31 was prepared from compound 69 using the method described in Example 4.

Example 183

Preparation of Compound 73

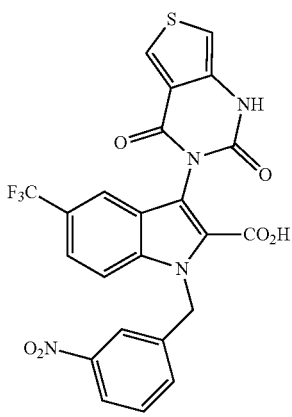
73

Compound 73 was prepared using the method described in Example 1 and using 2-fluoro-5-trifluoromethylbenzonitrile and 3-nitrobenzylamine in Step A and 4-aminothiophene-3-carboxylic acid methyl ester in Step D.

Example 184

Preparation of Compound 36

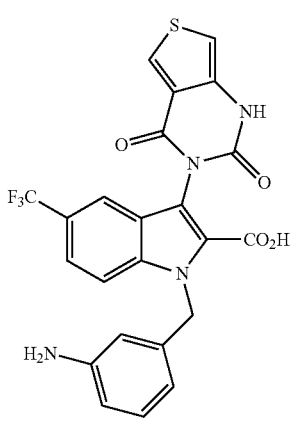

36

Compound 36 was prepared from compound 73 using the method described in Example 4.

Example 185

Preparation of Compound 53

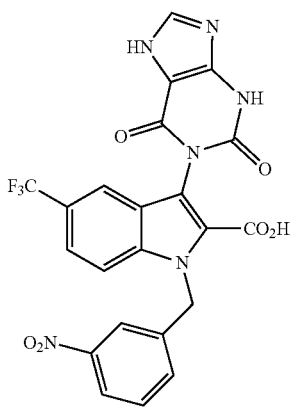

53

Compound 53 was prepared using the method described in Example 1 and using 2-fluoro-5-trifluoromethylbenzonitrile and 3-nitrobenzylamine in Step A, 4-aminothiophene-3-carboxylic acid methyl ester in Step D, and trifluoroacetic acid in a microwave reactor at 120° C. for 30 minutes in Step F.

Example 186

Preparation of Compound 24

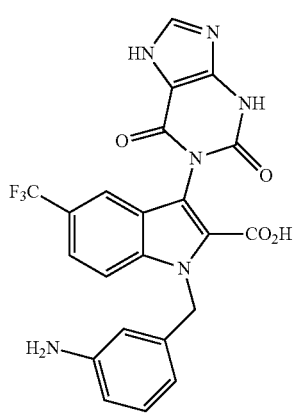

24

Compound 24 was prepared from compound 53 using the method described in Example 4.

Example 187

Preparation of Compound 232

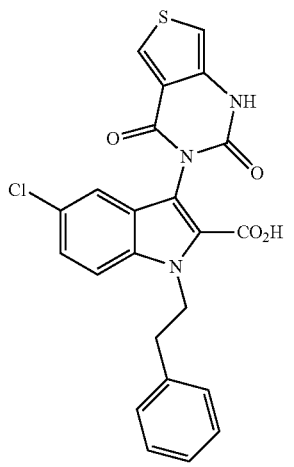

232

Compound 232 was prepared using the method described in Example 1 and using 5-chloro-2-fluorobenzonitrile and phenethylamine in Step A and 4-aminothiophene-3-carboxylic acid methyl ester in Step D.

Example 188

Preparation of Compound 233

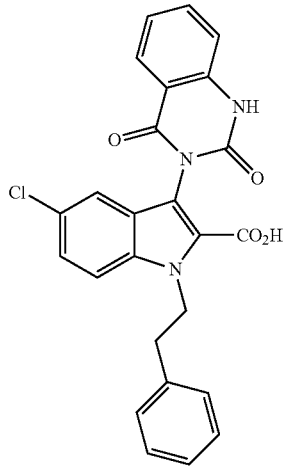

Compound 233 was prepared using the method described in Example 1 and using 5-chloro-2-fluorobenzonitrile and phenethylamine in Step A and methyl anthranilate in Step D.

Example 189

Preparation of Compound 20

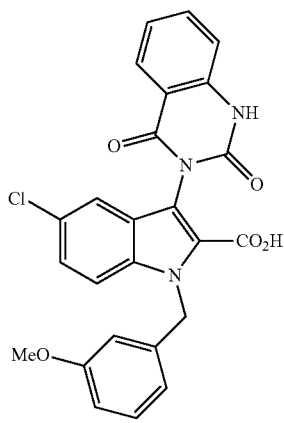

Compound 20 was prepared using the method described in Example 1 and using 5-chloro-2-fluorobenzonitrile and 3-methoxybenzylamine in Step A and methyl anthranilate in Step D.

Example 190

Preparation of Compound 23

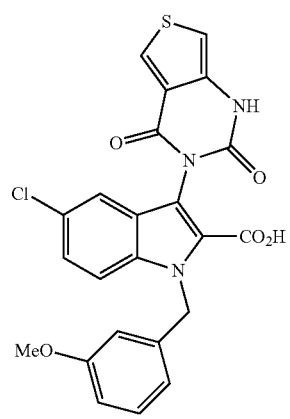

Compound 23 was prepared using the method described in Example 1 and using 5-chloro-2-fluorobenzonitrile and 3-methoxybenzylamine in Step A and 4-aminothiophene-3-carboxylic acid methyl ester in Step D.

Example 191

Preparation of Compound 234

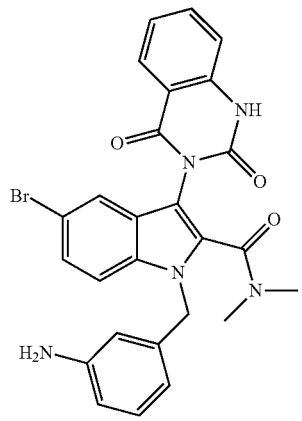

Compound 234 was prepared by first using the method described in Example 1 and using 5-bromo-2-fluorobenzonitrile and 3-nitrobenzylamine in Step A, and methyl anthranilate in Step D. This provided an intermediate an intermediate compound which was then reacted with diethylamine using the method described in Example 3. The resulting dim-

355 ethylamino intermediate was subsequently reduced using the method described in Example 4 to provide compound 234.

Example 192

Preparation of Compound 235

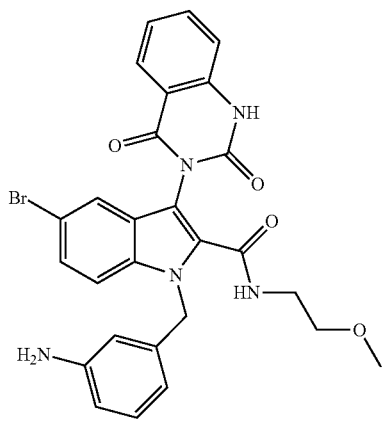

235

Compound 235 was prepared by first using the method described in Example 1 and using 5-bromo-2-fluorobenzonitrile and 3-nitrobenzylamine in Step A, and methyl anthranilate in Step D. This provided an intermediate an intermediate compound which was then reacted with 2-(methoxyethyl)amine using the method described in Example 3. The resulting dimethylamino intermediate was subsequently reduced using the method described in Example 4 to provide compound 235.

Example 193

Preparation of Compound 236

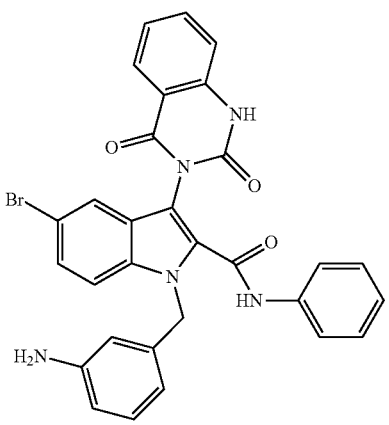

236

Compound 236 was prepared by first using the method described in Example 1 and using 5-bromo-2-fluorobenzonitrile and 3-nitrobenzylamine in Step A, and methyl anthranilate in Step D. This provided an intermediate an intermediate compound which was then reacted with aniline using the method described in Example 3. The resulting dimethy-

356 lamino intermediate was subsequently reduced using the method described in Example 4 to provide compound 236.

Example 194

Preparation of Compound 237

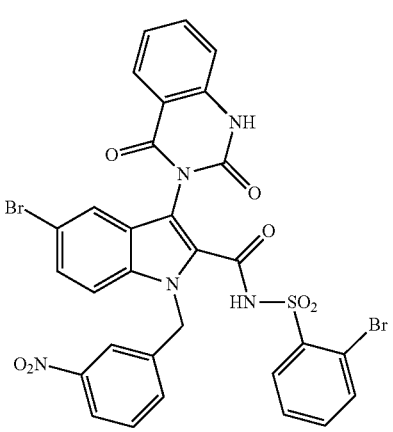

237

Compound 237 was prepared by first using the method described in Example 1 and using 5-bromo-2-fluorobenzonitrile and 3-nitrobenzylamine in Step A, and methyl anthranilate in Step D. This provided an intermediate an intermediate compound which was then reacted with 2-bromobenzenesulfonamide using the method described in Example 2 to provide compound 237.

Example 195

Preparation of Compound 238

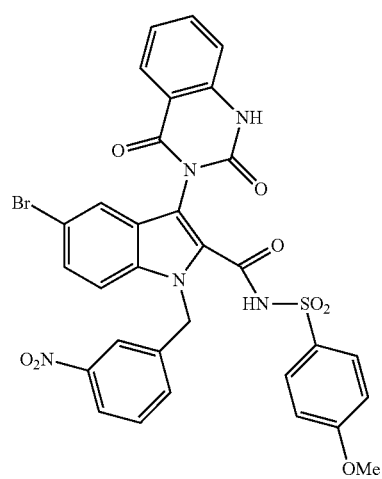

238

Compound 238 was prepared by first using the method described in Example 1 and using 5-bromo-2-fluorobenzonitrile and 3-nitrobenzylamine in Step A, and methyl anthranilate in Step D. This provided an intermediate an intermediate compound which was then reacted with Example 196

Preparation of Compound 94

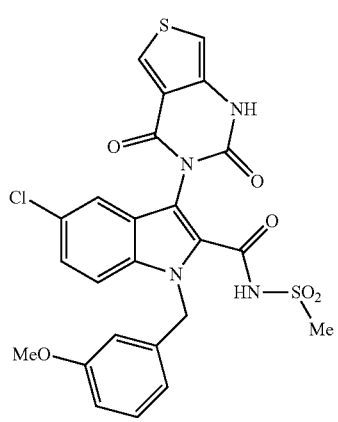
94

Compound 94 was prepared by reacting compound 23 with methanesulfonimide, using the method described in Example 2.

Example 197

Preparation of Compound 62

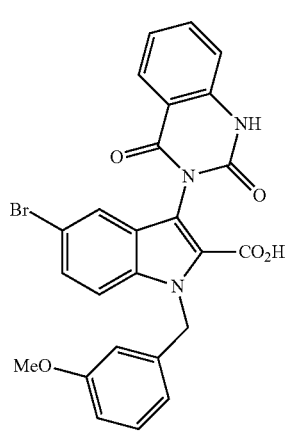
62

Compound 62 was prepared using the method described in Example 1 and using 5-bromo-2-fluorobenzonitrile and 3-methoxybenzylamine in Step A and methyl anthranilate in Step D.

Example 198

Preparation of Compound 70

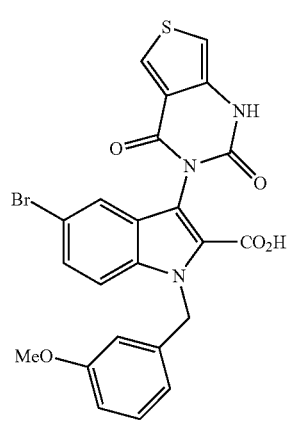
70

Compound 70 was prepared using the method described in Example 1 and using 5-bromo-2-fluorobenzonitrile and 3-methoxybenzylamine in Step A and 4-aminothiophene-3-carboxylic acid methyl ester was used in Step D.

Example 199

Preparation of Compound 46

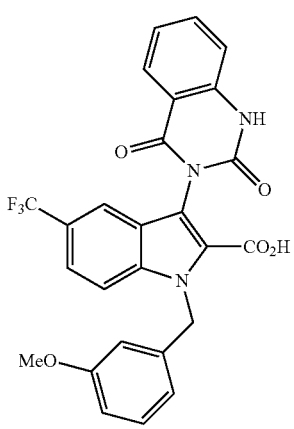
46

Compound 46 was prepared using the method described in Example 1 and using 2-fluoro-5-trifluoromethylbenzonitrile and 3-methoxybenzylamine in Step A and methyl anthranilate was used in Step D.

Example 200

Preparation of Compound 91

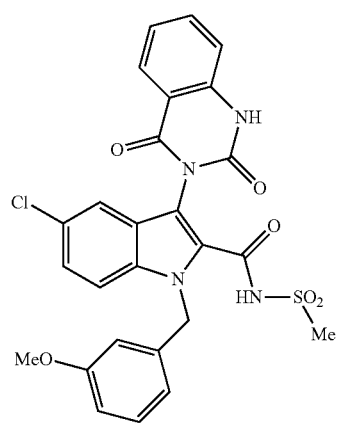

91

Compound 91 was prepared by reacting compound 20 with methanesulfonimide, using the method described in Example 2.

Example 201

Preparation of Compound 111

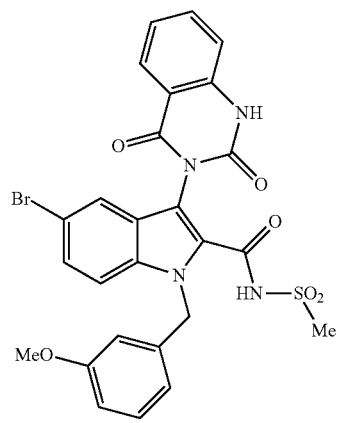

111

Compound 111 was prepared by reacting compound 62 with methanesulfonimide, using the method described in Example 2.

Example 202

Preparation of Compound 113

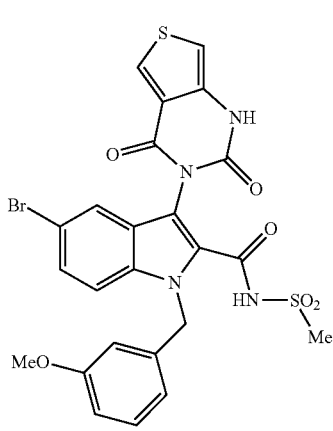

113

Compound 111 was prepared by reacting compound 70 with methanesulfonimide, using the method described in Example 2.

Example 203

Preparation of Compound 107

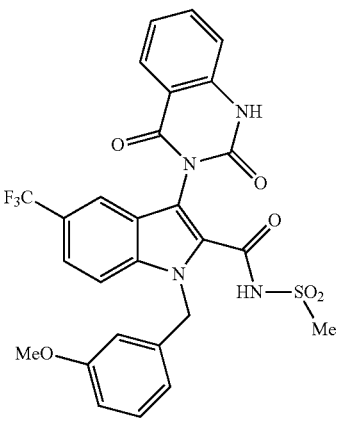

107

Compound 107 was prepared by reacting compound 46 with methanesulfonimide, using the method described in Example 2.

Example 204

Preparation of Compound 109

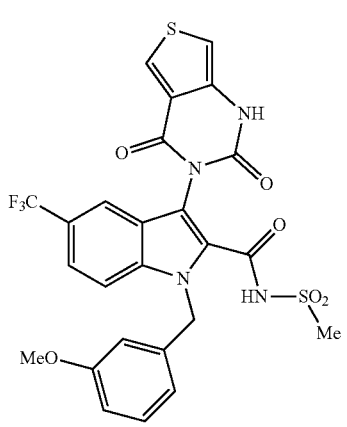

109

Compound 109 was prepared by first using the method described in Example 1 and using 2-fluoro-5-trifluoromethylbenzonitrile and 3-methoxybenzylamine in Step A, and 4-aminothiophene-3-carboxylic acid methyl ester in Step D. This provided an intermediate an intermediate compound which was then reacted with methanesulfonamide using the method described in Example 2 to provide compound 109.

Example 205

Preparation of Compound 82

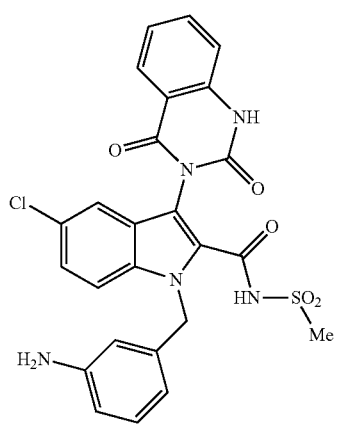

82

Compound 82 was prepared from compound 28 using methods shown in Example 2 (wherein methanesulfonamide was used) and Example 4.

Example 206

Preparation of Compound 100

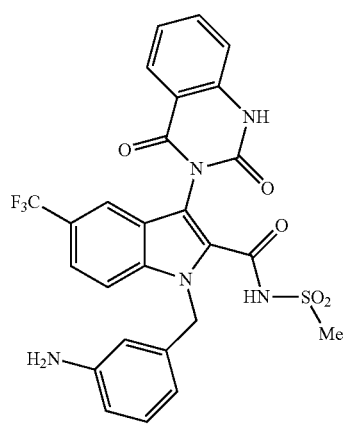

100

Compound 100 was prepared from compound 69 using methods shown in Example 2 (wherein methanesulfonamide was used) and Example 4.

Example 207

Preparation of Compound 102

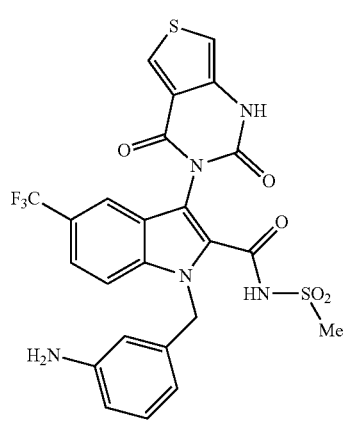

102

Compound 102 was prepared from compound 73 using methods shown in Example 2 (wherein methanesulfonamide was used) in Example 4.

Example 208

Preparation of Compound 116

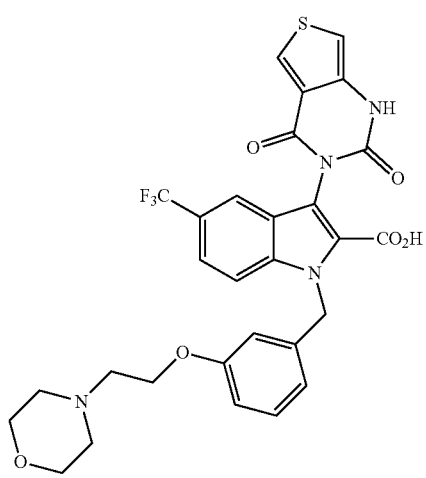

116

Compound 116 was prepared using the method described in Example 1 and using 2-fluoro-5-trifluoromethylbenzonitrile and 3-(2-morpholin-4-yl-ethoxy)benzylamine in Step A and 4-aminothiophene-3-carboxylic acid methyl ester was used in Step D.

Example 209

Preparation of Compound 239

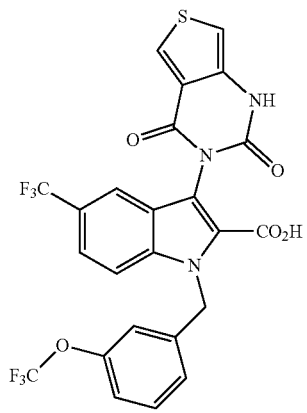

239

Compound 239 was prepared using the method described in Example 1 and using 2-fluoro-5-trifluoromethylbenzonitrile and 3-trifluoromethoxybenzylamine in Step A and 4-aminothiophene-3-carboxylic acid methyl ester was used in Step D.

Example 210

Preparation of Compound 240

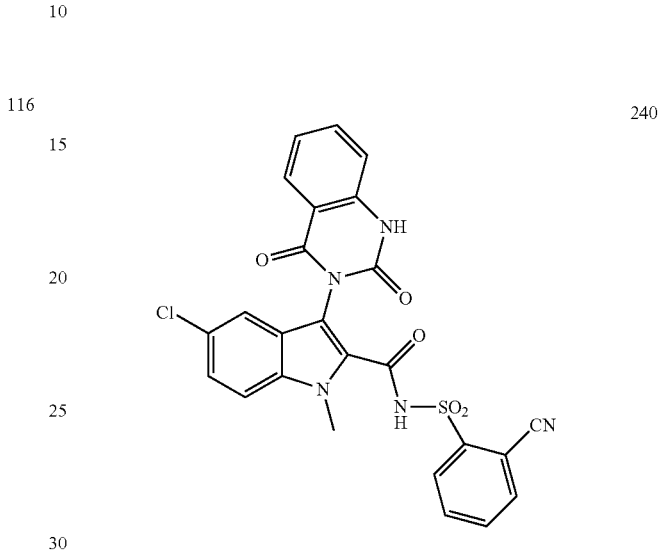

240

Compound 240 was prepared by reacting compound 138 with 2-cyanobenzenesulfonamide, using the method described in Example 2.

Example 211

Preparation of Compound 125

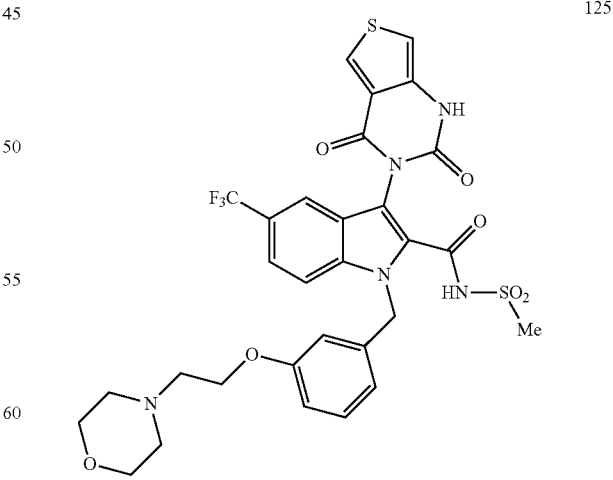

125

Compound 125 was prepared by reacting compound 116 with methanesulfonamide, using the method described in Example 2.

Example 212

Preparation of Compound 124

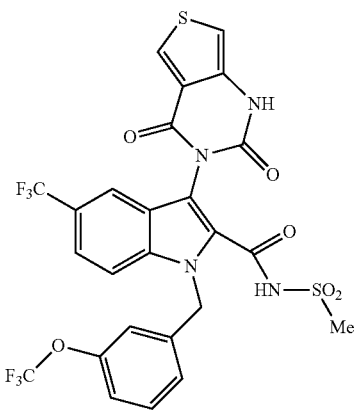

124

Compound 124 was prepared by reacting compound 241 with methanesulfonamide, using the method described in Example 2.

Example 213

Preparation of Compound 108

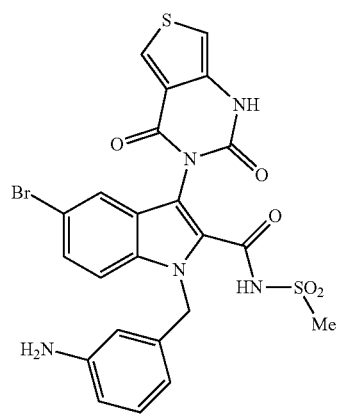

108

Compound 108 was prepared by first using the method described in Example 1 and using 5-bromo-2-fluorobenzonitrile and 3-nitrobenzylamine in Step A, and 4-aminothiophene-3-carboxylic acid methyl ester in Step D. This provided an intermediate an intermediate compound which was then reacted with methanesulfonamide using the method described in Example 2 to provide and intermediate compound which was subsequently reduced using the method set forth in Example 4 to provide compound 108.

Example 214

Preparation of Compound 86

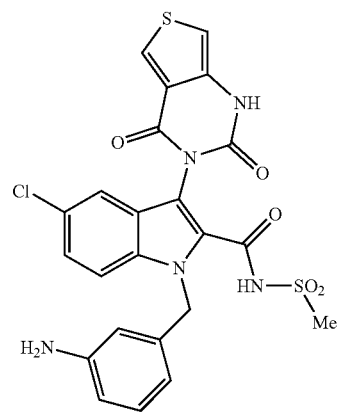

86

Compound 86 was prepared by first using the method described in Example 1 and using 5-chloro-2-fluorobenzonitrile and 3-nitrobenzylamine in Step A, and 4-aminothiophene-3-carboxylic acid methyl ester in Step D. This provided an intermediate an intermediate compound which was then reacted with methanesulfonamide using the method described in Example 2 to provide and intermediate compound which was subsequently reduced using the method set forth in Example 4 to provide compound 86.

Example 215

Preparation of Compound 30

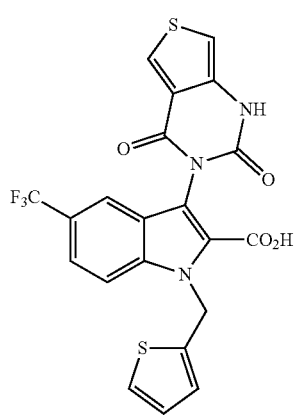

30

Compound 30 was prepared using the method described in Example 1 and using 2-fluoro-5-trifluoromethylbenzonitrile and thiophen-2-yl-methylamine in Step A and 4-aminothiophene-3-carboxylic acid methyl ester was used in Step D.

Example 216

Preparation of Compound 99

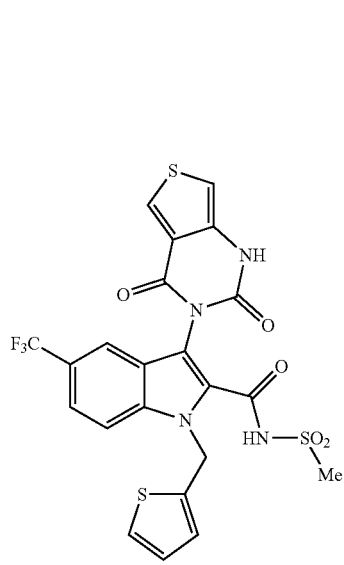

99

Compound 99 was prepared by reacting compound 30 with methanesulfonamide, using the method described in Example 2.

Example 217

Preparation of Compound 268

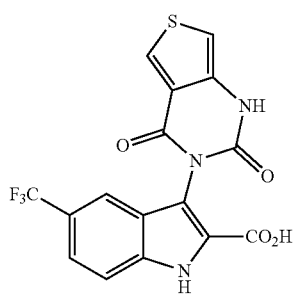

268

Compound 268 was prepared from compound 212 using the method described in Step F wherein trifluoroacetic acid was used in a microwave reactor at 120° C. for 30 minutes.

Example 218

Preparation of Compound 18

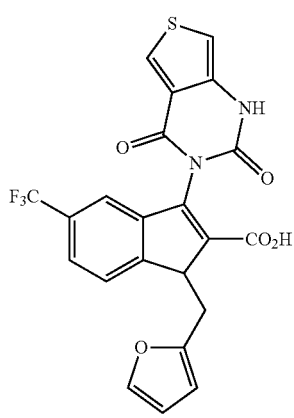

18

Compound 18 was prepared using the method described in Example 1 and using 2-fluoro-5-trifluoromethylbenzonitrile and furan-2-yl-methylamine in Step A, and 4-aminothiophene-3-carboxylic acid methyl ester in Step D.

Example 219

Preparation of Compound 90

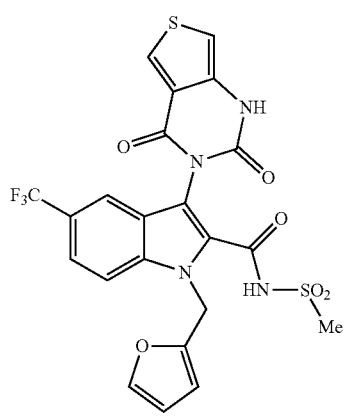

90

Compound 90 was prepared by reacting compound 18 with methanesulfonamide, using the method described in Example 2.

Example 220

Preparation of Compound 25

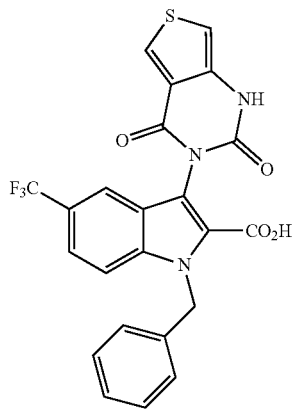
25

Compound 25 was prepared using the method described in Example 1 and using 2-fluoro-5-trifluoromethylbenzonitrile and benzylamine in Step A, and 4-aminothiophene-3-carboxylic acid methyl ester in Step D.

Example 221

Preparation of Compound 72

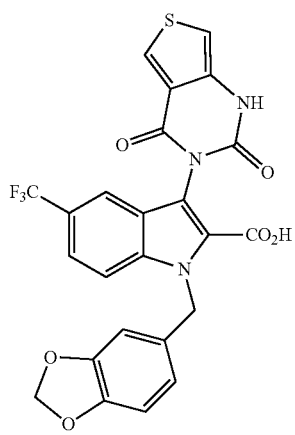
72

Compound 72 was prepared using the method described in Example 1 and using 2-fluoro-5-trifluoromethylbenzonitrile and 3,4-methylenedioxybenzylamine in Step A, and 4-aminothiophene-3-carboxylic acid methyl ester in Step D.

Example 222

Preparation of Compound 114

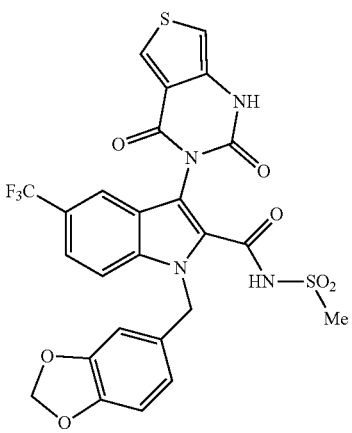
114

Compound 124 was prepared by reacting compound 72 with methanesulfonamide, using the method described in Example 2.

Example 223

Preparation of Compound 88

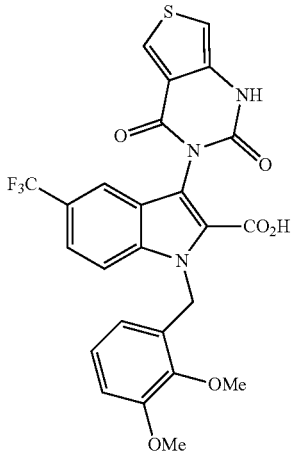
88

Compound 88 was prepared using the method described in Example 1 and using 2-fluoro-5-trifluoromethylbenzonitrile and 2,3-dimethoxybenzylamine in Step A, and 4-aminothiophene-3-carboxylic acid methyl ester in Step D.

Example 224

Preparation of Compound 120

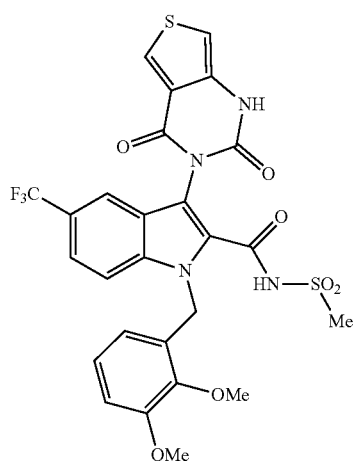

Compound 120 was prepared from compound 88 using the method described in Example 2, wherein methanesulfonamide was used.

Example 225

Preparation of Compound 87

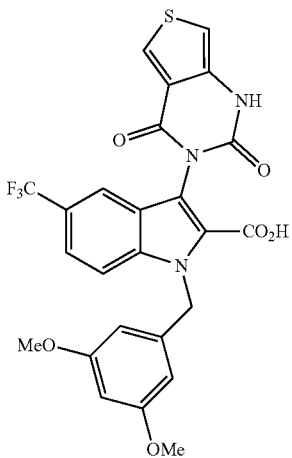

Compound 87 was prepared using the method described in Example 1 and using 2-fluoro-5-trifluoromethylbenzonitrile and 3,5-dimethoxybenzylamine in Step A, and 4-aminothiophene-3-carboxylic acid methyl ester in Step D.

Example 226

Preparation of Compound 119

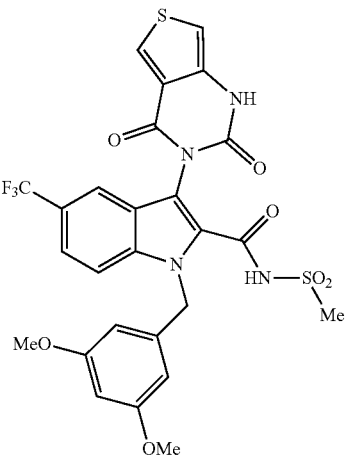

Compound 119 was prepared from compound 87 using the method described in Example 2, wherein methanesulfonamide was used.

Example 227

Preparation of Compound 83

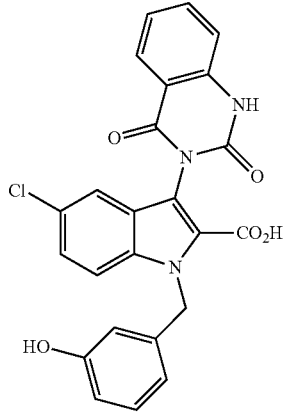

Compound 83 was prepared from compound 20 using the method described in Example 6.

Example 228

Preparation of Compound 38

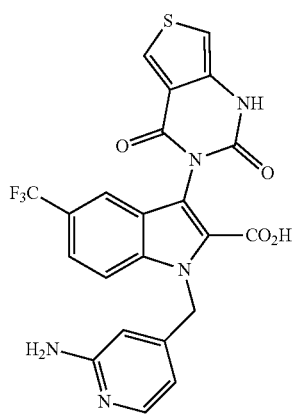

38

Compound 38 was prepared using the method described in Example 5, wherein 2-fluoro-5-trifluoromethylbenzonitrile was used in Step A, 4-aminothiophene-3-carboxylic acid methyl ester was used in Step D. This provided an intermediate compound which was then reacted with 2-tert-butoxycarbonylaminopyridin-4-yl-methyl bromide using the method described in Example 2. The resulting product of this reaction was subsequently converted to compound 38 using the method described in Example 3.

Example 229

Preparation of Compound 29

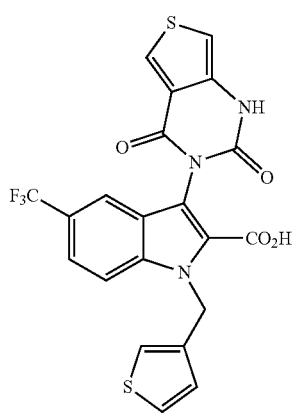

29

Compound 29 was prepared using the method described in Example 1 and using 2-fluoro-5-trifluoromethylbenzonitrile and thiophen-3-yl-methylamine in Step A, and 4-aminothiophene-3-carboxylic acid methyl ester in Step D.

Example 230

Preparation of Compound 98

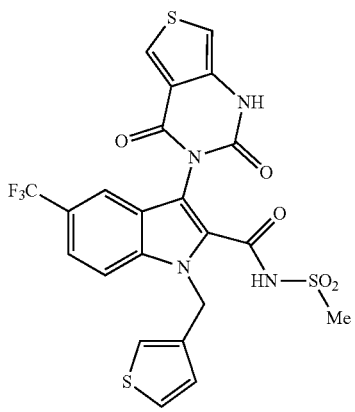

98

Compound 98 was prepared by reacting compound 29 with methanesulfonamide, using the method described in Example 2.

Example 231

Preparation of Compound 19

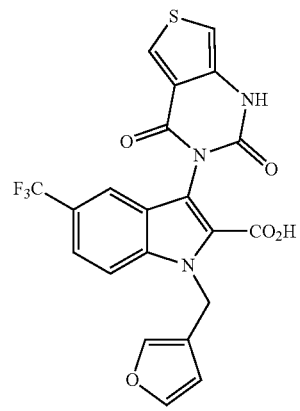

19

Compound 19 was prepared using the method described in Example 1 and using 2-fluoro-5-trifluoromethylbenzonitrile and furan-3-yl-methylamine in Step A, and 4-aminothiophene-3-carboxylic acid methyl ester in Step D.

Example 232

Preparation of Compound 89

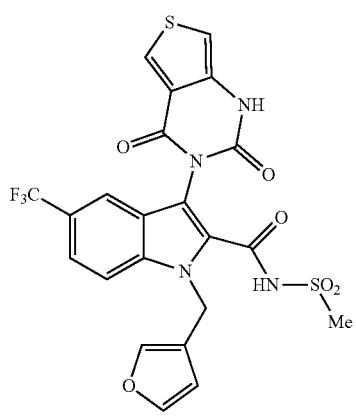

Compound 89 was prepared by reacting compound 19 with methanesulfonamide, using the method described in Example 2.

Example 233

Preparation of Compound 85

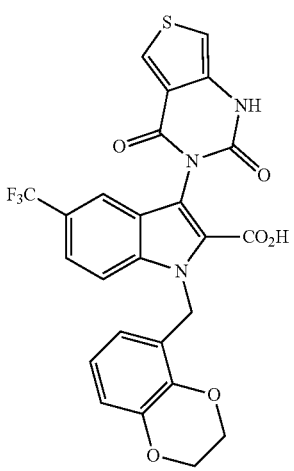

Compound 85 was prepared using the method described in Example 1 and using 2-fluoro-5-trifluoromethylbenzonitrile and 2,3-ethylenedioxybenzylamine in Step A, and 4-aminothiophene-3-carboxylic acid methyl ester in Step D.

Example 234

Preparation of Compound 118

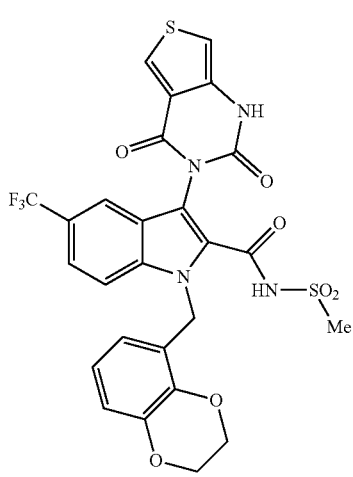

Compound 118 was prepared by reacting compound 85 with methanesulfonamide, using the method described in Example 2.

Example 235

Preparation of Compound 242

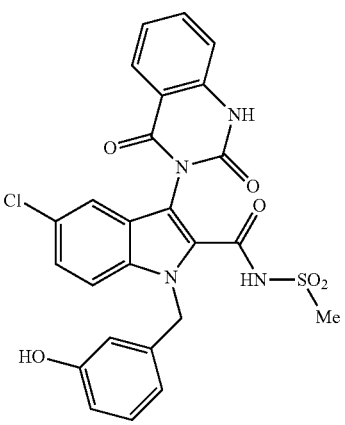

Compound 242 was prepared from compound 91 using the method described in Example 6.

Example 236

Preparation of Compound 103

103

Compound 103 was prepared from compound 109 using the method described in Example 6.

Example 237

Preparation of Compound 243

243

Compound 243 was prepared using the method described in Example 1 and using 5-chloro-2-fluorobenzonitrile and 3-methoxybenzylamine in Step A, and glycine methyl ester in Step D.

Example 238

Preparation of Compound 244

244

Compound 244 was prepared using the method described in Example 1 and using 5-chloro-2-fluorobenzonitrile and 3-methoxybenzylamine in Step A, and methyl 3-aminopropionate in Step D.

Example 239

Preparation of Compound 63

63

Compound 63 was prepared using the method described in Example 5, wherein 2-fluoro-5-trifluoromethylbenzonitrile was used in Step A, 4-aminothiophene-3-carboxylic acid methyl ester was used in Step D, and 5-nitrofuran-2-yl-methyl bromide was used in Step G.

Example 240

Preparation of Compound 269

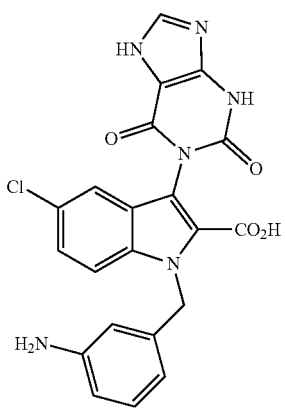
269

Compound 269 was prepared using methods shown in Example 1, wherein 5-chloro-2-fluorobenzonitrile and 3-nitrobenzylamine were used in Step A, -amino-3-(4-methoxybenzyl)-3H-imidazole-4-carboxylic acid methyl ester was used in Step D, and trifluoroacetic acid was used in a microwave reactor at 120° C. for 30 minutes in Step F. The nitro group of the resulting product was then reduced using the method described in Example 4 to provide compound 269.

Example 241

Preparation of Compound 245

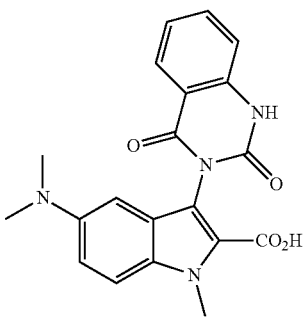
245

Compound 245 was prepared using methods shown in Example 1, wherein 2-fluoro-5-nitrobenzonitrile and methylamine were used in Step A and methyl anthranilate was used in Step D. Reduction of the 5-nitro group was carried out using stannous chloride in ethanol to provide the corresponding 5-amino indole intermediate. Dimethylation of the 5-amino group was carried out using aqueous formaldehyde solution (37% w/w, 10 eq.) and MP-cyanoborohydride resion (2.42 mmol/g, 1.5 eq.) in methanol:acetic acid (9:1, v/v) at room temperature for about 15 hours.

Example 242

Preparation of Compound 84

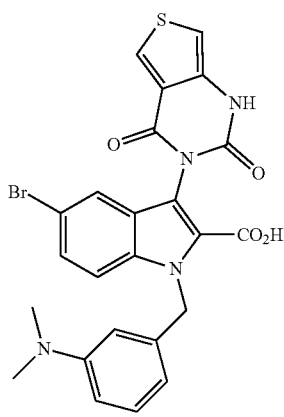
84

Compound 84 was prepared using methods shown in Example 1, wherein 2-fluoro-5-nitrobenzonitrile was reacted with 3-nitrobenzyl amine in Step A. Following steps B through E, the 3-nitrobenzyl intermediate was reduced using stannous chloride in ethanol to provide the corresponding 5-amino indole intermediate. Dimethylation of the 5-amino group was carried out using aqueous formaldehyde solution (37% w/w, 10 eq.) and MP-cyanoborohydride resion (2.42 mmol/g, 1.5 eq.) in methanol:acetic acid (9:1, v/v) at room temperature for about 15 hours.

Example 243

Preparation of Compound 246

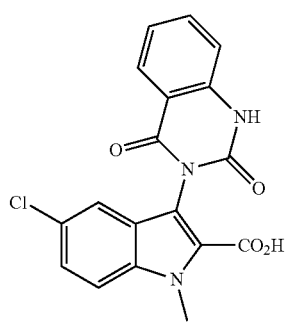
246

Compound 246 was prepared using the method described in Example 1 and using 5-chloro-2-fluorobenzonitrile and methylamine in Step A, and methyl anthranilate in Step D.

Example 244

Preparation of Compound 247

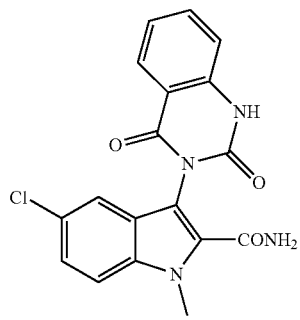

247

Compound 247 was prepared by reacting compound 246 with ammonia, using the method described in Example 3.

Example 245

Preparation of Compound 250

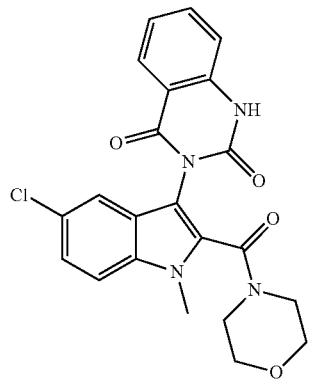

250

Compound 250 was prepared by reacting compound 246 with morpholine, using the method described in Example 3.

Example 246

Preparation of Compound 249

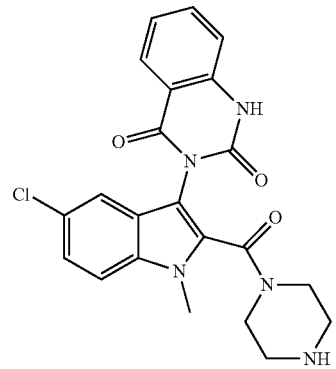

249

Compound 249 was prepared by reacting compound 246 with piperazine, using the method described in Example 3.

Example 247

Preparation of Compound 270

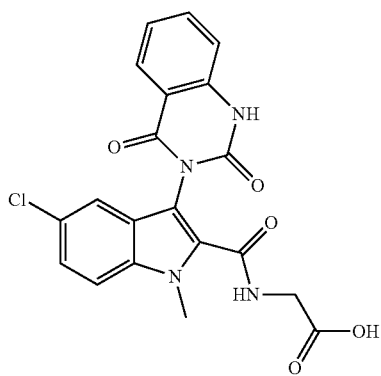

270

Compound 270 was prepared by reacting compound 246 with glycine tert-butyl ester, using the method described in Example 3.

Example 248

Preparation of Compound 9

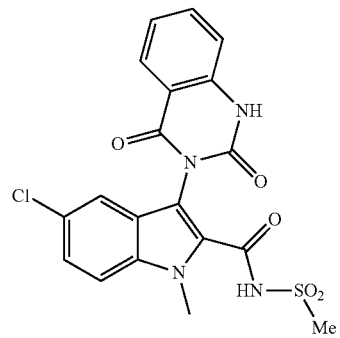

9

Compound 98 was prepared by reacting compound 246 with methanesulfonamide, using the method described in Example 2.

Example 249

Preparation of Compound 251

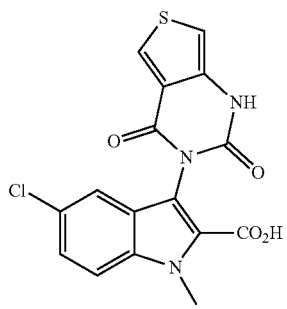

Compound 251 was prepared using the method described in Example 1 and using 5-chloro-2-fluorobenzonitrile and methylamine in Step A, and 4-amino-thiophene-3-carboxylic acid methyl ester in Step D.

Example 250

HCV NS5B Polymerase Inhibition Assay

An in vitro transcribed heteropolymeric RNA known as D-RNA or DCoH has been shown to be an efficient template for HCV NS5B polymerase (S.-E. Behrens et al., EMBO J. 15: 12-22 (1996); WO 96/37619). A chemically synthesized 75-mer version, designated DCoH75, whose sequence matches the 3'-end of D-RNA, and DCoH75ddC, where the 3'-terminal cytidine of DCoH75 is replaced by dideoxycytidine, were used for assaying the NS5B enzyme activity as described in Ferrari et al., 12$^{th}$ International Symposium on HCV and Related Viruses, P-306 (2005). A soluble C-terminal 21-amino acid truncated NS5B enzyme form (NS5BDeltaCT21) was produced and purified from *Escherichia coli* as C-terminal polyhistidine-tagged fusion protein as described in Ferrari et al., *J. Virol.* 73:1649-1654 (1999). A typical assay contained 20 mM Hepes pH 7.3, 10 mM MgCl$_2$, 60 mM NaCl, 100 µg/ml BSA, 20 units/ml RNasin, 7.5 mM DTT, 0.1 µM ATP/GTP/UTP, 0.026 µM CTP, 0.25 mM GAU, 0.03 µM RNA template, 20 µCi/ml [$^{33}$P]-CTP, 2% DMSO, and 30 or 150 nM NS5B enzyme. Reactions were incubated at 22° C. for 2 hours, then stopped by adding 150 mM EDTA, washed in DE81 filter plate in 0.5M di-basic sodium phosphate buffer, pH 7.0, and counted using Packard TopCount after the addition of scintillation cocktail. Polynucleotide synthesis was monitored by the incorporation of radiolabeled CTP. The effect of the 3-Heterocyclic Substituted Indole Derivatives on the polymerase activity was evaluated by adding various concentrations of a 3-Heterocyclic Substituted Indole Derivative, typically in 10 serial 2-fold dilutions, to the assay mixture. The starting concentrations of the indole derivatives ranged from 200 µM to 1 µM. An IC$_{50}$ value for the inhibitor, defined as the compound concentration that provides 50% inhibition of polymerase activity, was determined by fitting the cpm data to the Hill equation Y=100/(1+ 10^(((LogIC50−X)*HillSlope)), where X is the logarithm of compound concentration, and Y is the % inhibition. Ferrari et al., 12$^{th}$ International Symposium on HCV and Related Viruses, P-306 (2005) described in detail this assay procedure. It should be noted that such an assay as described is exemplary and not intended to limit the scope of the invention. The skilled practitioner can appreciate that modifications including but not limited to RNA template, primer, nucleotides, NS5B polymerase form, buffer composition, can be made to develop similar assays that yield the same result for the efficacy of the compounds and compositions described in the invention.

NS5B polymerase inhibition data for selected 3-Heterocyclic Substituted Indole Derivatives was obtained using the above method and calculated IC$_{50}$ values ranged from about 1 µM to about 14000 µM.

Example 251

Cell-Based HCV Replicon Assay

To measure cell-based anti-HCV activity of the a 3-Heterocyclic Substituted Indole Derivative, replicon cells were seeded at 5000 cells/well in 96-well collagen I-coated Nunc plates in the presence of the 3-Heterocyclic Substituted Indole Derivative. Various concentrations of a 3-Heterocyclic Substituted Indole Derivative, typically in 10 serial 2-fold dilutions, were added to the assay mixture, the starting concentration of the compound ranging from 250 uM to 1 uM. The final concentration of DMSO was 0.5%, fetal bovine serum was 5%, in the assay media. Cells were harvested on day 3 by the addition of 1× cell lysis buffer (Ambion cat #8721). The replicon RNA level was measured using real time PCR (Taqman assay). The amplicon was located in 5B. The PCR primers were: 5B.2F, ATGGACAGGCGCCCTGA; 5B.2R, TTGATGGGCAGCTTGGTTTC; the probe sequence was FAM-labeled CACGCCATGCGCTGCGG. GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM 7900HT Sequence Detection System using the following program: 48° C. for 30 min, 95° C. for 10 min, 40 cycles of 95° C. for 15 sec, 60° C. for 1 min. The ΔCT values (CT$_{5B}$-CT$_{GAPDH}$) were plotted against the concentration of test compound and fitted to the sigmoid dose-response model using XLfit4 (MDL). EC$_{50}$ was defined as the concentration of inhibitor necessary to achieve ΔCT=1 over the projected baseline; EC$_{90}$ the concentration necessary to achieve ΔCT=3.2 over the baseline. Alternatively, to quantitate the absolute amount of replicon RNA, a standard curve was established by including serially diluted T7 transcripts of replicon RNA in the Taqman assay. All Taqman reagents were from PE Applied Biosystems. Such an assay procedure was described in detail in e.g. Malcolm et al., *Antimicrobial Agents and Chemotherapy* 50: 1013-1020 (2006).

HCV Replicon assay data for selected 3-Heterocyclic Substituted Indole Derivatives was obtained using the above method and calculated EC$_{50}$ values ranged from about 1 µM to about 14000 µM.

Uses of the 3-Heterocyclic Substituted Indole Derivatives

The 3-Heterocyclic Substituted Indole Derivatives are useful in human and veterinary medicine for treating or preventing a viral infection or a virus-related disorder in a patient. In accordance with the invention, the 3-Heterocyclic Substituted Indole Derivatives can be administered to a patient in need of treatment or prevention of a viral infection or a virus-related disorder.

Accordingly, in one embodiment, the invention provides methods for treating a viral infection in a patient comprising administering to the patient an effective amount of at least one 3-Heterocyclic Substituted Indole Derivative or a pharmaceutically acceptable salt, solvate, ester or prodrug thereof. In another embodiment, the invention provides methods for treating a virus-related disorder in a patient comprising administering to the patient an effective amount of at least one 3-Heterocyclic Substituted Indole Derivative or a pharmaceutically acceptable salt, solvate, ester or prodrug thereof.

Treatment or Prevention of a Viral Infection

The 3-Heterocyclic Substituted Indole Derivatives can be used to treat or prevent a viral infection. In one embodiment, the 3-Heterocyclic Substituted Indole Derivatives can be inhibitors of viral replication. In a specific embodiment, the 3-Heterocyclic Substituted Indole Derivatives can be inhibitors of HCV replication. Accordingly, the 3-Heterocyclic Substituted Indole Derivatives are useful for treating viral diseases and disorders related to the activity of a virus, such as HCV polymerase.

Examples of viral infections that can be treated or prevented using the present methods, include but are not limited to, hepatitis A infection, hepatitis B infection and hepatitis C infection.

In one embodiment, the viral infection is hepatitis C infection.

In one embodiment, the hepatitis C infection is acute hepatitis C. In another embodiment, the hepatitis C infection is chronic hepatitis C.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a, 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al, *J Gen Virol*, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Treatment or Prevention of a Virus-Related Disorder

The 3-Heterocyclic Substituted Indole Derivatives can be used to treat or prevent a virus-related disorder. Accordingly, the 3-Heterocyclic Substituted Indole Derivatives are useful for treating disorders related to the activity of a virus, such as liver inflammation or cirrhosis. Virus-related disorders include, but are not limited to, RNA-dependent polymerase-related disorders and disorders related to HCV infection.

Treatment or Prevention of a RNA-Dependent Polymerase-Related Disorder

The 3-Heterocyclic Substituted Indole Derivatives are useful for treating or preventing a RNA dependent polymerase (RdRp) related disorder in a patient. Such disorders include viral infections wherein the infective virus contain a RdRp enzyme.

Accordingly, in one embodiment, the present invention provides a method for treating a RNA dependent polymerase-related disorder in a patient, comprising administering to the patient an effective amount of at least one 3-Heterocyclic Substituted Indole Derivative or a pharmaceutically acceptable salt, solvate, ester or prodrug thereof.

Treatment or Prevention of a Disorder Related to HCV Infection

The 3-Heterocyclic Substituted Indole Derivatives can also be useful for treating or preventing a disorder related to an HCV infection. Examples of such disorders include, but are not limited to, cirrhosis, portal hypertension, ascites, bone pain, varices, jaundice, hepatic encephalopathy, thyroiditis, porphyria cutanea tarda, cryoglobulinemia, glomerulonephritis, sicca syndrome, thrombocytopenia, lichen planus and diabetes mellitus.

Accordingly, in one embodiment, the invention provides methods for treating an HCV-related disorder in a patient, wherein the method comprises administering to the patient a therapeutically effective amount of at least one 3-Heterocyclic Substituted Indole Derivative, or a pharmaceutically acceptable salt, solvate, ester or prodrug thereof.

Combination Therapy

In another embodiment, the present methods for treating or preventing a viral infection can further comprise the administration of one or more additional therapeutic agents which are not 3-Heterocyclic Substituted Indole Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one 3-Heterocyclic Substituted Indole Derivative, or a pharmaceutically acceptable salt, solvate, ester or prodrug thereof, and (ii) at least one other antiviral agent that is other than a 3-Heterocyclic Substituted Indole Derivative, wherein the amounts administered are together effective to treat or prevent a viral infection.

When administering a combination therapy of the invention to a patient, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a 3-Heterocyclic Substituted Indole Derivative and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

In one embodiment, the at least one 3-Heterocyclic Substituted Indole Derivative is administered during at time when the additional antiviral agent(s) exert their prophylactic or therapeutic effect, or vice versa.

In another embodiment, the at least one 3-Heterocyclic Substituted Indole Derivative and the additional antiviral agent(s) are administered in doses commonly employed when such agents are used as monotherapy for treating a viral infection.

In another embodiment, the at least one 3-Heterocyclic Substituted Indole Derivative and the additional antiviral agent(s) are administered in doses lower than the doses commonly employed when such agents are used as monotherapy for treating a viral infection.

In still another embodiment, the at least one 3-Heterocyclic Substituted Indole Derivative and the additional antiviral agent(s) act synergistically and are administered in doses lower than the doses commonly employed when such agents are used as monotherapy for treating a viral infection.

In one embodiment, the at least one 3-Heterocyclic Substituted Indole Derivative and the additional antiviral agent(s) are present in the same composition. In one embodiment, this composition is suitable for oral administration. In another embodiment, this composition is suitable for intravenous administration.

Viral infections and virus-related disorders that can be treated or prevented using the combination therapy methods of the present invention include, but are not limited to, those listed above.

In one embodiment, the viral infection is HCV infection.

The at least one 3-Heterocyclic Substituted Indole Derivative and the additional antiviral agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of at least one 3-Heterocyclic Substituted Indole Derivative and the additional antiviral agent(s) may inhibit the resistance of a viral infection to these agents.

Non-limiting examples of other therapeutic agents useful in the present compositions and methods include an HCV polymerase inhibitor, an interferon, a viral replication inhibitor, an antisense agent, a therapeutic vaccine, a viral protease inhibitor, a virion production inhibitor, an antibody therapy (monoclonal or polyclonal), and any agent useful for treating an RNA-dependent polymerase-related disorder.

In one embodiment, the other antiviral agent is a viral protease inhibitor.

In another embodiment, the other antiviral agent is an HCV protease inhibitor.

In another embodiment, the other antiviral agent is an interferon.

In still another embodiment, the other antiviral agent is a viral replication inhibitor.

In another embodiment, the other antiviral agent is an antisense agent.

In another embodiment, the other antiviral agent is a therapeutic vaccine.

In a further embodiment, the other antiviral agent is an virion production inhibitor.

In another embodiment, the other antiviral agent is antibody therapy.

In another embodiment, the other antiviral agents comprise a protease inhibitor and a polymerase inhibitor.

In still another embodiment, the other antiviral agents comprise a protease inhibitor and an immunosuppressive agent.

In yet another embodiment, the other antiviral agents comprise a polymerase inhibitor and an immunosuppressive agent.

In a further embodiment, the other antiviral agents comprise a protease inhibitor, a polymerase inhibitor and an immunosuppressive agent.

In another embodiment the other agent is ribavirin.

HCV polymerase inhibitors useful in the present methods and compositions include, but are not limited to VP-19744 (Wyeth/ViroPharma), HCV-796 (Wyeth/ViroPharma), NM-283 (Idenix/Novartis), R-1626 (Roche), MK-0608 (Merck), A848837 (Abbott), GSK-71185 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Interferons useful in the present methods and compositions include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, Boehringer Ingelheim, Ingelheim, Germany), interferon alpha fusion polypeptides, or consensus interferon as defined by determination of a consensus sequence of naturally occurring interferon alphas (Infergen™, Amgen, Thousand Oaks, Calif.).

Antibody therapy agents useful in the present methods and compositions include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like). Viral protease inhibitors useful in the present methods and compositions include, but are not limited to, NS3 serine protease inhibitors (including, but are not limited to, those disclosed in U.S. Pat. Nos. 7,012,066, 6,914,122, 6,911,428, 6,846,802, 6,838,475, 6,800,434, 5,017,380, 4,933,443, 4,812,561 and 4,634,697; and U.S. Patent Publication Nos. US20020160962, US20050176648 and US20050249702), HCV protease inhibitors (e.g., SCH503034 (Schering-Plough), VX-950 (Vertex), GS-9132 (Gilead/Achillion), ITMN-191 (InterMune/Roche)), amprenavir, atazanavir, fosemprenavir, indinavir, lopinavir, ritonavir, nelfinavir, saquinavir, tipranavir and TMC114.

Viral replication inhibitors useful in the present methods and compositions include, but are not limited to, NS3 helicase inhibitors, NS5A inhibitors, ribavirin, viramidine, A-831 (Arrow Therapeutics); an antisense agent or a therapeutic vaccine.

In one embodiment, viral replication inhibitors useful in the present methods and compositions include, but are not limited to, NS3 helicase inhibitors or NS5A inhibitors.

Examples of protease inhibitors useful in the present methods include, but are not limited to, an HCV protease inhibitor and a NS-3 serine protease inhibitor.

Examples of HCV protease inhibitors useful in the present methods include, but are not limited to, those disclosed in Landro et al., *Biochemistry*, 36(31):9340-9348 (1997); Ingallinella et al., *Biochemistry*, 37(25):8906-8914 (1998); Llinàs-Brunet et al., *Bioorg Med Chem Lett*, 8(13):1713-1718 (1998); Martin et al., *Biochemistry*, 37(33):11459-11468 (1998); Dimasi et al., *J Virol*, 71(10):7461-7469 (1997); Martin et al., *Protein Eng*, 10(5):607-614 (1997); Elzouki et al., *J Hepat*, 27(1):42-48 (1997); *BioWorld Today*, 9(217):4 (Nov. 10, 1998); and International Publication Nos. WO 98/14181; WO 98/17679, WO 98/17679, WO 98/22496 and WO 99/07734.

Further examples of protease inhibitors useful in the present methods include, but are not limited to, Additional examples of other therapeutic agents useful in the present methods include, but are not limited to, Levovirin™ (ICN Pharmaceuticals, Costa Mesa, Calif.), VP 50406™ (Viropharma, Incorporated, Exton, Pa.), ISIS 14803™ (ISIS Pharmaceuticals, Carlsbad, Calif.), Heptazyme™ (Ribozyme Pharmaceuticals, Boulder, Colo.), VX-950™ (Vertex Pharmaceuticals, Cambridge, Mass.), Thymosin™ (SciClone Pharmaceuticals, San Mateo, Calif.), Maxamine™ (Maxim Pharmaceuticals, San Diego, Calif.), NKB-122 (JenKen Bioscience Inc., North Carolina), mycophenolate mofetil (Hoffman-LaRoche, Nutley, N.J.).

The doses and dosage regimen of the other agents used in the combination therapies of the present invention for the treatment or prevention of a viral infection can be determined by the attending clinician, taking into consideration the approved doses and dosage regimen in the package insert; the age, sex and general health of the patient; and the type and severity of the viral infection or related disease or disorder. When administered in combination, the 3-Heterocyclic Substituted Indole Derivative(s) and the other agent(s) for treating diseases or conditions listed above can be administered simultaneously (i.e., in the same composition or in separate compositions one right after the other) or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the at least one 3-Heterocyclic Substituted Indole Derivative and the additional antiviral agent(s), when administered as combination therapy, can range from about 0.1 to about 2000 mg per day, although variations will necessarily occur depending on the target of the therapy, the patient and the route of administration. In one embodiment, the dosage is from about 10 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the other therapeutic agent is INTRON-A interferon alpha 2b (commercially available from Schering-Plough Corp.), this agent is administered by subcutaneous injection at 3MIU(12 mcg)/0.5 mL/TIW is for 24 weeks or 48 weeks for first time treatment.

In another embodiment, when the other therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the other therapeutic agent is ROFERON A interferon alpha 2a (commercially available from Hoffmann-La Roche), this agent is administered by subcutaneous or intramuscular injection at 3MIU(11.1 mcg/mL)/TIW for at least 48 to 52 weeks, or alternatively 6MIU/TIW for 12 weeks followed by 3MIU/TIW for 36 weeks.

In still another embodiment, when the other therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the other therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the other therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

Compositions and Administration

Due to their activity, the 3-Heterocyclic Substituted Indole Derivatives are useful in veterinary and human medicine. As described above, the 3-Heterocyclic Substituted Indole Derivatives are useful for treating or preventing a viral infection or a virus-related disorder in a patient in need thereof.

When administered to a patient, the IDs can be administered as a component of a composition that comprises a pharmaceutically acceptable carrier or vehicle. The present invention provides pharmaceutical compositions comprising an effective amount of at least one 3-Heterocyclic Substituted Indole Derivative and a pharmaceutically acceptable carrier. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The 3-Heterocyclic Substituted Indole Derivatives of the present invention may also be deliverable transdermally. The transdermal compositions can take the form of creams, lotions, aerosols and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize the therapeutic effects, i.e. anti-inflammatory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more 3-Heterocyclic Substituted Indole Derivatives are administered orally.

In another embodiment, the one or more 3-Heterocyclic Substituted Indole Derivatives are administered intravenously.

In another embodiment, the one or more 3-Heterocyclic Substituted Indole Derivatives are administered topically.

In still another embodiment, the one or more 3-Heterocyclic Substituted Indole Derivatives are administered sublingually.

In one embodiment, a pharmaceutical preparation comprising at least one 3-Heterocyclic Substituted Indole Derivative is in unit dosage form. In such form, the preparation is subdivided into unit doses containing appropriate quantities of the active component, e.g., an effective amount to achieve the desired purpose.

Compositions can be prepared according to conventional mixing, granulating or coating methods, respectively, and the present compositions can contain, in one embodiment, from about 0.1% to about 99% of the 3-Heterocyclic Substituted Indole Derivative(s) by weight or volume. In various embodiments, the present compositions can contain, in one embodiment, from about 1% to about 70% or from about 5% to about 60% of the 3-Heterocyclic Substituted Indole Derivative(s) by weight or volume.

The quantity of 3-Heterocyclic Substituted Indole Derivative in a unit dose of preparation may be varied or adjusted from about 0.1 mg to about 2000 mg. In various embodiment, the quantity is from about 1 mg to about 2000 mg, 100 mg to about 200 mg, 500 mg to about 2000 mg, 100 mg to about 1000 mg, and 1 mg to about 500 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the 3-Heterocyclic Substituted Indole Derivatives will be regulated according to the judgment of the attending clinician considering such factors as age, condition and size of the patient as well as severity of the symptoms being treated. Generally, a total daily dosage of the 3-Heterocyclic Substituted Indole Derivatives range from about 0.1 to about 2000 mg per day, although variations will necessarily occur depending on the target of the therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one 3-Heterocyclic Substituted Indole Derivative or a pharmaceutically acceptable salt, solvate, ester or prodrug thereof; (ii) one or more additional therapeutic agents that are not a 3-Heterocyclic Substituted Indole Derivative; and (iii) a pharmaceutically acceptable carrier, wherein the amounts in the composition are together effective to treat a viral infection or a virus-related disorder.

Kits

In one aspect, the present invention provides a kit comprising a therapeutically effective amount of at least one 3-Heterocyclic Substituted Indole Derivative, or a pharmaceutically acceptable salt, solvate, ester or prodrug of said compound and a pharmaceutically acceptable carrier, vehicle or diluent.

In another aspect the present invention provides a kit comprising an amount of at least one 3-Heterocyclic Substituted Indole Derivative, or a pharmaceutically acceptable salt, solvate, ester or prodrug of said compound and an amount of at least one additional therapeutic agent listed above, wherein the amounts of the two or more ingredients result in a desired therapeutic effect.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound having the formula:

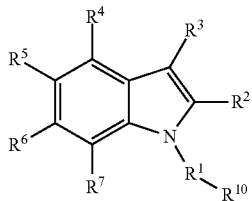

(I)

or a pharmaceutically acceptable salt thereof,
wherein:
$R^1$ is a bond, $—[C(R^{12})_2]_r—$, $—[C(R^{12})_2]_r—O—[C(R^{12})_2]_q—$, $—[C(R^{12})_2]_r—N(R^9)—[C(R^{12})_2]_q—$, $—[C(R^{12})_2]_q—CH=CH—[C(R^{12})_2]_q—$, $—[C(R^{12})_2]_q—C≡C—[C(R^{12})_2]_q—$, or $—[C(R^{12})_2]_q—SO_2—[C(R^{12})_2]_q—$;
$R^2$ is $—[C(R^{12})_2]_q—C(O)N(R^9)SOR^{11}$, $—[C(R^{12})_2]_q—C(O)N(R^9)SO_2R^{11}$, $—[C(R^{12})_2]_q—C(O)N(R^9)SO_2N(R^{11})_2$,

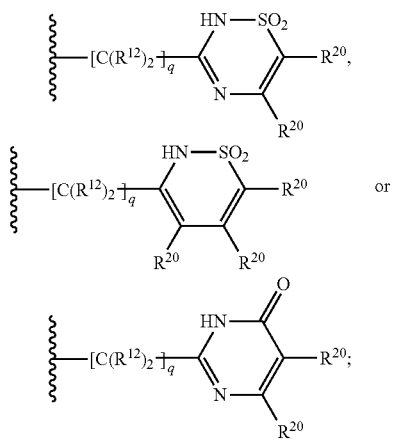

$R^3$ is:

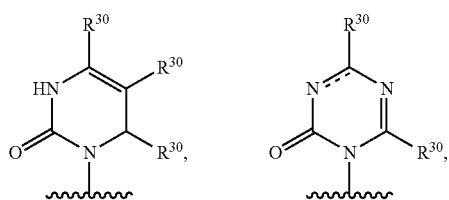

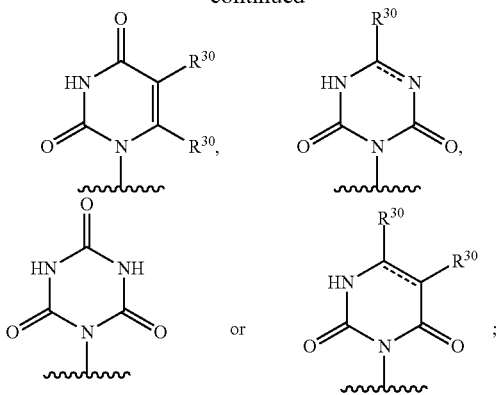

wherein the dotted line indicates an optional and additional bond such that when the optional and additional bond is absent, a hydrogen atom is understood to be present on the two ring atoms connected by the dotted line;
$R^4$, $R^5$, $R^6$ and $R^7$ are each, independently, H, alkyl, alkenyl, alkynyl, aryl, $—[C(R^{12})_2]_q$-cycloalkyl, $—[C(R^{12})_2]_q$-cycloalkenyl, $—[C(R^{12})_2]_q$-heterocycloalkyl, $—[C(R^{12})_2]_q$-heterocycloalkenyl, $—[C(R^{12})_2]_q$-heteroaryl, $—[C(R^{12})_2]_q$-haloalkyl, $—[C(R^{12})_2]_q$-hydroxyalkyl, halo, hydroxy, $—OR^9$, $—CN$, $—[C(R^{12})_2]_q—C(O)R^8$, $—[C(R^{12})_2]_q—C(O)OR^9$, $—[C(R^{12})_2]_q—C(O)N(R^9)_2$, $—[C(R^{12})_2]_q—OR^9$, $—[C(R^{12})_2]_q—N(R^9)_2$, $—[C(R^{12})_2]_q—NHC(O)R^8$, $—[C(R^{12})_2]_q—NR^8C(O)N(R^9)_2$, $—[C(R^{12})_2]_q—NHSO_2R^{11}$, $—[C(R^{12})_2]_q—S(O)_p R^{11}$, $—[C(R^{12})_2]_q—SO_2N(R^9)_2$ or $—SO_2N(R^9)C(O)N(R^9)_2$;
each occurrence of $R^8$ is independently H, alkyl, alkenyl, alkynyl, $—[C(R^{12})_2]_q$-aryl, $—[C(R^{12})_2]_q$-cycloalkyl, $—[C(R^{12})_2]_q$-cycloalkenyl, $—[C(R^{12})_2]_q$-heterocycloalkyl, $—[C(R^{12})_2]_q$-heterocycloalkenyl, $—[C(R^{12})_2]_q$-heteroaryl, haloalkyl or hydroxyalkyl;
each occurrence of $R^9$ is independently H, alkyl, alkenyl, alkynyl, $—[C(R^{12})_2]_q$-aryl, $—[C(R^{12})_2]_q$-cycloalkyl, $—[C(R^{12})_2]_q$-cycloalkenyl, $—[C(R^{12})_2]_q$-heterocycloalkyl, $—[C(R^{12})_2]_q$-heterocycloalkenyl, $—[C(R^{12})_2]_q$-heteroaryl, haloalkyl or hydroxyalkyl;
$R^{10}$ is H, cycloalkyl, cycloalkenyl, heterocycloalkyl, heterocycloalkenyl, aryl, or heteroaryl, wherein a cycloalkyl, cycloalkenyl, heterocycloalkyl, heterocycloalkenyl, aryl or heteroaryl group can be optionally substituted with up to 4 substituents, which are each independently selected from H, alkyl, alkenyl, alkynyl, aryl, $—[C(R^{12})_2]_q$-cycloalkyl, $—O—[C(R^{12})_2]_q$-cycloalkyl, $—[C(R^{12})_2]_q$-cycloalkenyl, $—[C(R^{12})_2]_q$-heterocycloalkyl, $—[C(R^{12})_2]_q$-heterocycloalkenyl, $—[C(R^{12})_2]_q$-heteroaryl, $—[C(R^{12})_2]_q$-haloalkyl, $—[C(R^{12})_2]_q$-hydroxyalkyl, halo, hydroxy, $—NO_2$, $—OR^9$, $—CN$, $—[C(R^{12})_2]_q—C(O)R^8$, $—[C(R^{12})_2]_q—C(O)OR^9$, $—[C(R^{12})_2]_q—C(O)N(R^9)_2$, $—[C(R^{12})_2]_q—OR^9$, $—[C(R^{12})_2]_q—N(R^9)_2$, $—[C(R^{12})_2]_q—NHC(O)R^8$, $—[C(R^{12})_2]_q—NR^8C(O)N(R^9)_2$, $—[C(R^{12})_2]_q—NHSO_2R^{11}$, $—[C(R^{12})_2]_q—S(O)_p R^{11}$, $—[C(R^{12})_2]_q—SO_2N(R^9)_2$ and $—SO_2N(R^9)C(O)N(R^9)_2$, such that when $R^1$ is a bond, $R^{10}$ is not H;
each occurrence of $R^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally substituted with up to 4 substituents, which are each independently selected from H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, hydroxy, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$alkyl, —[C(R$^{12}$)$_2$]$_q$—NHSO$_2$cycloalkyl, —[C(R$^{12}$)$_2$]$_q$—NHSO$_2$aryl, —[C(R$^{12}$)$_2$]$_q$—SO$_2$N(R$^9$)$_2$ and —SO$_2$N(R$^9$)C(O)N(R$^9$)$_2$;

each occurrence of R$^{12}$ is independently H, halo, —N(R$^9$)$_2$, —OR$^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally substituted with up to 4 substituents, which are each independently selected from alkyl, halo, haloalkyl, hydroxyalkyl, hydroxy, —CN, —C(O)alkyl, —C(O)Oalkyl, —C(O)NHalkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two R$^{12}$ groups, together with the carbon atoms to which they are attached, join to form a cycloalkyl, heterocycloalkyl or C═O group;

each occurrence of R$^{20}$ is independently alkyl, aryl, cycloalkyl, heterocycloalkyl or heteroaryl, or both R$^{20}$ groups and the carbon atoms to which they are attached, join to form a cycloalkyl, cycloheteroalkyl, aryl or heteroaryl group wherein a cycloalkyl, cycloheteroalkyl, aryl or heteroaryl group can be optionally substituted with up to 4 groups, which are each independently selected from alkyl, alkenyl, alkynyl, halo, hydroxy, —OR$^9$, —CN, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-haloalkyl, —[C(R$^{12}$)$_2$]$_q$-hydroxyalkyl, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$;

each occurrence of R$^{30}$ is independently, H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, hydroxy, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ or —SO$_2$N(R$^9$)C(O)N(R$^9$)$_2$, or two adjacent R$^{30}$ groups, together with the carbon atoms to which they are attached, join to form a cycloalkyl, heterocycloalkyl, aryl or heteroaryl group;

each occurrence of p is independently 0, 1 or 2;
each occurrence of q is independently an integer ranging from 0 to 4; and
each occurrence of r is independently an integer ranging from 1 to 4.

2. The compound of claim 1, wherein R$^2$ is —C(O)NHSO$_2$R$^{11}$ and R$^{11}$ is alkyl, aryl, cycloalkyl, haloalkyl, heteroaryl, heterocycloalkyl or hydroxyalkyl.

3. The compound of claim 1, wherein R$^2$ is —C(O)NHSO$_2$N(R$^{11}$)$_2$.

4. The compound of claim 1, wherein R$^3$ is:

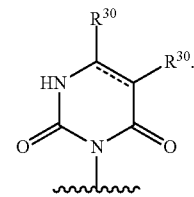

5. The compound of claim 1, wherein R$^1$ is —[C(R$^{12}$)$_2$]$_r$— and R$^{10}$ is:

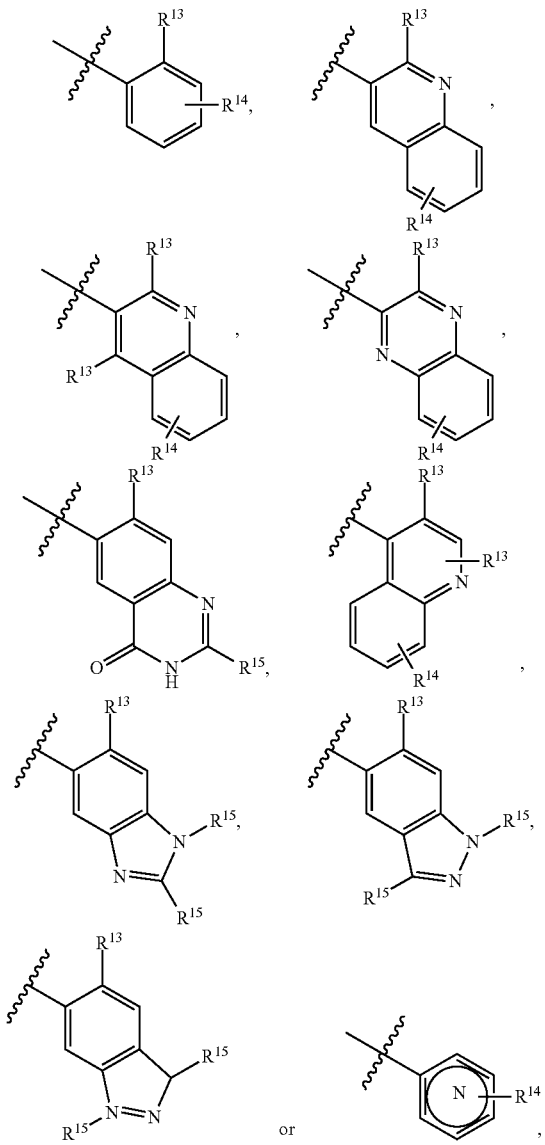

wherein R$^{13}$ is H, F, Br or Cl; R$^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, hydroxy, —NH$_2$, —SO₂alkyl, —SO₂NHalkyl, —S-alkyl, —CH₂NH₂, —CH₂OH, —SO₂NH₂, —NHC(O)-alkyl, —C(O)O-alkyl, —C(O)-heterocycloalkyl and heteroaryl; and

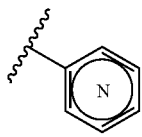

represents a pyridyl group, wherein the ring nitrogen atom can be at any of the five unsubstituted ring atom positions.

6. The compound of claim 1, wherein R⁴, R⁶ and R⁷ are each H, and R⁵ is H, halo or haloalkyl.

7. The compound of claim 1 having the formula:

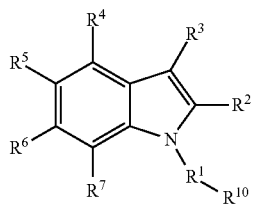
(Ia)

or a pharmaceutically acceptable salt thereof, wherein:
R¹ is —CH₂—;
R² is —C(O)NHSO₂R¹¹;
R³ is:

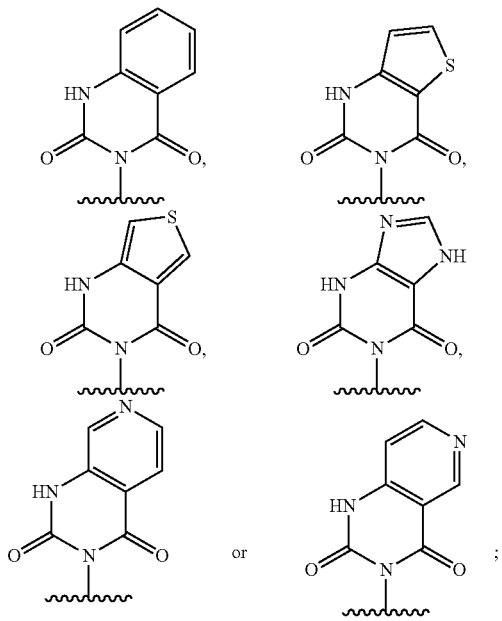

R⁴, R⁶ and R⁷ are each H;
R⁵ is H, alkyl, —O-alkyl, halo or haloalkyl;
R¹⁰ is H, aryl, cycloalkyl or heteroaryl, wherein a cycloalkyl, aryl or heteroaryl group can be optionally substituted with up to 4 substituents, which are each independently selected from alkyl, —O-alkyl, halo, —O-haloalkyl, —OH, —NH₂, —NH(alkyl), —N(alkyl)₂, —NO₂, —CN, —NHC(O)-alkyl, —O-alkylene-heterocycloalkyl —C(O)O-alkyl and —O-haloalkyl;

R¹¹ is alkyl, aryl or cycloalkyl;

each occurrence of R¹² is H, alkyl or halo, or two geminal R¹² groups, together with the common carbon atom to which they are attached, join to form a 3- to 6-membered cycloalkyl group; and r is an integer ranging from 1 to 4.

8. A compound having the formula:

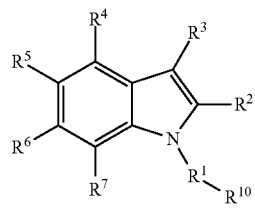
(II)

or a pharmaceutically acceptable salt thereof,
wherein:

R¹ is a bond, —[C(R¹²)₂]ᵣ—, —[C(R¹²)₂]ᵣ—O—[C(R¹²)₂]_q—, —[C(R¹²)₂]ᵣ—N(R⁹)—[C(R¹²)₂]_q—, —[C(R¹²)₂]_q—CH=CH—[C(R¹²)₂]_q—, —[C(R¹²)₂]_q—C≡C—[C(R¹²)₂]₄—, or —[C(R¹²)₂]_q—SO₂—[C(R¹²)₂]_q—;

R² is —C(O)R⁹, —C(O)OR⁹, —C(O)OCH₂OR⁹, —C(O)N(R⁹)₂, —[C(R¹²)₂]—C(O)OR⁹, —[C(R¹²)₂]_q—C(O)N(R⁹)₂, -alkyl, —[C(R¹²)₂]_q-aryl, —[C(R¹²)₂]_q-cycloalkyl, —[C(R¹²)₂]_q-cycloalkenyl, —[C(R¹²)₂]_q-heterocycloalkyl, —[C(R¹²)₂]_q-heteroaryl or —[C(R¹²)₂]_q-heterocycloalkenyl, wherein an aryl, cycloalkyl, cycloalkenyl, heterocycloalkyl, heterocycloalkenyl or heteroaryl, group can be optionally substituted with up to 4 substituents, which are each independently selected from alkyl, alkenyl, alkynyl, aryl, —[C(R¹²)₂]_q-cycloalkyl, —[C(R¹²)₂]_q-cycloalkenyl, —[C(R¹²)₂]_q-heterocycloalkyl, —[C(R¹²)₂]_q-heterocycloalkenyl, —[C(R¹²)₂]_q-heteroaryl, —[C(R¹²)₂]_q-haloalkyl, —[C(R¹²)₂]_q-hydroxyalkyl, halo, hydroxy, —OR⁹, —CN, —[C(R¹²)₂]_q—C(O)R⁸, —[C(R¹²)₂]_q—C(O)OR⁹, —[C(R¹²)₂]_q-C(O)N(R⁹)₂, —[C(R¹²)₂]_q—OR⁹, —[C(R¹²)₂]_q—N(R⁹)₂, —[C(R¹²)₂]_q—NHC(O)R⁸, —[C(R¹²)₂]_q-NR⁸C(O)N(R⁹)₂, —[C(R¹²)₂]_q—NHSO₂R¹¹, —[C(R¹²)₂]_q—S(O)_pR¹¹, —[C(R¹²)₂]_q—SO₂N(R⁹)₂ and —SO₂N(R⁹)C(O)N(R⁹)₂;

R³ is:

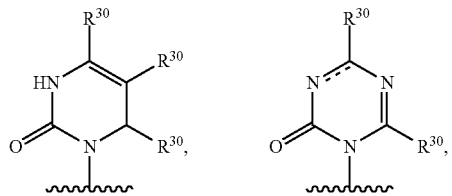

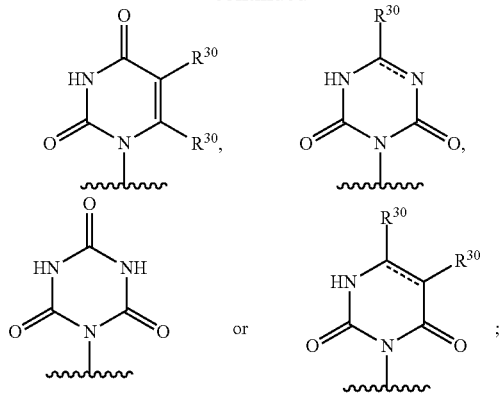

wherein the dotted line indicates an optional and additional bond such that when the optional and additional bond is absent, a hydrogen atom is understood to be present on the two ring atoms connected by the dotted line;

$R^4$, $R^5$, $R^6$ and $R^7$ are each, independently, H, alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, hydroxy, —$OR^9$, —CN, —[C($R^{12}$)$_2$]$_q$—C(O)$R^8$, —[C($R^{12}$)$_2$]$_q$—C(O)$OR^9$, —[C($R^{12}$)$_2$]$_q$—C(O)$_N$($R^9$)$_2$, —[C($R^{12}$)$_2$]$_q$—$OR^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—$NR^8$C(O)N($R^9$)$_2$, —[C($R^{12}$)$_2$]$_q$—NHSO$_2$$R^{11}$, —[C($R^{12}$)$_2$]$_q$—S(O)$_p$$R^{11}$, —[C($R^{12}$)$_2$]$_q$—SO$_2$N($R^9$)$_2$ or —SO$_2$N($R^9$)C(O)N($R^9$)$_2$;

each occurrence of $R^8$ is independently H, alkyl, alkenyl, alkynyl, —[C($R^{12}$)$_2$]$_q$-aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, haloalkyl or hydroxyalkyl;

each occurrence of $R^9$ is independently H, alkyl, alkenyl, alkynyl, —[C($R^{12}$)$_2$]$_q$-aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, haloalkyl or hydroxyalkyl;

$R^{10}$ is H, cycloalkyl, cycloalkenyl, heterocycloalkyl, heterocycloalkenyl, aryl, or heteroaryl, wherein a cycloalkyl, cycloalkenyl, heterocycloalkyl, heterocycloalkenyl, aryl or heteroaryl group can be optionally substituted with up to 4 substituents, which are each independently selected from H, alkyl, alkenyl, alkynyl, aryl, NO$_2$, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, hydroxy, —$OR^9$, —CN, —[C($R^{12}$)$_2$]$_q$—C(O)$R^8$, —[C($R^{12}$)$_2$]$_q$—C(O)$OR^9$, —[C($R^{12}$)$_2$]$_q$—C(O)N($R^9$)$_2$, —[C($R^{12}$)$_2$]$_q$—$OR^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—$NR^8$C(O)N($R^9$)$_2$, —[C($R^{12}$)$_2$]$_q$—NHSO$_2$$R^{11}$, —[C($R^{12}$)$_2$]$_q$—S(O)$_p$$R^{11}$, —[C($R^{12}$)$_2$]$_q$—SO$_2$N($R^9$)$_2$ and —SO$_2$N($R^9$)C(O)N($R^9$)$_2$, such that when $R^1$ is a bond, $R^{10}$ is not H;

each occurrence of $R^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally substituted with up to 4 substituents, which are each independently selected from H, alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, hydroxy, —$OR^9$, —CN, —[C($R^{12}$)$_2$]$_q$—C(O)$R^8$, —[C($R^{12}$)$_2$]$_q$—C(O)$OR^9$, —[C($R^{12}$)$_2$]$_q$—C(O)N($R^9$)$_2$, —[C($R^{12}$)$_2$]$_q$—$OR^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—$NR^8$C(O)N($R^9$)$_2$, —[C($R^{12}$)$_2$]$_q$—NHSO$_2$alkyl, —[C($R^{12}$)$_2$]$_q$—NHSO$_2$cycloalkyl, —[C($R^{12}$)$_2$]$_q$—NHSO$_2$aryl, —[C($R^{12}$)$_2$]$_q$—SO$_2$N($R^9$)$_2$ and —SO$_2$N($R^9$)C(O)N($R^9$)$_2$;

each occurrence of $R^{12}$ is independently H, halo, —N($R^9$)$_2$, —$OR^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally substituted with up to 4 substituents, which are each independently selected from alkyl, halo, haloalkyl, hydroxyalkyl, hydroxy, —CN, —C(O)alkyl, —C(O)Oalkyl, —C(O)NHalkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two $R^{12}$ groups, together with the carbon atoms to which they are attached, join to form a cycloalkyl, heterocycloalkyl or C=O group;

each occurrence of $R^{30}$ is independently, H, alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, hydroxy, —$OR^9$, —CN, —[C($R^{12}$)$_2$]$_q$—C(O)$R^8$, —[C($R^{12}$)$_2$]$_q$—C(O)$OR^9$, —[C($R^{12}$)$_2$]$_q$—C(O)N($R^9$)$_2$, —[C($R^{12}$)$_2$]$_q$—$OR^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—$NR^8$C(O)N($R^9$)$_2$, —[C($R^{12}$)$_2$]$_q$—NHSO$_2$$R^{11}$, —[C($R^{12}$)$_2$]$_q$—S(O)$_p$$R^{11}$, —[C($R^{12}$)$_2$]$_q$—SO$_2$N($R^9$)$_2$ or —SO$_2$N($R^9$)C(O)N($R^9$)$_2$, or two adjacent $R^{30}$ groups, together with the carbon atoms to which they are attached, join to form a cycloalkyl, heterocycloalkyl, aryl or heteroaryl group;

each occurrence of p is independently 0, 1 or 2;

each occurrence of q is independently an integer ranging from 0 to 4; and each occurrence of r is independently an integer ranging from 1 to 4.

9. The compound of claim 8, wherein $R^2$ is —C(O)$OR^9$ or —C(O)N($R^9$)$_2$.

10. The compound of claim 8, wherein $R^3$ is:

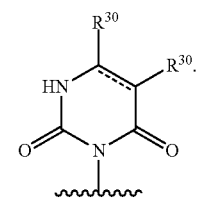

11. The compound of claim 8, wherein $R^1$ is —[C($R^{12}$)$_2$]$_r$— and $R^{10}$ is:

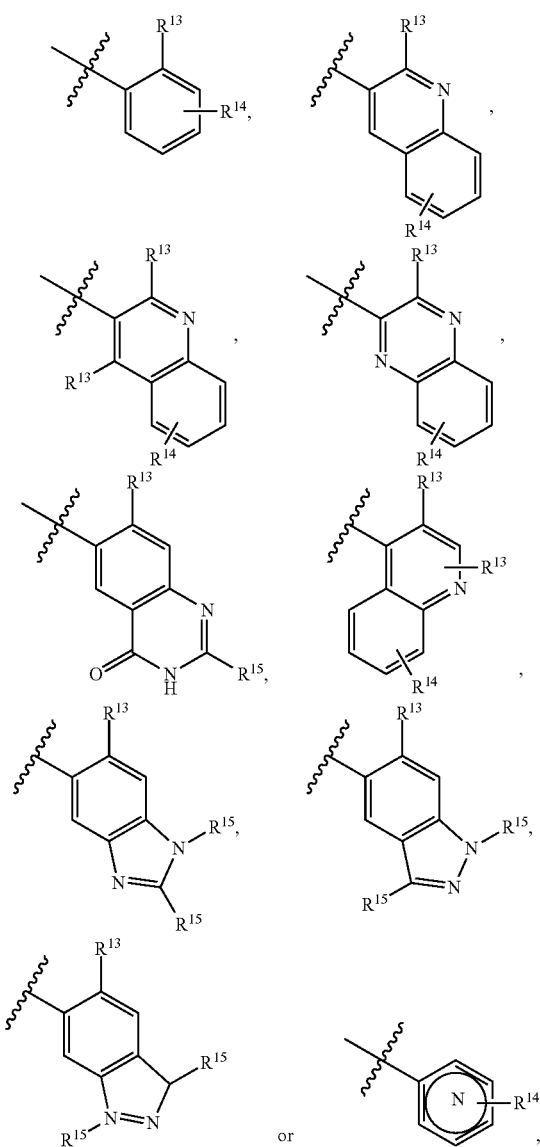

wherein R¹³ is H, F, Br or Cl; R¹⁴ represents up to 4 optional and additional substituents, each independently selected from alkyl, cycloalkyl, CF₃, —CN, halo, —O-alkyl, —O-haloalkyl, —NHSO₂-alkyl, —NO₂, —C(O)NH₂, —C(O)NH-alkyl, —C(O)OH, hydroxy, —NH₂, —SO₂alkyl, —SO₂NHalkyl, —S-alkyl, —CH₂NH₂, —CH₂OH, —SO₂NH₂, —NHC(O)-alkyl, —C(O)O-alkyl, —C(O)-heterocycloalkyl and heteroaryl; and

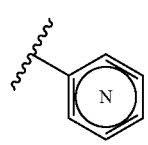

represents a pyridyl group, wherein the ring nitrogen atom can be at any of the five unsubstituted ring atom positions.

12. The compound of claim 8, wherein R⁴, R⁶ and R⁷ are each H, and R⁵ is H, halo or haloalkyl.

13. The compound of claim 8 having the formula:

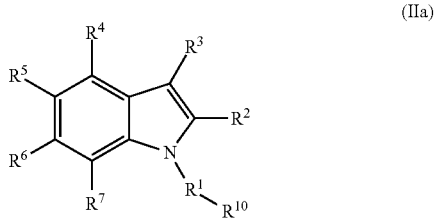

(IIa)

or a pharmaceutically acceptable salt thereof, wherein:
R¹ is —CH₂—;
R² is —C(O)OH or —C(O)NH₂;
R³ is:

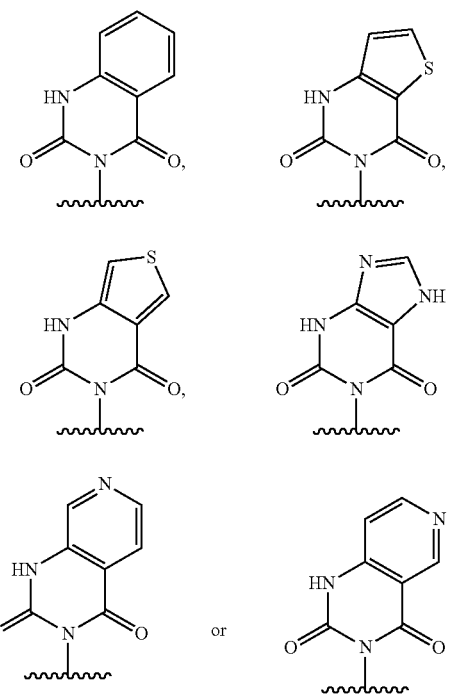

R⁴, R⁶ and R⁷ are each H;
R⁵ is H, halo or haloalkyl;
R¹⁰ is H aryl, cycloalkyl or heteroaryl, wherein a cycloalkyl, aryl or heteroaryl group can be optionally substituted with one or more substituents, which are each independently selected from alkyl, —O-alkyl, halo, —O-haloalkyl, —OH, —NH₂, —NH(alkyl), —N(alkyl)₂, —NO₂, —CN, —NHC(O)-alkyl, —O-alkylene-heterocycloalkyl —C(O)O-alkyl and —O-haloalkyl; and r is an integer ranging from 1 to 4.

14. A compound having the structure
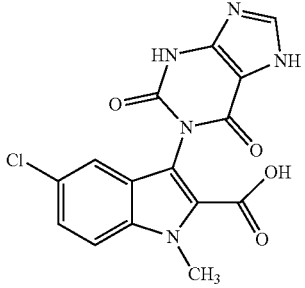
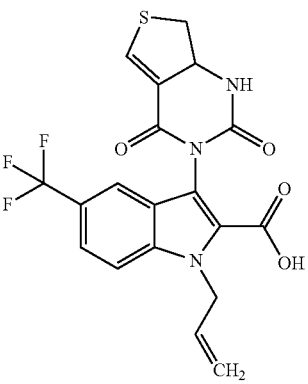
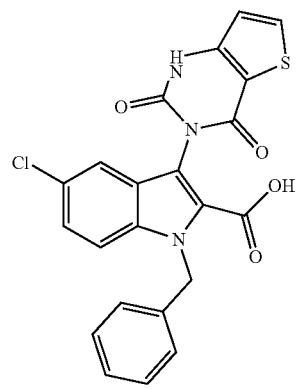
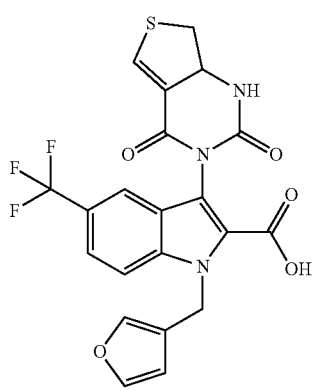
-continued
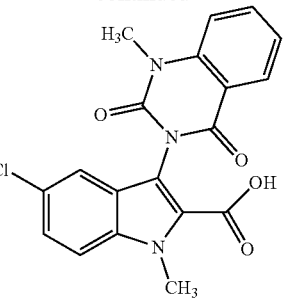
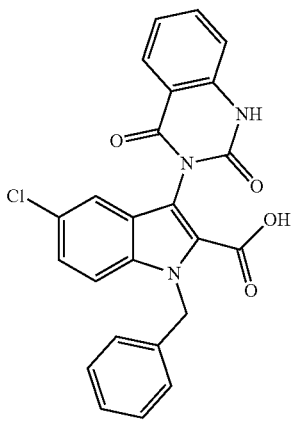
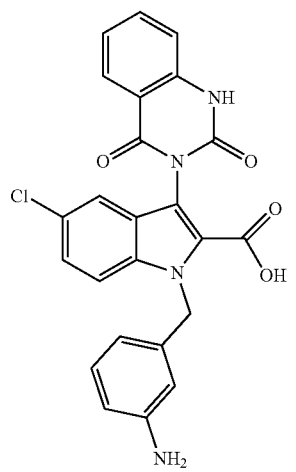
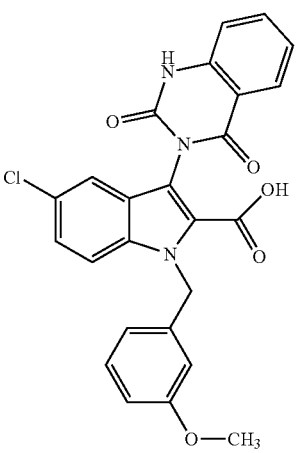

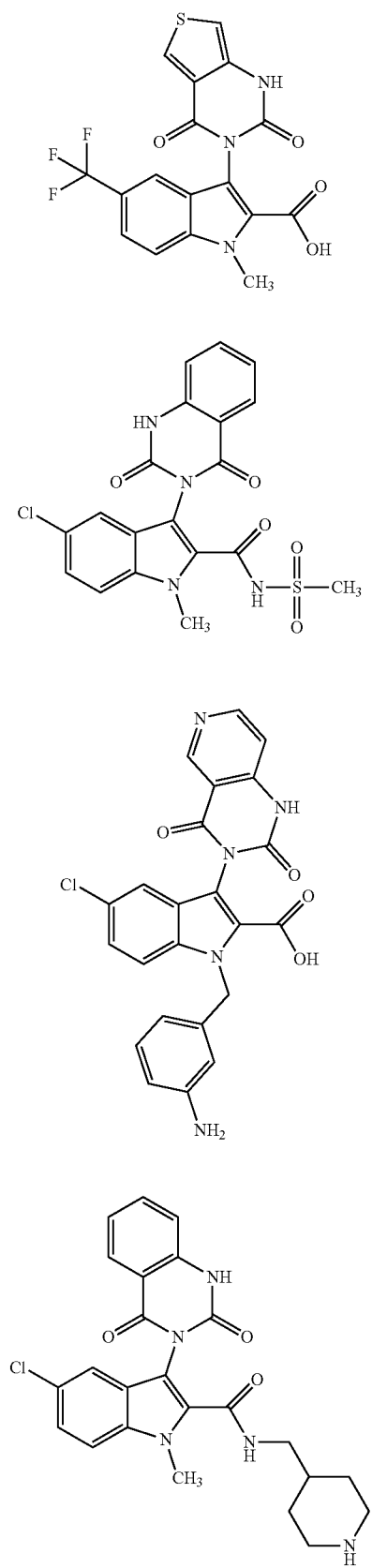
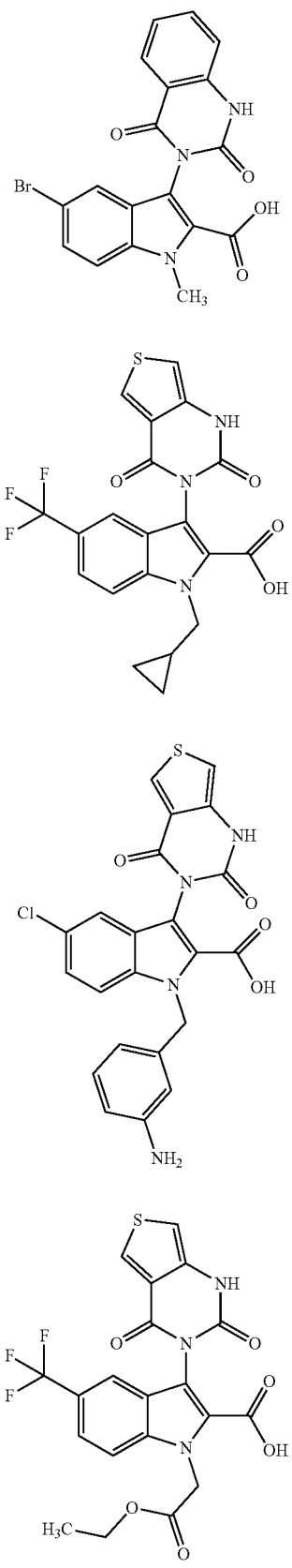

407
-continued
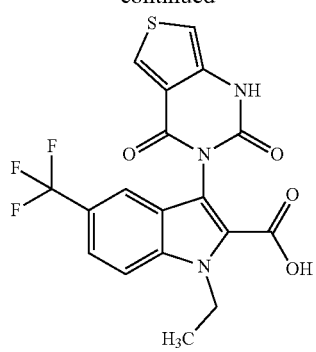
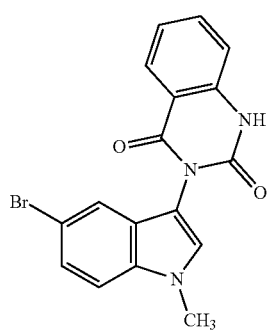
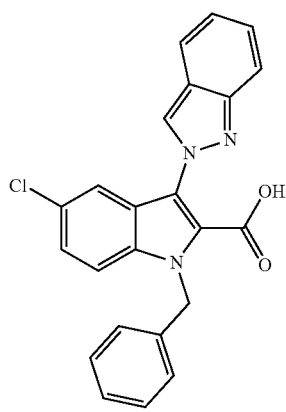
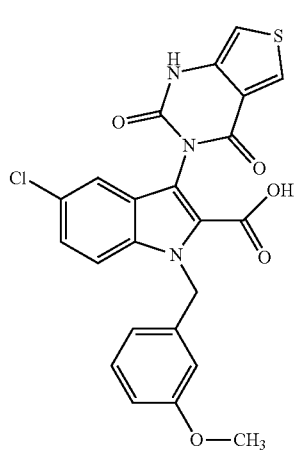
408
-continued
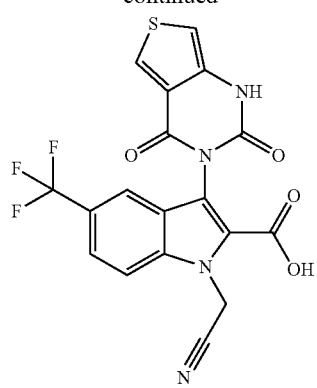
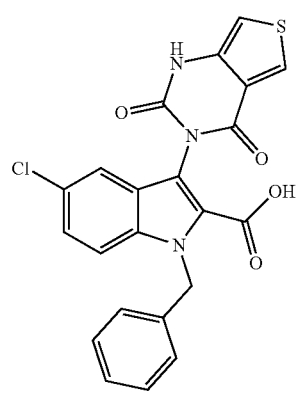
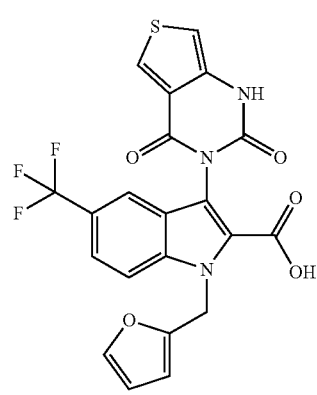
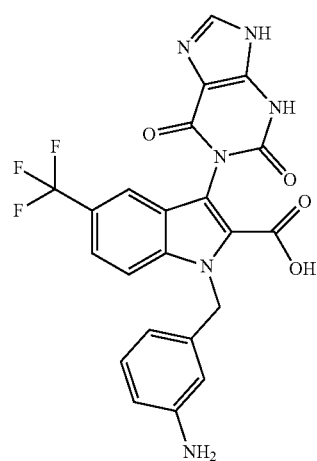

409
-continued
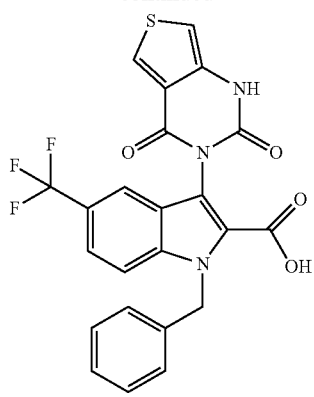
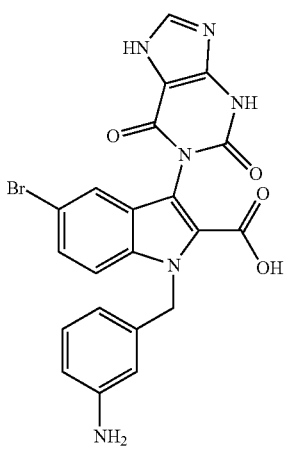
410
-continued
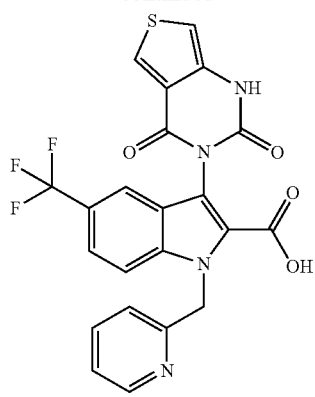
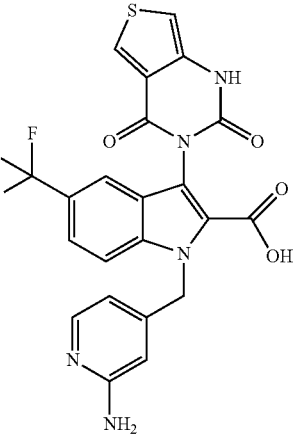

411
-continued
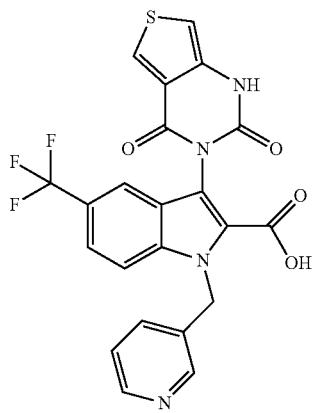
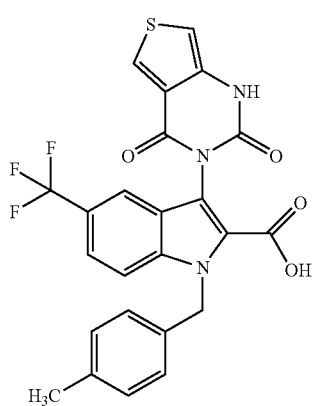
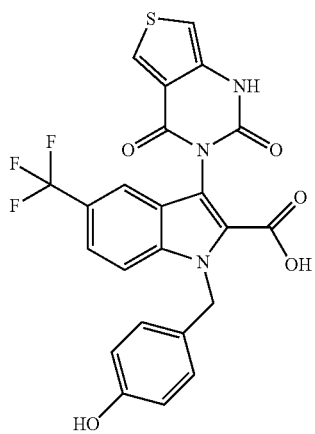
412
-continued
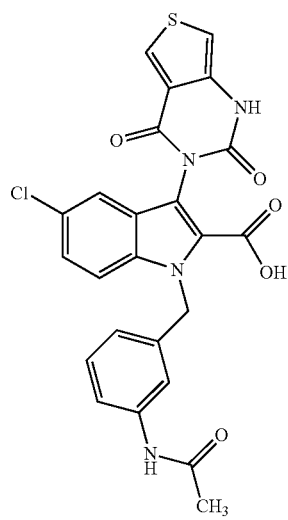
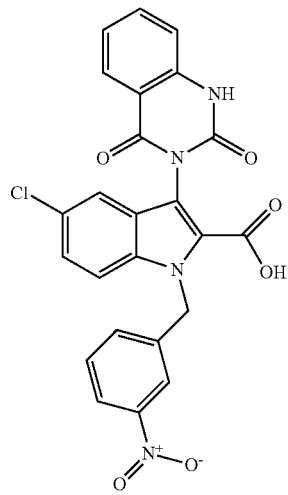
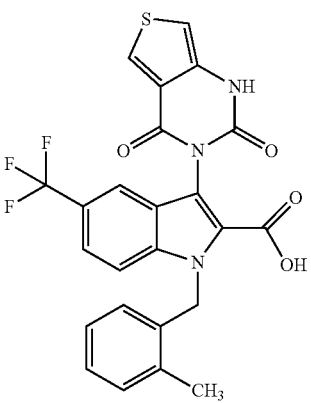

413
-continued
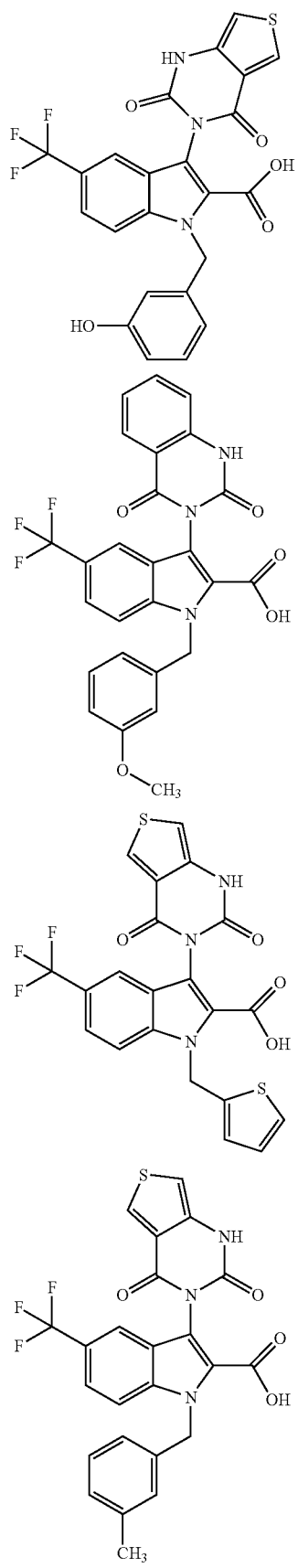
414
-continued
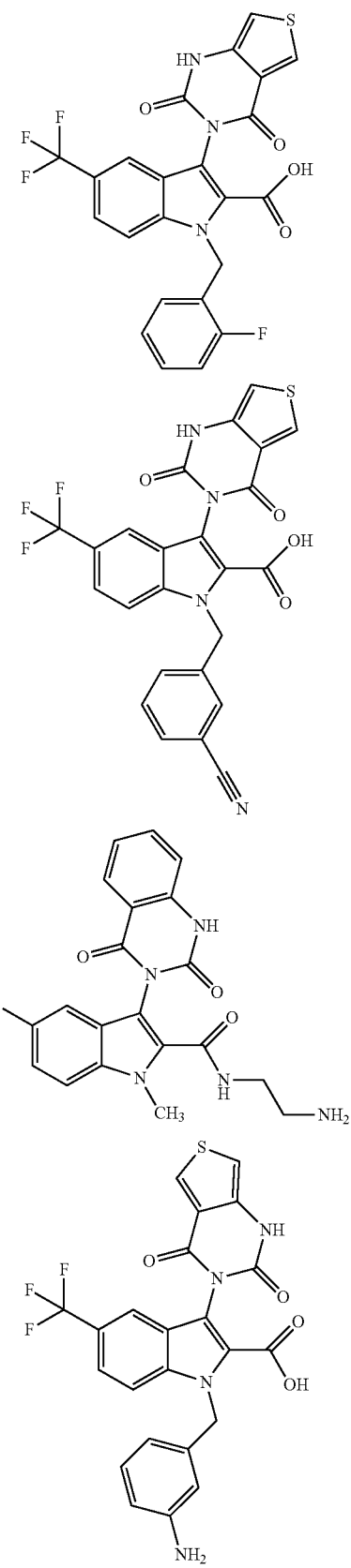

415
-continued
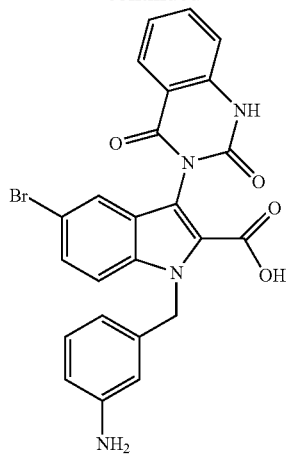
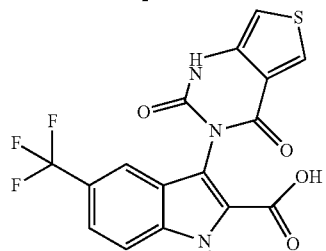
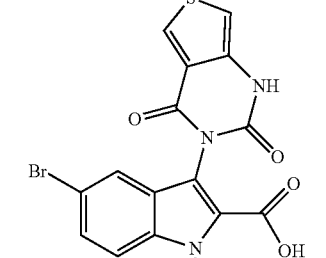
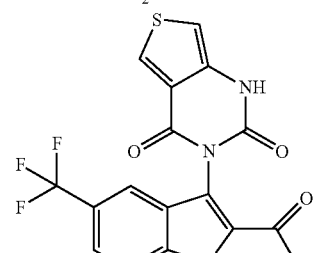
416
-continued
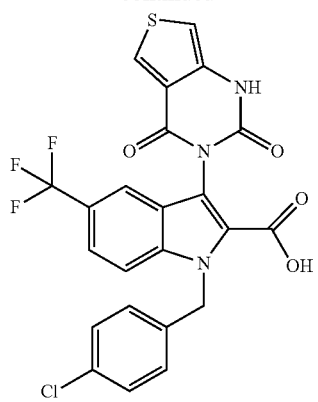
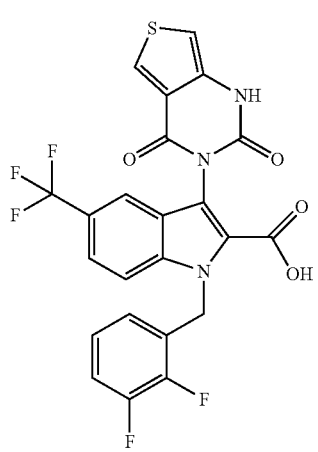
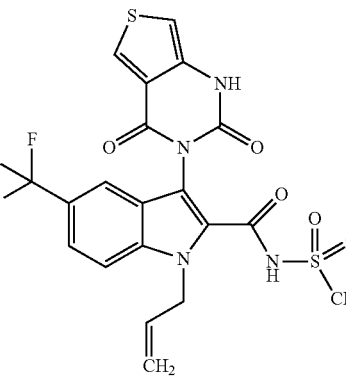
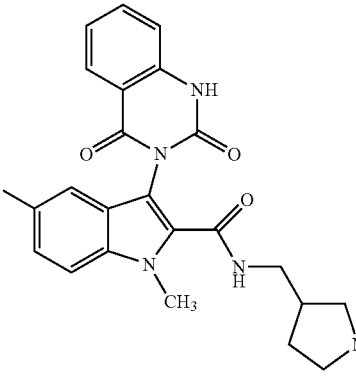

417
-continued
418
-continued
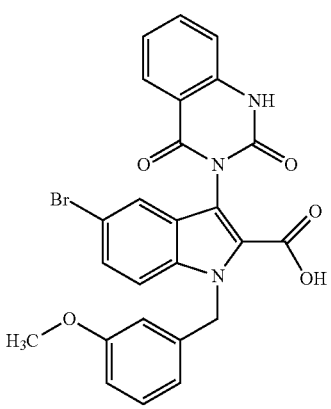
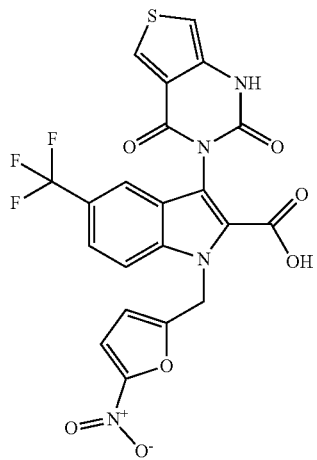
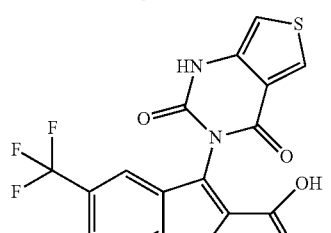
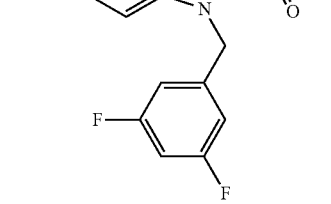
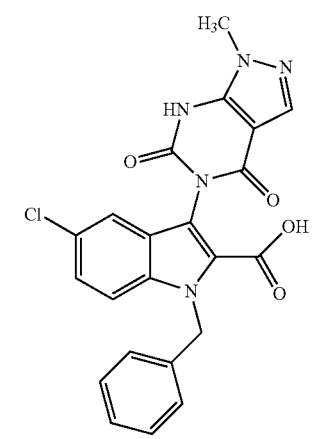
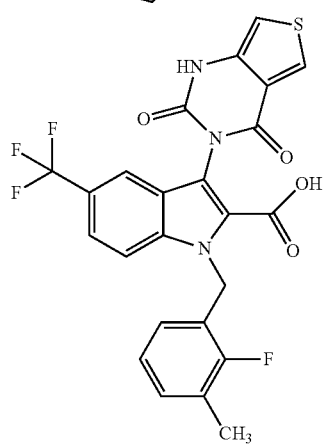
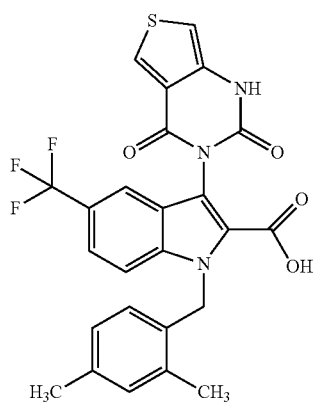

419
-continued
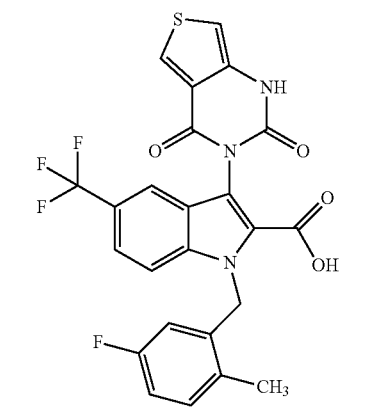
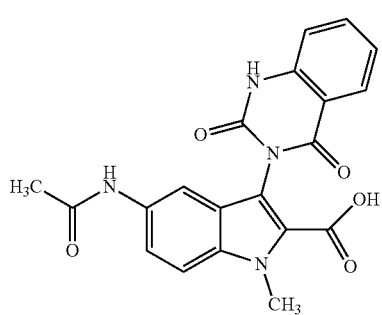
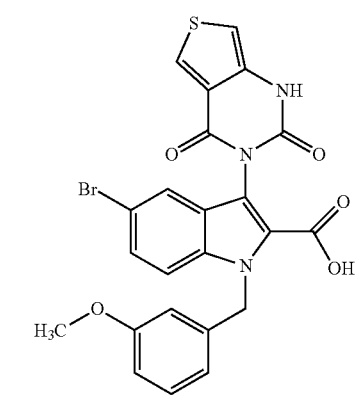
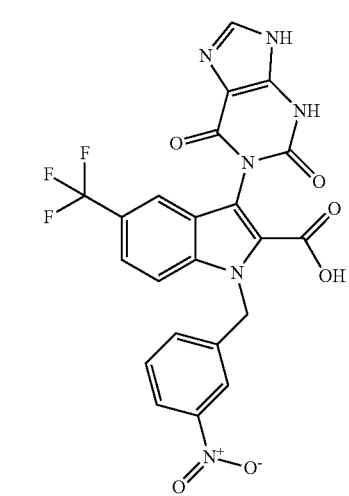
420
-continued
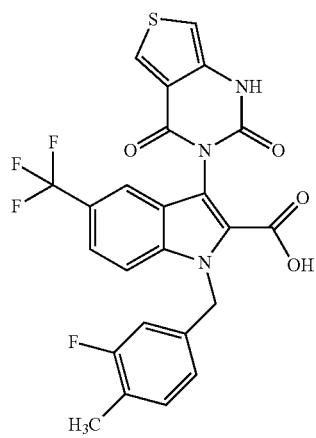
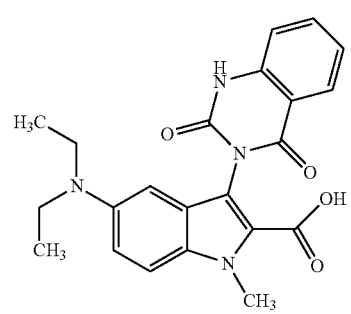
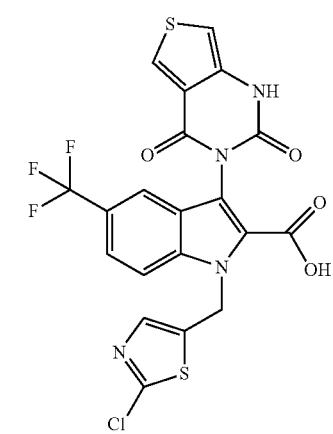
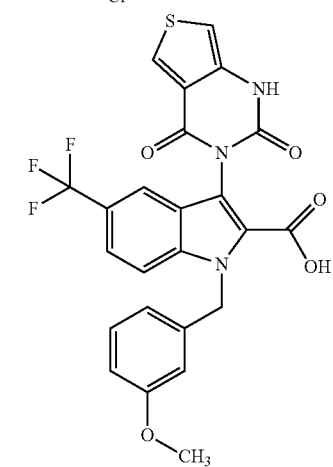

421
-continued
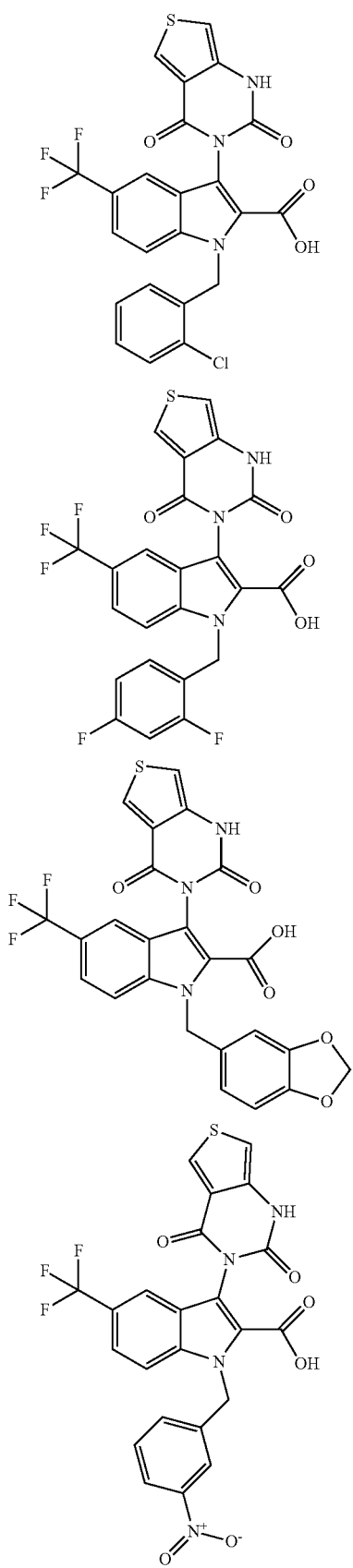
422
-continued
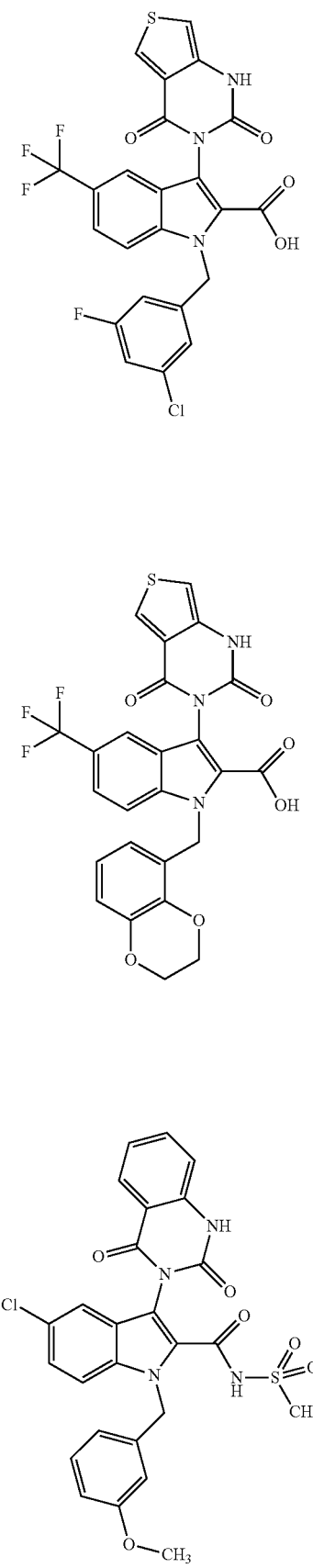

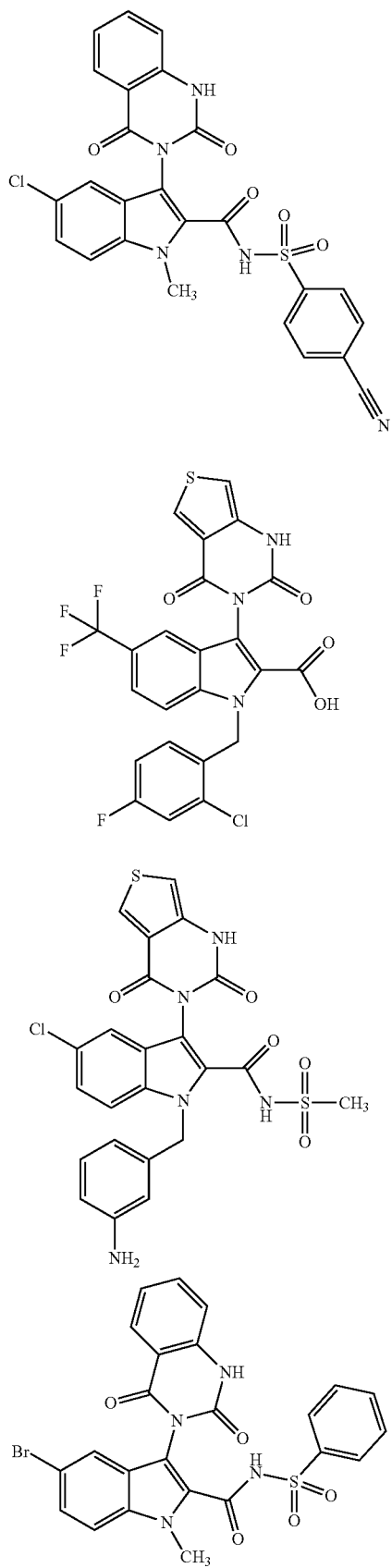
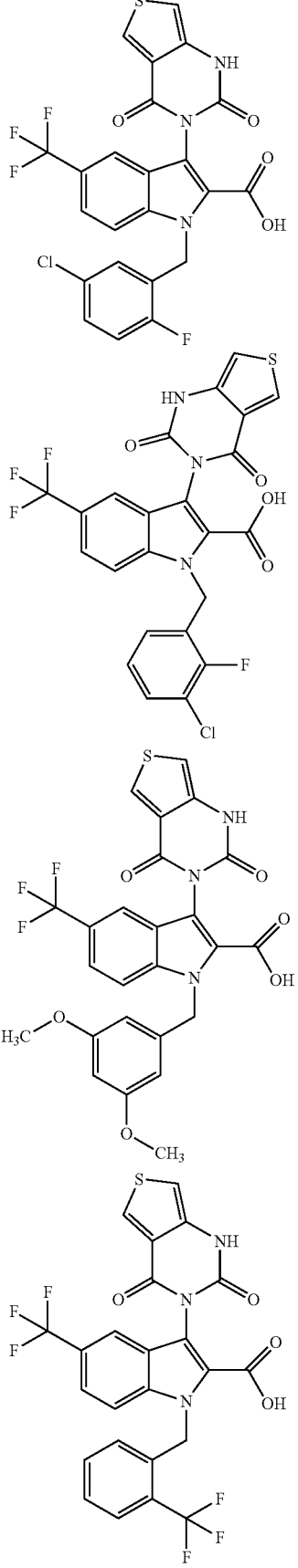

425
-continued
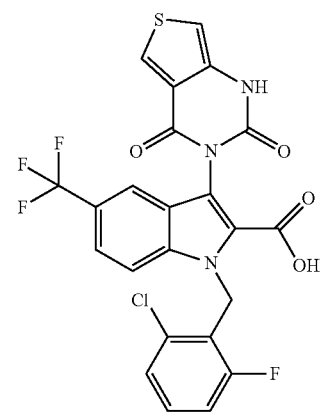
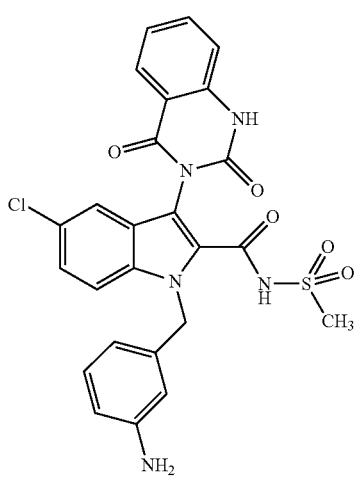
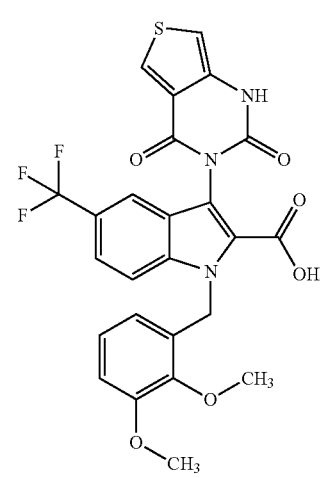
426
-continued
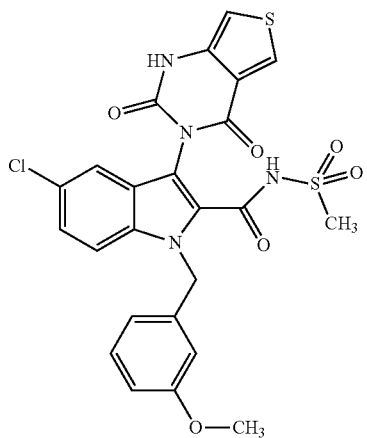
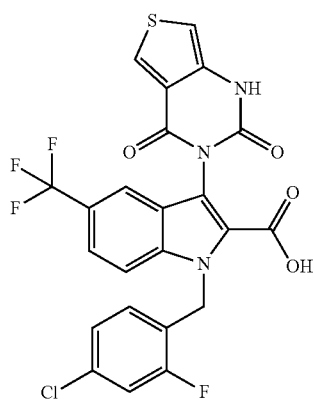
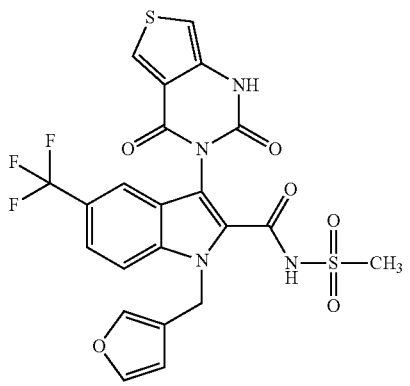

427
-continued
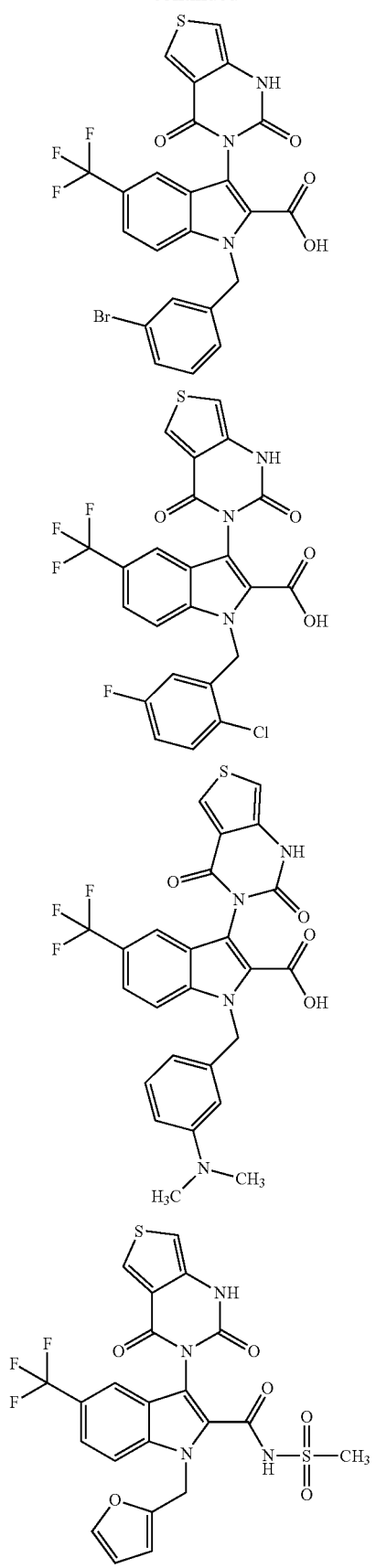
428
-continued
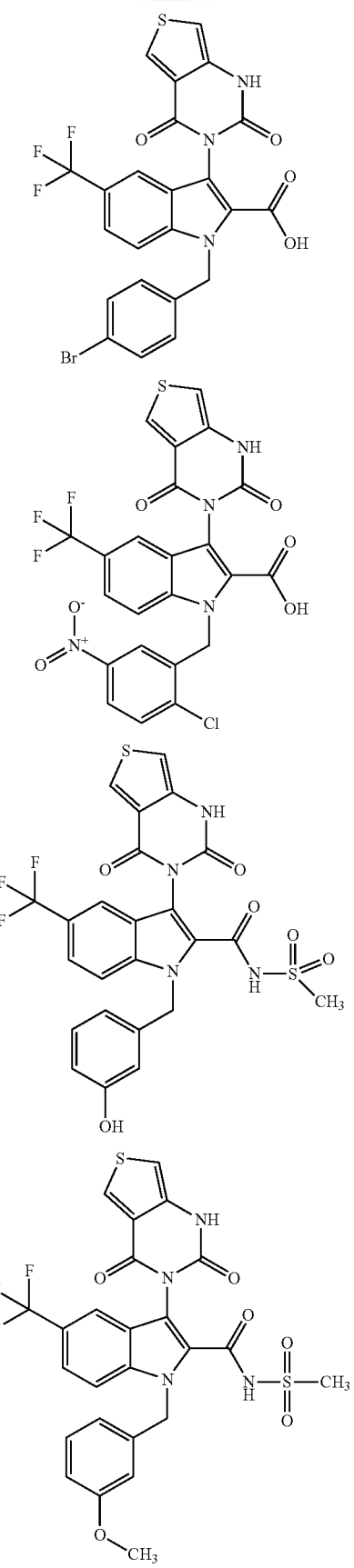

429
-continued
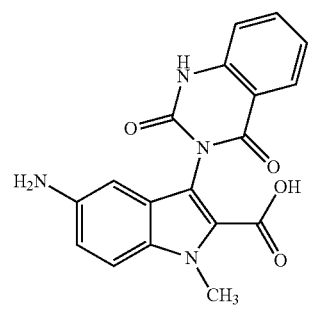
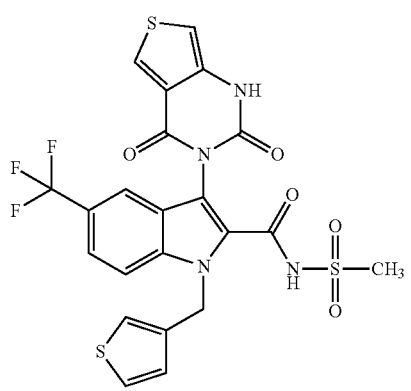
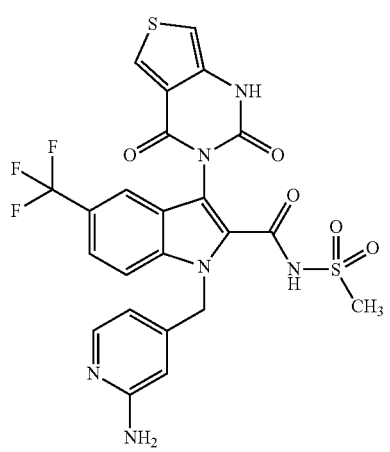
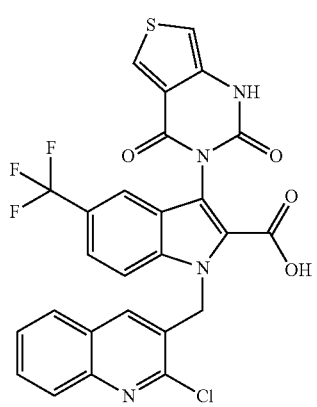
430
-continued
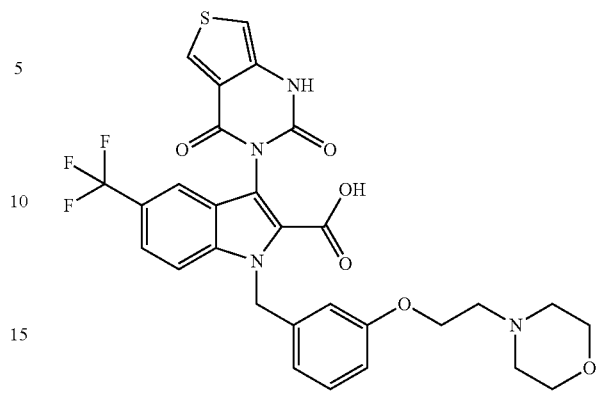
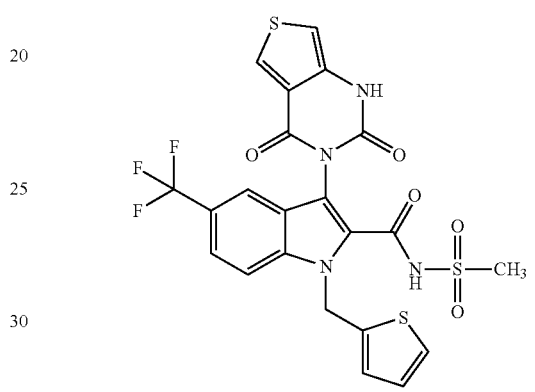
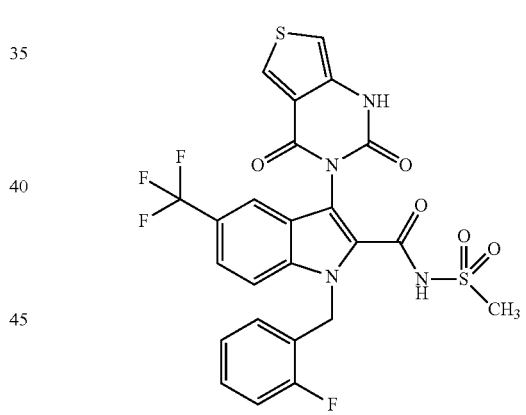
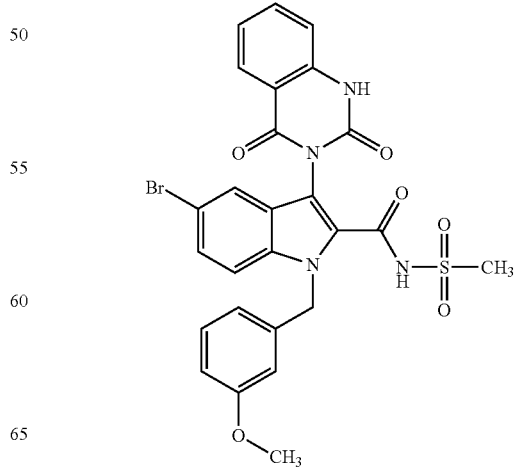

431
-continued
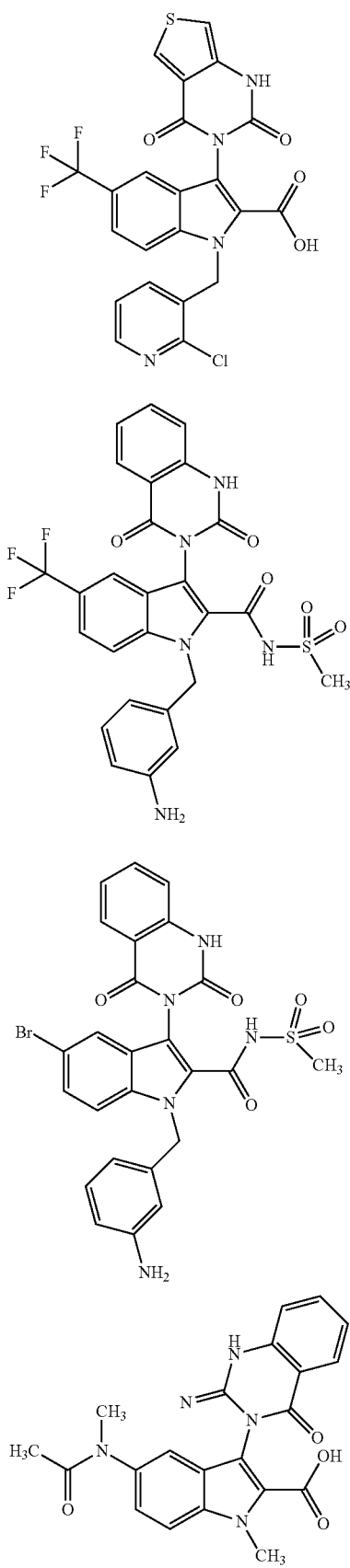
432
-continued
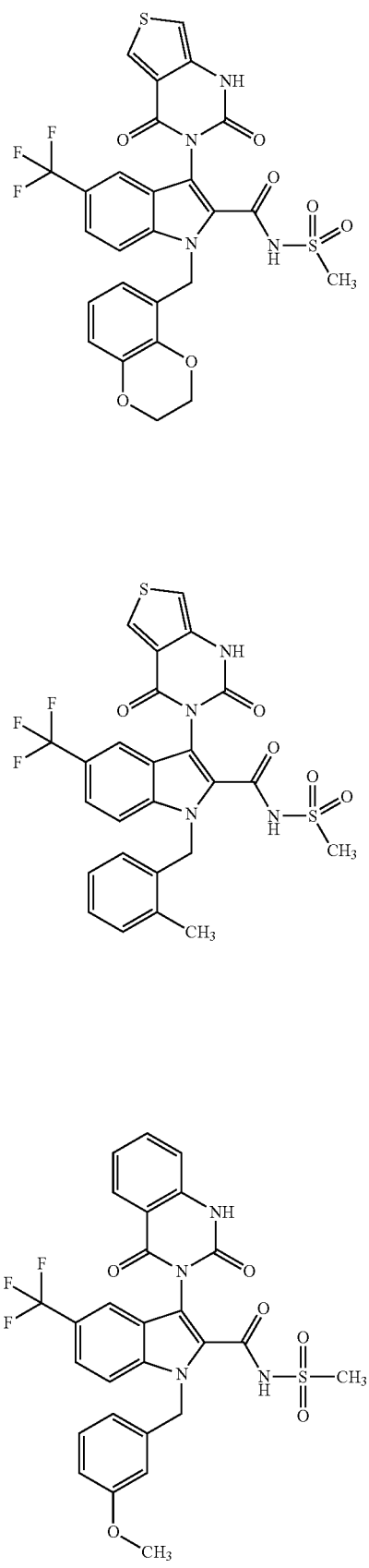

433
-continued
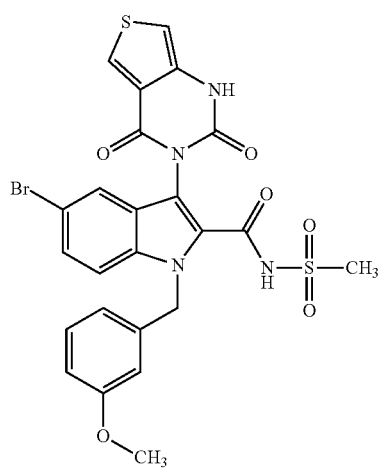
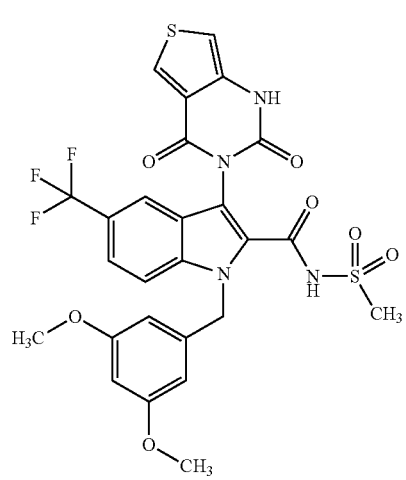
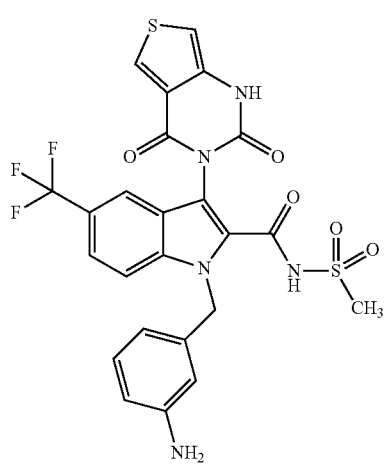
434
-continued
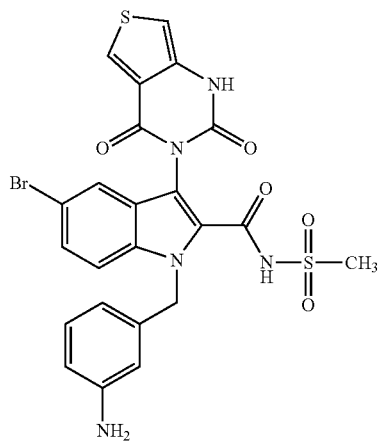
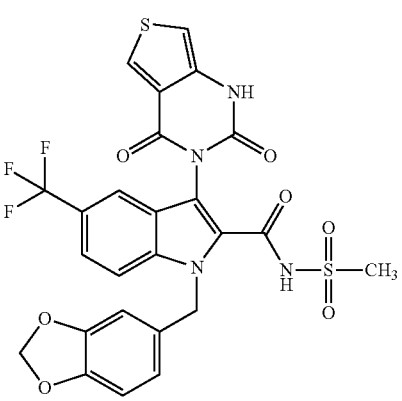
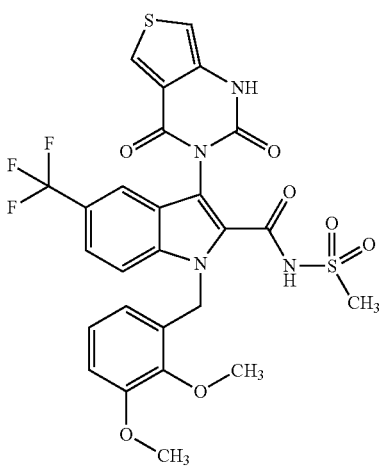

435
-continued
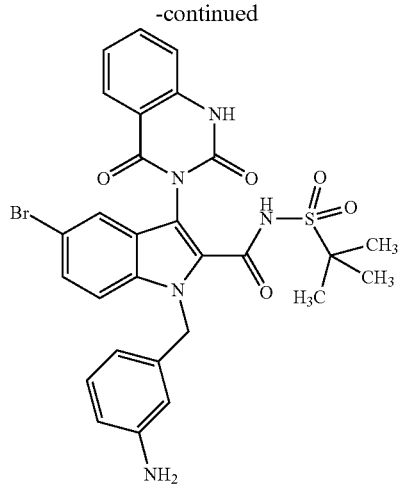
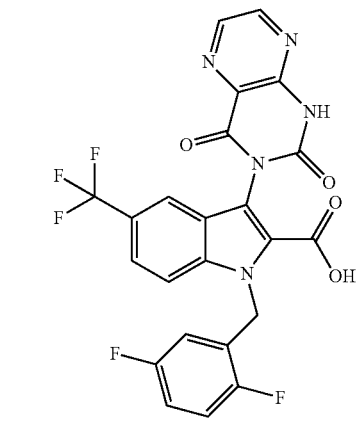
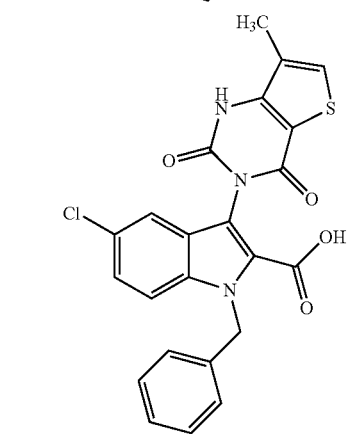
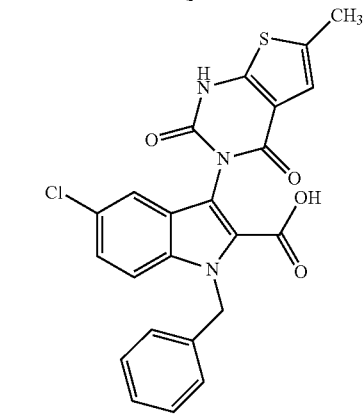
436
-continued
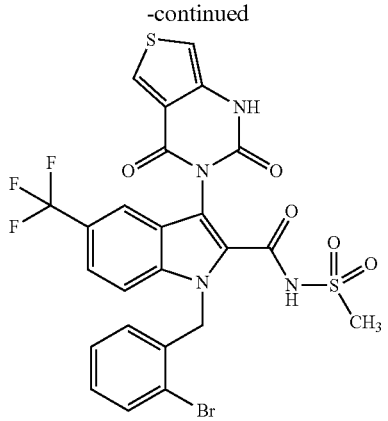
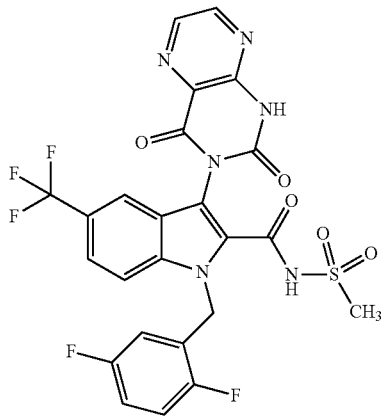
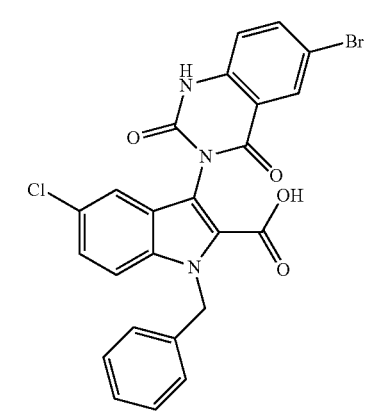
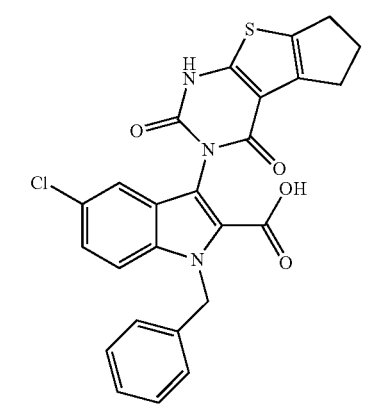

437
-continued
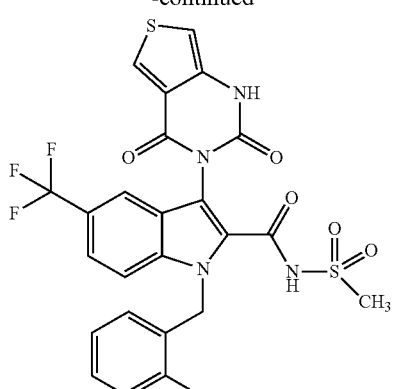
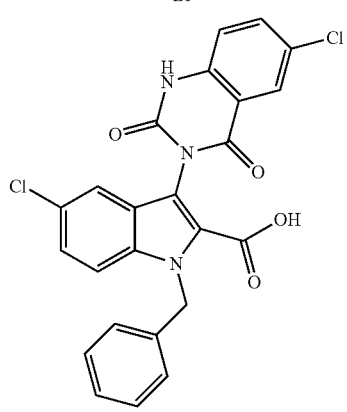
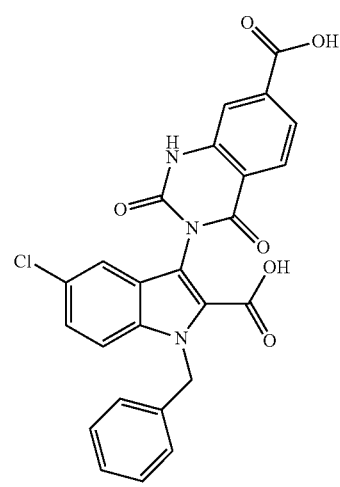
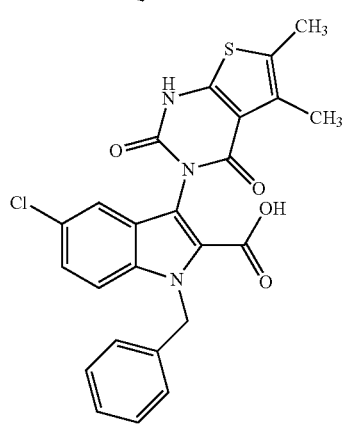
438
-continued
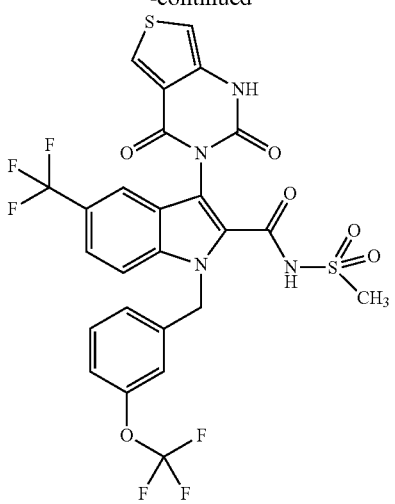
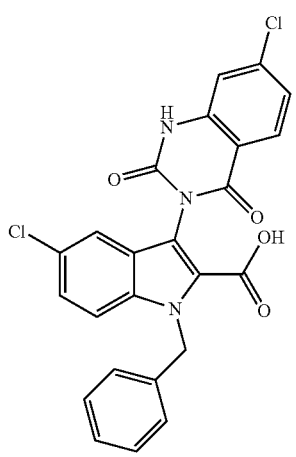
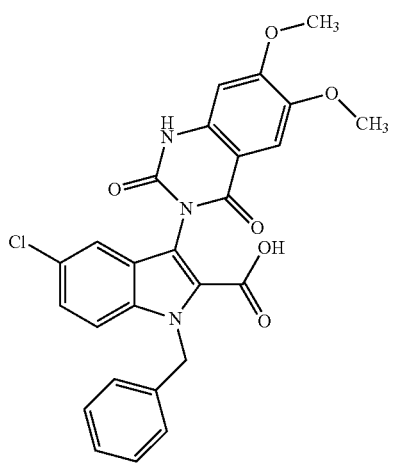

439
-continued
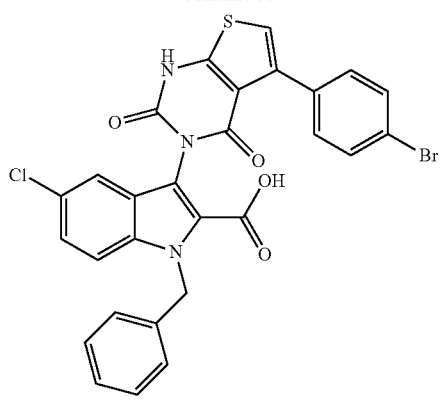
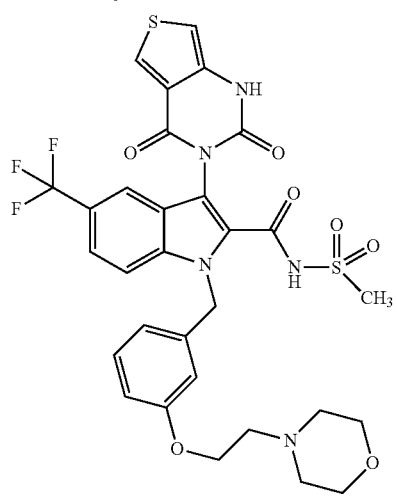
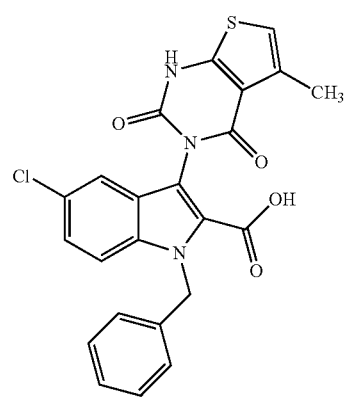
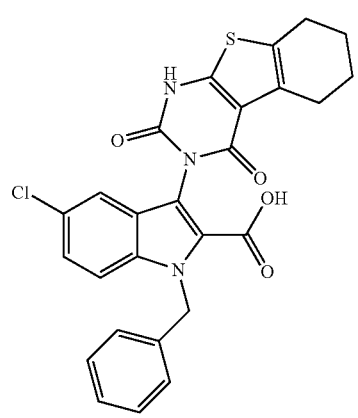
440
-continued
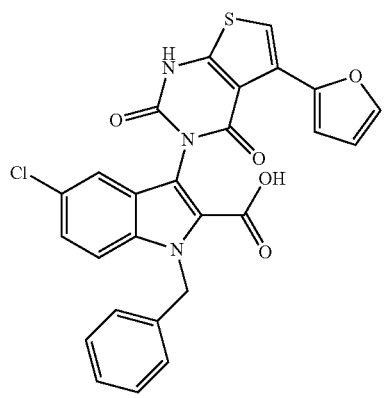
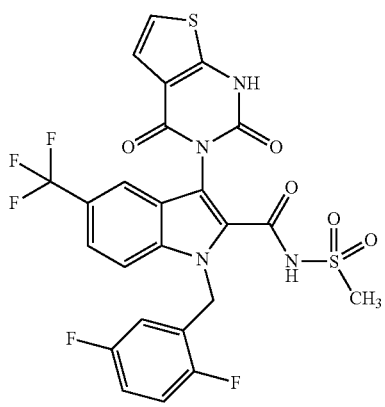
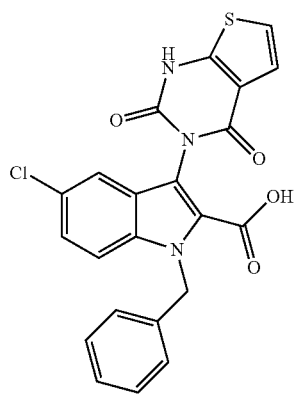
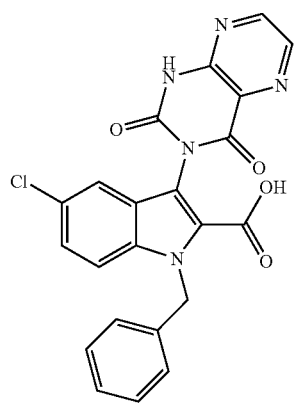

441
-continued
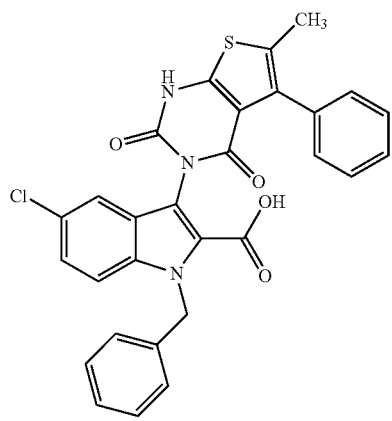
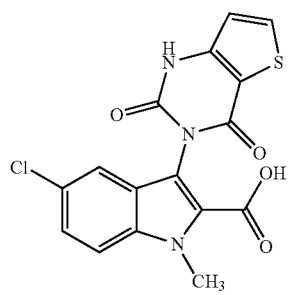
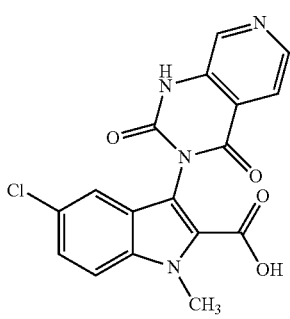
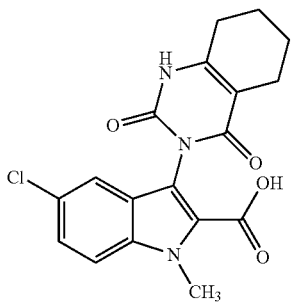
442
-continued
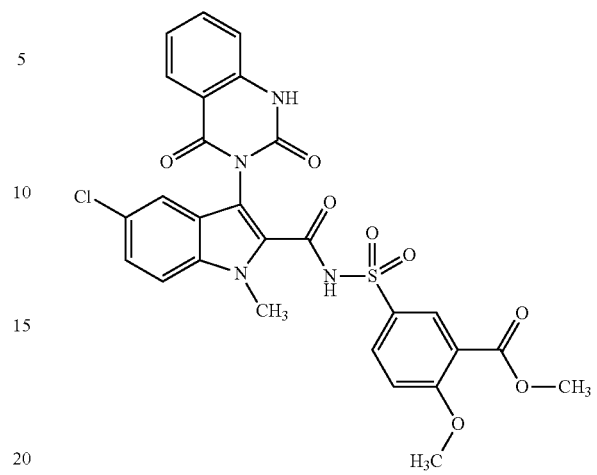
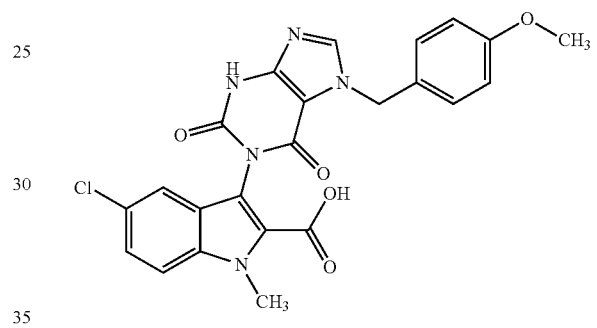
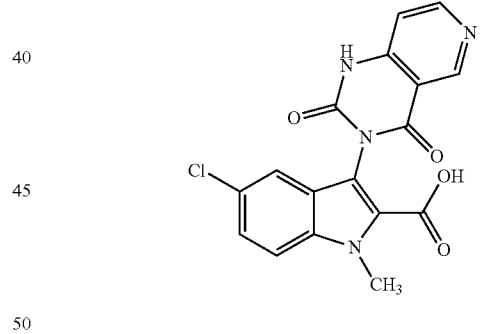
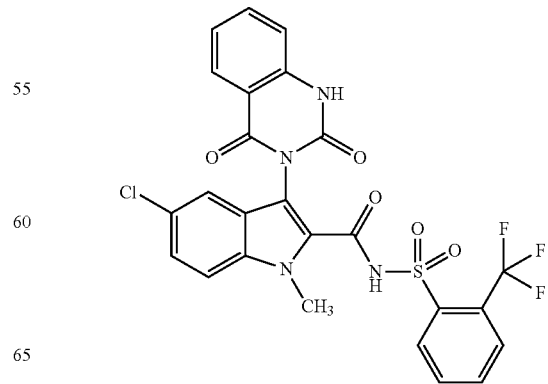

443
-continued
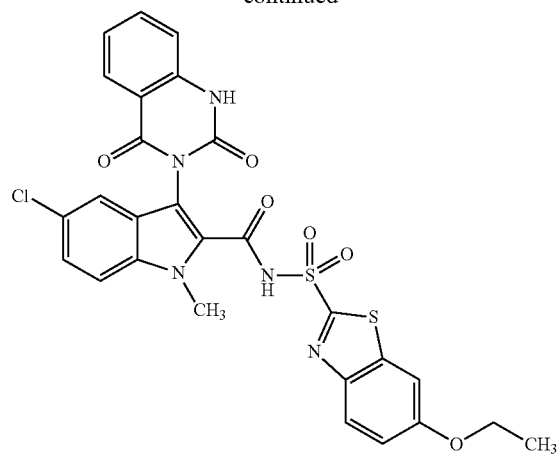
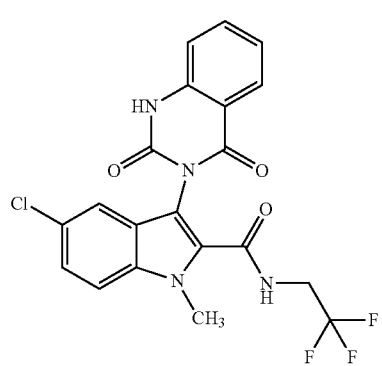
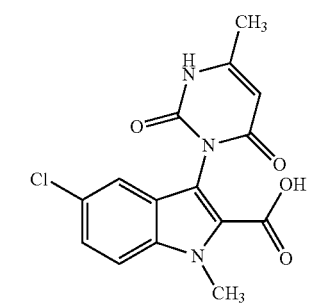
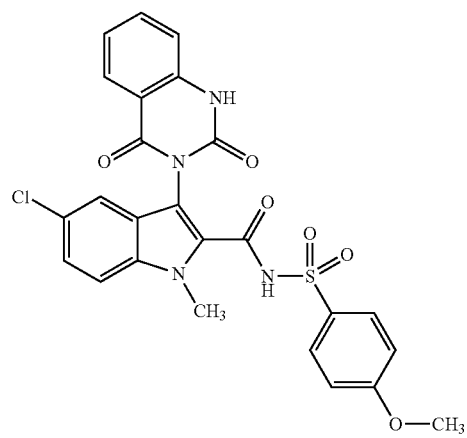
444
-continued
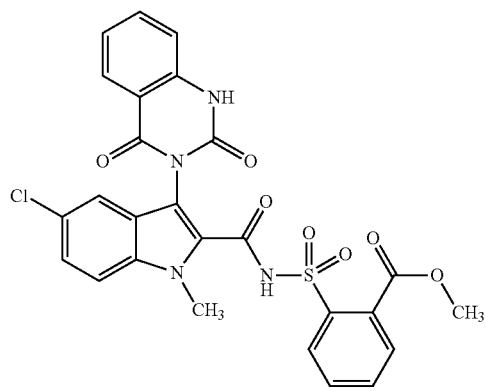
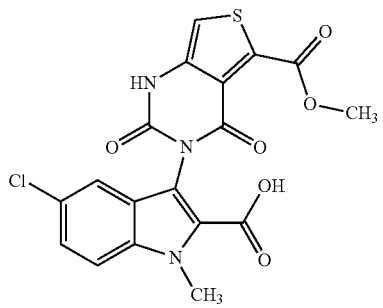
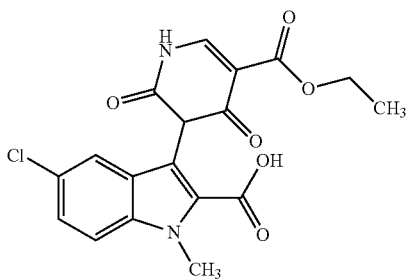
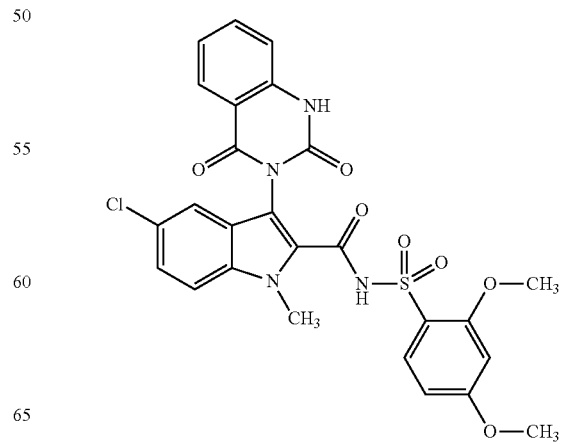

445
-continued
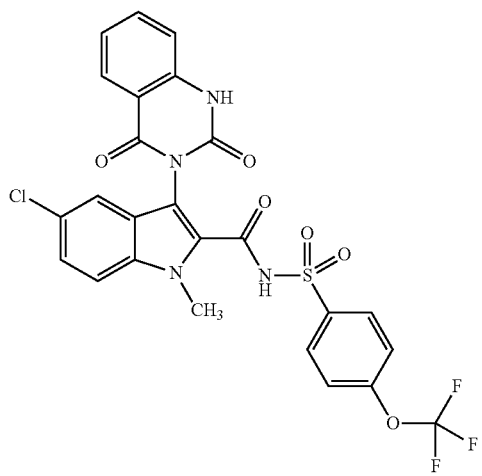
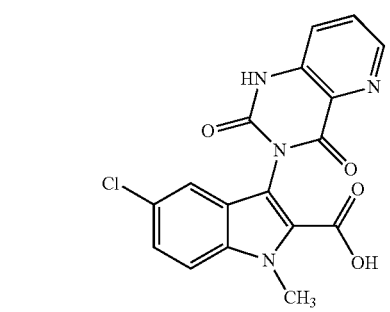
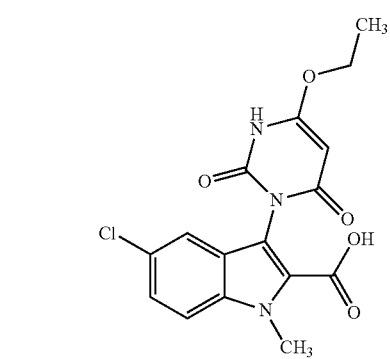
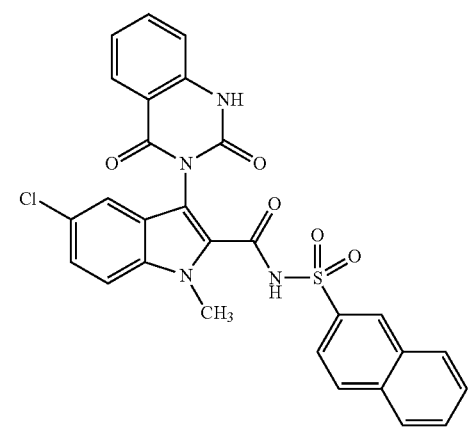
446
-continued
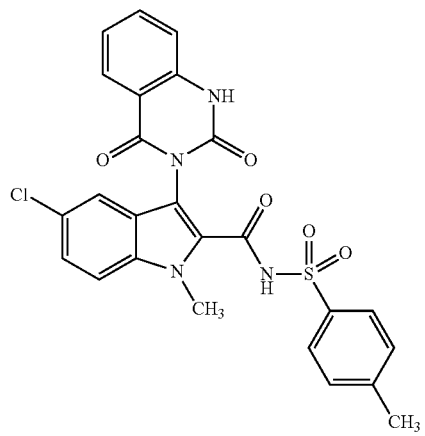
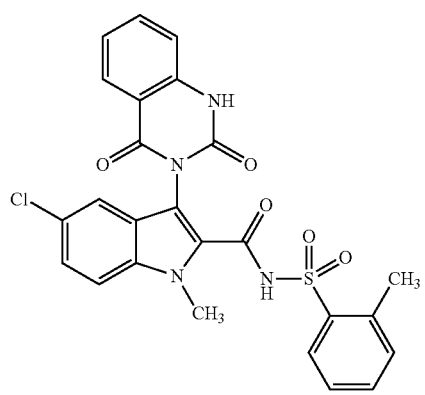
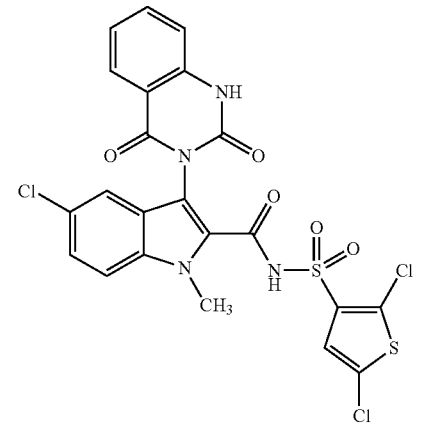

447
-continued
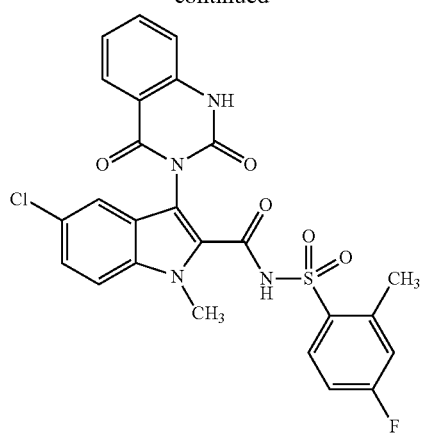
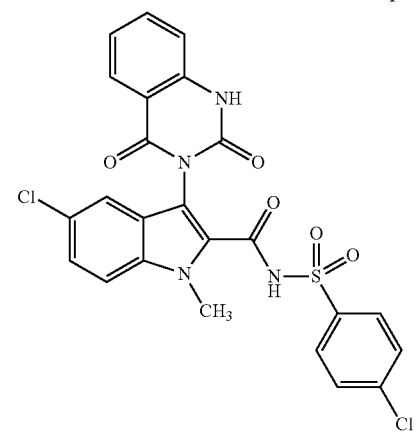
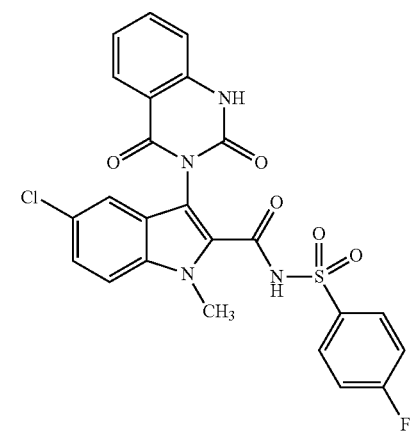
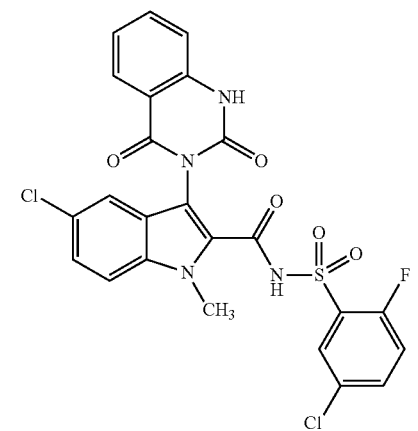
448
-continued
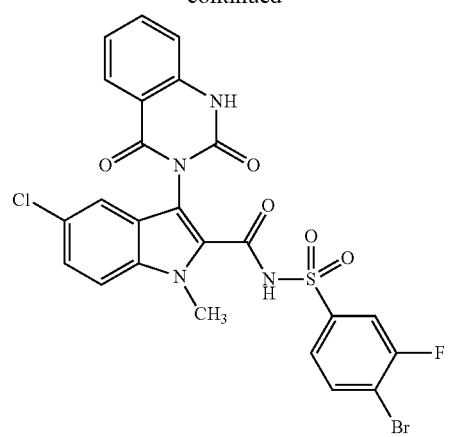
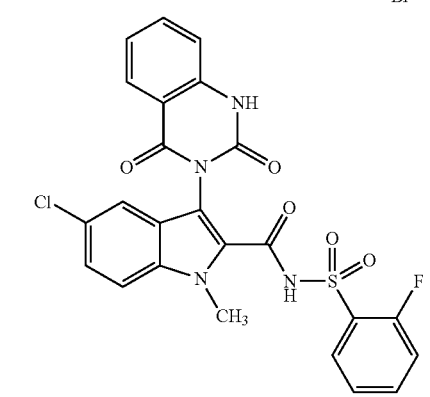
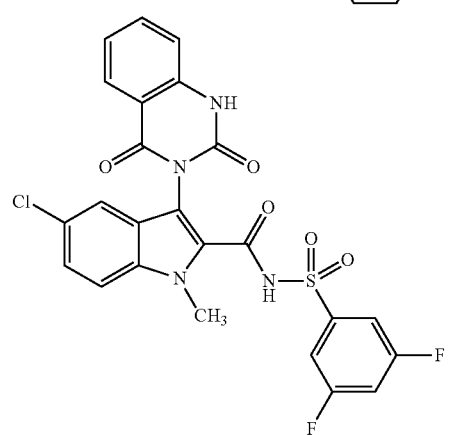
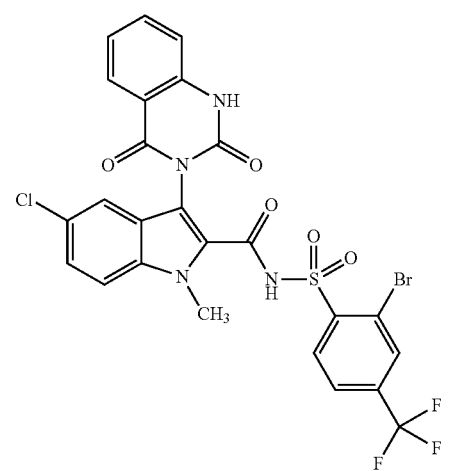

| 449 -continued | 450 -continued |
|---|---|
| 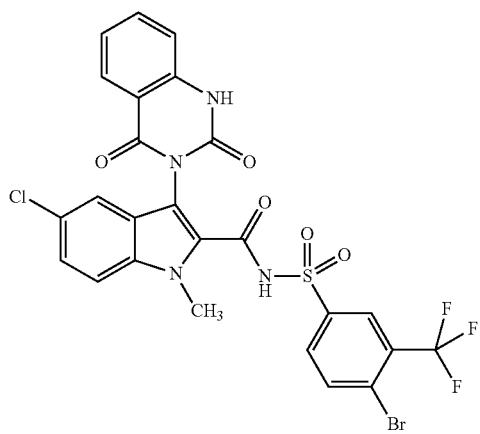 | 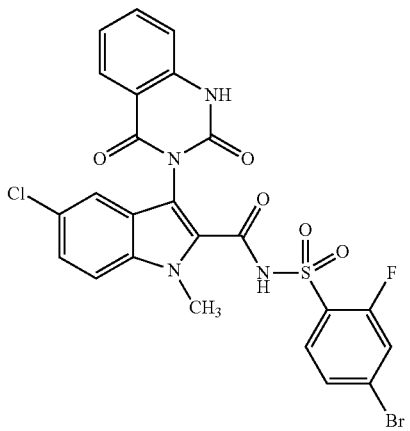 |
| 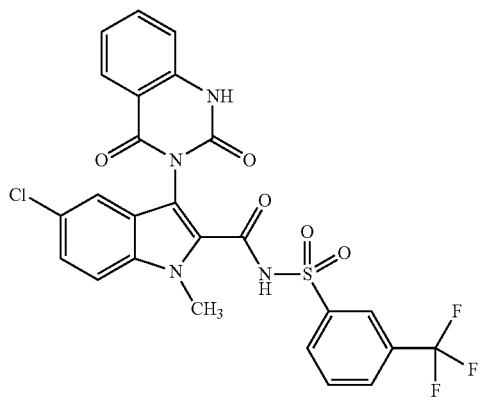 | 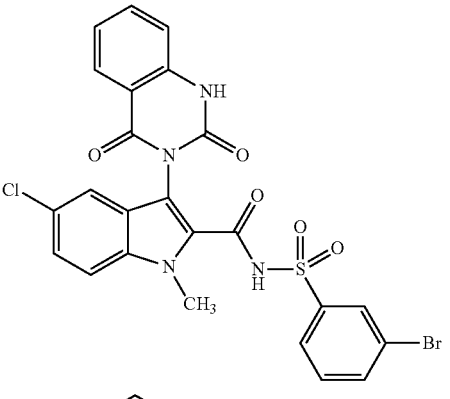 |
| 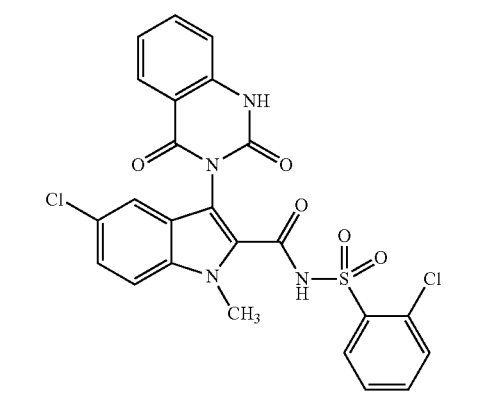 | 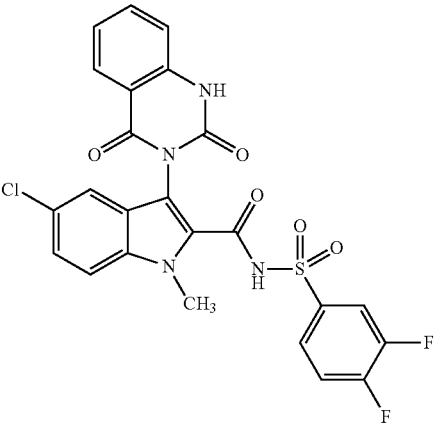 |
| 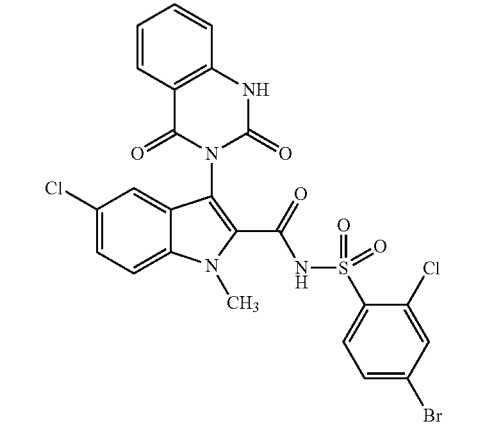 | 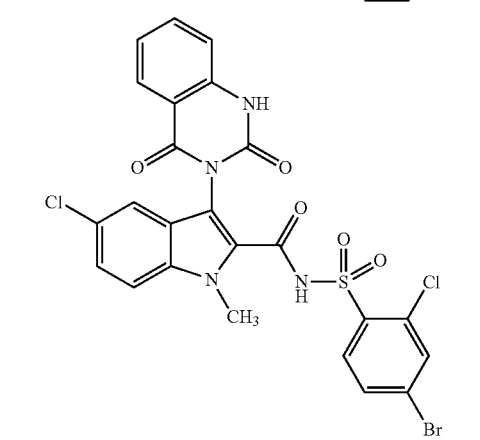 |

451
-continued
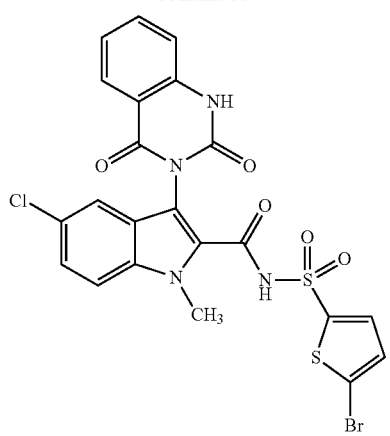
452
-continued
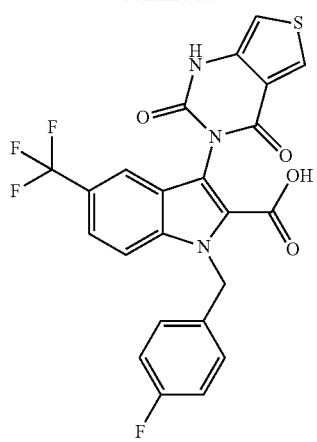
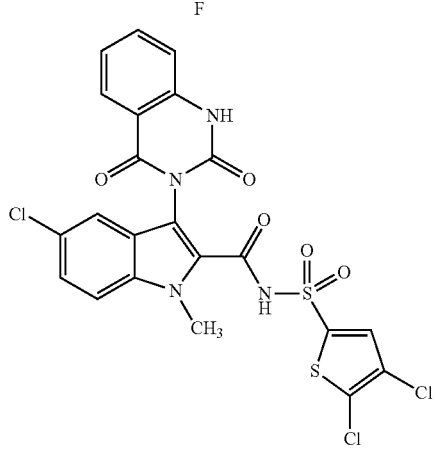
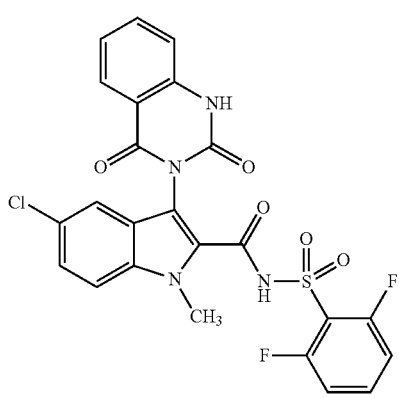
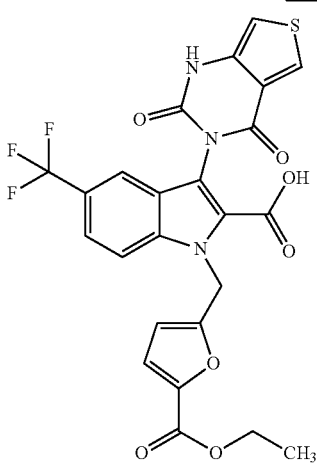

453
-continued
454
-continued
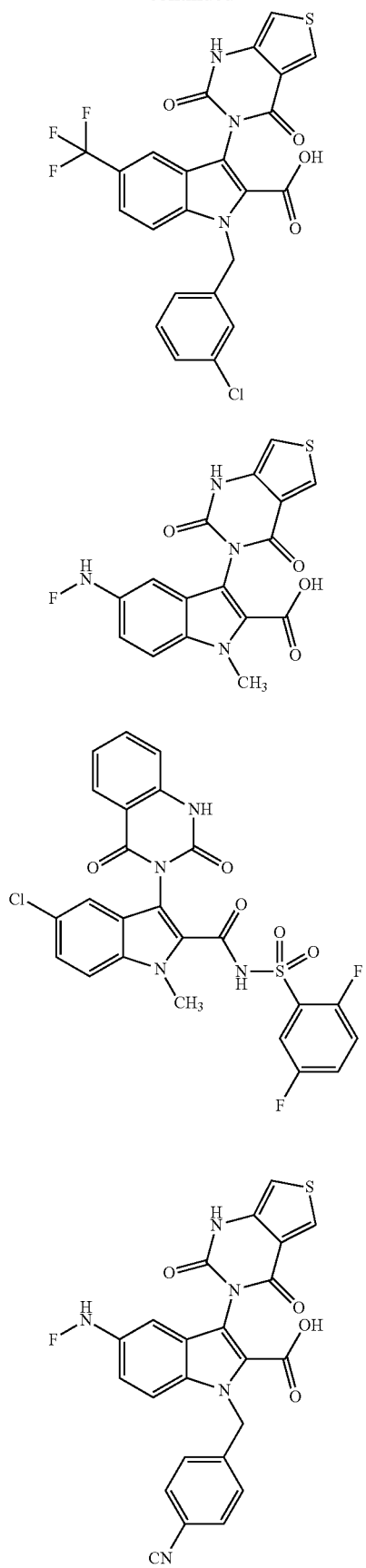
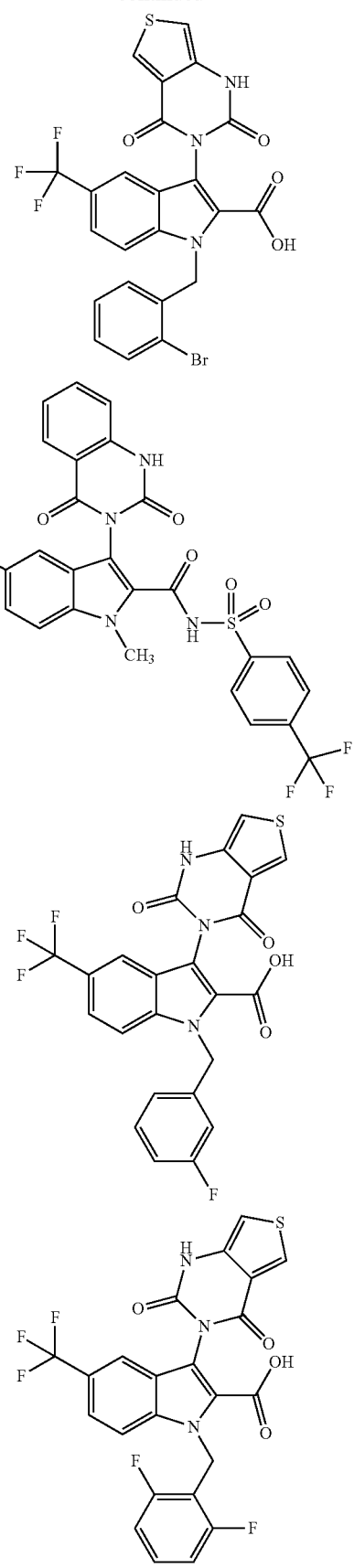

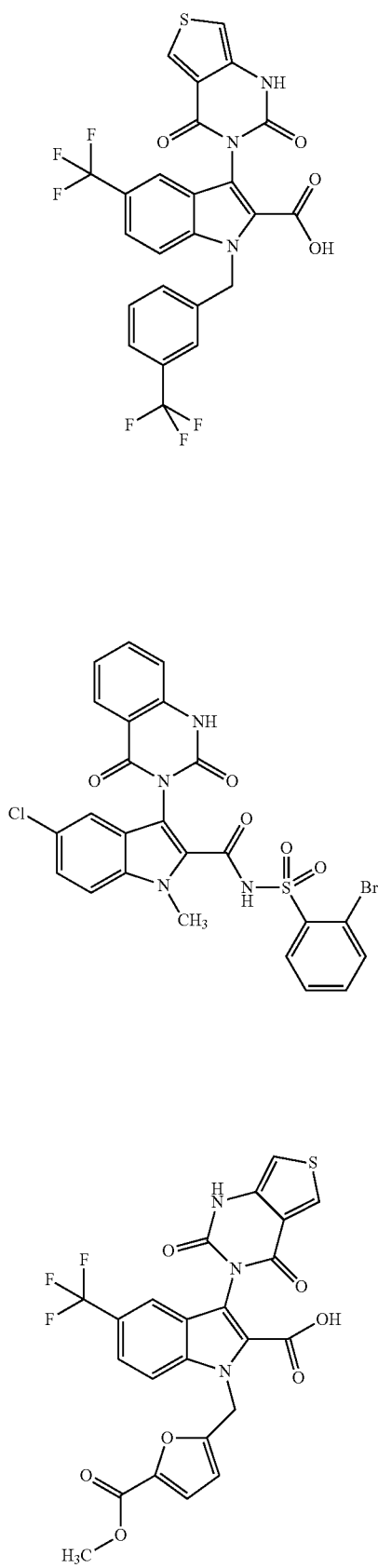
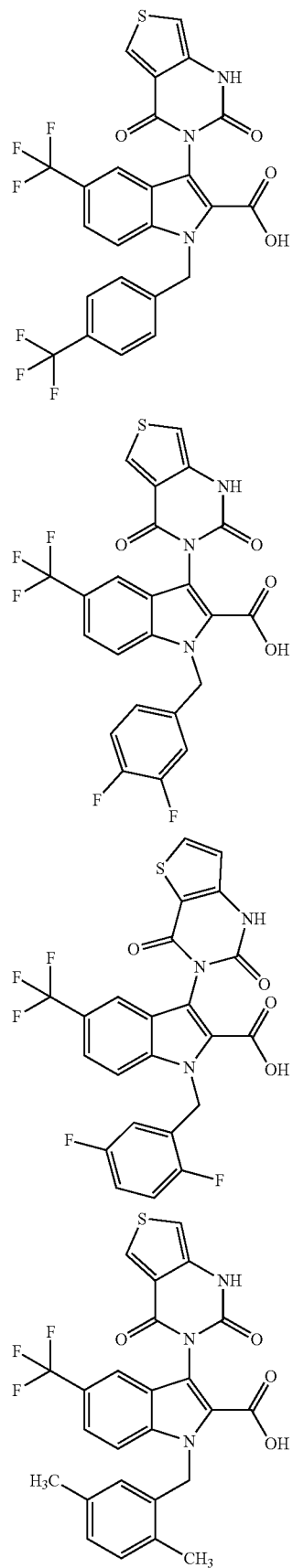

457
-continued
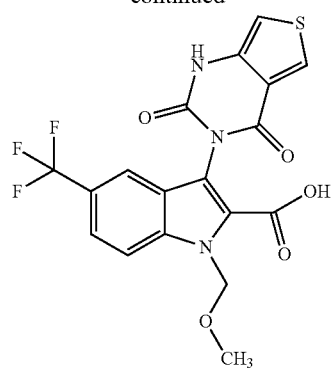
458
-continued
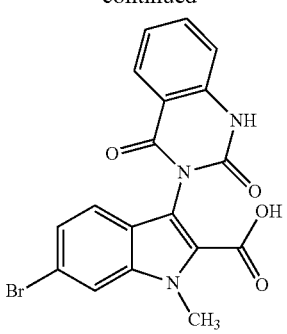
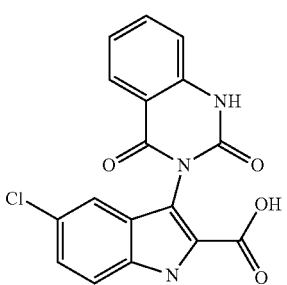
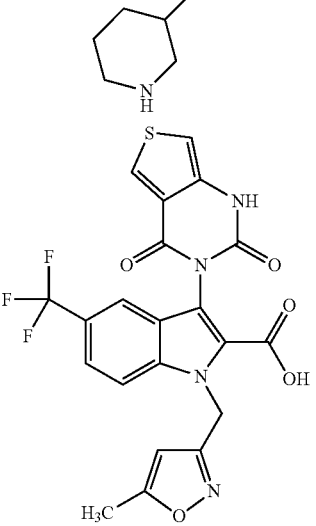
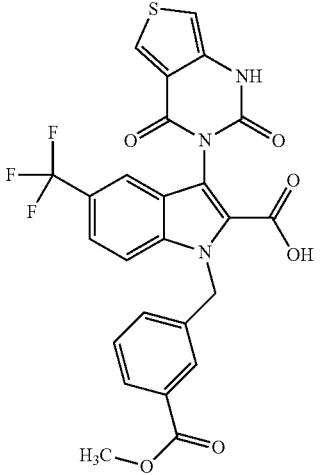

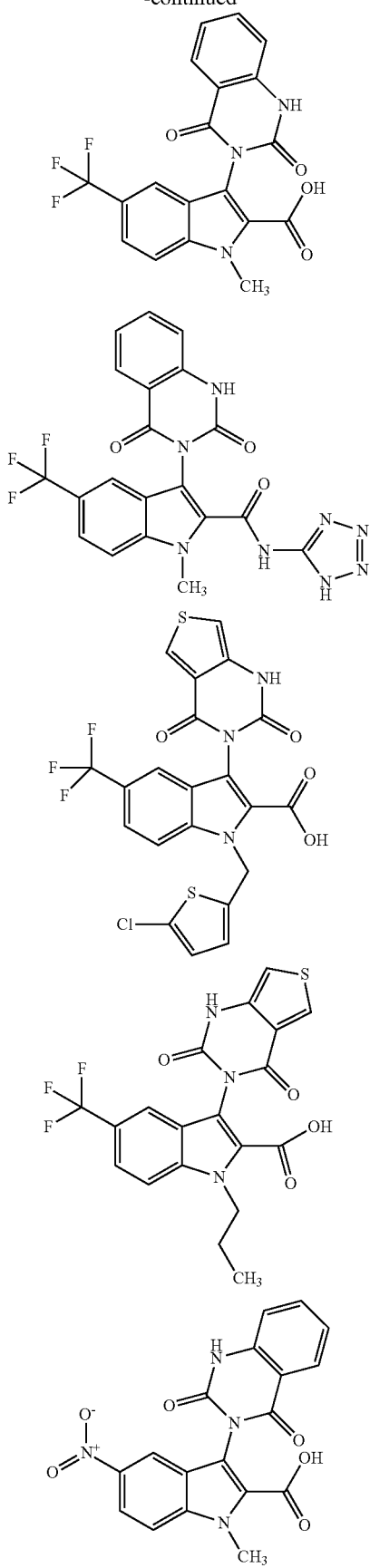
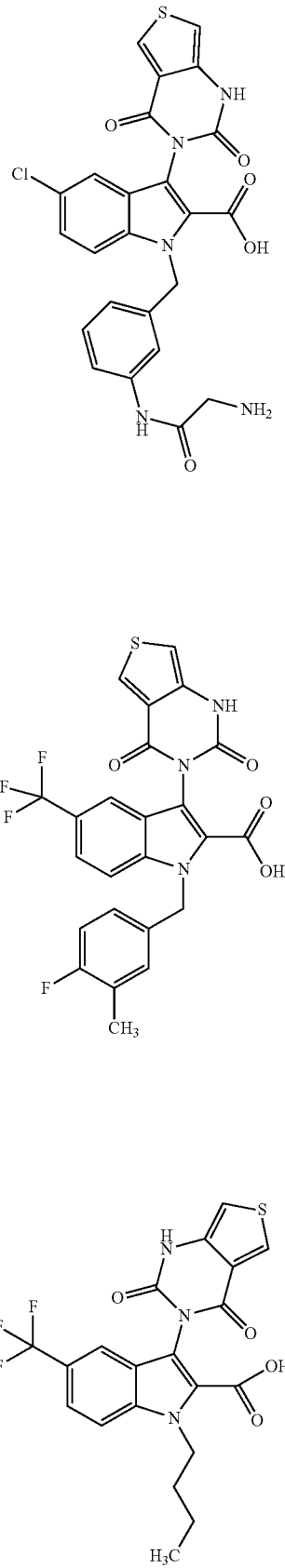

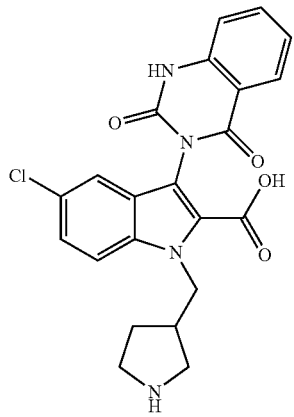
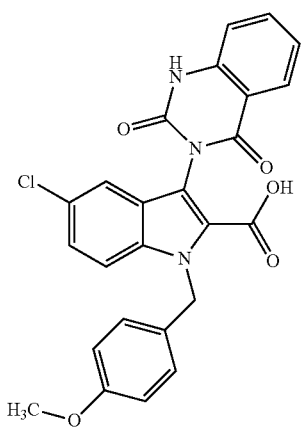
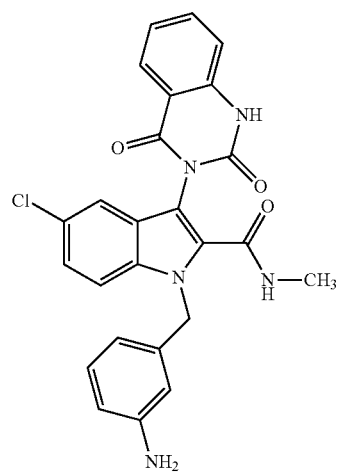
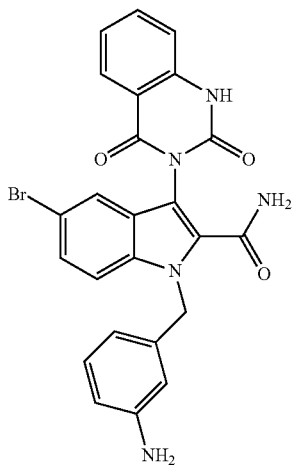
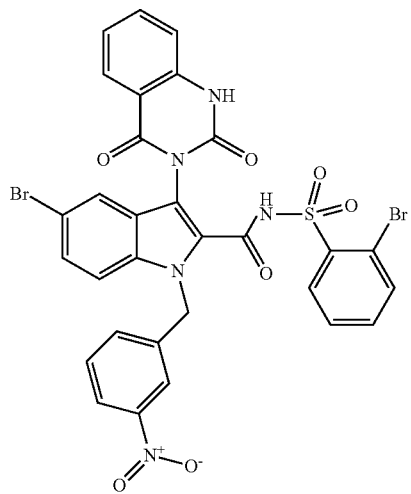
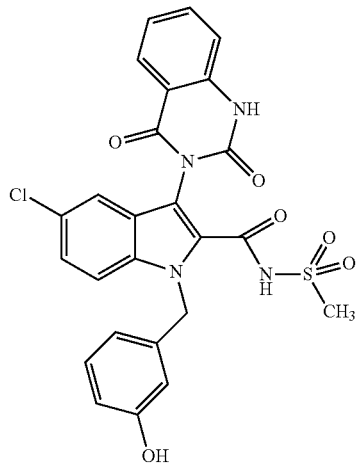

463
-continued
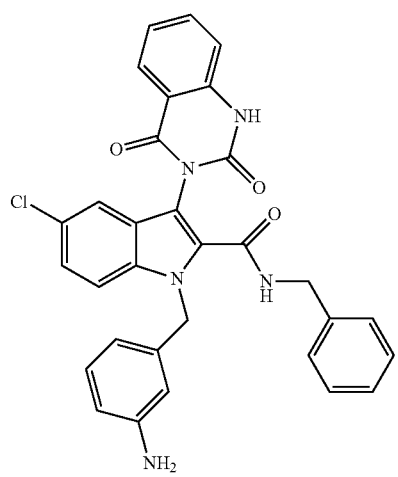
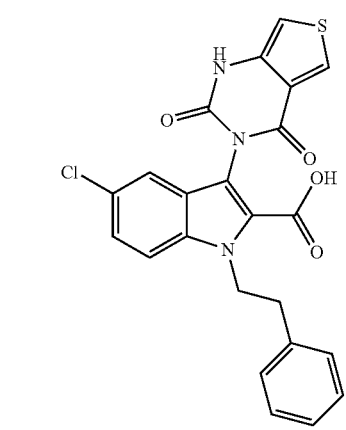
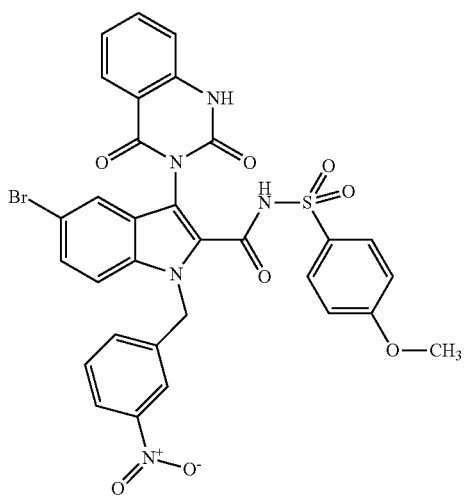
464
-continued
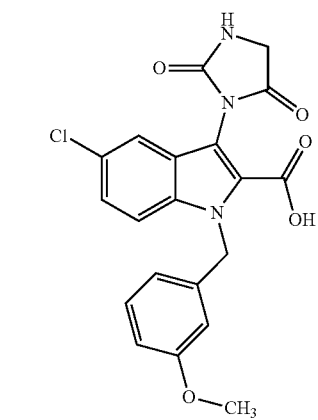
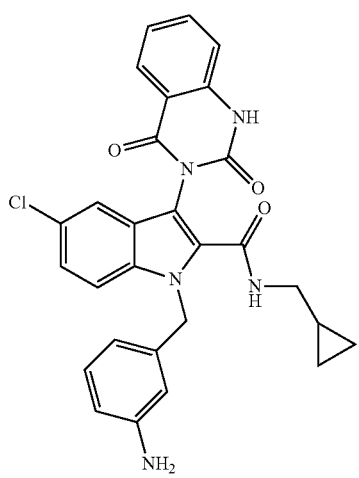
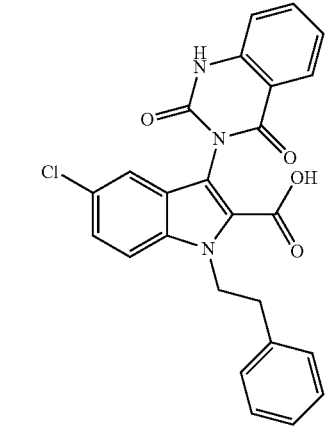
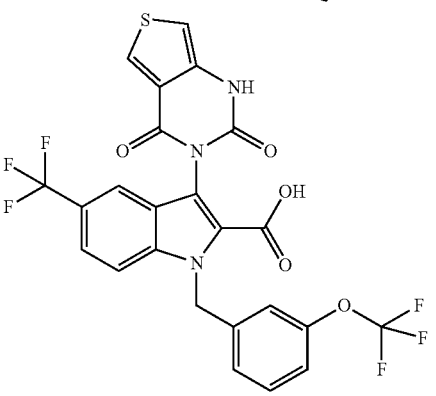

465
-continued
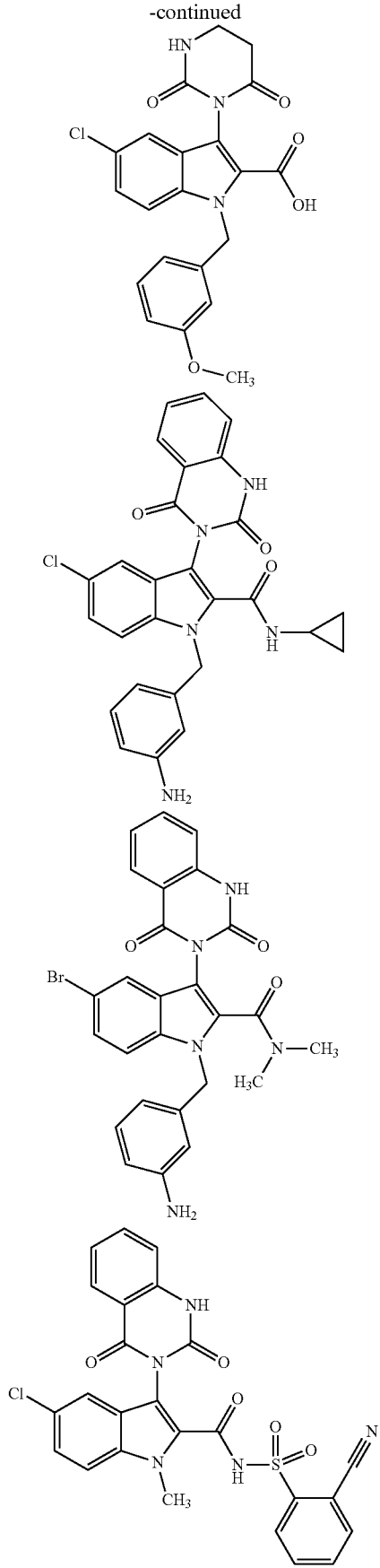
466
-continued
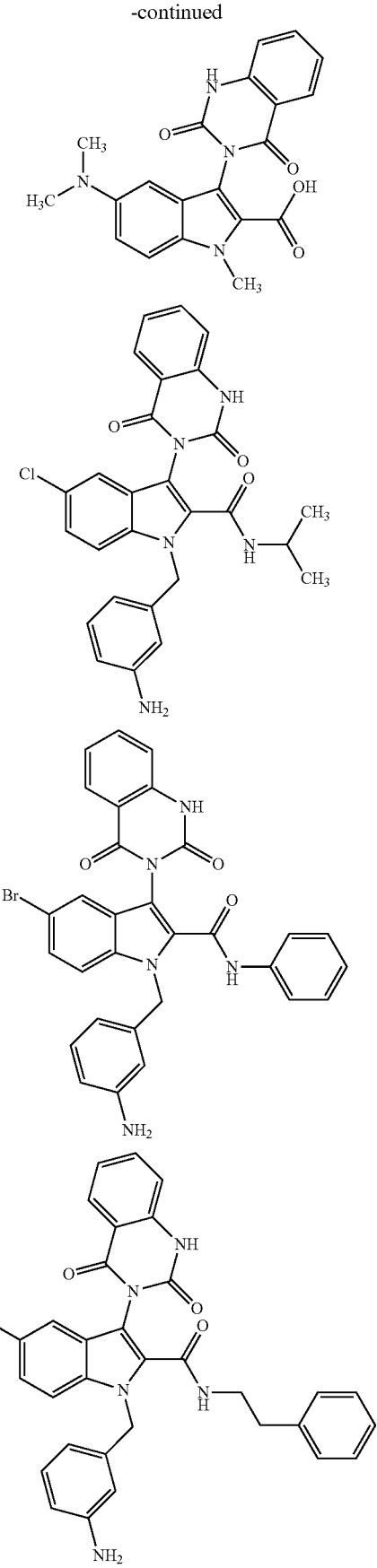

467
-continued
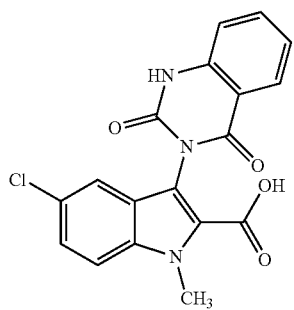
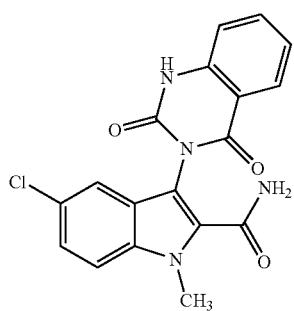
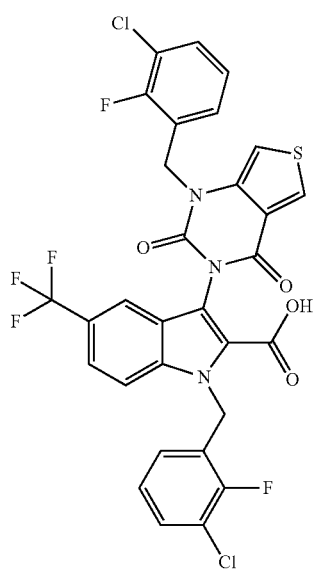
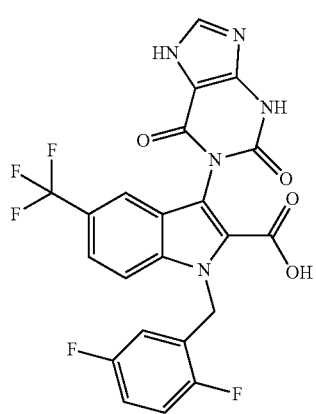
468
-continued
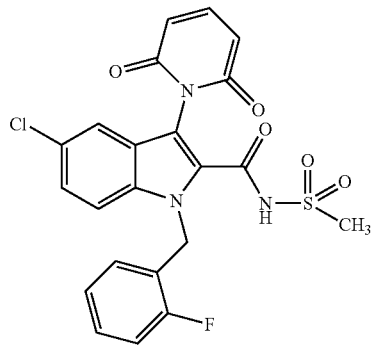
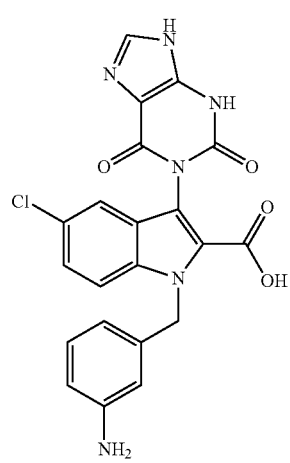
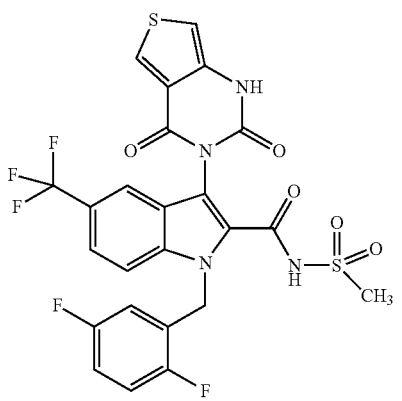
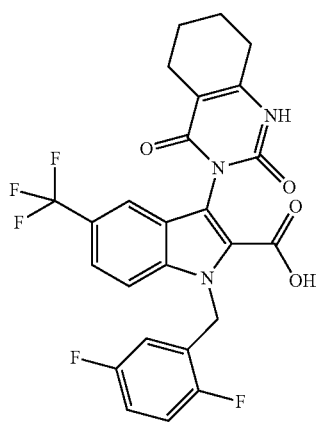

469
-continued
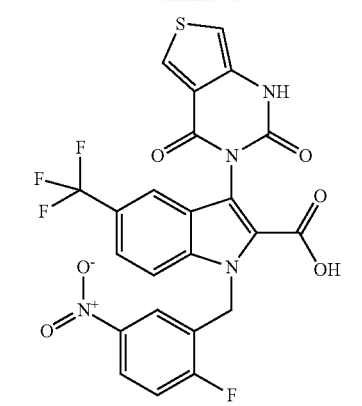
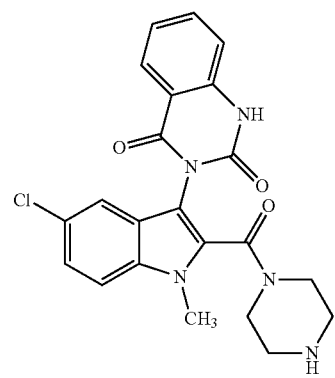
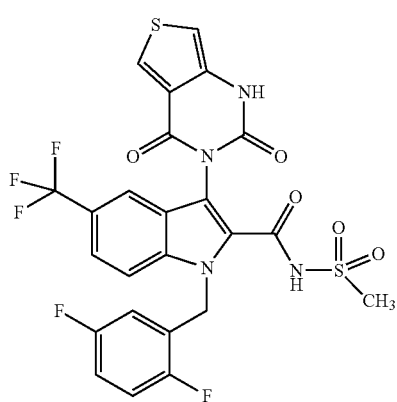
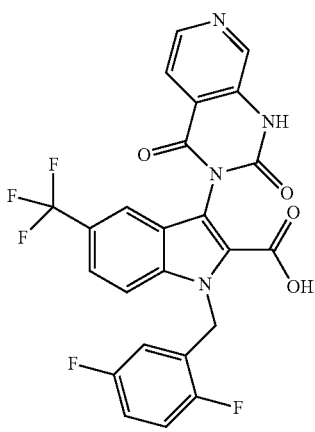
470
-continued
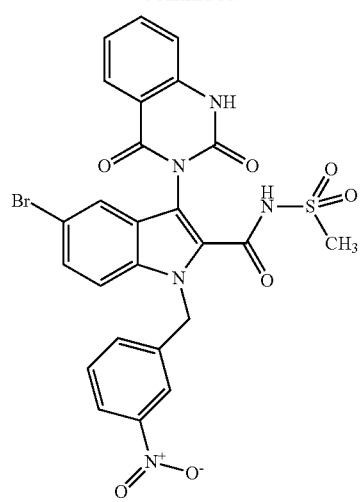
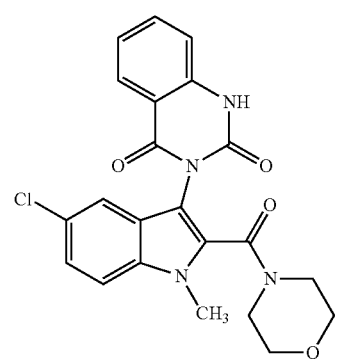
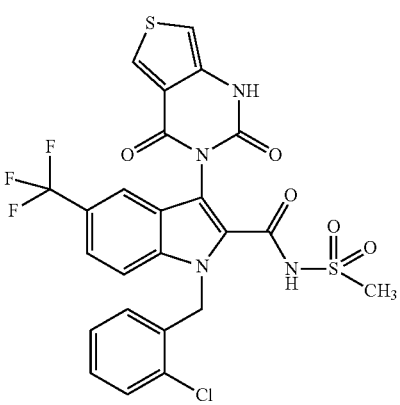
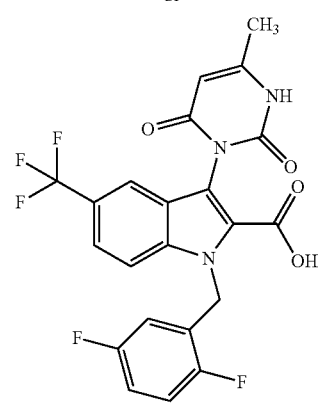

471
-continued
472
-continued
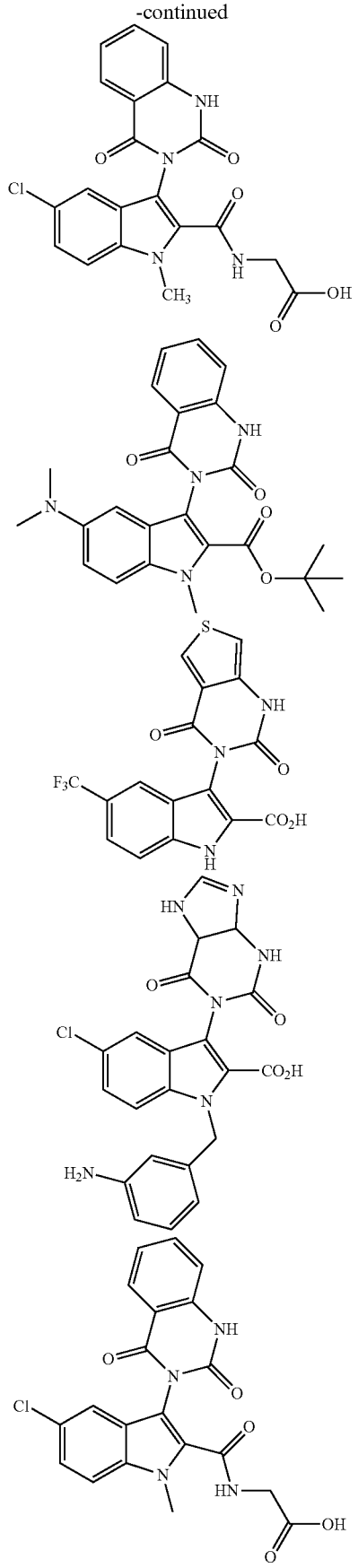
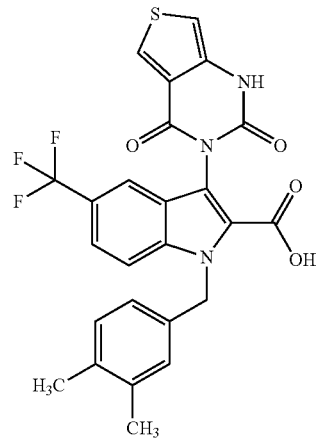
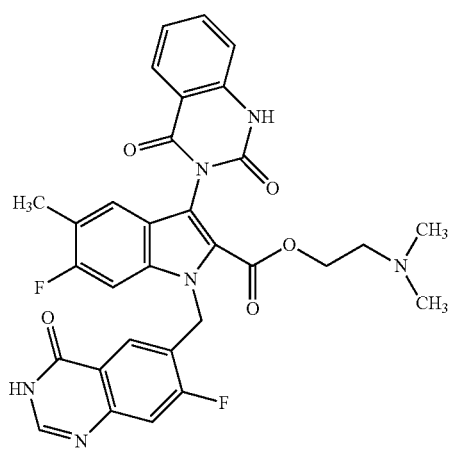
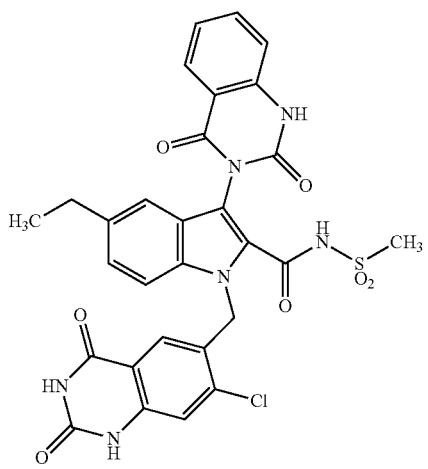

473
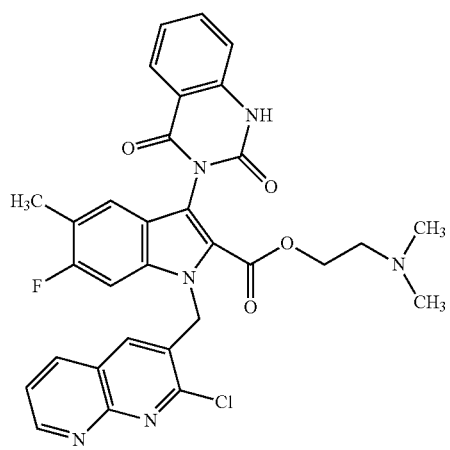
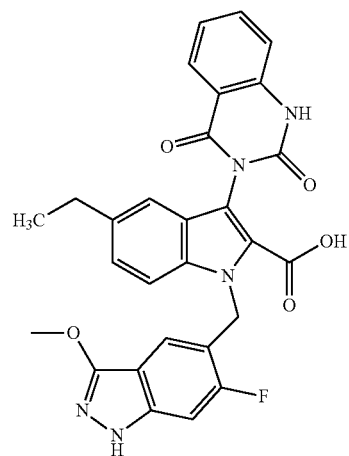
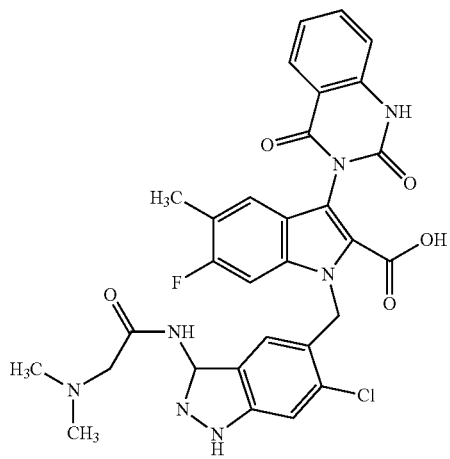
474
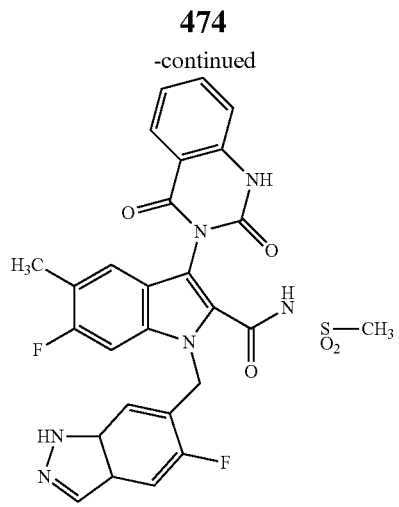
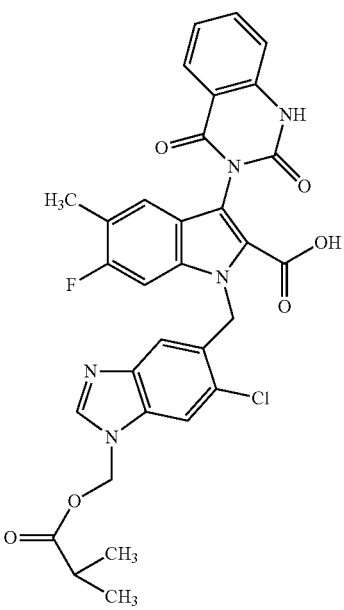
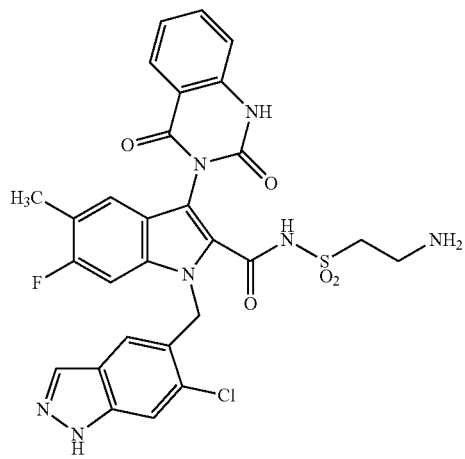

-continued

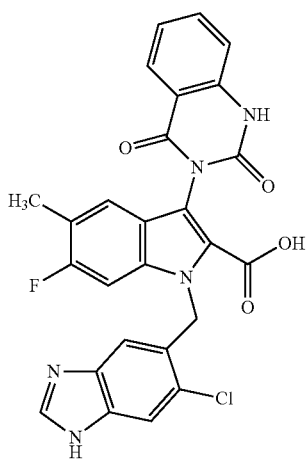

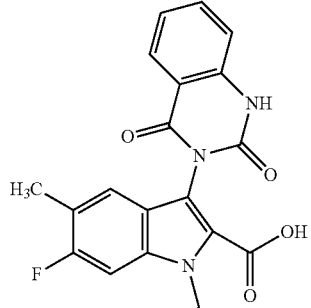

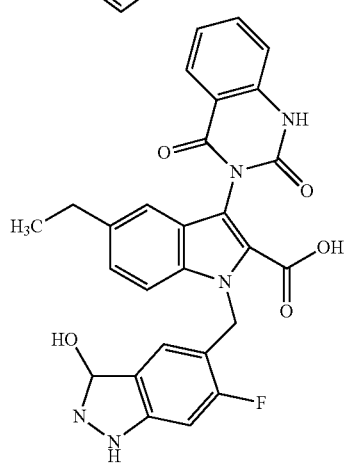

or

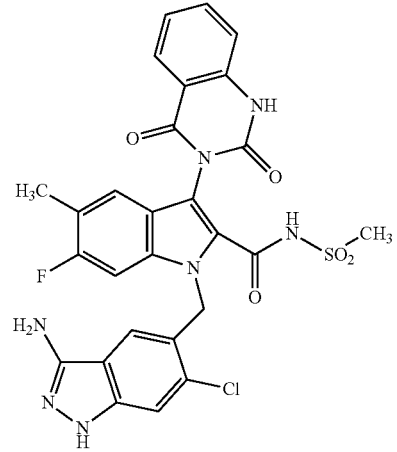 [SMILES: Cc1cc2c(-n3c(=O)[nH]c4ccccc4c3=O)c(C(=O)NS(C)(=O)=O)n(Cc3cc4c(N)n[nH]c4cc3Cl)c2cc1F]

or a pharmaceutically acceptable salt thereof.

15. A composition comprising at least one compound of claim 1 or a pharmaceutically acceptable salt thereof, and at least one pharmaceutically acceptable carrier.

16. A composition comprising at least one compound of claim 8 or a pharmaceutically acceptable salt thereof, and at least one pharmaceutically acceptable carrier.

17. A method for treating Hepatitis C Virus (HCV) infection in a patient, the method comprising administering to the patient an effective amount of at least one compound of claim 1 or a pharmaceutically acceptable salt thereof.

18. A method for treating Hepatitis B Virus (HBV) infection in a patient, the method comprising administering to the patient an effective amount of at least one compound of claim 8 or a pharmaceutically acceptable salt thereof.

19. The method of claim 17, further comprising administering to the patient at least one additional antiviral agent, wherein the additional agent is selected from an HCV polymerase inhibitor, an interferon, a viral replication inhibitor, an antisense agent, a therapeutic vaccine, a viral protease inhibitor, a virion production inhibitor, an antibody therapy (monoclonal or polyclonal), and any agent useful for treating HCV infection.

20. The method of claim 18, further comprising administering to the patient at least one additional antiviral agent, wherein the additional agent is selected from an HCV polymerase inhibitor, an interferon, a viral replication inhibitor, an antisense agent, a therapeutic vaccine, a viral protease inhibitor, a virion production inhibitor, an antibody therapy (monoclonal or polyclonal), and any agent useful for treating HBV infection.

* * * * *